US005756291A

United States Patent [19]
Griffin et al.

[11] Patent Number: 5,756,291
[45] Date of Patent: May 26, 1998

[54] APTAMERS SPECIFIC FOR BIOMOLECULES AND METHODS OF MAKING

[75] Inventors: Linda Griffin, Atherton; Glenn Albrecht, Redwood City; John Latham, Palo Alto; Lawrence Leung, Hillsborough; Eric Vermaas, Oakland; John J. Toole, Burlingame, all of Calif.

[73] Assignee: Gilead Sciences, Inc., Foster City, Calif.

[21] Appl. No.: 484,192

[22] Filed: Jun. 7, 1995

Related U.S. Application Data

[63] Continuation of Ser. No. 934,387, Aug. 21, 1992, abandoned, which is a continuation-in-part of PCT/US92/01383, Feb. 21, 1992.

[51] Int. Cl.$^6$ ............... C12Q 1/68; C07K 1/14; C07H 21/04; C07H 21/02
[52] U.S. Cl. ............... 435/6; 536/23.1; 530/413; 935/77; 935/78
[58] Field of Search ............... 435/6; 935/77, 935/78; 530/413; 536/23.1

[56] References Cited

U.S. PATENT DOCUMENTS 4,748,156  5/1988  Aoki et al.
5,270,163  12/1993  Gold et al.

FOREIGN PATENT DOCUMENTS

WO 91/02750  of 0000  WIPO
WO 91/19813  of 0000  WIPO

OTHER PUBLICATIONS

Bock et al., Nature 356:564–566 (6 Feb. 1992).
Kadonaga et al., PNAS, USA 83: 5889–5893 (Aug. 1986).
Ullman et al., "Principles of Homogeneous Enzyme–Immunoassay," Enzyme–Immunoassay 5:105–134 (1988).
Van Lente et al, "Determination of Thyroxine by Enzyme–Immunoassay," Enzyme–Immunoassay 6:135–153 (1988).
Blackwell et al., "Differences and Similarities in DNA–Binding Preferences of MyoD and E2A Protein Complexes Revealed by Binding Site Selection," Science (1990) 250:1104–1110.
Blackwell et al., "Sequence–Specific DNA Binding by the c–Myc Protein," Science (1990) 250:1149–1152.
Tuerk and Gold, "Systematic Evolution of Ligands by Exponential Enrichment: RNA Ligands to Bacteriophage T4 DNA Polymerase," Science (1990) 249:505–510.
Saiki et al., "Primer–Directed Enzymatic Amplification of DNA with a Thermostable DNA Polymerase," Science (1988) 239:487–491.
Kinzler and Vogelstein, "Whole Genome PCR: Application to the Identification of Sequences Bound by Gene Regulatory Proteins," Nucleic Acids Res. (1989) 17:3645–3653.
Kinzler and Vogelstein, "The GLI Gene Encodes a Nuclear Protein Which Binds Specific Sequences in the Human Genome," Mol. Cell. Biol. (1990) 10:634–642.

Ellington and Szostak, "In Vitro Selection of RNA Molecules that Bind Specific Ligands," Nature (1990) 346:818–822.
Thiesen and Bach, "Target Detection Assay (TDA): A Versatile Procedure to Determine DNA Binding Sites as Demonstrated on SP1 Protein," Nucleic Acids Res. (1990) 18(11):3203–3208.
Springer, T.A., "Adhesion Receptors of the Immune System," Nature (1990) 346:425–434.
Isobe, M., et al., "Specific Acceptance of Cardiac Allograft After Treatment with Antibodies to ICAM–1 and LFA–1," Science (1992) 255:425–434.
Oppenheimer–Marks et al., "Differential Utilization of ICAM–1 and VCAM–1 During the Adhesion and Transendothelial Migration of Human T Lymphocytes," Immunol. (1991) 147:2913–2921.
Straunton et al., "The Arrangement of the Immunoglobulin–like Domains of ICAM–1 and the Binding Sites for LFA–1 and Rhinovirus," Cell (1990) 61:243–254.
Ferns et al., "Inhibition of Neointimal Smooth Muscle Accumulation After Angioplasty by an Antibody to PDGF," Science (1992) 253:1129.
Libby et al., "Production of Platelet–Derived Growth Factor–Like Mitogen by Smooth–Muscle Cells from Human Atheroma," NEJM (1988) 318:1493.
Kavanaugh et al., "Transcriptional Regulation of the A and B Chain Genes of Platelet–derived Growth Factor in Microvascular Endothelial Cells," J. Biol. Chem. (1988) 263:8470.
Lindner et al., "Role of Basic Fibroblast Growth Factor in Vascular Lesion Formation," Circulation Research (1991) 68:106.
Mann et al., "Prothrombin," Meth. Enzymol. (1981) 80:286–302.

(List continued on next page.)

Primary Examiner—Stephanie W. Zitomer
Attorney, Agent, or Firm—Mark L. Bosse

[57] ABSTRACT

A method for identifying oligomer sequences, optionally comprising modified base, which specifically bind target molecules such as serum proteins, kinins, eicosanoids and extracellular proteins is described. The method is used to generate aptamers that bind to serum Factor X, PDGF, FGF, ICAM, VCAM, E-selectin, thrombin, bradykinin, PGF2 and cell surface molecules. The technique involves complexation of the target molecule with a mixture of oligonucleotides containing random sequences and sequences which serve as primer for PCR under conditions wherein a complex is formed with the specifically binding sequences, but not with the other members of the oligonucleotide mixture. The complex is then separated from uncomplexed oligonucleotides and the complexed members of the oligonucleotide mixture are recovered from the separated complex using the polymerase chain reaction. The recovered oligonucleotides may be sequenced, and successive rounds of selection using complexation, separation, amplification and recovery can be employed. The oligonucleotides can be used for therapeutic and diagnostic purposes and for generating secondary aptamers.

12 Claims, 6 Drawing Sheets

OTHER PUBLICATIONS

Ellington et al., "Selection in vitro of single-stranded DNA molecules that fold into specific ligand-binding structures," *Nature* (1992) 355:850–852.

Riordan et al., "Oligonucleotide-based therapeutics," *Nature* (1992) 350:442–443.

Oliphant et al., "Defining the Consensus Sequences of *E. coli* Promoter Elements by Random Selection," *Nucl. Acids Res.* (1988) 16(15):7673–7683.

Oliphant et al., "Defining the Sequence Specificity of DNA-Binding Proteins by Selecting Binding Sites from Random-Sequence Oligonucleotides: Analysis of Yeast GCN4 Protein," *Mol. Cell Biol.* (1989) 9(7):2944–2949.

Chittenden et al., "The T/E1A-Binding Domain of Retinoblastoma Product Can Interact Selectively with a Sequence-Specific DNA-Binding Protein," *Cell* (Jun. 14, 1991) 65:1073–1082.

Huynh-Dinh et al., "Modified oligonucleotide as alternatives to the synthesis of mixed probes for the screening of cDNA libraries," *PNAS* (1985) 32:7510–7514.

Kirk-Othmer, "Encyclopedia of Chemical Technology," 3rd Ed., 6:35–54 (1979), John Wiley & Sons, NY.

| # | * | | | | | | | | | | | | | | | | | |
|---|---|---|---|---|---|---|---|---|---|---|---|---|---|---|---|---|---|---|
| 1 | 26 | G | G | G | T | T | G | G | - | - | G | T | C | G | G | T | T | G | G | T |
| 2 | 20 | G | G | G | A | T | G | G | - | - | T | T | T | G | G | T | T | G | G | G |
| 3 | 32 | A | G | G | T | T | G | G | - | - | - | G | A | G | G | G | T | G | G | G |
| 4 | 41 | T | G | G | T | T | G | G | - | - | C | G | A | G | G | A | T | G | G | A |
| 5 | 56 | A | G | G | T | T | G | G | - | G | T | A | G | T | G | T | T | G | G | T |
| 6 | 29 | A | G | G | T | T | G | G | - | - | G | C | T | G | G | T | T | G | G | G |
| 7 | 17 | G | G | G | T | T | G | G | - | - | - | G | A | G | T | T | G | G | A |
| 8 | 44 | T | G | G | T | T | G | G | - | - | G | T | C | G | G | T | T | G | G | G |
| 9 | 50 | G | G | G | A | T | G | G | - | - | T | G | T | G | G | T | T | G | G | C |
| 10 | 30 | T | G | G | T | T | G | G | - | - | C | A | G | G | G | A | T | G | G | G |
| 11 | 25 | T | G | G | A | T | G | G | - | - | T | G | A | G | T | T | G | G | A |
| 12 | 28 | G | G | G | G | T | G | G | - | - | T | T | A | G | T | T | G | G | T |
| 13 | 47 | A | G | G | G | T | G | G | - | - | T | T | A | G | T | T | G | G | T |
| 14 | 42 | C | G | G | T | T | G | G | - | G | T | T | G | G | G | A | T | G | G | A |
| 15 | 41 | C | G | G | T | T | G | G | - | - | T | G | T | G | G | T | T | G | G | T |
| 16 | 53 | A | G | G | T | T | G | G | - | - | T | G | T | G | G | G | T | G | G | G |
| 17 | 15 | C | G | G | G | T | G | G | - | - | A | T | A | G | G | T | T | G | G | A |
| 18 | 24 | G | G | T | G | T | G | G | T | A | G | T | T | T | G | T | T | G | G | G |
| 19 | 23 | T | G | G | T | T | G | G | T | T | A | C | T | G | G | T | T | G | G | G |
| 20 | 27 | G | G | G | T | T | G | G | - | - | T | C | T | G | G | G | T | G | G | A |
| 21 | 36 | T | G | G | T | T | G | G | - | - | G | T | T | G | G | G | T | G | G | A |
| 22 | 25 | T | G | G | T | T | G | G | - | - | C | C | A | G | G | T | T | G | G | A |
| 23 | 12 | C | T | A | G | C | G | G | - | C | A | G | T | G | G | T | T | G | G | G |
| 24 | 25 | T | G | G | G | T | G | G | - | - | G | G | A | G | G | T | T | G | G | T |
| 25 | 49 | A | G | G | T | T | G | G | - | - | T | T | T | G | G | G | T | G | G | T |
| 26 | 28 | A | G | G | T | T | G | G | - | T | T | A | G | G | T | T | G | G | T |
| 27 | 18 | G | G | G | A | T | G | C | - | - | G | G | T | G | G | T | T | G | G | G |
| 28 | 55 | T | G | G | T | T | G | G | - | T | T | A | T | G | G | T | T | G | G | T |
| 29 | 23 | A | G | G | T | T | G | G | - | - | T | G | T | G | G | T | T | G | G | C |
| 30 | 40 | A | G | G | T | T | G | G | - | - | T | G | T | G | G | G | T | G | G | G |
| 31 | 41 | T | G | G | T | T | G | G | - | - | - | G | A | G | T | T | G | G | T |
| 32 | 42 | G | G | G | T | T | G | G | T | G | G | T | G | G | A | T | G | G | T |
| | | | | | | | Consensus Sequence | | | | | | | | | | | |
| | | | G | G | T | T | G | G | (N)3 | | | | | G | G | T | T | G | G | |
| | G | | 9 | 31 | 30 | 6 | 0 | 32 | 31 | | | | | 30 | 32 | 6 | 0 | 32 | 32 | 11 |
| | A | | 9 | 0 | 1 | 4 | 0 | 0 | 0 | | | | | 0 | 0 | 4 | 0 | 0 | 0 | 8 |
| | T | | 10 | 1 | 1 | 22 | 31 | 0 | 0 | | | | | 2 | 0 | 22 | 32 | 0 | 0 | 11 |
| | C | | 4 | 0 | 0 | 0 | 1 | 0 | 1 | | | | | 0 | 0 | 0 | 0 | 0 | 0 | 2 |

Fig. 1

| clone 1 | A G G A T A T A T G A T A T G A T T C G |
|---|---|
| 2 | T C A G T A T T A G G C C C C T C G A A |
| 3 | C A G A G T A C A G G C C A T G T G C A |
| 4 | T A G T A T G T A T T A T G T G T A G |
| 5 | G T A T A T A G T A T A G T A T T G G C |
| 7 | G A C T A A A C G C A T T G T G C C C C |
| 8 | T A C C A T C C C G T G G A C G T A A C |
| 10 | G T A C A T T C A G G C T G C C T G C C |
| 13 | G A C G C A T C C A G T T T A G G T C G |
| 14 | A A C G A A G C G C A C G C C G G C T G |
| 17 | G T A T A T A G T A T A G T A T T G G C |
| 18 | T A C T A T C A T G T A T A T T A C C C |
| 19 | A T A G A G T A T A T A T G C T G T C T |
| 20 | C A C C A A A C G C A T T G C A T T C C |
| 21 | A C G G A T G G T C T G G C T G C A C A |
| 22 | C A T T A A A C G C G A G C T T T T T G |
| 23 | G A C G C A C C G T A C C C C G T |
| 24 | G T A T A T A G T A T A G T A T T G G C |
| 26 | C T C C C A T A A T G C C C T A G C C G |
| 27 | C A G T T T A C G T G C C A C T G T A C |
| 28 | T G G A T A G C A C A T T G G G T G T A |
| 29 | G T G T A G T T T A C G T C C C A C C C |
| 31 | G A A C A A A A C G C A T T G T C C C C |
| 32 | T A T A G A G T A T A G T A T G T G C T |
| 33 | A G T A C A T G C A G G T A G T T C A C |
| 34 | G C C C A A C A C G C A T T G T T C C C |
| 36 | G A G T T C A C G T G C G A T G T G A C |

APTAMERS SPECIFIC FOR BIOMOLECULES AND METHODS OF MAKING

CROSS-REFERENCE TO RELATED APPLICATION

This is a continuation of application Ser. No. 07/934,387 filed on Aug. 21, 1992, now abandoned, which is a continuation-in-part of PCT/US92/01383, filed Feb. 21, 1992, which is based on U.S. Ser. Nos. 658,849; 659,114; 659,103; 658,796; 659,113, 659,980 and 659,981, all filed Feb. 21, 1991, 744,870 and 745,215, both filed Aug. 14, 1991 and 787,921, filed Nov. 6, 1991, all now abandoned, the disclosures of each of which are incorporated herein by reference. This application is also related in part to application Ser. No. 934,385, filed Aug. 21, 1992, now abandoned, also incorporated herein by reference.

1. Technical Field

The present invention is directed to compositions and methods for identifying oligonucleotide sequences which specifically bind biomolecules, including peptides, hydrophobic molecules, and target features on cell surfaces, in particular extracellular proteins, and the use of these sequences to detect and/or isolate the target molecules and the resulting compositions. The instant invention is exemplified by obtaining compositions, through the use of disclosed methods, that comprise oligonucleotide sequences which bind to Factor X, thrombin, kinins, eicosanoids, extracellular proteins, PDGF, aFGF, ICAM-1, VCAM-1, E-Selectin and fragments or peptides thereof.

The invention is also directed to improvements in methods to identify specific binding sequences (aptamers) for target substances and methods of use of such specific binding sequences. More specifically, it concerns: (1) methods for the selection of aptamers containing modified monomers that bind to specific target molecules; (2) the use of oligonucleotides containing modified monomer residues to expand the repertoire of candidate oligomer sequences; (3) the use of identifying and amplifying oligonucleotides without attached flanking regions or structural constraints, but which nevertheless are capable of specific binding to desired targets; (4) the design and use of conjugates designed to bind specific target cells and induce an immune response to the target cells; (5) methods of identifying oligonucleotide sequences which specifically bind target features on cell surfaces, and in particular, extracellular proteins, more specifically, it concerns methods of identifying, isolating and amplifying oligonucleotide sequences which bind to extracellular proteins on particular human cell lines; (6) methods to identify specific binding oligo nucleotide sequences by incubating a pool of oligonucleotides with support-bound target molecules and detaching the resulting target-oligonucleotide complexes from the support; (7) the use of improved methods to obtain aptamers that bind to selected target molecules such as Factor X, PDGF, aFGF, ICAM-1, VACM-1, E-selectin and fragments thereof; and (8) compositions obtained from the application of the disclosed methods.

2. Background and Related Art

Conventional methods of therapeutic treatment based on binding and inhibition of therapeutic target molecules as well as detection and isolation of proteins and other molecules have employed small molecules, antibodies and the like which specifically bind such substances. Recently, however, the de novo design of specifically binding oligonucleotides for certain non-oligonucleotide targets has been described. See, e.g., Blackwell et al., Science (1990) 250:1104–1110; Blackwell et al., Science (1990) 250:1149–1151; Tuerk, C., and Gold, L., Science (1990) 249:505–510; Ellington et al., Nature (1990) 346:818–822. The Tuerk reference describes the use of an in vitro selection and enrichment procedure to obtain RNA molecules that bind to an RNA binding protein. In this method, a pool of RNAs that are completely randomized at specific positions is subjected to selection for binding to a desired nucleic acid binding protein. The selected RNAs are then amplified as double-stranded DNA that is competent for subsequent in vitro transcription. The newly transcribed RNA is then enriched for better binding sequences and recycled through this procedure. The amplified selected sequences are subjected to dideoxy sequence determination. This procedure was applied to determination of RNA molecules which are bound by T4 DNA polymerase. The method utilizes the polymerase chain reaction (PCR) technique, as described by Saiki, R. K., et al., Science (1988) 239:487–491, to amplify the selected RNAS.

Kinzler, K. W., et al., Nucleic Acids Res (1989) 17:3645–3653, describes the use of PCR to identify genomic DNA sequences that are bound by nucleic acid binding proteins that regulate gene expression. In the reported work, total genomic DNA is first converted to a form that is suitable for amplification by PCR and the DNA sequences of interest are selected by binding to the target regulatory protein. The recovered bound sequences are then amplified by PCR. The selection and amplification process are repeated as needed. The process as described was applied to identify genomic DNA sequences which bind to the *Xenopus laevis* transcription factor 3A. The same authors (Kinzler et al.) in a later paper, Mol Cell Biol (1990) 10:634–642, applied this technique to identify the portion of the human genome which is bound by the GLI gene product produced as a recombinant fusion protein. The GLI gene is amplified in a subset of human tumors and is a DNA binding protein.

Ellington, A. D., et al., Nature (1990) 346:818–822, describe the production of a large number of random sequence RNA molecules and identification of those which bind specifically to selected molecules, for instance, organic dyes such as Cibacron blue. Randomly synthesized DNA yielding approximately $10^{15}$ individual sequences was amplified by PCR and transcribed into RNA. It was thought that the complexity of the pool was reduced in the amplification/transcription steps to approximately $10^{13}$ different sequences. The pool was then applied to an affinity column containing the dye and the bound sequences subsequently eluted, treated with reverse transcriptase and amplified by PCR. The results showed that about one in $10^{10}$ random sequence RNA molecules folds in such a way as to bind specifically to the ligand.

Thiesen, H.-J., and Bach, C., Nucleic Acids Res (1990) 18:3203–3208, describe what they call a target detection assay (TDA) to determine DNA binding sites for putative DNA binding proteins. In their approach, a purified functionally active DNA binding protein and a pool of genomic double-stranded oligonucleotides which contain PCR primer sites at each end were incubated with the protein. The resulting DNA complexes with the protein (in their case, the SP1 regulatory protein) were separated from the unbound oligomers in the mixture by band-shift electrophoresis and the complex oligonucleotides were rescued by PCR and cloned, and then sequenced using double-stranded mini-prep DNA sequencing.

None of the above references, however, describes the identification of oligonucleotides which specifically bind biomolecules that are not known to interact with oligonucleotides. In particular, these references do not describe the identification of oligonucleotides which specifically bind peptide molecules such as serum proteins, kinins, hydrophobic molecules such as eicosanoids, or extracellular proteins.

Ellington, A. D. et al., Nature (1992) 355:850–852, describe isolation of single stranded DNA molecules from a pool of molecules containing a 120 base region of random sequence. DNA molecules were shown to bind to organic dyes such as Cibacron Blue after selection and amplification of molecules that were retained on columns containing immobilized dye.

Gold, L. et al., international publication number WO/91/19813 describes selection of single-stranded RNA molecules that bind to molecules such as the polymerase of bacteriophage T4 or the reverse transcriptase of HIV-1.

In copending application U.S. Ser. No. 07/586,759, filed 21 Sep. 1990, Weintraub and Blackwell describe a system for identifying oligonucleotides which bind targets specifically wherein the target is incubated with double stranded DNA, randomized in one section but bracketed by PCR templates, and separating the resulting complexes using an electrophoretic gel shift method. The separation of the complex is then followed by PCR amplification and cloning. This method was published in Science (1990) 250:1104–1110; ibid., 1149–1151.

The art has not demonstrated (i) in vivo therapeutic (mammalian or primate) efficacy of selected oligonucleotides for any clinical indication, (ii) binding of single-stranded DNA oligonucleotides to biomolecules that do not ordinarily bind to nucleic acid as part of their normal function, (iii) interference with the function of a target molecule by a bound a oligonucleotide or aptamer, (iv) target molecule binding mediated by single-stranded DNA, (v) target-specific binding of short oligonucleotides or oligonucleotide analogs that are derived from a larger full-length parent oligonucleotide (aptamer) molecule, (vi) selection of single-stranded DNAs that bind to selected target biomolecules by a gel shift or functional selection methods, (vii) recognition of the problem that flanking primer sequences represent with respect to selection for truly optimal binding agents, or (viii) methods in which aptamer DNA- target complexes are isolated by coupling a target to a column support, and then purified by uncoupling the target-aptamer complex.

The invention herein provides an approach and utilizes binding selection methods combined with PCR or other amplification methods to develop aptamers that bind to various target molecules such as protein or peptide molecules such as Factor X, PDGF, FGF, ICAM, VCAM or E-selectin; kinins; hydrophobic molecules such as ecosanoids; and extracellular proteins. In this method, selected and amplified aptamers that specifically bind to these targets are obtained starting from a pool of randomized oligonucleotides, optionally containing modified monomers.

Intercellular Adhesion Molecules and Inflammation. Cell adhesion molecules such as intercellular adhesion molecule-1 (ICAM-1), vascular adhesion molecule-1 (VCAM-1) and E-Selectin (ELAM-1) play an important role in the complex series of events associated with inflammatory responses after tissue damage or in response to infection. Inflammatory responses involve recruitment of inflammatory cells to the site of injury, infection or foreign cells (Springer, T. A., Nature (1990) 346:425–434; Isobe, M., et al., Science (1992) 255:1125–1127), followed by clearance or removal of the damaged or foreign cells. In cases where normal homeostatic mechanisms fail to attenuate the inflammatory response, disease conditions result through damage to normal tissue and cells. A hallmark of the inflammatory response is cell-cell interactions that are required for activation of the cells involved. The cell-cell interactions are mediated by the presence of intercellular adhesion molecules that permit attachment of white blood cells or leukocytes through specific binding interactions with vascular endothelial cells (EC).

Extravasation of circulating T-cells and neutrophils through the endothelium and into the perivascular tissue requires the recognition of cell adhesion molecules which are glycoproteins present on the surface of activated EC (Oppenheimer-Marks, N., et al., I Immunol (1991) 147:2913–2921). Cytokines, released locally at sites of inflammation from neighboring cells due to injury, activate expression of a specific set of genes in EC including several adhesion receptors: E-Selectin, ICAM-1 and VCAM-1. The time course of expression after stimulation and the individual roles each plays in this process has been extensively examined and indicates that a multi-step process requiring each component is essential for extravasation. This process has been broken down into three steps, 1) neutrophil binding (rolling), 2) strengthening, signal transduction and shape change and finally 3) migration and extravasation. E-Selectin has been implicated in the rolling process, ICAM-1 in the second step and VCAM-1 in the migration step. Several lines of evidence indicate that this process may be interrupted at each of these steps resulting in decreased inflammation.

ICAM-1 is probably the best studied adhesion molecule of the three and is characterized by the presence of active domains that participate in binding interactions (Staunton, D. E., et al., Cell (1990) 61:243–254). It is a member of the Ig super-gene family consisting of five IgG domains. Amino acids in domains one and two play a direct role in interacting with the inducible lymphocyte adhesion receptor LFA-1. Antibodies which recognize these amino acids and thus block ICAM-1/LFA-1 interactions have been tested in an in vitro model and shown to decrease trans-migration of activated T-cells.

Other adhesion molecules such as ICAM-2, ELAM-1 and granule membrane protein-140 and their cognate white cell glycoprotein receptors such as LFA-1, Mac-1 and p150,95 are also believed to play a role in the inflammatory response. Modulation of the inflammatory response by specific binding to adhesion molecules and interfering with cell-cell interactions reduces inflammation in appropriate animal models. Aptamers which are used as specific binding agents can thus be used as therapeutics for treatment of inflammatory diseases or conditions such as vascular damage due to inflammation associated with heart attacks or other acute or chronic cardiac conditions. The inflammatory component associated with asthma, rheumatoid arthritis, allograft rejection, psoriasis and the like can also be treated in a similar manner.

In addition to their use as therapeutic agents, aptamers that specifically bind to adhesion molecules can be used for diagnostic purposes when appropriately labeled or marked. Such diagnostic agents can be used in in vivo or in vitro assays.

Growth Factors. Aptamers that bind to smooth muscle cell (SMC) growth factors, such as platelet derived growth factor (PDGF), basic fibroblast growth factor (bFGF) and acidic fibroblast growth factor (aFGF) can be used in postangioplasty treatments to prevent or reduce restenosis. Reduction of accelerated atherosclerosis after heart transplant and coronary bypass may also be treated using aptamers that bind FGFs to prevent excessive neovascularization in "angiogenic" diseases (e.g. diabetic retinopathy, rheumatoid arthritis, psoriasis). Aptamers that bind to PDGF may be used to treat certain fibrotic diseases (e.g. pulmonary fibrosis).

Current data obtained from animal models suggest that bFGF and PDGF play different but overlapping roles in myointimal thickening after vessel injury. bFGF appears to mediate the Phase I medial SMC proliferation (peak at 48 hr) while PDGF is important in Phase II (4–14 days) causing SMC migration into the intima as well as proliferation in the intima (which is also partially dependent on bFGF). Clinical indications for bFGF aptamers or PDGF thus include inhibition of myointimal thickening or restenosis associated with various conditions including angioplasty procedures.

Anti-PDGF IgG (polyclonal) was shown to decrease intimal thickening by 40% after angioplasty in a rat model (Ross et al., Science 253:1129, 1992). The mechanism of inhibition may be mediated mainly by inhibition of chemotaxis of SMC. Anti-PDGF antibodies are much more potent against exogenous PDGF than endogenous PDGF (isoform AA) induced by IL-1 or TGF-b because cell bound PDGF is less accessible to intact IgG.

Production of PDGF-like mitogen by SMC cultured from human atheroma has been described (Libby et al., NEJM, 318:1493, 1988). Anti-PDGF antibodies neutralized only 40% of mitogenic activity and mRNA for PDGF A chain, but not B chain which was detected in these cultured SMC. This data suggests that the PDGF AA isoform may be a preferred target compared to the AB or BB isoforms. However, human platelet PDGF is of the AB form. In other studies (e.g. Williams et al. J. Biol. Chem. (1988) 263:8470), human renal microvascular endothelial cells were found to express both A and B chain mRNA and both mRNA levels increase after cell stimulation with thrombin, TGF-b and PMA, with evidence of differential transcriptional control.

Rat carotid SMC's express bFGF by Northern and Western analysis. Systemic infusion of bFGF is a potent mitogen for SMC proliferation in injured carotid vessels (Lindner, et al. Circulation Research, 68:106, 1991). bFGF is a potent stimulator for angiogenesis. Clinical indications for the use of bFGF aptamers include treatment of angiogenic diseases such as diabetic retinopathy or tumor growth associated with angiogenic activity.

Factor Xa and Factor X. Factor Xa (F Xa) plays an important role in thrombosis as the penultimate enzyme in the clotting cascade. Plasma levels of F X are about 10-fold below those of thrombin, suggesting that FX or FXa inhibitors may be effective at lower concentrations in plasma relative to a thrombin inhibitor of equal relative potency. F Xa is a serine protease that converts human prothrombin to thrombin, the final enzyme in the clotting cascade, by cleavage of two peptide bonds in prothrombin (Mann et al., Meth Enzymol (1981) 80:286–302). Conversion of prothrombin to thrombin results in fibrin clot formation mediated by thrombin. Both the generation and activity of F Xa is strictly regulated to control thrombus formation at sites of thrombogenic stimulus. Aptamers that prevent conversion of F X to F Xa or that inhibit the activity of F Xa are thus suitable for antithrombotic therapeutics. Clinical applications for such agents include treatment of conditions associated with cardiovascular diseases such as stroke or for extracorporeal anticoagulation indications such as in coronary bypass surgery. F X or F Xa inhibitors are also useful in clinical applications where prophylactic anticoagulation treatments are used such as prior to surgery in hip replacement procedures and the like.

Clinical indications for inhibitors of F Xa or F X center on situations where partial or total occlusion of blood vessels by blood clots occur. Such diseases include myocardial infarction, deep vein thrombosis, pulmonary embolism, pheripheral arterial occlusion and the like. Treatment or prophylaxis of thrombotic diseases is based on inhibition of clotting and/or acceleration of thrombolysis. By modulating the activities of thrombin via preventing conversion of prothrombin to thrombin, thrombin activities such as fibrinogen to fibrin conversion, mitogenesis for vascular smooth muscle cells, stimulation of platelet aggregation, monocyte chemotaxis, stimulation of prostacyclin and platelet activating factor synthesis by vascular endothelial cells, induction of neutrophil adherence to vessel walls, generation of activated protein C from protein C and the like can also be modulated. Such activities are involved in restenosis, accelerated atherosclerosis after heart transplant, vascular graft reocclusion associated with vascular shunt implants, thrombus formation associated with cardiopulmonary bypass surgery, thrombus formation associated with extracoropreal circuits used in ex vivo procedures such as dialysis or apheresis, sepsis-related disseminated intravascular coagulation and the like.

Kinins. Kinins include a family of N-substituted derivatives of adenine and peptides which are formed in biological fluids by the activation of kininogens. Kinins have been shown to exert numerous physiological and pathological actions such as exhibiting hypotensive effects, causing pain, mediating reactive hyperaemia in exocrine glands, playing a role in vascular and cellular events that accompany the inflammatory processes, controlling protectivesure, and possibly acting as protective agents against hypertension. In pathological states, kinins have been implicated in asthma, inflammatory diseases such as rheumatoid arthritis and other forms of arthritis, vascular changes occurring in migraine, myocardial infarction, cardiovascular failure, carcinoid and postgastrectomy dumping syndromes, hyperbradykininism syndrome, hemorrhagic and endotoxic shock, as well as other pathological conditions. For a review of kinins, see Regoli, D., and Barabe, J., Pharmacological Review (1980) 32:1–46.

Eicosanoids. Eicosanoids are a family of fatty acid derivatives which include the various prostaglandins, thromboxanes, leukotrienes and prostacyclin. Eicosanoids are widespread and produce a remarkably broad spectrum of effects embracing nearly every biological function. For example, eicosanoids have been shown to affect the cardiovascular system, blood, smooth muscle, kidney and urine formation, the central nervous system, inflammatory and immune responses, afferent nerves and pain, as well as several metabolic functions. For a general review of eicosanoids and their biological significance, see Moncada, S., et al., in The Pharmacological Basis of Therapeutics, Gilman, A. G., et al., eds. (MacMillan Publishing Company, New York), 7th Edition, pages 660–671.

Many of these molecules (both kinins and eicosanoids) are so ubiquitous that antibody production in laboratory animals against the native molecules can be difficult unless they are chemically modified to become antigenic. Labeled kinins with sufficient specific activity are not available and bradykinin antibodies tend to cross-react with kininogen. Therefore, conventional immunodiagnostic and isolation techniques are not easily available with respect to these substances. It would therefore be desirable to develop alternative methods for working with these agents.

Additionally, there are numerous difficulties related to collecting biological samples while avoiding the formation or the inactivation of kinins. Thus, previous assay methods have focused on measuring the particular kininogens rather than the activation peptides thereof. For a review of the problems associated with the use of conventional diagnostic techniques and kinins, see Goodfriend, T. L., and Odya, C. E., in Methods of Hormone Radioimmunoassays, B. N. Jaffee and H. R. Behrman, eds. (Academic Press, New York), 1979, pages 909–923; and Talamo, R. C., and Goodfriend, T. L., Handbook Exp. Pharmacol. (1979) 25 (Suppl.):301–309. It would therefore be desirable to develop alternative methods for working with these agents.

Cell Surface Molecules. Particular cells can be characterized by the presence of certain proteins on their surface. These proteins can serve a variety of functions including providing binding sites for other biomolecules and/or virus receptors. It is also known that it is possible to differentiate normal cells of a given type from abnormal cells by the type and/or amount of characteristic protein on the cells' surface. Since it is known that it is possible to differentiate different types of cells by the characteristic proteins present on their surface, different methodologies have been developed in attempts to characterize cells by the ability of certain molecules to bind to the characteristic proteins on those cells.

The present inventors postulated that oligonucleotides could be used to bind to characteristic proteins at the cell surface. Although such binding does occur, it is not highly specific, i.e., a given oligonucleotide may bind to cellular proteins on two very different types of cell lines. Further, even if a particular oligonucleotide is found to be specific to a particular characteristic protein, it is difficult to isolate the desired oligonucleotide and produce it in sufficient amounts so as to allow it to be useful as a probe to identify particular cell lines having particular characteristic proteins thereon.

Immune Recognition Mechanisms. This invention is also related to the use of specific binding oligomers in immune recognition mechanisms. Various immune recognition mechanisms exist which permit recognition and immune destruction of malignant or infected cells in an organism. Malignant cells often express antigens that are not found in normal cells; some of these antigens are found at the surface of the cell. Similarly pathogen-infected cells often express pathogen-encoded antigens at the cell surface. In both cases, the surface antigen represents a potential target for a CTL (cytotoxic T-cell) immune response.

Unfortunately, immune responses against unwanted cells are not always effective; moreover, such responses can, in some instances, be suppressed. A variety of mechanisms may play a role in the reduction or suppression of immune responses to pathologic cells. For example, tumors are associated with a decreased level of the histocompatibility antigens that may play a role in eliciting a CTL response. Viruses have also been able to mask viral antigens at the cell surface. In the case of HIV, heavy glycosylation of the envelope protein (normally found at the cell surface) may play a role in preventing an effective immune response against infected cells. The propensity of pathologic cells to reduce or escape effective CTL responses probably plays a role in the progression of various infections and disorders.

While some vaccines in current use consist of only portions of a pathogen (such as a viral envelope protein in the case of HBV virus), immune responses against an intact pathogen, such as a virus or bacterium, are often more effective than responses against individual components of the pathogen. Attenuated virus vaccines, for example, are used in some cases in order to expose the immune system to antigens that present epitopes in as natural a form as possible. The resulting immune response appears in general to result in more effective protection against the pathogen than the corresponding response to only a portion of the pathogen.

Many CTL responses appear to be based upon specific contacts between a plurality of surface antigens serving as signals for both self and non-self cells. Normal immune function is believed to involve a combined response to this plurality of surface antigens. Hence, it is reasonable to expect that a modified immune response would result if one or more of these surface features were somehow modified or masked.

In addition to the use of antibodies specific for one or more of the subject surface features, considerable attention has also been directed recently to the use of oligonucleotides of similar specificity. De novo recovery of specifically binding oligonucleotides is possible with respect to non-oligonucleotide targets, as discussed above.

It would clearly be advantageous to devise methods which permit the modulation of immune response to natural antigens in a manner such that optimum immune protection against a pathogen or malignant cell may be obtained, or such that an undesired component of the response may be eliminated. In particular, it would be desirable to take advantage of the involvement of a plurality of epitopes in the normal immune response by developing immunomodulatory agents which target one or more specific epitopes involved in generating the immune response.

Modified Bases in Polymerization Reactions. A large number of modifications which behave in a known manner in polymerase reactions are known. Otvos, L., et al., Nucleic Acids Res (1987) 1763–1777, report the enzyme catalyzed incorporation of 5-(1-alkenyl)-2'-deoxyuridines into DNA. As reported in this paper, 5-vinyl-dUP behaved in the DNA polymerase I reaction catalyzed by the Klenow fragment in a manner similar to dTTP; (E)-5-(1-heptenyl) and (E)-5-(1-octenyl)-dUDPs were poor substrates; however, all of these residues are read as thymidine in the polymerization.

Allen, D. J., et al., Biochemistry (1989) 28:4601–4607, report the incorporation of 5-(propylamino) uridine into oligomers and its labeling, using the propylamine function, with mansyl chloride. This complex was used to study interaction with DNA polymerase I (Klenow fragment) and was shown to interact with the enzyme. This base residue is also recognized as thymidine.

Langer, P. R., et al., Proc Natl Acad Sci USA (1981) 78:6633–6637, described the synthesis of DNA and RNA using dUTP and UTP residues labeled with biotin through a linker at the C5 position. These labeled forms of dUTP and UTP were utilized by a number of DNA and RNA polymerases and are recognized by these enzymes when included in the oligomer template as thymidine or uridine.

Gebyehu, G., et al., Nucleic Acids Res (1987) 15:4513, reported biotin-labeling of dATP and dCTP nucleotide analogs through the 6-position of adenine and 4-position of cytosine. They were incorporated into DNA probes by standard nick translation protocols and probes labeled with biotin derivatives of these nucleotides were effectively hybridized to target DNA sequences. Thus, the modified forms of dATP and dCTP, when incorporated into oligomers are recognized as A and C, respectively. Similarly, Gillam, I. C., et al., Anal Biochem (1986) 199–207, described the incorporation of N⁴ (6-aminohexyl) cytidine and deoxycytidine nucleotides into DNA enzymatically.

Trainor, G. L., et al., Nucleic Acids Res (1988) 16:11846, describe the ability of succinyl-fluorescein-labeled dideoxynucleoside triphosphates as substrates for terminal deoxynucleotidyl transferase and their use in the preparation of 3'-fluorescence-tagged DNA.

Mizusawa, S., et al., Nucleic Acids Res (1986) 14, described the replacement of dGTP in polymerase reactions by deoxy-7-deazaguanidine triphosphate; this is also described in the context of a PCR reaction by Innis, M. A., in "PCR Protocols: A Guide to Methods and Applications" (1990) Academic Press Inc.

The incorporation of 5-azido-dUTP appears to substitute for dTTP in polymerase reactions as reported by Evans, R. K., et al., Biochemistry (1987) 26:269–276; Proc Natl USA (1986) 83:5382–5386.

Oligonucleotides which contain covalently-bound mercury at specific base residues was described by Dale, R. M. K., et al., Proc Natl Acad Sci USA (1973) 70:2238–2242.

Finally, a terminal fluorescence residue using purines linked to fluorescing moieties is described by Prober, J. M., et al., Science 238:336.

Further, as set forth in the foregoing publications, not only is the modified base specifically recognized as such in a template sequence; nucleotide triphosphates utilizing the modified base are also capable of incorporation into the newly synthesized strand by polymerase enzymes.

Oligomers. Aptamers containing modifications may have superior binding qualities which are attributable to the modifications per se and this inclusion of modifications thus expands or alters the repertoire of candidates subjected to the initial screen. The present invention is related in part to an improvement in the above-described methods wherein oligomers containing modifications not found in native nucleic acids can be included among the candidates for specific binding.

Furthermore, although PCR has made possible the isolation and analysis of specific nucleic acid fragments from a wide variety of sources, application of PCR to isolate and analyze a particular nucleic acid region heretofore has required knowledge of the nucleic acid sequences either flanking or within the region of interest. The requirement of prior knowledge of the flanking region is particularly troublesome when trying to identify aptamers. Flanking primer sequences impose limits on aptamer structural diversity: either the ability to bind is affected by the primers, thereby eliminating from consideration a class of binding agents, or occasionally, the primers actually participate in or facilitate binding by conferring structure. Flanking sequence thus may impose constraints which make aptamers so identified suboptimal for drug development. These problems with the processes of selection for truly optimal binding agents or aptamers have severely limited drug development.

Clearly, it would be advantageous to devise methods which permit the identification of optimal aptamers. Methods such as those described by Ellington, A. D. et al., Nature (1990) 346:818–822, estimate that 1 in 10¹⁰ aptamers bind in that system. The novel methods herein described and claimed, including those for amplifying nucleic acids with no known base sequences may revise this ratio downward to 1 in 10⁹ or 1 in 10⁸.

Furthermore, none of the cited references describe the identification of aptamers capable of binding to proteins such as thrombin. The use of DNA aptamers according to this invention has several advantages over RNA including increased nuclease stability and ease of amplification by PCR or other methods. RNA generally is converted to DNA prior to amplification using reverse transcriptase, a process that is not equally efficient with all sequences, resulting in loss of some aptamers from a selected pool.

SUMMARY OF THE INVENTION

The invention described herein provides specifically binding oligonucleotides or "aptamers", including modified oligonucleotides or "aptamers", that are stable, versatile, and highly specific for their intended targets as exemplified by Factor X, aFGF, ICAM-1, peptides or fragments thereof and the like. Furthermore, the aptamers of the invention may be determined as well as synthesized using modified nucleotides and internucleotide linkages. In addition, these aptamers may be obtained from mixtures of candidate oligomers with completely unpredetermined sequences, without the necessity for inclusion of PCR primer sequences in the candidate pool. In addition, improved methods for generation of such aptamers are described. In one method, the efficiency of the method to determine suitable aptamers is further enhanced by separation of the complex containing successful candidate oligonucleotides bound to target from uncomplexed oligonucleotides and elution of the complex from solid support. In other methods, single-stranded aptamers composed of DNA analogs that bind target molecules are separated from nonbinding species by electrophoresis.

The aptamers of the present invention find a variety of utilities including therapeutic and diagnostic utilities as well as functioning as laboratory and industrial reagents. The aptamers of the invention can be coupled to various auxiliary substances such as labels or solid supports.

Thus, in one aspect, the invention is directed to aptamers and improved methods to obtain aptamers containing at least one binding region capable of binding specifically to a target molecule wherein the aptamer is a single-stranded DNA or DNA analog. Such single-stranded DNA aptamers can be constructed to bind specifically to a wide variety of target substances including proteins, peptides, glycoproteins, lipids, glycolipids, carbohydrates, various small molecules, and the like. Preferred targets include protein or peptide molecules such as Factor X, PDGF, FGF, ICAM, VCAM or E-selectin (ELAM-1), kinins, hydrophobic molecules such as ecosanoids, and extracellular proteins or fragments thereof. Such single-stranded DNA aptamers are advantageously stable as compared to RNA counterparts. It has been heretofore thought that the three-dimensional structure of double-stranded DNA limited the structural diversity of the molecule. The inventors herein are unaware of any prior demonstration of structural diversity for single- or double-stranded DNA sufficient to provide the range of conformations necessary to provide aptamers to biomolecules that do not normally bind to nucleic acids. For example, known RNA structures, such as pseudoknots, have not been described for single-stranded DNA.

In another aspect, the invention is directed to methods to obtain single stranded DNA aptamers by solution phase selection followed by separation using solid columns including immobized substrate columns and gels such as agarose or polyacrylamide.

In another aspect, the invention is directed to aptamers, optionally having one or more modified nucleotide residues, that have relatively short specific binding regions of less than 15 nucleotide residues and which may, themselves, be relatively small molecules containing less than 16 nucleotide residues. The limited length of these aptamers is advantageous in facilitating administration and synthesis. Further, in still other aspects, the invention is directed to aptamers with very low dissociation constants with respect to their target molecules (that do not normally bind oligonucleotides) of about 500 nM and in some cases less than $20 \times 10^{-9}$; and with high specificity for their targets of at least 5-fold differential in binding affinity as compared to competing substances. These enhanced specificities and binding affinities are clearly advantageous in the applications for which the aptamers of the invention are useful.

In another aspect, the invention is directed to functional selection methods that permit isolation of aptamers that both bind to and inhibit or otherwise modulate one or more biological functions of target biomolecules as exemplified by thrombin and Factor X.

In another aspect, the invention is directed to aptamers or modified aptamers that bind to a wide variety of target molecules, especially those selected from the group consisting of bradykinin, PGF2, CD4, HER2, IL-1 receptor, Factor X, thrombin, PDGF, aFGF, ICAM-1, VCAM-1, E-Selectin, and peptides or one or more fragments thereof. The versatility of aptamers in specifically binding even small and hydrophobic molecules expands the range of their utility.

It is also an object of the present invention to provide aptamers as specific binding agents for therapeutic application in the treatment of diseases with an immunological component such as inflammation. Methods are disclosed that can be used to obtain aptamers that bind to adhesion molecules. Such agents may act, at least in part, by specific binding to adhesion molecules such as ICAM-1, VCAM-1 E-Selectin and the like, thereby interfering with their function in immune responses.

In other aspects, the invention is directed to complexes of the target molecules and the aptamers or modified aptamers of the invention and to methods to obtain and to use the aptamers of the invention.

In another aspect, the invention is directed to complexes of a desired target substance with oligomers which contain at least one modified monomeric residue or linkage, said complex being free of cellular components normally associated with the target.

In still other aspects, the invention is directed to improved methods to obtain aptamers in general. These improved methods include the ability to utilize in a candidate pool of oligonucleotides completely undetermined sequences; to incorporate modified oligonucleotides in the candidate pool and to include modified nucleotides in the amplifying step of the method; to enhance the efficiency of the method by isolating the complex between the successful members of the candidate pool and the target molecule; and to obtain aptamers that bind cell surface factors using a subtraction technique.

In still another aspect of the invention, aptamers may be used as specific binding agents in conjugates designed to modulate the immune system.

BRIEF DESCRIPTION OF THE FIGURES

FIG. 1 is a chart depicting thrombin aptamer consensus-related sequences.

FIG. 3 is a chart depicting aptamer sequences obtained from round 6 with 5-pentynyl dU in the mixture of oligomers in Example 20.

FIG. 6 is a graph of a chart depicting sequences for cloned Factor X aptamers.

DETAILED DESCRIPTION

Figure 2:
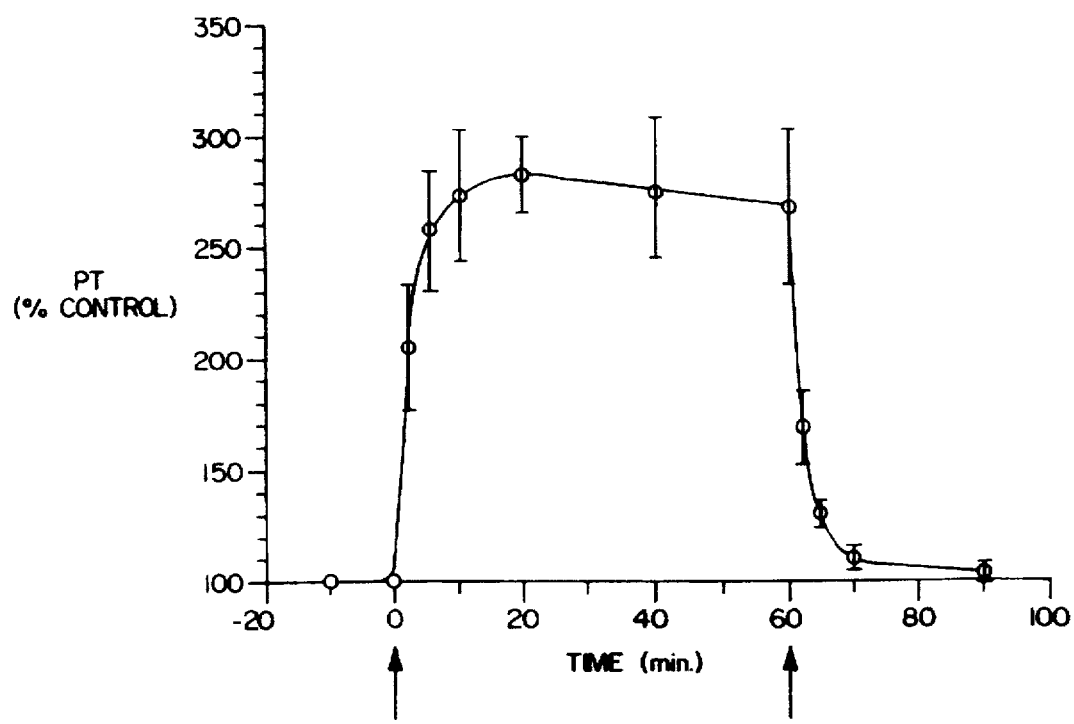
FIG. 2 is a plot of in vivo thrombin inhibition obtained from primates using a 15-mer aptamer.

The practice of the present invention will employ, unless otherwise indicated, conventional techniques of chemistry, molecular biology, biochemistry, protein chemistry, and recombinant DNA technology, which are within the skill of the art. Such techniques are explained fully in the literature. See, e.g., oligonucleotide Synthesis (M. J. Gait ed. 1984); Nucleic Acid Hybridization (B. D. Hames & S. J. Higgins eds. 1984); Sambrook, Fritsch & Maniatis, Molecular Cloning: A Laboratory Manual, Second Edition (1989); and the series Methods in Enzymology (S. Colowick and N. Kaplan eds., Academic Press, Inc.).

The invention is directed to a method which permits the recovery and deduction of aptamers which bind specifically to desired targets including those illustrated hereinbelow such as factor X, PDGF, FGF, ICAM, kinins (including bradykinin) as well as other small peptide hormones such as the vasoconstrictor endothelin (a 21-mer peptide), small hydrophobic molecules such as eicosanoids (including PGF2), and extracellular proteins, such as thrombin, as well as molecules that are contained at the cell surface such as IL-1 receptor and CD4. As a result of application of this method, aptamers or modified aptamers which contain the specifically binding sequences can be prepared and used in oligonucleotide-based therapy, in the detection and isolation of the target substance, as well as in other applications.

The aptamers described herein can be used as a separation means for retrieving the targets to which they specifically bind. By coupling the oligonucleotides containing the specifically binding sequences to a solid support, for example, the target substances can be recovered in useful quantities. In addition, these oligonucleotides can be used in diagnosis by employing them in specific binding assays for the target substances. When suitably labeled using detectable moieties including radioisotopes such as $^{19}F$, $^{99m}Tc$, $^{131}I$, $^{90}Y$, $^{111}In$, $^{123}I$, $^{15}N$ or $^{32}P$, the specifically binding oligonucleotides can also be used for in vivo or in vitro diagnosis, imaging or histological analysis by techniques known in the art.

For application in such various uses, the aptamers of the invention may be coupled to auxiliary substances that enhance or complement the function of the aptamer. Such auxiliary substances include, for example, labels such as radioisotopes, fluorescent labels, enzyme labels and the like; specific binding reagents such as antibodies, additional aptamer sequence, cell surface receptor ligands, receptors per se and the like; toxins such as diphtheria toxin, tetanus toxin or ricin; drugs such as antiinflammatory, antibiotic, or metabolic regulator pharmaceuticals, solid supports such as chromatographic or electrophoretic supports, and the like. Suitable techniques for coupling of aptamers to desired auxiliary substances are generally known for a variety of such auxiliary substances, and the specific nature of the coupling procedure will depend on the nature of the auxiliary substance chosen. Coupling may be direct covalent coupling or may involve the use of synthetic linkers such as those marketed by Pierce Chemical Co., Rockford, Ill.

Thus, the aptamers or modified aptamers of the invention may be used alone in therapeutic applications or may be used as targeting agents to deliver pharmaceuticals or toxins to desired targets. The aptamers may be used in diagnostic procedures and advantageously in this application include label. They way be used as reagents to separate target molecules from contaminants in samples containing the target molecules in which application they are advantageously coupled to solid support. A particularly advantageous application of the aptamers of the invention includes their use in an immune recruitment procedure as targeting agents for the immunomodulating substance used in this procedure, as further described below.

Definitions. As used in the disclosure and claims, the following terms are defined as follows. All references cited are incorporated by reference.

As used herein, a "target" or "target molecule" refers to a biomolecule that could be the focus of a therapeutic drug strategy or diagnostic assay, including, without limitation, proteins or portions thereof, enzymes, peptides, enzyme inhibitors, hormones, carbohydrates, glycoproteins, lipids, phospholipids, nucleic acids, and generally, any biomolecule capable of turning a biochemical pathway on or off or modulating it, or which is involved in a predictable biological response. Targets may be free in solution, like thrombin, or associated with cells or viruses, as in receptors or envelope proteins. Any ligand which is of sufficient size to be specifically recognized by an oligonucleotide sequence can be used as the target.

Thus, glycoproteins, proteins, carbohydrates, membrane structures, receptors, organelles, and the like can be used as the complexation targets.

It should be noted that excluded from target molecules are substances to which DNA sequences normally bind such as nucleases, substrates wherein binding is effected by Watson-Crick base pairing modes of binding to nucleic acids, specific triple helix binding to nucleic acid sequences, and the like. Thus, excluded from target molecules are those substances which natively bind the specific form of aptamer at issue. Thus, excluded therefore are nucleases that bind to single-stranded DNA, restriction endonucleases that bind to double-stranded DNA with respect to single-stranded DNA and double-stranded DNA, respectively. Also excluded are cell surface receptors specific for DNA or RNA.

A wide variety of materials can serve as targets. These materials include intracellular, extracellular, and cell surface proteins, peptides, glycoproteins, carbohydrates, including glycosaminoglycans, lipids, including glycolipids and certain oligonucleotides. A representative list of targets for which the aptamers of the invention may be prepared is set forth herein in Table 1 which follows the examples in the present specification.

Some of the useful targets are peptides such as kinins and small low molecular weight carbohydrates such as prostaglandins. These targets have particular features as follows:

By "kinin" is meant any of the peptide components enzymatically released by the activation of the various kininogens (hormogens). Thus, the term "kinin" includes the mammalian kinins such as, but not limited to, bradykinin (BK), Lys-BK, Met-Lys-BK, leukokinins, colostrokinin, neurokinin; the various nonmammalian kinins; and metabolites of the above. Kinins include a family of N-substituted derivatives of adenine and small peptides having, on the average, 9–11 amino acids. As described above, there are several inherent problems associated with the use of conventional immunotechniques for working with kinins. Thus, the present invention provides an efficient method for the detection and isolation of these important substances. For a review of kinins and their significance, see Regoli, D., and Barabe, J., Pharmacological Reviews (1980) 32:1–46, incorporated herein by reference in its entirety.

The subject invention is also useful for the detection and/or isolation of low molecular weight hydrophobic molecules. By "hydrophobic" is meant a compound having non-polar groups such that the compound as a whole has a relatively low affinity for water and other polar solvents. The hydrophobic molecules of the instant invention lack large numbers of groups that may participate in establishing noncovalent binding interactions with aptamers. Such interactions include base stacking via aromatic rings in the target, polar and ionic interactions, and hydrogen bonding.

The invention is particularly useful with fatty acid derivatives such as eicosanoids. By "eicosanoid" is meant any of the several members of the family of substances derived from 20-carbon essential fatty acids that contain three, four or five double bonds: 8,11,14-eicosatrienoic acid (dihomolinolenic acid); 5,8,11,14-eicosatetraenoic acid (arachidonic acid) and 5,8,11,14,17-eicosapentaenoic acid. Such substances encompass the various prostaglandins, including but not limited to PGA, PGB, PGC, PGD, PGE, PGE1, PGE2, PGE2, PGF, PGF1G, PGF2, PGG, PGG2, PGH, PGH2; the thromboxanes such as but not limited to TXA2 and TXB2; prostacyclin (PGI2) and 6-keto-PGT1; leukotrienes and precursors thereof such as LTB4 (a 5,12-dihydroxy compound), LTC4 (a 5-hydroxy derivative that is conjugated with glutathione), LTA4 (a 5,6-epoxide), LTD4 (synthesized by the removal of glutamic acid from LTC4), LTE4 (resulting from the subsequent cleavage of glycine), LTF4 (an -glutamyl, cysteinyl derivative), SRS-A (a mixture of LTC4 and LTD4 known as the "slow-reacting substance of anaphylaxis"), HPETE (hydroperoxyeicosatetraenoic acid) and HETE (monohydroxyeicosatetraenoic acid). Eicosanoids are also intended to include synthetic eicosanoid analogs such as 16-methoxy-16-methyl-PGF2 and 15-methyl-PGF2 (Guzzi, et al., J. Med. Chem. (1986) 29:1826–1832; Cheng, et al., Acta Acad. Med. Shanghai (1990) 17:378–381) or in vivo generated eicosanoid metabolites (Morrow, et al., Proc Natl. Acad. Sci (USA) (1990) 87:9383–9387). Eicosanoids are relatively low molecular weight compounds which are generally hydrophobic in nature. These substances normally have molecular weights under 400, but some naturally occurring variants are conjugated to one or several amino acids and these will have higher molecular weights. These variants are also encompassed by the subject invention. As described above, several eicosanoids have not heretofore been easily detectable or isolatable using standard immunotechniques due to their ubiquitous nature. Thus, the present invention provides an efficient method for the detection and isolation of these important substances. For a review of eicosanoids and their significance, see Moncada, S., et al., in The Pharmacological Basis of Therapeutics, Gilman, A. G., et al., eds. (MacMillan Publishing Company, New York), 7th Edition, pages 660–671, incorporated herein by reference in its entirety.

The above small molecule and hydrophobic targets have not heretofore been considered to be potential target molecules for aptamer selection as oligonucleotides are very hydrophilic and highly hydrated. Previous methods for obtaining oligonucleotides that bind to targets utilized protein targets that normally bind to nucleic acids, or in the work described by Ellington, et al., Nature (1990) 346:818–822, target molecules with many possible hydrogen-bond donor and acceptor groups as well as planar surfaces for stacking interactions. In the case of nucleic acid binding proteins, binding to nucleic acid oligonucleotides is aided by the inherent binding properties of the proteins. In the case of molecules used by Ellington et al., numerous chemical structures are present that can participate in noncovalent binding interactions including planar aromatic rings that may interact with nucleic acids via base stacking interactions. In contrast, many eicosanoids such as PGF2 have relatively little structural diversity. It is thus unexpected that fatty acid-like molecules may serve as binding targets for single stranded DNA. One representative eicosanoid, PGF2, as used in the present invention, has only 3 hydroxyl groups, two double bonds between adjacent methylene groups, a carboxylic acid group (which, as used herein, is present as an amide linkage for covalent attachment to a solid support) and a cyclopentyl ring. By comparison with almost all other classes of potential biological target molecules, the eicosanoids are extremely deficient in groups that may participate in noncovalent binding interactions.

Target molecules that are not conventionally considered to be biomolecules are also appropriate for the methods described herein. Examples of "non-biomolecule" targets include intermediates or end-products generated by chemical synthesis of compounds used in therapeutic, manufacturing or cosmetic applications, including polymer surfaces, especially those useful in medical applications. Aptamer oligonucleotides may be used to specifically bind to most organic compounds and are suitably used for isolation or detection of such compounds.

As used herein, "specifically binding oligonucleotides" or "aptamers" refers to oligonucleotides having specific binding regions which are capable of forming complexes with an intended target molecule in an environment wherein other substances in the same environment are not complexed to the oligonucleotide. The specificity of the binding is defined in terms of the comparative dissociation constants (Kd) of the aptamer for target as compared to the dissociation constant with respect to the aptamer and other materials in the environment or unrelated molecules in general. Typically, the Kd for the aptamer with respect to the target will be 2-fold, preferably 5-fold, more preferably 10-fold less than Kd with respect to target and the unrelated material or accompanying material in the environment. Even more preferably the Kd will be 50-fold less, more preferably 100-fold less, and more preferably 200-fold less.

The binding affinity of the aptamers herein with respect to targets and other molecules is defined in terms of Kd. The value of this dissociation constant can be determined directly by well-known methods, and can be computed even for complex mixtures by methods such as those, for example, set forth in Caceci, M., et al., Byte (1984) 9:340–362. It has been observed, however, that for some small oligonucleotides, direct determination of Kd is difficult, and can lead to misleadingly high results. Under these circumstances, a competitive binding assay for the target molecule or other candidate substance may be conducted with respect to substances known to bind the target or candidate. The value of the concentration at which 50% inhibition occurs (Ki) is, under ideal conditions, equivalent to Kd. However, in no event can Ki be less than Kd. Thus, determination of Ki, in the alternative, sets a maximal value for the value of Kd. Under those circumstances where technical difficulties preclude accurate measurement of Kd, measurement of Ki can conveniently be substituted to provide an upper limit for Kd.

As specificity is defined in terms of Kd as set forth above, excluded from the categories of unrelated materials and materials accompanying the target in the target's environment are those materials which are sufficiently related to the target to be immunologically crossreactive therewith, and materials which natively bind oligonucleotides of particular sequences such as nucleases, restriction enzymes, and the like. By "immunologically crossreactive" is meant that antibodies raised with respect to the target crossreact under standard assay conditions with the candidate material.

Generally, for antibodies to crossreact in standard assays, the binding affinities of the antibodies for crossreactive materials as compared to targets should be in the range of 5-fold to 100-fold, generally about 10-fold.

Thus, aptamers which contain specific binding regions are specific with respect to unrelated materials and with respect to materials which do not normally bind such oligonucleotides such as nucleases and restriction enzymes.

In general, a minimum of approximately 6 nucleotides, preferably 10, and more preferably 14 or 15 nucleotides, are necessary to effect specific binding. The only apparent limitations on the binding specificity of the target/oligonucleotide couples of the invention concern sufficient sequence to be distinctive in the binding oligonucleotide and sufficient binding capacity of the target substance to obtain the necessary interaction. Aptamers of binding regions containing sequences shorter than 10, e.g., 6-mers, are feasible if the appropriate interaction can be obtained in the context of the environment in which the target is placed. Thus, if there are few interferences by other materials, less specificity and less strength of binding may be required.

As used herein, "aptamer" refers in general to either an oligonucleotide of a single defined sequence or a mixture of said oligonucleotides, wherein the mixture retains the properties of binding specifically to the target molecule. Thus, as used herein "aptamer" denotes both singular and plural sequences of oligonucleotides, as defined hereinabove.

Structurally, the aptamers of the invention are specifically binding oligonucleotides, wherein "oligonucleotide" is as defined herein. As set forth herein, oligonucleotides include not only those with conventional bases, sugar residues and internucleotide linkages, but also those which contain modifications of any or all of these three moieties.

"Single-stranded" oligonucleotides, as the term is used herein, refers to those oligonucleotides which contain a single covalently linked series of nucleotide residues.

"Oligomers" or "oligonucleotides" include RNA or DNA sequences of more than one nucleotide in either single chain or duplex form and specifically includes short sequences such as dimers and trimers, in either single chain or duplex form, which may be intermediates in the production of the specifically binding oligonucleotides. "Modified" forms used in candidate pools contain at least one non-native residue.

"Oligonucleotide" or "oligomer" is generic to polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base or abasic nucleotides.

The oligomers of the invention may be formed using conventional phosphodiester-linked nucleotides and synthesized using standard solid phase (or solution phase) oligonucleotide synthesis techniques, which are now commercially available. However, the oligomers of the invention may also contain one or more "substitute" linkages as is generally understood in the art. Some of these substitute linkages are non-polar and contribute to the desired ability of the oligomer to diffuse across membranes. These "substitute" linkages are defined herein as conventional alternative linkages such as phosphorothioate or phosphoramidate, are synthesized as described in the generally available literature. Alternative linking groups include, but are not limited to embodiments wherein a moiety of the formula P(O)S, ("thioate"), P(S)S ("dithioate"), P(O)NR'$_2$, P(O)R', P(O)OR$^6$, CO, or CONR'$_2$, wherein R' is H (or a salt) or alkyl (1–12C) and R$^6$ is alkyl (1–9C) is joined to adjacent nucleotides through —O— or —S—. Dithioate linkages are disclosed and claimed in commonly owned U.S. application Ser. No. 248,517. Substitute linkages that may be used in the oligomers disclosed herein also include nonphosphorous-based internucleotide linkages such as the 3'-thioformacetal (—S—CH$_2$—O—), formacetal (—O—CH$_2$—O—) and 3'-amine (—NH—CH$_2$—CH$_2$—) internucleotide linkages disclosed and claimed in commonly owned pending U.S. patent application Ser. Nos. 690,786 and 763,130, both incorporated herein by reference. One or more substitute linkages may be utilized in the oligomers in order to further facilitate binding with complementary target nucleic acid sequences or to increase the stability of the oligomers toward nucleases, as well as to confer permeation ability. (Not all such linkages in the same oligomer need be identical.)

The term "nucleoside" or "nucleotide" is similarly generic to ribonucleosides or ribonucleotides, deoxyribonucleosides or deoxyribonucleotides, or to any other nucleoside which is an N-glycoside or C-glycoside of a purine or pyrimidine base, or modified purine or pyrimidine base. Thus, the stereochemistry of the sugar carbons may be other than that of D-ribose in one or more residues. Also included are analogs where the ribose or deoxyribose moiety is replaced by an alternate structure such as the 6-membered morpholino ring described in U.S. Pat. No. 5,034,506 or where an acyclic structure serves as a scaffold that positions the base analogs described herein in a manner that permits efficient binding to target nucleic acid sequences or other targets. Elements ordinarily found in oligomers, such as the furanose ring or the phosphodiester linkage may be replaced with any suitable functionally equivalent element. As the anomer binds to targets in a manner similar to that for the anomers, one or more nucleotides may contain this linkage or a domain thereof. (Praseuth, D., et al., Proc Natl Acad Sci (USA) (1988) 85:1349–1353). Modifications in the sugar moiety, for example, wherein one or more of the hydroxyl groups are replaced with halogen, aliphatic groups, or functionalized as ethers, amines, and the like, are also included.

"Nucleoside" and "nucleotide" include those moieties which contain not only the natively found purine and pyrimidine bases A, T, C, G and U, but also modified or analogous forms thereof. Modifications include alkylated purines or pyrimidines, acylated purines or pyrimidines, or other heterocycles. Such "analogous purines" and "analogous pyrimidines" are those generally known in the art, many of which are used as chemotherapeutic agents. An exemplary but not exhaustive list includes pseudoisocytosine, N$^4$, N$^4$-ethanocytosine, 8-hydroxy-N$^6$methyladenine, 4-acetylcytosine, 5-(carboxyhydroxylmethyl) uracil, 5-fluorouracil, 7-deazaadenine, 7-deazaguanine, 5-bromouracil, 5-carboxymethylaminomethyl-2-thiouracil, 5-carboxymethylaminomethyl uracil, dihydrouracil, inosine, N$^6$isopentenyl-adenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N$^6$methyladenine, 7-methylguanine, 5-methylaminomethyl uracil, 5-methoxyaminomethyl-2-thiouracil, beta-D-mannosylqueosine, 5'-methoxycarbonylmethyluracil, 5-methoxyuracil, 2-methylthio-N$^6$isopentenyladenine, uracil-5-oxyacetic acid methyl ester, pseudouracil, 2-thiocytosine, 5-methyl-2-thiouracil, 2-thiouracil, 4-thiouracil, 5-methyluracil, N-uracil-5-oxyacetic acid methylester, uracil-5-oxyacetic acid, queosine, 2-thiocytosine, 5-propyluracil, 5-propylcytosine, 5-ethyluracil, 5-ethylcytosine, 5-butyluracil, 5-butylcytosine, 5-pentyluracil, 5-pentylcytosine, and 2,6-diaminopurine.

In addition to the modified bases above, nucleotide residues which are devoid of a purine or a pyrimidine base may also be included in the aptamers of the invention and in the methods for their obtention.

The sugar residues in the oligonucleotides of the invention may also be other than conventional ribose and deoxyribose residues. In particular, substitution at the 2'-position of the furanose residue is particularly important with regard to enhanced nuclease stability.

Aptamer oligonucleotides may contain analogous forms of ribose or deoxyribose sugars that are generally known in the art. An exemplary, but not exhaustive list includes 2' substituted sugars such as 2'-O-methyl-, 2'-O-alkyl, 2'-O-allyl, 2'-S-alkyl, 2'-S-allyl, 2'-fluoro-, 2'-halo, or 2'-azido-ribose, carbocyclic sugar analogs, -anomeric ribose, epimeric sugars such as arabinose, xyloses or lyxoses, pyranose sugars, furanose sugars, sedoheptuloses, acyclic analogs and abasic nucleoside analogs such as methyl riboside, ethyl riboside or propyl riboside.

Although the conventional sugars and bases will be used in applying the method of the invention, substitution of analogous forms of sugars, purines and pyrimidines can be advantageous in designing the final product. Additional techniques, such as methods of synthesis of 2'-modified sugars or carbocyclic sugar analogs, are described in Sproat, B. S. et al., Nucl Acid Res (1991) 19:733–738; Cotten, M. et al., Nuc Acid Res (1991) 19:2629–2635; Hobbs, J. et al., Biochemistry (1973) 12:5138–5145; and Perbost, M. et al., Biochem Biophys Res Comm (1989) 165:742–747 (carbocyclics).

As used herein, "primer" refers to a sequence which is capable of serving as an initiator molecule for a DNA polymerase when bound to complementary DNA which is usually between 3–25 nucleotides in length.

As used herein, a "type II restriction enzyme site" refers to a site possessed by the class of restriction enzymes which cleaves one or both DNA strands at internucleotide linkages that are located outside of those associated with bases in the recognition sequence. This term is also meant herein to refer to a restriction enzyme such as Bcg I (New England Biolabs, catalog no. 545L) that makes two double stranded DNA cuts outside of its recognition sequence.

One of the objects of the invention is to identify aptamers useful as drugs per se or useful in drug development. Toward this end, selection criteria for targets and aptamers include:

1. The aptamer should selectively bind to the desired target, thereby inhibiting a biochemical pathway or generating a specific response (e.g., modulating an immune response or disrupting binding interactions between a receptor and its ligand);

2. The aptamer selected for use in diagnostic applications should have specificity for analyte (ligand) binding in those cases where the aptamer will be immobilized to a support;

3. The biochemical pathway that is inhibited or the biological response generated should be related to a pathological disease state in such a way that inhibition of that pathway or the biological response generated in a patient is therapeutic;

4. Desirably, the aptamer is specific so that it does not appreciably inhibit other pathways or generate additional unwanted biological responses;

5. Preferred aptamers have or are capable of being adapted to have the pharmacokinetic characteristics of a practical drug (i.e., they must be absorbed, must penetrate to the site of action and must have a reasonably predictable dose response relationship and duration of action);

6. Desirably, the aptamer has an acceptable toxicological profile in animals and the results of human clinical trials must demonstrate an appropriate therapeutic use.

Methods to Prepare the Invention Aptamers. In general, the method for preparing the aptamers of the invention involves incubating a desired target molecule with a mixture of oligonucleotides under conditions wherein some but not all of the members of the oligonucleotide mixture form complexes with the target molecules. The resulting complexes are then separated from the uncomplexed members of the oligonucleotide mixture and the complexed members which constitute an aptamer (at this stage the aptamer generally being a population of a multiplicity of oligonucleotide sequences) is recovered from the complex and amplified. The resulting aptamer (mixture) may then be substituted for the starting mixture in repeated iterations of this series of steps. When satisfactory specificity is obtained, the aptamer may be used as a obtained or may be sequenced and synthetic forms of the aptamer prepared. In this most generalized form of the method, the oligonucleotides used as members of the starting mixture may be single-stranded or double-stranded DNA or RNA, or modified forms thereof. However, single-stranded DNA is preferred. The use of DNA eliminates the need for conversion of RNA aptamers to DNA by reverse transcriptase prior to PCR amplification. Furthermore, DNA is less susceptible to nuclease degradation than RNA.

The oligonucleotides that bind to the target are separated from the rest of the mixture and recovered and amplified. Amplification may be conducted before or after separation from the target molecule. The oligonucleotides are conveniently amplified by PCR to give a pool of DNA sequences. The PCR method is well known in the art and described in, e.g., U.S. Pat. Nos. 4,683,195 and 4,683,202, and 4,800,159 and Saiki, R. K., et al., Science (1988) 239:487–491, European patent applications 86302298.4, 86302299.2 and 87300203.4, as well as Methods in Enzymology (1987) 155:335–350. If RNA is initially used, the amplified DNA sequences are transcribed into RNA. The recovered DNA or RNA, in the original single-stranded or duplex form, is then used in another round of selection and amplification. After three to six rounds of selection/amplification, oligomers that bind with an affinity in the mM to M range can be obtained for most targets and affinities below the M range are possible for some targets. PCR may also be performed in the presence of target.

Other methods of amplification may be employed including standard cloning, ligase chain reaction, etc. (See e.g., Chu, et al., U.S. Pat. No. 4,957,858). For example, to practice this invention using cloning, once the aptamer has been identified, linkers may be attached to each side to facilitate cloning into standard vectors. Aptamers, either in single or double stranded form, may be cloned and recovered thereby providing an alternative amplification method.

Amplified sequences can be applied to sequencing gels after any round to determine the nature of the aptamers being selected by target molecules. The entire process then may be repeated using the recovered and amplified duplex if sufficient resolution is not obtained.

Amplified sequences can be cloned and individual oligonucleotides then sequenced. The entire process can then be repeated using the recovered and amplified oligomers as needed. Once an aptamer that binds specifically to a target has been selected, it may be recovered as DNA or RNA in single-stranded or duplex form using conventional techniques.

Similarly, a selected aptamer may be sequenced and resynthesized using one or more modified bases, sugars and linkages using conventional techniques. The specifically binding oligonucleotides need to contain the sequence-conferring specificity, but may be extended with flanking regions and otherwise derivatized.

The starting mixture of oligonucleotide may be of undetermined sequence or may preferably contain a randomized portion, generally including from about 3 to about 400 nucleotides, more preferably 10 to 100 nucleotides. The randomization may be complete, or there may be a preponderance of certain sequences in the mixture, or a preponderance of certain residues at particular positions. Although, as described hereinbelow, it is not essential, the randomized sequence is preferably flanked by primer sequences which permit the application of the polymerase chain reaction directly to the recovered oligonucleotide from the complex. The flanking sequences may also contain other convenient features, such as restriction sites which permit the cloning of the amplified sequence. These primer hybridization regions generally contain 10 to 30, more preferably 15 to 25, and most preferably 18 to 20, bases of known sequence.

The oligonucleotides of the starting mixture may be conventional oligonucleotides, most preferably single-stranded DNA, or may be modified forms of these conventional oligomers as described hereinabove. For oligonucleotides containing conventional phosphodiester linkages or closely related forms thereof, standard oligonucleotide synthesis techniques may be employed. Such techniques are well known in the art, such methods being described, for example, in Froehler, B., et al., Nucleic Acids Research (1986) 14:5399–5467; Nucleic Acids Research (1988) 16:4831–4839; Nucleosides and Nucleotides (1987) 6:287–291; Froehler, B., Tet Lett (1986) 27:5575–5578. Oligonucleotides may also be synthesized using solution phase methods such as triester synthesis, known in the art. The nature of the mixture is determined by the manner of the conduct of synthesis. Randomization can be achieved, if desired, by supplying mixtures of nucleotides for the positions at which randomization is desired. Any proportion of nucleotides and any desired number of such nucleotides can be supplied at any particular step. Thus, any degree of randomization may be employed. Some positions may be randomized by mixtures of only two or three bases rather than the conventional four. Randomized positions may alternate with those which have been specified. It may be helpful if some portions of the candidate randomized sequence are in fact known.

In one embodiment, the oligonucleotides used as starting materials in the process of the invention to determine specific binding sequences may be single-stranded or double-stranded DNA or RNA. Single-stranded DNA is preferred. In any case, the starting material oligonucleotide will contain a randomized sequence portion containing at least one residue modification usually flanked by primer sequences which permit the application of the polymerase chain reaction to the recovered oligonucleotide from the complex, or these flanking sequences may be added after complexation. These flanking sequences may also contain other convenient features such as restriction sites which permit the cloning of the amplified sequence.

The randomized portion may be constructed using conventional solid phase techniques using mixtures of nucleotides at the positions where randomization is desired. In general, the modification is included by use of a modified monomer in the synthesis mixture. Of course, any degree of randomization may be employed; some positions may be randomized by mixtures of only two or three bases rather than the conventional four; randomized positions may alternate with those which have been specified. Indeed, it may be helpful if some portions of the candidate randomized sequence are in fact known.

In one embodiment of the method of the invention, the starting mixture of oligonucleotides subjected to the invention method will have a binding affinity for the target characterized by a Kd of 1 m or greater. Binding affinities of the original mixture for target may range from about 100M to 10M to 1M, but, of course, the smaller the value of the dissociation constant, the more initial affinity there is in the starting material for the target. This may or may not be advantageous as specificity may be sacrificed by starting the procedure with materials with high binding affinity.

By application of the method of the invention as described herein, improvements in the binding affinity over one or several iterations of the above steps of at least a factor of 50, preferably of a factor of 100, and more preferably of a factor of 200 may be achieved. As defined herein, a ratio of binding affinity reflects the ratio of Kds of the comparative complexes. Even more preferred in the conduct of the method of the invention is the achievement of an enhancement of an affinity of a factor of 500 or more.

Thus, the method of the invention can be conducted to obtain the invention aptamers wherein the aptamers are characterized by consisting of single-stranded DNA, or by having a binding affinity to a target that does not normally bind oligonucleotides represented by a Kd of $20 \times 10^{-9}$ or less, or by having a specificity representing by a factor of at least 2, preferably 5, and more preferably 10 with respect to unrelated molecules, or by having a binding region of less than 15 nucleotide residues or a total size of less than 16 nucleotide residues, or by binding to particular target molecules. The invention processes are also characterized by accommodating starting mixtures of oligonucleotides having a binding affinity for target characterized by a Kd of 1M or more by an enhancement of binding affinity of 50 or more, and by being conducted under physiological conditions.

As used herein, physiological conditions means the salt concentration and ionic strength in an aqueous solution which characterize fluids found in human metabolism commonly referred to as physiological buffer or physiological saline. In general, these are represented by an intracellular pH of 7.1 and salt concentrations (in mM) of $Na^+$: 3–15; $K^+$: 140; $Mg^{+2}$: 6.3; $Ca^{+2}$: $10^{-4}$; $Cl^-$: 3–15, and an extracellular pH of 7.4 and salt concentrations (in mM) of $Na^+$: 145; $K^+$: 3; $Mg^{+2}$: 1–2; $Ca^{+2}$: 1–2; and $Cl^-$: 110.

The use of physiological conditions in the aptamer selection method is important, particularly with respect to those aptamers that may be intended for therapeutic use. As is understood in the art, the concentration of various ions, in particular, the ionic strength, and the pH value impact on the value of the dissociation constant of the target/aptamer complex.

Selection of Single Stranded Aptamers by Gel Shift Methods. The application of gel shift methods to the isolation of single-stranded DNA aptamers bound to target molecules not known to normally bind nucleic acids is shown in the present invention to be an efficient solution phase selection method. Gel shift methods were used to obtain aptamers that specifically bind to peptides having sequences found in active domains of ICAM-1 and to proteins such as thrombin and Factor X. Thus the method is generally applicable to the selection of aptamers for a variety of target biomolecules. It was also found that efficient selection of aptamers is possible when aptamer pools from intermediate rounds of selection on columns is applied to gel shift selections. The combination of column selection with gel shift selection unexpectedly gave rapid isolation of specific binding aptamer pools.

Selection of specifically binding aptamer species is based at least in part on an effective increase in the mass of the bound aptamer in aptamer-target complex compared to unbound DNA. In cases where the effective charge of the aptamer is reduced through interactions with the target molecule, a decreased rate of migration compared to uncomplexed DNAs can also contribute to separation of unbound species during electrophoresis on the gel. Such selection with single stranded DNA have not previously been demonstrated for biomolecules that do not normally bind to nucleic acids. Gel selections were conducted in a low salt buffer which allows stable ionic interactions to occur between aptamer DNA and target molecules. The selections can be carried out at temperatures between 4 C. and about 40 C. for most target molecules. Gel shift selections have a number of advantages over previously described methods such as columns containing immobilized target molecules. First, for target molecules of limited availability or high cost, smaller amounts of target molecule is required for each round of selection. Selections were accomplished using about 100 to 10,000 fold less target molecule compared to selections on columns containing immobilized target molecules. Second, gel selections are suitable for solution phase determination of $K_D$ values for binding of aptamer DNA to its target. Third, gel selections are also suitable for selection of aptamers using limiting amounts of target. Because the target is in solution, the amount of target used for a selection can be precisely determined and controlled. A difference between selections on gels after binding compared to selections using immobilized target molecules is that matrix effects, for example DNA binding to the immobilization matrix, do not occur until selection and separation of complexed and uncomplexed species (i.e. electrophoresis) is applied.

This selection process should yield moderate to high affinity aptamers to target molecules in an efficient manner.

Generation of Aptamers by Functional Selection Using Gel Shift Methods and other Separation Methods. Another aspect of the present invention is to provide methods for selection of aptamers that both specifically bind to and interfere with some aspect of biological function of the target molecule. Aptamers that bind to a target molecule may or may not interfere with target function, depending on the binding site on the target. Functional selection using a solid column including gel shift methods may be accomplished in a number of ways. For example, aptamers that inhibit conversion of a preprotein such as Factor X (F X) to Factor Xa (F Xa) can be used as antithrombotic agents. Conversion of F X to F Xa is mediated via proteolytic cleavage by Factor VIIa, Factor IXa or Russell Viper Venom. Aptamers that bind to the site of cleavage on F X will inhibit the proteolytic cleavage mediated by F VIIa or F IXa. The selection would be conducted by incubating F X in the presence of aptamer DNA followed by addition of F VIIa to effect cleavage of F X molecules that are not protected by bound aptamer. Separation of F X from F Xa followed by isolation of aptamer species bound to F X will result in enrichment for F X binding species that interfere with proteolysis. Separation of F X from F Xa can be carried out by gel electrophoresis, preferably in low salt (about 50 mM) buffer. In this type of protocol, functional selection occurs prior to enrichment for aptamers that interfere with or modulate target molecule function. A characteristic of aptamers obtained from such selections is that the aptamer binds to a structure found in the precursor (F X) that is not found in the product molecule (F Xa).

Isolation of aptamers that bind to thrombin and mimic the binding of thrombomodulin can also be accomplished by functional selection methods. Thrombomodulin is an integral membrane glycoprotein found on the surface of endothelial cells that binds thrombin and converts the enzyme from a procoagulant protease to an anticoagulant protease by changing the substrate specificity of thrombin from fibrinogen to Protein C (Esmon, C. T. J. Biol. Chem (1989) 264:4743–4746). The thrombomodulin-dependent alteration is substrate specificity from fibrinogen to protein C appears to be effected through a combination of an allosteric change in the active site conformation of thrombin and an overlap of the thrombomodulin and fibrinogen binding sites on thrombin. The peptide cleavage sites on fibrinogen that are recognized by thrombin are CPRTNR, with cleavage at the RT peptide bond, while the RL bond in the DPRLID sequence of protein C is cleaved. A functional selection for a thrombomodulin-like aptamer (i.e. an aptamer that binds to thrombin and effects a change that mimics the binding of thrombomodulin) can be achieved by several methods. One approach is to incubate a pool of oligonucleotides with random region(s) with thrombin and isolate or separate thrombin molecules (designated herein thrombin*) with bound aptamers that mimic the binding of thrombomodulin from other thrombin molecules. Such a separation could be effected on the basis of substrate binding specificity differences between thrombin and thrombin*. Thrombin molecules that do not bind to a protein C-like substrate can be separated from thrombin* molecules using fibrinogen-like or protein C-like substrates. For example, the thrombin*-aptamer complexes can be passed over a column containing immobilized peptide protein C substrate (which may be a suicide substrate or a protein C peptide or peptide analog) and those able to bind to the substrate can be separated from those thrombin-aptamer complexes which are unable to bind a protein C type substrate. A negative selection could be performed in a similar manner with a fibrinogen substrate column.

An additional approach to select for aptamers that mimic the thrombomodulin mediated alteration of thrombin specificity is to immobilize a pool of oligonucleotides on beads such that each bead contains a unique oligonucleotide species. Such libraries could be generated by a "split synthesis" approach as has been demonstrated for random peptide libraries (Lam, K. S. et al., Nature (1991) 354:82–84). In addition to a unique aptamer, each bead would also display a chromophore linked to the bead via a Protein C peptide or peptide analog. Upon the addition of thrombin to the library of beads, beads displaying aptamers that mimic thrombomodulin and confer specificity towards Protein C peptides will be distinguishable by a color change due to the cleavage of the peptide linking the chromophore to the bead.

Several approaches may be used to select aptamers that block thrombin's activity towards fibrinogen and the thrombin receptor but do not affect the binding of thrombomodulin and activity towards Protein C. These approaches all involve the use of multiple selections to derive aptamers with highly specific properties. In the first example, a pool of oligonucleotides is subjected to two rounds of selection. The first round involves selecting oligonucleotides that bind to thrombin, the second round involves selecting those oligonucleotides that also bind to a complex between thrombin and thrombomodulin. Aptamers derived from such a dual selection strategy will be directed against regions of thrombin apart from the thrombomodulin binding site and will be unlikely to interfere with thrombomodulin binding and activity against Protein C.

Additional approaches involve multiple selections using mutant or variant thrombin molecules. From site-directed mutagenesis studies on thrombin it is apparent that there are distinct but overlapping binding sites on thrombin for fibrinogen, thrombin receptor and thrombomodulin. The substitution of Lysine-52 and Arginine-68 in thrombin with Glutamate residues caused a decrease in the recognition of fibrinogen and the thrombin receptor, implicating these residues in the binding site for these molecules. Conversely, the substitution of Arginine-68 and Arginine-70 in thrombin with Glutamate caused a decrease in the recognition of thrombomodulin, implicating these residues in the binding site for thrombomodulin (Wu, W. et al, Proc. Natl. Acad. Sci. USA (1991) 88:6775–6779. Mutant thrombin molecules where specific residues implicated in the binding of substrate and effector molecules, from mutagenesis, structural or biochemical studies, are substituted can be used in positive and negative selections to identify aptamers that are directed away from or towards the substituted residues within the binding site. In one example, a pool of oligonucleotides is screened for those that bind to thrombin, in a second round those oligonucleotides that also bind to a mutant thrombin, where Arginine-68 and Arginine-70 have been substituted with other amino-acids, are selected. This dual selection identifies aptamers that do not recognize Arginine-68 and Arginine-70 and therefore do not block the thrombomodulin binding site. In a second example, a pool of oligonucleotides is screened for those that bind to thrombin, in a second round of negative selection the oligonucleotides that do not bind to a mutant thrombin, where Lysine-52 has been substituted, are selected. This dual selection identifies aptamers that recognize Lysine-52 within the fibrinogen/thrombin receptor binding site but outside the thrombomodulin binding site.

Such functional selections can also be carried out using other proteins that are proteolytically processed to generate active species. Examples of additional processed molecules that may serve as target molecules in functional selections include prothrombin, F VII, F IX, Factor XII, serum complement proteins, plasminogen, endothelin and the like.

In addition to separation by gel electrophoresis, separations may also be based on column methods such as affinity columns. An affinity column containing immobilized substrate for F Xa such as a peptide or peptide analog containing the sequence arg-gly-arg would retain F Xa to a greater extent than F X. In the case of selections for aptamers that bind to the site of proteolytic cleavage on prothrombin, columns containing an immobilized substrate such as D-phenylalanyl-L-prolyl-L-arginine chloromethyl ketone (Green, G. D., Thromb Res (1986) 44:175–184) will permit separation of prothrombin from thrombin which will migrate more slowly on the column. Immobilized substrates for enzymes could be suicide substrates (Clarke, D. D., Neurochem Res (1991) 16:1055–1058), substrate analogs or standard substrates. Such substrates may be immobilized on columns or covalently linked to gel polymers such as agarose or acrylamide using methods known in the art.

Other variations of functional selections can be conducted using appropriate modifications of targets and separation methods. For example, aptamers that bind a cofactor binding site or to the active site of an enzyme or to the ligand binding region of a receptor (or receptor fragment that retains ligand binding function) respectively. In this type of protocol, the functional selection occurs concurrently with enrichment for aptamers that interfere with or modulate target molecule function.

Use of Modified Nucleotides and Oligonucleotides. In one embodiment of the invention method, the initial mixture of candidate oligonucleotides will include oligomers which contain at least one modified nucleotide residue or linking group.

If certain specific modifications are included in the amplification process as well, advantage can be taken of additional properties of any modified nucleotides, such as the presence of specific affinity agents in the purification of the desired materials.

In order for the modified oligomer to yield useful results, the modification must result in a residue which is "read" in a known way by the polymerizing enzyme used in the amplification procedure. It is not necessary that the modified residue be incorporated into the oligomers in the amplification process, as long it is possible to discern from the nucleotide incorporated at the corresponding position the nature of the modification contained in the candidate, and provided only one round of complexation/amplification is needed. However, many of the modified residues of the invention are also susceptible to enzymatic incorporation into oligonucleotides by the commonly used polymerase enzymes and the resulting oligomers will then directly read on the nature of the candidate actually contained in the initial complex. It should be noted that if more than one round of complexation is needed, the amplified sequence must include the modified residue, unless the entire pool is sequenced and resynthesized to include the modified residue.

Certain modifications can be made to the base residues in a oligonucleotide sequence without impairing the function of polymerizing enzymes to recognize the modified base in the template or to incorporate the modified residue. These modifications include alkylation of the 5-position of uridine, deoxyuridine, cytidine and deoxycytidine; the $N^4$ position of cytidine and deoxycytidine; the $N^6$ position of adenine and deoxyadenine; the 7-position of 7-deazaguanine, 7-deazadeoxyguanine, 7-deazaadenine and 7-deazadeoxyadenine. A modified base may be included in the oligomeric mixtures useful in the method of the invention, particularly when the nature of the recognition is known.

The nature of the sugar moiety may also be modified without affecting the capacity of the sequence to be usable as a specific template in the synthesis of new DNA or RNA.

The efficacy of the process of selection and amplification depends on the ability of the PCR reaction faithfully to reproduce the sequence actually complexed to the target substance. Thus, if the target substance contains modified forms of cytosine (C*), the PCR reaction must recognize this as a modified cytosine and yield an oligomer in the cloned and sequenced product which reflect this characterization. If the modified form of cytosine (C*) is included in the PCR reaction as dC*TP, the resulting mixture will contain C* at positions represented by this residue in the original member of the candidate mixture. (It is seen that the PCR reaction cannot distinguish between various locations of C* in the original candidate; all C residue locations will appear as C*.) Conversely, dCTP could be used in the PCR reaction and it would be understood that one or more of the positions now occupied by C was occupied in the original candidate mixture by C*, provided only one round of complexation/ amplification is needed. If the amplified mixture is used in a second round, this new mixture must contain the modification.

Of course, if the selected aptamer is sequenced and resynthesized, modified oligonucleotides and linking groups may be used in the synthesized form of the aptamer.

The oligomers found to bind the target may be resynthesized de novo based on the determined sequence to contain additional modifications. Some of the modifications which may be included in these aptamers of the invention are as follows:

Any of the hydroxyl groups ordinarily present on the sugar moieties may be replaced by phosphonate groups, phosphate groups, protected by a standard protecting group, or activated to prepare additional linkages to additional nucleotides, or may be conjugated to solid supports. The 5' terminal OH is conventionally phosphorylated; any 2'-OH or OH substituents at the 3' terminus may also be phosphorylated. The hydroxyls may also be derivatized to standard protecting groups.

One or more phosphodiester linkages may be replaced by alternative linking groups in the specifically binding oligonucleotide ultimately obtained. These alternative linking groups include, but are not limited to embodiments wherein P(O)O is replaced by P(O)S, P(O)NR$_2$, P(O)R, P(O)OR', CO, or CNR$_2$, wherein R is H or alkyl (1–6C) and R' is alkyl (1–6C); in addition, this group may be attached to adjacent nucleotide through O or S. Not all linkages in the same oligomer need to be identical.

Inclusion of modified oligonucleotides in the methods and aptamers of the invention provides a tool for expansion of the repertoire of candidates to include large numbers of additional oligonucleotide sequences. Such expansion of the candidate pool may be especially important as the demonstration of binding to proteins, for example, in the prior art is limited to those proteins known to have the capability to bind DNA. Modifications of the oligonucleotide may be necessary to include all desired substances among those targets for which specific binding can be achieved.

Thus, one preferred method comprises incubating the target with a mixture of oligonucleotides, wherein these oligonucleotides contain at least one modified nucleotide residue or linkage, under conditions wherein complexation occurs with some but not all members of the mixture; separating the complexed from uncomplexed oligonucleotides, recovering and amplifying the complexed oligonucleotides and optionally determining the sequence of the recovered nucleotides. In an additional preferred embodiment, amplification is also conducted in the presence of modified nucleotides.

Use of Starting Oligonucleotide Mixtures of Unpredetermined Sequence. In another embodiment, a method for making aptamers is provided, based on the discovery that the presence of flanking sequences (usually primer binding sequences) on the oligonucleotides of the candidate mixture may limit aptamer structural diversity and/or inhibit binding, thereby resulting in less than the full range of structural variation that is possible in a given pool of aptamers. This embodiment may use mixtures of unbiased oligonucleotide pools, and provides the ability to then engineer appropriate means for amplifying the desired oligonucleotides (putative aptamers).

Once single stranded aptamers are generated, linkers may be added to both ends as described herein (much in the same manner as a sticky end ligation). Preferably the linkers are partially double stranded and have some overhang to and at both ends to facilitate cloning into a standard cloning vector. One of the overhangs should be a random sequence to provide complementarity to permit binding to the aptamer. The other overhang may provide necessary bases for sticky end ligation.

In one embodiment the method comprises:
(a) providing a mixture of oligonucleotides of unknown, non-predetermined or substantially non-predetermined, said mixture comprising a quantity of oligonucleotides sufficiently reflective of the structural complexity of said target as to statistically ensure the presence of at least one oligonucleotide capable of binding said target;
(b) incubating said mixture of oligonucleotides with said target under conditions wherein complexation occurs between some oligonucleotides and said target, said complexed oligonucleotides defining an aptamer population;
(c) recovering said aptamers in substantially single stranded form;
(d) attaching a known nucleotide sequence to at least one end of said aptamers;
(e) amplifying said aptamers; and
(f) removing said known nucleotide sequence from said aptamers.

In the first step, the oligonucleotides comprising the mixture way be of completely unknown sequence. The oligonucleotides comprising the pool also may be of partially known sequence, but without flanking primer regions. The invention is not limited to first generation aptamers, but way be practiced to identify second and third generation aptamers as well. oligonucleotides comprising the pool from which second and third generation aptamers may be identified, may have, for example, 40%–70% of their sequences known or predetermined.

One skilled in the art will recognize that the diversity of the oligonucleotide pool from which aptamers are identified may be reduced, either by using known sequences, or through the processes of retention and selection by which these aptamers are made. As pool size and pool diversity is reduced, more aptamers capable of more specific binding are recovered. Stated in another way, the quantity of oligonucleotides in the pool and the diversity and/or complexity of the pool are inversely related.

These aspects of the invention are elucidated in the following embodiment which adds additional steps to steps (a)–(f) listed above:
(g) repeating steps a-f using said first aptamers of step (f), or a portion thereof, to comprise a second pool of oligonucleotides for use in step (a), thereby generating a second aptamer population which may be used to repeat steps (a)–(f), and optionally
(h) repeating steps (a)–(f) using said second aptamers of step (g), or a portion thereof, a sufficient number of times so as to identify an optimal aptamer population from which at least one consensus region may identified in at least two of the aptamers from said optimal aptamer population, the presence of which may be correlated with aptamer to target binding or to aptamer structure.

This method includes methods for selectively attaching and removing flanking regions to aptamers, thereby permitting aptamer recovery in high yield. One such method comprises, after separating oligonucleotides in the method above in substantially single stranded form from the pool capable of binding target;

attaching a 5' linker of known sequence to a first (the 5') end of the oligonucleotides, the 5' linker having a first type II restriction enzyme recognition site at its 3' end, attaching a 3' linker of known sequence to a second (the 31) end of the oligonucleotides, the 3' linker having a second type II restriction enzyme recognition site different from the site at the 5' end;

amplifying the oligonucleotides, thereby generating a duplex comprising a first (upper) strand, having a 5' linker complement portion, an oligonucleotide complement portion and a 3' linker complement portion, and a second (lower) strand, comprising a 5' linker portion, an oligonucleotide portion and a 3' linker portion;

removing the 5' and the 3' linker portions from the oligonucleotides; and recovering the oligonucleotides in substantially single stranded form.

Another method of effecting amplification comprises, after recovering oligonucleotides from the above bound pool in substantially single stranded form;

attaching a double stranded DNA linker of known sequence having at least 2–4 bases of random sequence present as a 3' overhang, said 2–4 bases capable of hybridizing to the 3' end of said oligonucleotides, the linker having a first type II restriction enzyme recognition site;

attaching a double stranded DNA linker of known sequence having at least 2–4 bases of random sequence present as a 3' overhang, the 2–4 bases capable of hybridizing to the 5' end of the oligonucleotides, said linker having a second type II restriction enzyme recognition site;

amplifying said oligonucleotides, thereby generating duplexes comprising a first (upper) strand, having a 5' linker complement portion, an oligonucleotide complement portion and a 3' linker complement portion, and a second (lower) strand, comprising a 5' linker portion, an oligonucleotide portion and a 3' linker portion;

removing the 3' linker portion from the oligonucleotide by attaching the product of step 4 above to a solid support, removing the 3' linker by digesting with a type II restriction enzyme capable of recognizing said first type II restriction enzyme binding site, removing the 5' linker complement and the oligonucleotide complement by heat denaturation, annealing a 5' linker complement to the upper strand, and removing the 5' linker portion by digesting with a type II restriction enzyme capable of recognizing the second type II restriction enzyme site; and recovering the oligonucleotides in substantially single stranded form.

In another approach, the method includes attaching a single RNA residue to the 5' linker portion and removing it after amplification by cleaving the RNA linkage.

A Subtraction Method for Aptamer Preparation. It is often advantageous in enhancing the specificity of the aptamer obtained to remove members of the starting oligonucleotide mixture which bind to a second substance from which the target molecule is to be distinguished. This method is particularly useful in obtaining aptamers which bind to targets that reside on cell surfaces since a large number of contaminating materials will surround the desired target. In such subtraction methods, at least two rounds of selection and amplification will be conducted. In a positive/negative selection approach, the target will be incubated with the starting mixture of oligonucleotides and, as usual, the complexes formed are separated from uncomplexed oligonucleotides. The complexed oligonucleotides, which are now an aptamer, are recovered and amplified from the complex. The recovered aptamer is then mixed with the second, undesired, substance from which the target is to be distinguished under conditions wherein members of the aptamer population which bind to said second substance can be complexed. This complex is then separated from the remaining oligonucleotides of the aptamer. The resulting unbound second aptamer population is then recovered and amplified. The second aptamer population is highly specific for the target as compared to the second substance.

In an alternative approach, the negative selection step may be conducted first, thus mixing the original oligonucleotide mixture with the undesired substance to complex away the members of the oligonucleotide mixture which bind to the second substance; the uncomplexed oligonucleotides are then recovered and amplified and incubated with the target under conditions wherein those members of the oligonucleotide mixture which bind targets are complexed. The resulting complexes then removed from the uncomplexed oligonucleotides and the bound aptamer population is recovered and amplified as usual.

When applied to the preparation of aptamers which bind specifically targets residing on cell surfaces, the positive round is conducted preferably with the target expressed at the surface of a cell, said expression typically occurring through recombinant transformation or by virtue of the native properties of the cell. The negative round of selection is conducted with similar cells which have similar surface materials associated with them, but which do not express the desired target.

The methods and aptamers of the present invention can also be directed to cell surface proteins. To prepare these aptamers, a pool of oligonucleotides is brought into contact with a first known cell line which is known to express a particular cell surface protein which is uniquely identified with that cell line and sufficient time is allowed for the oligonucleotides to bind to the protein on the cell surfaces. The cells are isolated with oligonucleotides bound thereto and the oligonucleotides are removed. This procedure is referred to herein as "positive screening". Thereafter, the removed oligonucleotides are brought into contact with a second cell line which is identical to the first cell line, except that the second cell line does not express the particular identifying cell surface protein; binding is allowed to occur and any oligonucleotides which bind to the second cell line are isolated and discarded. This procedure is referred to as "negative screening". The "positive" and "negative" screening steps can be repeated a multiplicity of times in order to obtain oligonucleotides which are highly specific for the cell surface proteins being expressed on the first cell line. The highly specific oligonucleotides may then be amplified and sequenced.

A preferred variation for selection of aptamers that bind to surface antigens involves a procedure wherein negative selection is first carried out followed by a positive selection. In accordance with this procedure, a pool of random oligonucleotides is combined with a tissue culture medium. The oligonucleotides are allowed to remain in contact with the cell cultures for a sufficient period of time to allow binding between oligonucleotides and cell surfaces which lack the target molecule. When this binding occurs, a negative selection process has been carried out, i.e., oligonucleotides which are not the desired aptamers can be eliminated by their binding to nontarget surfaces. Following this negative selection, a positive selection step is carried out. This is done by combining the oligonucleotides which did not bind to the surfaces lacking target molecules thereon with a cell culture containing the target molecule on their surface. Such a negative-positive selection protocol can be carried out in a medium containing human or bovine serum in order to select aptamers under simulated physiological conditions. It is desirable to replicate physiological conditions as closely as possible when carrying out the selection processes in that one endeavors to find oligonucleotides (aptamers) which bind to the target molecules under physiological conditions so that such aptamers can later be used in vivo.

In more detail, the oligonucleotide mixture is brought into contact with a first known cell line which is known to express a particular cell surface protein which is uniquely identified with that cell line. After allowing sufficient time for the oligonucleotides to bind to the protein on the cell surfaces, procedures are carried out to isolate the cells with oligonucleotides bound thereto and the oligonucleotides are removed. This procedure is referred to herein as "positive screening".

After treatments with the candidate oligonucleotide mixtures, the cells containing the targeted surface protein may be extensively washed in buffered saline or in tissue culture medium to remove low affinity aptamers and uncomplexed oligonucleotides. Following washing, the cells are treated with one or more of a number of agents that permit recovery of bound aptamers. The cells may be treated enzymatically with trypsin or other proteases to cleave the targets at the cell surface, thus releasing the bound aptamers. Alternatively, the cells containing bound aptamers may be washed in a detergent or high ionic strength solution in order to disrupt binding between the cells and aptamers. The aptamers recovered at this point consist of a pool of different sequences that bind to different cell surface targets, including the target of interest.

Aptamers from the first tissue culture cells may be recovered from solution by precipitation or may be used directly if reagents used to remove aptamers do not significantly affect cells in the second tissue culture.

The aptamer mixture is then incubated with the second (null) cell culture under similar conditions. The mixture brought into contact with a second cell line which is identical to the first cell line, except that the second cell line does not express the particular identifying cell surface protein. Binding is allowed to occur and any oligonucleotides which bind to the second cell line are isolated and discarded. This procedure is referred to as "negative screening". The "positive" and "negative" screening steps can be repeated a multiplicity of times in order to obtain oligonucleotides which are highly specific for the cell surface proteins being expressed on the first cell line. When the highly specific oligonucleotides have been determined and isolated, they are subjected to PCR technology for amplification as above. The resulting "aptamers" can be labeled and thereafter effectively used to identify the presence of the first cell line expressing the particular cell surface protein.

This method identifies target features on cell surfaces such as proteins, especially hetero- or homodimers or multimers. Selecting high-affinity ligands specific for such transmembrane proteins outside the natural cellular context has heretofore been exceedingly difficult, if not impossible. Many transmembrane proteins cannot be isolated from cells without loss of their native structure and function. This is due, in part, to a requirement for detergents to disrupt cellular membranes that anchor transmembrane proteins (Helenius, A., et al., Biochem. Biophys. Acta (1975) 415:27–79). Detergents that solubilize membranes also tend to denature proteins, leading to loss of function and alteration of native structure.

A preferred variation of this method involves a procedure wherein negative selection is first carried out followed by a positive selection. In accordance with this procedure, a pool of random oligonucleotides is combined with a tissue culture medium. The oligonucleotides are allowed to remain in contact with the cell cultures for a sufficient period of time to allow binding between oligonucleotides and cell surfaces which lack the target molecule. When this binding occurs, a negative selection process has been carried out, i.e., oligonucleotides which are not the desired aptamers can be eliminated by their binding to nontarget surfaces. Following this negative selection, a positive selection step is carried out. This is done by combining the oligonucleotides which did not bind to the surfaces with no target molecules thereon with a cell culture containing the target molecule on their surface. Such a negative-positive selection protocol can be carried out in a medium containing human or bovine serum in order to select aptamers under simulated physiological conditions. It is desirable to replicate physiological conditions as closely as possible when carrying out the selection processes in that one endeavors to find oligonucleotides (aptamers) which bind to the target molecules under physiological conditions so that such aptamers can later be used in vivo.

Aptamers which are selected in the presence of serum may be rendered nuclease-stable by the use of PCR primers with modified internucleotide linkages that are nuclease-stable as described in commonly assigned copending Application Publication No. WO90/15065 (incorporated herein by reference).

An alternative variation of the use of serum for aptamer selection is also possible. In accordance with this alternative protocol, candidate aptamers are added to a tissue culture medium lacking serum. The serum-free medium is incubated with cells which lack the target molecules on their surfaces. Following the incubation, a cell culture which contains the target molecules on their surfaces is combined with any oligonucleotides which did not bind to the first cell culture which did not have the target molecule thereon. This step in the protocol provides for positive selection. After continuing the incubation for the positive selection for 20–40 minutes, serum is added in order to provide a final concentration in the range of about 5% to 10% of serum. At this point, any oligonucleotides which are not tightly complexed with the target molecule begin to degrade due to the nucleases present in the added serum. However, the oligonucleotides which are tightly bound to the target molecules on the cells are nuclease resistant as they are inaccessible to the nucleases due to their physical association with the target molecules. After exposure to the nucleases for 10–30 minutes, the medium (i.e., the serum containing the nucleases) is removed and the cells are washed and caused to release the oligonucleotides or aptamers bound thereto by treatment of the cells with proteases and/or detergents. Any oligomers which are substantially degraded by the nucleases will not be amplified during amplification processing.

In more detail, the present inventors have found that the nuclease activity present within the serum is primarily a 3' exonuclease activity. The presence of 3' exonuclease activity during target binding may be used with a candidate aptamer pool that has a short primer at the 3' end as a nuclease target. Accordingly, if the 3' end, which includes the primer, is degraded by the nuclease, the oligonucleotides attached to the degraded primers will not be amplified during amplification processing and will thereby be eliminated. A similar short primer sequence (6–10 bases) at the 5' end could also be utilized in the same manner if 5' exonucleases are added to the medium during the selection protocol.

At various stages of the screening process, advantage may be taken of PCR techniques for amplification of selected aptamer pools. While the material recovered after a single cycle of positive and negative selection may in some instances be suitable after amplification for sequencing directly, it is often advantageous to repeat the cycle until a lower dissociation constant (Kd) is obtained for binding of the single-stranded oligonucleotide species to the transfectant cells (the first tissue culture cells) relative to the parental cells (the second tissue culture cells). Usually, multiple rounds of selection and aptamer amplification will be necessary in order to provide multiple opportunities to enrich for aptamers that specifically bind to the target structure. In addition, it is clearly within the scope of the present invention to amplify the selected pools of aptamer after each screening (positive or negative).

If an agonist or other substance already known to bind the desired target is available, competitive binding analyses can be performed using the selected oligonucleotide species and radiolabeled substance. Depending upon the results of such competitive analyses, it can be determined whether it would be desirable to proceed with additional positive/negative screening cycles.

One could also determine whether the selected oligonucleotide species can inhibit the target protein in a functional assay. For example, oligonucleotides selected for binding to CD4, the human lymphocyte transmembrane protein, may be tested for their ability to inhibit HIV-1 infection of human lymphocytes in culture.

Modified Method Wherein Target/Aptamer Complexes are Separated from Solid Support. As set forth hereinabove, the original oligonucleotide mixture can be synthesized according to the desired contents of the mixture and can be separated by adding the oligonucleotide mixture to a column containing covalently attached target molecules (see, Ellington, A. D., et al., Nature (1990) 346:818–822) or to the target agents in solution (see Blackwell et al., Science (1990) 250:1104–1110; Blackwell et al., Science (1990) 250:1149–1151; or to the target agent bound to a filter (see Tuerk, C., and Gold, L., Science (1990) 249:505–510). Complexes between the aptamer and targeted agent are separated from uncomplexed aptamers using any suitable technique, depending on the method used for complexation. For example, if columns are used, non-binding species are simply washed from the column using an appropriate buffer. Specifically bound material can then be eluted.

If binding occurs in solution, the complexes can be separated from the uncomplexed oligonucleotides using, for example, the mobility shift in electrophoresis technique (EMSA), described in Davis, R. L., et al., Cell (1990) 60:733. In this method, aptamer-target molecule complexes are run on a gel and aptamers removed from the region of the gel where the target molecule runs. Unbound oligomers migrate outside these regions and are separated away. Finally, if complexes are formed on filters, unbound aptamers are eluted using standard techniques and the desired aptamer recovered from the filters.

In a preferred method, separation of the complexes involves detachment of target-aptamer complexes from column matrices as follows.

A column or other support matrix having covalently or noncovalently coupled target molecules is synthesized. Any standard coupling reagent or procedure may be utilized, depending on the nature of the support and the target molecule. For example, covalent binding may include the formation of disulfide, ether, ester or amide linkages. The length of the linkers used may be varied by conventional means. Noncovalent linkages include antibody-antigen interactions, protein-sugar interactions, as between, for example, a lectin column and a naturally-occurring oligosaccharide unit on a peptide.

Lectins are proteins or glycoproteins that can bind to complex carbohydrates or oligosaccharide units on glycoproteins, and are well-described in The Lectins (I. E. Liener et al., eds., Academic Press 1986). Lectins are isolated from a wide variety of natural sources, including peas, beans, lentils, pokeweed and snails. Concanavalin A is a particularly useful lectin.

Other linking chemistries are also available. For example, disulfide-derivatized biotin (Pierce) may be linked to a target molecule by coupling through an amine or other functional group. The resulting target-S-S-biotin complex could then be used in combination with avidin-derivatized support. Oligonucleotide-target complexes could then be recovered by disulfide bond cleavage. Alternatively, target may be coupled via a cis-diol linker, and oligonucleotide-target complexes may be recovered by mild oxidation of the vicinal diol bond using $NaIO_4$ or other appropriate reagents. Linking chemistries will be selected on the basis of (i) conditions or reagents necessary for maintaining the structure or activity of the target molecule, and/or (ii) chemical groups or moieties on the target molecule available for linking to the support.

The oligomer mixture is added to and incubated with the support to permit oligonucleotide-target complexation. Complexes between the oligonucleotides and target molecule are separated from uncomplexed oligonucleotides by removing unbound oligomers from the support environment. For example, by removing unbound oligomers from the nonbinding species are simply washed from the column using an appropriate buffer.

Following removal of unbound oligomers, the target molecules are uncoupled from the support. The uncoupling procedure depends on the nature of the coupling, as described above. Targets bound through disulfide linkages, for example, may be removed by adding a sulfhydryl reagent such as dithiothreitol or -mercaptoethanol. Targets bound to lectin supports may be removed by adding a complementary monosaccharide (e.g., -methyl-mannoside, N-acetylglucosamine, glucose, N-acetylgalactosamine, galactose or other saccharides for concanavalin A). Oligonucleotides specifically bound to the target can then be recovered by standard denaturation techniques such as phenol extraction.

The method of elution of target-oligonucleotide complex from a support has superior unexpected properties when compared with standard oligonucleotide elution techniques. This invention is not dependent on the mechanism by which these superior properties occur. However, without wishing to be limited by any one mechanism, the following explanation is offered as to how more efficient elution is obtained. Certain support effects result from the binding of oligonucleotides to the support, or the support in conjunction with oligonucleotide or target. Removing oligonucleotide-target complexes enables the recovery of oligonucleotides specific to target only, while eliminating oligonucleotides binding to the support, or the support in conjunction with oligonucleotide or target. At each cycle of selection, this method may give up to 1,000-fold enrichment for specifically binding species. Selection with targets remaining bound to support gives less enrichment per cycle, making it necessary to go through many more cycles in order to get a good aptamer population.

Aptamer Pools of Varying Length. Aptamers can also be selected in the above methods using a pool of oligonucleotides that vary in length as the starting material. Thus, several pools of oligonucleotides having random sequences are synthesized that vary in length from e.g. 50 to 60 bases for each pool and containing the same flanking primer-binding sequences. Equal molar amounts of each pool are mixed and the variable-length pool is then used to select for aptamers that bind to the desired target substance, as described above. This protocol selects for the optimal species for target binding from the starting pool and does not limit aptamers to those of a given length.

Alternatively, several pools of mixed length aptamers can be used in parallel in separate selections and then combined and further selected to obtain the optimal binders from the size range initially used. For example, three pools, A, B and C, can be used. Pool A can consist of oligonucleotides having random sequences that vary in length from e.g. 30 to 40 bases; pool B can have sequences varying in length from e.g. 40 to 50 bases; and pool C can have sequences varying in length from 50 to 60 bases. It is to be understood that the lengths described above are for illustrative purposes only. After selection to obtain binders from A, B, and C, all aptamers are mixed together. A number of rounds of selection are done as described above to obtain the best binders from the initial species selected in the 30-to 60-base range. Note that with this technique, not all possible species in some of the pools are used for selection. If the number of sites available for binding are increased, i.e., if a column is used and the size of the column increased, more species can be included for selection. Furthermore, this method allows for the selection of oligomers from the initial starting pool that are of optimal length for binding the targeted agent.

Derivatization. Aptamers containing the specific binding sequences discerned through the method of the invention can also be derivatized in various ways. For example, if the aptamer is to be used for separation of the target substance, conventionally the oligonucleotide will be derivatized to a solid support to permit chromatographic separation. If the oligonucleotide is to be used to label cellular components or otherwise for attaching a detectable moiety to target, the oligonucleotide will be derivatized to include a radionuclide, a fluorescent molecule, a chromophore, an affinity ligand or the like. If the oligonucleotide is to be used in specific binding assays, coupling to solid support or detectable label, and the like are also desirable. If it is to be used in therapy, the oligonucleotide may be derivatized to include ligands which permit easier transit of cellular barriers, toxic moieties which aid in the therapeutic effect, or enzymatic activities which perform desired functions at the targeted site. The aptamer may also be included in a suitable expression system to provide for in situ generation of the desired sequence. The generation of aptamers by invivo expression systems would also permit binding to intracellular targets.

Consensus Sequences. When a number of individual, distinct aptamer sequences for a single target molecule have been obtained and sequenced as described above, the sequences may be examined for "consensus sequences." As used herein, "consensus sequence" refers to a nucleotide sequence or region (which may or may not be made up of contiguous nucleotides), which is found in one or more regions of at least two aptamers, the presence of which may be correlated with aptamer-to-target-binding or with aptamer structure.

A consensus sequence may be as short as three nucleotides long. It also may be made up of one or more noncontiguous sequences with nucleotide sequences or polymers of hundreds of bases long interspersed between the consensus sequences. Consensus sequences may be identified by sequence comparisons between individual aptamer species, which comparisons may be aided by computer programs and other tools for modeling secondary and tertiary structure from sequence information. Generally, the consensus sequence will contain at least about 3 to 20 nucleotides, more commonly from 6 to 10 nucleotides.

As used herein "consensus sequence" means that certain positions, not necessarily contiguous, of an oligonucleotide are specified. By specified is meant that the composition of the position is other than completely random. Not all oligonucleotides in a mixture may have the same nucleotide at such position; for example, the consensus sequence may contain a known ratio of particular nucleotides. For example, a consensus sequence might consist of a series of four positions wherein the first position in all members of the mixture is A, the second position is 25% A, 35% T and 40% C, the third position is T in all oligonucleotides, and the fourth position is G in 50% of the oligonucleotides and C in 50% of the oligonucleotides.

When a consensus sequence is identified, oligonucleotides that contain that sequence may be made by conventional synthetic or recombinant means. These aptamers, termed "secondary aptamers," may also function as target-specific aptamers of this invention. A secondary aptamer may conserve the entire nucleotide sequence of an isolated aptamer, or may contain one or more additions, deletions or substitutions in the nucleotide sequence, as long as a consensus sequence is conserved. A mixture of secondary aptamers may also function as target-specific aptamers, wherein the mixture is a set of aptamers with a portion or portions of their nucleotide sequence being random or varying, and a conserved region which contains the consensus sequence. Additionally, secondary aptamers may be synthesized using one or more of the modified bases, sugars and linkages described herein using conventional techniques and those described herein.

In some embodiments of this invention, aptamers may be sequenced or mutagenized to identify consensus regions or domains which are participating in aptamer binding to target, and/or aptamer structure. This information is used for generating second and subsequent pools of aptamers of partially known or predetermined sequence. Sequencing, used alone or in combination with the retention and selection processes of this invention, may be used to generate less diverse oligonucleotide pools from which aptamers may be made. Further selection according to these methods may be carried out to generate aptamers having preferred characteristics for diagnostic or therapeutic applications. That is, domains which facilitate, for example, drug delivery could be engineered into the aptamers selected according to this invention.

Although this invention is directed to making aptamers using screening from pools of non-predetermined sequences of oligonucleotides, it also may be used to make second generation aptamers from pools of known or partially known sequences of oligonucleotides. A pool is considered diverse even if one or both ends of the oligonucleotides comprising it are not identical from one oligonucleotide pool member to another, or if one or both ends of the oligonucleotides comprising the pool are identical with nonidentical intermediate regions from one pool member to another. Toward this objective, knowledge of the structure and organization of the target protein can be useful to distinguish features which are important for biochemical pathway inhibition or biological response generation in the first generation aptamers. Structural features may be considered in generating a second (less random) pool of oligonucleotides for generating second round aptamers.

Those skilled in the art will appreciate that comparisons of the complete or partial amino acid sequences of the purified protein target to identify variable and conserved regions is useful. Comparison of sequences of aptamers made according to this invention provides information about the consensus regions and consensus sequences responsible of binding. It is expected that certain nucleotides will be rigidly specified and certain positions will exclusively require certain bases. Likewise, studying localized regions of a protein to identify secondary structure may be useful. Localized regions of a protein may adopt a number of different conformations including beta strands, alpha helices, turns (induced principally by proline or glycine residues) or random structure. Different regions of a polypeptide interact with each other through hydrophobic and electrostatic interactions and also by formation of salt bridges, disulfide bridges, etc. to form the secondary and tertiary structures. Defined conformations can be formed within the protein organization, including beta sheets, beta barrels, and clusters of alpha helices.

It sometimes is possible to determine the shape of a protein target or portion thereof by crystallography X ray diffraction or by other physical or chemical techniques known to those skilled in the art. Many different computer programs are available for predicting protein secondary and tertiary structure, the most common being those described in Chou, P. Y. and Fasman, G. D. (1978) Biochemistry, 13:222–245, and Garnier et al. (1978) J. Mol. Biol., 120:97–120. Generally, these and other available programs are based on the physical and chemical properties of individual amino acids (hydrophobicity, size, charge and presence of side chains) and on the amino acids' collective tendency to form identifiable structures in proteins whose secondary structure has been determined. Many programs attempt to weight structural data with their known influences. For example, amino acids such as proline or glycine are often present where polypeptides have share turns. Long stretches of hydrophobic amino acids (as determined by hydropathy plot), usually have a strong affinity for lipids.

Data obtained by the methods described above and other conventional methods and tools can be correlated with the presence of particular sequences of nucleotides in the first and second generation aptamers to engineer second and third generation aptamers. Further, according to this invention, second generation aptamers may be identified simply by sequentially screening from pools of oligonucleotides having more predetermined sequences than the pools used in earlier rounds of selection.

These methods may be used to design optimal binding sequences for any desired protein target (which may be portions of aptamers or entire aptamers) and/or to engineer into aptamers any number of desired targeted functions or features. Optimal binding sequences will be those which exhibit high relative affinity for target, i.e., affinity measured in $K_D$ in at least in the millimolar range, more preferably in the micromolar range, and, for certain drug applications, the nanomolar range. In practicing this invention, studying the binding energies of aptamers using standard methods known generally in the art may be useful generally, consensus regions may be identified by comparing the conservation of nucleotides for appreciable enhancement in binding.

Structural knowledge can be used to engineer aptamers made according to this invention. For example, stem structures in the aptamer pool may be vital components in some embodiments where increased aptamer rigidity is desired. According to the teachings of the instant invention, a randomly generated pool of oligonucleotides having the stem sequences may be generated. After aptamers are identified which contain the stem (i.e., use the stem in primers), one may put cross-linkers in the stem to covalently fix the stem in the aptamer structure. For an example of a cross-linker which may be used in this way see co-pending application Ser. No. 529,346 entitled "Use of Novel oligonucleotides in Target Specific Binding" filed on May 25, 1990 which is hereby incorporated by reference. Cross-linkers also may be used to fix an aptamer to a target.

Once an aptamer has been identified, it may be used, either by linkage to, or use in combination with, other aptamers identified according to these methods. One or more aptamers may be used in this manner to bind to one or more tartets.

Utility of the Aptamers. The aptamers and modified aptamers of the invention are useful in diagnostic, research and therapeutic contexts. For diagnostic applications, aptamers are particularly well suited for binding to biomolecules that are identical or similar between different species. Classes of molecules such as kinins and eicosanoids generally do not serve as good antigens because they are not easily recognized as foreign by the immune systems of animals that can be used to generate antibodies. Antibodies are generally used to bind analytes that are detected or quantitated in various diagnostic assays. Aptamers represent a class of molecules that may be used in place of antibodies for diagnostic and purification purposes.

The aptamers of the invention are therefore particularly useful as diagnostic reagents to detect the presence or absence of the target substances to which they specifically bind. Such diagnostic tests are conducted by contacting a sample with the specifically binding oligonucleotide to obtain a complex which is then detected by conventional means. For example, the aptamers may be labeled using radioactive, fluorescent, or chromogenic labels and the presence of label bound to solid support to which the target substance has been bound through a specific or nonspecific binding means detected. Alternatively, the specifically binding aptamers may be used to effect initial complexation to the support. Means for conducting assays using such oligomers as specific binding partners are generally known to track those for standard specific binding partner based assays.

This invention also permits the recovery and deduction of oligomeric sequences which bind specifically to cell surface proteins and specific portions thereof. Therefore, these oligonucleotides can be used as a separation tool for retrieving the substances to which they specifically bind. By coupling the oligonucleotides containing the specifically binding sequences to a solid support, for example, proteins or other cellular components to which they bind can be recovered in useful quantities. In addition, these oligonucleotides can be used in diagnosis by employing them in specific binding assays for the target substances. When suitably labeled using detectable moieties such as radioisotopes, the specifically binding oligonucleotides can also be used for in vivo imaging or histological analysis.

It may be commented that the mechanism by which the specifically binding oligomers of the invention interfere with or inhibit the activity of a target substance is not always established, and is not a part of the invention. The oligomers of the invention are characterized by their ability to target specific substances regardless of the mechanisms of targeting or the mechanism of the effect thereof.

For use in research, the specifically binding oligonucleotides of the invention are especially helpful in effecting the isolation and purification of substances to which they bind. For this application, typically, the oligonucleotide containing the specific binding sequences is conjugated to a solid support and used as an affinity ligand in chromatographic separation of the target substance. The affinity ligand can also be used to recover previously unknown substances from sources which do not contain the target substance by virtue of binding similarity between the intended target and the unknown substances. Furthermore, as data accumulate with respect to the nature of the nonoligonucleotide/ oligonucleotide-specific binding, insight may be gained as to the mechanisms for control of gene expression.

In therapeutic applications, the aptamers of the invention can be formulated for a variety of modes of administration, including systemic and topical or localized administration. Techniques and formulations generally may be found in Remington's Pharmaceutical Sciences, Mack Publishing Co., Easton, Pa., latest edition.

For systemic administration, injection is preferred, including intramuscular, intravenous, intraperitoneal, and subcutaneous. For injection, the aptamers of the invention are formulated in liquid solutions, preferably in physiologically compatible buffers such as Hank's solution or Ringer's solution. In addition, the aptamers may be formulated in solid form and redissolved or suspended immediately prior to use. Lyophilized forms are also included.

Systemic administration can also be by transmucosal or transdermal means, or the oligomers can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the oligomers are formulated into conventional oral administration forms such as capsules, tablets, and tonics.

For topical administration including ocular administration, the oligomers of the invention are formulated into ointments, salves, gels, or creams, as is generally known in the art.

The oligonucleotides may also be employed in expression systems, which are administered according to techniques applicable, for instance, in applying gene therapy.

Immune Recruitment/Immune Response Modulation. The present invention also provides a method whereby immune response is elicited in a desired manner through the use of agents which are directed to specific targets on cells involved in a pathological condition of interest. The aptamers prepared herein are useful as targeting agents in this method. In a particular embodiment of the invention, the known ability of various materials to elicit strong immune responses is exploited so as, in turn, to stimulate the immune response to target pathologic cells, which may themselves otherwise have the ability to reduce or escape effective CTL responses.

Pursuant to this method of the invention, in a first step a targeting agent is identified that specifically binds to a surface feature of the pathologic cells of interest. Once such a selective targeting agent has been identified, in a second step a conjugate is formed with a moiety known to act itself as an immunogen, for example as an antigen for eliciting a strong CTL response in the organism. By virtue of the selective binding of the targeting agent component of the conjugate to cells containing the target, these cells are in effect modified so as to exhibit the immunologic character of the associated immunogenic component of the conjugate. Thus, when the associated moiety is an antigen which elicits a strong CTL response, the cells are effectively marked for destruction by the antigen component of the conjugate.

In accordance with one preferred embodiment of the invention, the targeting agent is an oligonucleotide which binds to a specific target on a cell surface, and the immunomodulatory component of the conjugate is a polypeptide which elicits a strong CTL response.

Targeting Agents. For use as targeting agents, any of a number of different materials which bind to cell surface antigens may be employed. When available, antibodies to target cell surface antigens will generally exhibit the necessary specificity for the target. Similarly, ligands for any receptors on the surface of the pathologic cells of interest may suitably be employed as targeting agent. Yet another class of potentially valuable targeting agents is oligonucleotides of the requisite binding selectivity.

Typically, for reaction with antigenic determinants on proteins, antibodies raised against these proteins, either polyclonal or monoclonal, may be used. Polyclonal anti-sera are prepared in conventional ways, for example by infecting a suitable mammal with antigen to which antibody is desired, assaying the antibody level in serum against the antigen, and preparing anti-sera when the titers are high. Monoclonal antibody preparations may also be prepared conventionally, such as by the method of Koehler and Milstein using, e.g., peripheral blood lymphocytes or spleen cells from immunized animals and immortalizing these cells either by viral infection, by fusion with myelomas, or by other conventional procedures and screening for the production of the desired antibodies by isolated colonies.

In addition to antibodies, suitable immunoreactive fragments may also be employed, such as the Fab, Fab', or F(ab')$_2$ fragments. Many antibodies suitable for use in forming the targeting mechanism are already available in the art. For example, the use of immunologically reactive fragments as substitutes for whole antibodies is described by Spiegelberg, H. L., in "Immunoassays in the Clinical Laboratory" (1978) 3:1–23.

One known surface antigen to which antibodies can be raised, for example, is the extracellular domain of the HER2/nu associated with breast tumors. As set forth by Fendly, B. M. et al. J Biol Resp Mod (1990) 9:449–455, antibodies to HER/nu can be raised in alternate hosts (since the antigen is not foreign to the host-bearing tumor) and can be used in immunoconjugates to bind specifically to the tumor. As applied in the method of the invention, the antibody or fragment thereof would be coupled not to a toxin, but to an immunomodulatory agent which would mount a CTL response.

In addition to immunoreactivity, targeting can be effected by utilizing receptor ligands which target receptors at the target cell surface, for example on the basis of complementarity of contours or charge patterns between the receptor and ligand. As used herein, the term "receptor ligand" refers to any substance, natural or synthetic, which binds specifically to a cell surface receptor, protein or glycoprotein found at the surface of the desired target cell population. These receptor ligands include lymphokine factors, for example, IL2 or viral or tumor antigens.

Oligonucleotides identified as binding to one or more surface antigen of the pathologic cells may also be used to form conjugates in a known manner, and are particularly preferred for use as targeting agents in accordance with the present invention.

Immunomodulatory Agents. An "immunological response" as discussed herein generally refers to the development in a mammal of either a cell- or antibody-mediated immune response to an agent of interest. Typically, such a response consists of the mammal producing antibodies and/or cytotoxic T-cells directed specifically to a particular agent. In the context of the present invention, however, an "immunological response different from that elicited by the pathologic cell itself in the absence of the conjugate" may constitute, e.g., the failure to produce antibodies or cytotoxic T-cells under circumstances (for example, in the presence of a particular antigen) which would normally result in the induction of a specific response.

Examples of moieties known to act as antigens for eliciting a strong CTL response include a wide range of biologically active materials. Particularly suitable for use in this regard are short peptide sequences, such as those which may correspond to the antigenic determinants of known immunogenic proteins. For example, sequences derived from viral or bacterial pathogens may be useful in stimulating a strong CTL response in the infected host organism.

Other immunomodulatory agents useful in the invention include fragments of the HLA Class I glycoproteins. The ability of such HLA Class I glycoproteins or fragments thereof to stimulate a CTL response has been documented by Symington, F. W. et al., Invest Dermatol (1990) 95:224–228. Also known to elicit CTL responses are short regions of viral antigens such as those of the influenza virus nucleoprotein (Rothbard, J. B. et al., EMBO J (1989) 8:2321–2328) and sections of the murine minor histocompatibility antigens such as H-25.3 cell surface antigen (Lai, P. K., Transplantation (1985) 39:638–643). Other known agents which expand CTL as opposed to helper T-cells include interleukin-6 and cyclosporin A.

Techniques for Coupling Targeting Agents and Immunomodulatory Agents. Coupling of the targeting agents with the immunomodulatory agents may be carried out using any of a variety of different techniques which are well known per se to those working in the field. The particular choice of coupling method depends on the chemical nature of the specific targeting and immunomodulatory agents. Selection of the most appropriate method of coupling from among the variety of available alternatives for any given types of targeting and immunomodulatory agents may in some instances require routine screening to determine empirically which conjugates provide the optimum combination of targeting specificity and desired immunomodulatory effect.

When at least one of the agents which constitute the conjugate is a polypeptide, well-known chemical methods for formation of chemical bonds with, e.g., functional groups on amino acid side-chains or preferably N-terminal amino or C-terminal carboxyl groups, may be employed. One common approach is the use of linkers which may be homobifunctional or heterobifunctional, and typically involve highly reactive functional groups on the linker. Another approach is the use of dehydrating agents, such as carbodiimides, to effect the formation of new bonds by reaction of a carboxyl moiety on one member of the conjugate with a free amino group on the other. Particularly suitable methods involving the use of conjugation reagents (i.e., reagents which result in elimination of water to form a new covalent bond) are discussed in, e.g., U.S. Pat. No.

4,843,147 to Levy et al., which is hereby incorporated by reference. Additional techniques for formation of conjugates between polypeptides and various types of biologically active molecules have been described in the art with respect to the formation of cytotoxic conjugates; for example, a variety of different conjugate-forming reactions are described in U.S. Pat. No. 4,507,234 to Kato et al., which is also hereby incorporated by reference.

Similarly, methods are known for attaching a variety of different species to oligonucleotides. For example, Asseline, U. et al. (Proc Natl Acad Sci 81, 3297–3301 (1984)) describes the covalent linking of an intercalating agent via a polymethylene linker through a 3'-phosphate group. Mori, K. et al. (FEBS Letters 249:213–218 (1989)) describes the covalent attachment of groups via a methylene linker at the 5'-terminus of oligonucleotides. PCT application WO89/05853 published Jun. 29, 1989, the entire disclosure of which is hereby incorporated by reference, describes a variety of methods for formation of conjugates between nucleotide sequences and chelating agents; the chelating agent is joined to the nucleotides sequence by either a covalent bond or a linking unit derived from a polyvalent functional group. Other methods will of course be readily apparent to those working in the field.

Identification of Suitable Targets for the Conjugates. Suitable targets for binding a targeting agent include cell surface antigens which are specific to the pathologic cells which it is desired to treat. For example, most tumor antigens (such as the carcinoembryonic antigen associated with several types of cancer) do not generally elicit an effective CTL response. The presence of the antigens on the surface of tumor cells enables the use of appropriately tailored targeting agents to deliver conjugate specifically to those cells.

In addition to eliciting CTL type responses, other types of immunomodulatory effects may be achieved through the use of the inventive conjugates. For example, the conjugates of the invention may be useful in preventing the progression or the cure of autoimmune disease.

Diseases with an autoimmune component, such as diabetes or arthritis, appear to involve response to specific self antigens. By using conjugates of the invention to elicit an immune response against those immune cells which mediate the attack on self tissues, a positive effect on the course of the disease may be achieved. In principle, a group of antigenically related immune cells that mediate the systemically inappropriate response could be targeted using a single conjugate specific for that antigen. Destruction of this marked population by the immune system should lead to an amelioration of the disease condition.

Alternatively, the binding of appropriate conjugates to target antigens on cells could be employed as a means to mask recognition of those antigens or of the cell bearing the antigens. This could prevent the destruction of the cell carrying the antigens, and thus result in stasis of autoimmune disease progression.

Further, an immune response stimulated by the immunomodulatory portion of the conjugate may result in other desirable immunologic responses in the organism. In particular, by virtue of the cell death process initiated in response to the conjugate, a highly desirable response to other unmarked cells of the same type may result. Thus, by identifying a particular class of cells for recognition by various components of the immune system via the immunomodulatory portion of the conjugate, it may be possible to induce a particular category of response (e.g., CTL-mediated destruction) to that category of cells as a whole, regardless of whether or not the cells are marked by conjugate.

Specific Embodiments. One aspect of the invention (Aptamer A) is directed to an aptamer containing at least one binding region capable of binding specifically to a target molecule or a fragment of a target molecule comprising:

Factor X, PDGF, aFGF, ICAM-1, VCAM-1 or E-selectin.

Another aspect of the invention (Aptamer B) is directed to Aptamer A which comprises single-stranded DNA.

Another aspect of the invention (Aptamer C) is directed to Aptamer B which contains a binding region of less than 14 nucleotide residues.

Another aspect of the invention (Aptamer D) is directed to Aptamer B-C which contains a binding region of less than 10 nucleotide residues.

Another aspect of the invention (Aptamer E) is directed to Aptamer B-C which contains 6–100 nucleotide residues.

Another aspect of the invention (Aptamer F) is directed to Aptamer B-D which contains 6–50 nucleotide residues.

Another aspect of the invention (Aptamer G) is directed to Aptamer B-E wherein said aptamer is capable of binding specifically to a target molecule at physiological conditions.

Another aspect of the invention (Aptamer H) is directed to Aptamer A wherein the target is ICAM-1.

Another aspect of the invention (Aptamer I) is directed to Aptamer A-H which is a secondary aptamer.

Another aspect of the invention (Method A) is directed to a method for obtaining an aptamer containing at least one binding region that specifically binds a target or a fragment of a target comprising Factor X, PDGF, aFGF, ICAM-1, VCAM-1 or E-selectin, which method comprises:

(a) incubating said target with a mixture of member oligonucleotides under conditions wherein the target complexes with some, but not all members of the mixture to form oligonucleotide-target complexes;

(b) separating the oligonucleotide-target complexes from uncompleted oligonucleotides;

(c) recovering and amplifying the complexed oligonucleotides from said complexes to obtain an aptamer; and (d) optionally determining the sequence of the recovered aptamer, wherein said aptamer is a single-stranded DNA, or wherein said aptamer contains at least one binding region capable of binding specifically to a target molecule that does not normally bind oligonucleotides with a dissociation constant (Kd) less than about 20 nM, or wherein said aptamer contains at least one binding region capable of binding specifically to a target molecule, wherein the Kd with respect to the aptamer and said target molecule is less by a factor of at least 5, as compared to the Kd for said aptamer and other molecules, or wherein said aptamer contains at least one binding region capable of binding specifically to a target molecule wherein said binding region contains less than 15 nucleotide residues, or wherein said aptamer contains at least one binding region capable of binding specifically to a target molecule wherein said aptamer contains less than 16 nucleotide residues.

Another aspect of the invention (Method B) is directed to the method of Method A wherein said mixture of oligonucleotides contains at least one modified oligonucleotide.

Another aspect of the invention (Method C) is directed to the method of Method A wherein said amplifying is conducted using at least one modified nucleotide.

Another aspect of the invention (Method D) is directed to the method of Method B-C wherein said mixture of oligonucleotides contains one randomized-sequence region.

Another aspect of the invention (Method E) is directed to the method of Method B-D which further includes repeating steps (a)–(c) using the recovered and amplified complexed oligonucleotides resulting from step (c) in succeeding step (a).

Another aspect of the invention (Method F) is directed to the method of Method B-E wherein the Kd with respect to the oligonucleotide mixture and target is at least 50-fold more than the Kd with respect to the aptamer and target.

Another aspect of the invention (Aptamer J) is directed to an aptamer prepared by the method of Method B-F.

Another aspect of the invention (Method G) is directed to a method to obtain a secondary aptamer that specifically binds to a target molecule or fragment of a target molecule comprising Factor X, PDGF, aFGF, ICAM-1, VCAM-1 or E-selectin, which method comprises:

(a) incubating said target molecule with a mixture of oligonucleotide sequences under conditions wherein complexation occurs with some, but not all, members of the mixture to form oligonucleotide-target complexes;

(b) separating the oligonucleotide-target complexes from uncomplexed oligonucleotides;

(c) recovering and amplifying the complexed oligonucleotides from said complexes;

(d) optionally repeating steps (a)–(c) with the recovered oligonucleotides of step (c);

(e) determining the sequences of the recovered oligonucleotides;

(f) determining a consensus sequence included in the recovered oligonucleotides; and (g) synthesizing a secondary aptamer which comprises the consensus sequence.

Another aspect of the invention (Aptamer K)) is directed to a secondary aptamer prepared by the method of Method G.

Another aspect of the invention (Method H) is directed to a method for obtaining an aptamer containing at least one binding region that specifically binds a target or a fragment of a target comprising Factor X, PDGF, aFGF, ICAM-1, VCAM-1 or E-selectin, which method comprises:

(a) incubating said target with a mixture of member oligonucleotides under conditions wherein the target complexes with some, but not all, members of the mixture to form oligonucleotide-target complexes;

(b) separating the oligonucleotide-target complexes from uncomplexed oligonucleotides;

(c) recovering and amplifying the complexed oligonucleotides from said complexes to obtain an aptamer; and (d) optionally determining the sequence of the recovered aptamer, wherein the dissociation constant (Kd) with respect to said target and mixture of oligonucleotides is less than about 20 nM, or wherein the Kd with respect to the aptamer and said target is less by a factor of at least 50 as compared to the Kd for said target and said mixture of oligonucleotides; or wherein steps (a) and (b) are conducted under physiological conditions, or wherein said mixture of oligonucleotides consists of single-stranded DNA.

Another aspect of the invention (Method I) is directed to the method of Method H which further includes repeating steps (a)–(c) using the recovered and amplified complexed oligonucleotides resulting from step (c) in succeeding step (a).

Another aspect of the invention (Method J) is directed to a method to obtain an aptamer containing a binding region which specifically binds a target molecule or a fragment of a target molecule comprising Factor X, FDGF, aFGF, ICAM-1, VCAM-1 or E-selectin, which method comprises:

(a) incubating the target molecule reversibly coupled to a support with a mixture of oligonucleotide sequences under conditions wherein the coupled target molecule complexes with some, but not all, members of the mixture to form support-bound oligonucleotide complexes;

(b) decoupling and recovering the oligonucleotide target complex from the support to obtain free aptamer-target complexes;

(c) recovering and amplifying the completed oligonucleotides from the free oligonucleotide-target complexes to obtain a population of aptamers;

(d) optionally repeating steps (a)–(c) using as said mixture the recovered population of aptamers of step (c); and (e) optionally determining the sequence of the recovered aptamers.

Another aspect of the invention (Method K) is directed to the method of Method J wherein the support is a lectin support and the target substance binds reversibly to lectin.

Another aspect of the invention (Method L) is directed to the method of Method K wherein in step (b), decoupling is accomplished by adding a monosaccharide.

Another aspect of the invention (Method M) is directed to the method of Method L wherein the monosaccharide is selected from the group consisting of -methyl-mannoside, N-acetylglucosamine, glucose, N-acetylgalactosamine and galactose.

Another aspect of the invention (Method N) is directed to a method to detect the presence or absence of a target molecule, which method comprises contacting a sample suspected of containing said target molecule with the aptamer of Aptamer A-I under conditions wherein a complex between said target molecule and the aptamer is formed, and detecting the presence or absence of said complex.

Another aspect of the invention (Method O) is directed to a method to purify a target molecule, which method comprises contacting a sample containing said target molecule with the aptamer of Aptamer A-I attached to solid support under conditions wherein said target molecule is bound to the aptamer coupled to solid support;

washing unbound components of the sample; and recovering the target molecule from said solid support.

Another aspect of the invention (Composition A) is directed to a pharmaceutical composition for medical use comprising the aptamer of Aptamer A-I in admixture with a physiologically acceptable excipient.

Another aspect of the invention (Composition B) is directed to a composition for diagnostic use which comprises the aptamer of Aptamer A-I.

Another aspect of the invention (Aptamer L) is directed to the aptamer of Aptamer A-I coupled to an auxiliary substance.

Another aspect of the invention (Aptamer M) is directed to the aptamer of Aptamer L wherein said auxiliary substance is selected from the group consisting of a drug, a toxin, a solid support, and specific binding reagent, a label, a radioisotope or a contrast agent.

Another aspect of the invention (Method P) is directed to a method for obtaining a single-stranded DNA aptamer which specifically binds to a target or a fragment of a target molecule that does not normally bind to nucleic acids, which method comprises:

(a) incubating said target with a solution comprising a mixture of oligonucleotides under conditions where complexation occurs with some, but not all, members of the mixture to form oligonucleotide-target complexes;

(b) separating the oligonucleotide-target complexes from uncompleted oligonucleotides using a solid column;

(c) recovering and amplifying the complexed oligonucleotides from said complexes; and (d) optionally determining the sequence of the recovered oligonucleotide.

Another aspect of the invention (Method Q) is directed to the method of Method P wherein the solid column is an agarose or polvacrylamide gel.

Another aspect of the invention (Method R) is directed to the method of Method Q wherein the target is a protein, glycoprotein, lipid, glycolipid, carbohydrate or small molecule.

Another aspect of the invention (Method S) is directed to the method according to Method Q wherein the target or the fragment of a target is Factor X, PDGF, aFGF, ICAM-1, VCAM-1 or E-selectin.

Another aspect of the invention (Method T) is directed to a method for obtaining an aptamer which specifically binds to a target that does not normally bind to nucleic acids and modulates or affects one or more functions of the target, which method comprises:

(a) incubating said target with a solution comprising a mixture of oligonucleotides under conditions where complexation occurs with some, but not all, members of the mixture to form oligonucleotide-target complexes;

(b) separating the oligonucleotide-target complexes from uncompleted oligonucleotides;

(c) recovering and amplifying the complexed oligonucleotides from said complexes; and (d) optionally determining the sequence of the recovered oligonucleotide.

Another aspect of the invention (Method U) is directed to the method of Method T wherein step (b) is conducted using a solid column.

Another aspect of the invention (Method V) is directed to the method of Method U wherein the solid column is an agarose gel or a polyacrylamide gel.

Another aspect of the invention (Method W) is directed to the method of Method T wherein the target is a protein, glycoprotein or enzyme.

Another aspect of the invention (Method X) is directed to the method according to Method W wherein the target is Factor X, PGDF, aFGF, ICAM-1, VCAM-1 or E-selectin.

Another aspect of the invention (Aptamer N) is directed to a single-stranded DNA aptamer containing at least one binding region capable of binding specifically to a target molecule.

Another aspect of the invention (Aptamer O) is directed to an aptamer containing at least one binding region capable of binding specifically to a target molecule that does not normally bind oligonucleotides with a dissociation constant (Kd) of less than $20 \times 10^{-9}$.

Another aspect of the invention (Aptamer P) is directed to an aptamer containing at least one binding region capable of binding specifically to a target molecule, wherein the Kd with respect to the aptamer and said target molecule is less by a factor of at least 5, as compared to the Kd for said aptamer and other unrelated molecules.

Another aspect of the invention (Aptamer Q) is directed to an aptamer containing at least one binding region capable of binding specifically to a target molecule wherein said binding region contains less than 15 nucleotide residues.

Another aspect of the invention (Aptamer R) is directed to an aptamer containing at least one binding region capable of binding specifically to a target molecule wherein said aptamer contains less than 16 nucleotide residues.

Another aspect of the invention (Aptamer S) is directed to an aptamer containing at least one binding region capable of binding specifically to a target molecule selected from the group consisting of:

bradykinin, PGF2, CD4, HER2, IL-1 receptor, Factor X, and thrombin.

Another aspect of the invention (Aptamer T) is directed to the aptamer of Aptamer N-R wherein the target molecule exhibits one or more biological functions.

Another aspect of the invention (Aptamer U) is directed to the aptamer of Aptamer T wherein the target molecule does not exhibit the biological function of binding nucleic acids.

Another aspect of the invention (Aptamer V) is directed to the aptamer of Aptamer N-R wherein the target molecule is a protein or peptide.

Another aspect of the invention (Aptamer W) is directed to the aptamer of Aptamer V wherein the target molecule is an extracellular protein.

Another aspect of the invention (Aptamer X) is directed to the aptamer of Aptamer W wherein the extracellular protein is selected from the group consisting of botulinum toxin and diphtheria toxin, collagenase, tumor necrosis factor, antithrombin III, interleukins, elastase, and PDGF (and) fibroblast growth factors.

Another aspect of the invention (Aptamer Y) is directed to the aptamer of Aptamer V wherein the target molecule is an intracellular protein.

Another aspect of the invention (Aptamer Z) is directed to the aptamer of Aptamer Y wherein the intracellular protein is selected from the group consisting of oncogene proteins, hydroxymethyl glutaryl CoA synthase and dihydrofolate reductase.

Another aspect of the invention (Aptamer AA) is directed to the aptamer of Aptamer V wherein the target molecule is a cell surface protein.

Another aspect of the invention (Aptamer AB) is directed to the aptamer of Aptamer AA wherein the cell surface protein is selected from the group consisting of HLA antigens, tumor necrosis factor receptors, EGF receptor, CD62, ICAM-1, ICAM-2, VCAM-1 and ELAM-1.

Another aspect of the invention (Aptamer AC) is directed to the aptamer of Aptamer V wherein the target molecule is a glycoprotein.

Another aspect of the invention (Aptamer AD) is directed to the aptamer of Aptamer N-R wherein the target molecule is a carbohydrate.

Another aspect of the invention (Aptamer AE) is directed to the aptamer of Aptamer AD wherein the carbohydrate is a selected from the group consisting of monosaccharide, disaccharide, polysaccharide, or is a glucosaminoglycan or fragment thereof.

Another aspect of the invention (Aptamer AF) is directed to the aptamer of Aptamer N-R wherein the target molecule is a lipid.

Another aspect of the invention (Aptamer AG) is directed to the aptamer of Aptamer AF wherein the lipid is a glycolipid.

Another aspect of the invention (Aptamer AH) is directed to the aptamer of Aptamer AF wherein the lipid is a steroid, or triglyceride.

Another aspect of the invention (Aptamer AI) is directed to the aptamer of Aptamer N-R wherein the target molecule is a small molecule selected from the group consisting of aflatoxin, histamine, and eicosanoids.

Another aspect of the invention (Aptamer AJ) is directed to the aptamer of Aptamer N-R wherein the target molecule has a molecular weight from about 100 to about 1000 daltons.

Another aspect of the invention (Aptamer AK) is directed to the aptamer of N-R wherein the target molecule has a molecular weight from about $10^3$ to about $10^4$ daltons.

Another aspect of the invention (Aptamer AL) is directed to the aptamer of N-R wherein the target molecule has a molecular weight from about $10^4$ to about $10^6$ daltons.

Another aspect of the invention (Aptamer AM) is directed to the aptamer of N-S which contains a binding region of less than 14 nucleotide residues.

Another aspect of the invention (Aptamer AN) is directed to the aptamer of Aptamer N-S which contains a binding region of less than 10 nucleotide residues.

Another aspect of the invention (Aptamer AO) is directed to the aptamer of Aptamer N-Q or S which contains 6–100 nucleotide residues.

Another aspect of the invention (Aptamer AP) is directed to the aptamer of Aptamer N-Q or S which contains 6–50 nucleotide residues.

Another aspect of the invention (Aptamer AQ) is directed to the aptamer of Aptamer N-AP wherein said aptamer is capable of binding specifically to a target molecule at physiological conditions.

Another aspect of the invention (Aptamer AR) is directed to the single-stranded DNA aptamer of Aptamer N-AQ wherein said aptamer binds to said target with a Kd of less than $20 \times 10^{-9}$.

Another aspect of the invention (Aptamer AS) is directed to the aptamer of Aptamer AR wherein said aptamer binds to the target with a Kd of less than $20 \times 10^{-9}$ at physiological conditions.

Another aspect of the invention (Aptamer AT) is directed to the aptamer of Aptamer N-AS wherein the Kd with respect to the aptamer and said target molecule is less by a factor of at least 5, as compared to the Kd for said aptamer and other unrelated molecules.

Another aspect of the invention (Aptamer AU) is directed to the aptamer of Aptamer N-AT wherein the aptamer contains at least one modified linking group, sugar residue and/or base.

Another aspect of the invention (Aptamer AV) is directed to the aptamer of Aptamer AU wherein the aptamer contains at least one linking group wherein P(O)O is replaced by P(O)S, P(S)S, P(O)NR$_2$, P(O)R, P(O)OR', CO or CH$_2$, wherein each R or R' is independently H or substituted or unsubstituted alkyl (1–20C) optionally containing an ether (—O—) linkage, aryl, alkenyl, cycloalkyl, cycloalkenyl or aralkyl; or the aptamer contains at least one linking group attached to an adjacent nucleotide through S or N; or the aptamer contains at least one modified form of purine or pyrimidine or at least one abasic site; or the aptamer contains at least one modified or analogous sugar other than underivatized ribose.

Another aspect of the invention (Aptamer AW) is directed to the aptamer of Aptamer AV which contains at least one linking group wherein P(O)o is replaced by P(O)S and said linking group is attached to each adjacent nucleotide through 0; or which contains at least one linking group wherein P(O)O is replaced by P(O)NH(CH$_2$CH$_2$CH$_3$) and said linking group is attached to each adjacent nucleotide through O; or contains at least one uracil (dU) base substituted for thymine; or contains at least one abasic site; or contains at least one 5-pentynyluracil base substituted for thymine, or contains a 2'-O-alkyl, 2'-O-allyl, 2'-S-alkyl, 2'-S-allyl or halo sugar residue.

Another aspect of the invention (Aptamer AX) is directed to the aptamer of Aptamer N-AW which is a secondary aptamer.

Another aspect of the invention (Method Y) is directed to a method for obtaining an aptamer containing at least one binding region that specifically binds a target, which method comprises:

(a) incubating said target with a mixture of member oligonucleotides under conditions wherein the target complexes with some, but not all, members of the mixture to form oligonucleotide-target complexes;

(b) separating the oligonucleotide-target complexes from uncompleted oligonucleotides;

(c) recovering and amplifying the completed oligonucleotides from said complexes to obtain an aptamer; and (d) optionally determining the sequence of the recovered aptamer, wherein said aptamer is a single-stranded DNA, or wherein said aptamer contains at least one binding region capable of binding specifically to a target molecule that does not normally bind oligonucleotides with a dissociation constant (Kd) of less than $20 \times 10^{-9}$, or wherein said aptamer contains at least one binding region capable of binding specifically to a target molecule, wherein the Kd with respect to the aptamer and said target molecule is less by a factor of at least 5, as compared to the Kd for said aptamer and other molecules, or wherein said aptamer contains at least one binding region capable of binding specifically to a target molecule wherein said binding region contains less than 15 nucleotide residues, or wherein said aptamer contains at least one binding region capable of binding specifically to a target molecule wherein said aptamer contains less than 16 nucleotide residues, or wherein said aptamer contains at least one binding region capable of binding specifically to a target molecule selected from the group consisting of exemplified targets.

Another aspect of the invention (Method Z) is directed to the method of Method Y wherein said mixture of oligonucleotides contains at least one modified oligonucleotide.

Another aspect of the invention (Method AA) is directed to the method of Method Y wherein said amplifying is conducted using at least one modified nucleotide.

Another aspect of the invention (Method AB) is directed to the method of Method Y-AA wherein said mixture of oligonucleotides contains at least one randomized-sequence region.

Another aspect of the invention (Method AC) is directed to the method of Method Y-AB which further includes repeating steps (a)–(c) using the recovered and amplified completed oligonucleotides resulting from step (c) in succeeding step (a).

Another aspect of the invention (Method AD) is directed to the method of Method Y-AC wherein the Kd with respect to the oligonucleotide mixture and target is at least 50-fold more than the Kd with respect to the aptamer and target.

Another aspect of the invention (Aptamer AY) is directed to an aptamer prepared by the method of Method Y-AD.

49

Another aspect of the invention (Method AE) is directed to a method to obtain a secondary aptamer that specifically binds to a target molecule which method comprises:
 (a) incubating said target molecule with a mixture of oligonucleotide sequences under conditions wherein complexation occurs with some, but not all, members of the mixture to form oligonucleotide-target complexes;
 (b) separating the oligonucleotide-target complexes from uncompleted oligonucleotides;
 (c) recovering and amplifying the complexed oligonucleotides from said complexes;
 (d) optionally repeating steps (a)–(c) with the recovered oligonucleotides of step (c);
 (e) determining the sequences of the recovered oligonucleotides;
 (f) determining a consensus sequence included in the recovered oligonucleotides; and
 (g) synthesizing a secondary aptamer which comprises the consensus sequence.

Another aspect of the invention (Aptamer AZ) is directed to a secondary aptamer prepared by the method of Method AE.

Another aspect of the invention (Method AF) is directed to a method for obtaining an aptamer containing at least one binding region that specifically binds a target, which method comprises:
 (a) incubating said target with a mixture of member oligonucleotides under conditions wherein the target complexes with some, but not all, members of the mixture to form oligonucleotide-target complexes;
 (b) separating the oligonucleotide-target complexes from uncompleted oligonucleotides;
 (c) recovering and amplifying the complexed oligonucleotides from said complexes to obtain an aptamer; and
 (d) optionally determining the sequence of the recovered aptamer,
 wherein the dissociation constant (Kd) with respect to said target and mixture of oligonucleotides is 1M, or
 wherein the Kd with respect to the aptamer and said target is less by a factor of at least 50 as compared to the Kd for said target and said mixture of oligonucleotides; or
 wherein steps (a) and (b) are conducted under physiological conditions, or
 wherein said mixture of oligonucleotides consists of single-stranded DNA.

Another aspect of the invention (Method AG) is directed to the method of Method AF wherein said mixture of oligonucleotides contains at least one modified oligonucleotide.

Another aspect of the invention (Method AH) is directed to the method of Method AF wherein said amplifying is conducted using at least one modified nucleotide.

Another aspect of the invention (Method AI) is directed to the method of Method AF-AH wherein said mixture of oligonucleotides contains at least one randomized-sequence region.

Another aspect of the invention (Method AJ) is directed to the method of Method AF-AH which further includes repeating steps (a)–(c) using the recovered and amplified complexed oligonucleotides resulting from step (c) in succeeding step (a).

Another aspect of the invention (Method AK) is directed to the method of Method AF wherein said mixture of oligonucleotides is of unpredetermined sequence.

50

Another aspect of the invention (Aptamer BA) is directed to an aptamer prepared by the method of Method AF-AK.

Another aspect of the invention (Method AL) is directed to a method to obtain an aptamer containing a binding region which specifically binds a target molecule which comprises:
 (a) incubating the target molecule reversibly coupled to a support with a mixture of oligonucleotide sequences under conditions wherein the coupled target molecule complexes with some, but not all, members of the mixture to form support-bound oligonucleotide complexes;
 (b) decoupling and recovering the oligonucleotide target complex from the support to obtain free aptamer-target complexes;
 (c) recovering and amplifying the complexed oligonucleotides from the free oligonucleotide-target complexes to obtain a population of aptamers;
 (d) optionally repeating steps (a)–(c) using as said mixture the recovered population of aptamers of step (c); and
 (e) optionally determining the sequence of the recovered aptamers. Another aspect of the invention (Method AM) is directed to the method of Method AL wherein in step (a) the target substance is reversibly coupled to the support using an activated thiol group on the support.

Another aspect of the invention (Method AN) is directed to the method of Method AL wherein in step (b), decoupling is accomplished by adding a reducing agent.

Another aspect of the invention (Method AO) is directed to the method of Method AN wherein the reducing agent is dithiothreitol or -mercaptoethanol.

Another aspect of the invention (Method AP) is directed to the method of Method AL wherein the support is a lectin support and the target substance binds reversibly to lectin.

Another aspect of the invention (Method AQ) is directed to the method of Method AP wherein in step (b), decoupling is accomplished by adding a monosaccharide.

Another aspect of the invention (Method AR) is directed to the method of Method AQ wherein the monosaccharide is selected from the group consisting of -methyl-mannoside, N-acetylglucosamine, glucose, N-acetylgalactosamine and galactose.

Another aspect of the invention (Method AS) is directed to a method for obtaining aptamers capable of binding a target, said method comprising:
 (a) providing a first pool of oligonucleotides of unpredetermined sequence, said pool comprising a quantity of oligonucleotides sufficiently reflective of the structural complexity of said target as to ensure the presence of at least one oligonucleotide capable of binding said target;
 (b) incubating said pool of oligonucleotides, or a portion thereof with said target under conditions wherein complexation occurs between some oligonucleotides and said target, said complexed oligonucleotides defining a first aptamer population;
 (c) recovering said first aptamers in substantially single stranded form from uncomplexed oligonucleotides;
 (d) attaching a known nucleotide sequence to at least one end of said first aptamers;
 (e) amplifying said first aptamers;
 (f) removing said known nucleotide sequence from said first aptamers;
 (g) optionally repeating steps (a)–(f) a sufficient number of times to generate an optimal aptamer population having high affinity for target.

Another aspect of the invention (Method AT) is directed to a method for obtaining an oligonucleotide capable of complexing to a desired target, said oligonucleotide being substantially non-predetermined sequence, said method comprising:

(a) incubating said target with a pool of oligonucleotides of non-predetermined or substantially non-predetermined sequence under conditions wherein some, but not all, oligonucleotides complex with said target;

(b) separating oligonucleotide:target complexes;

(c) recovering the oligonucleotides from step b in substantially single stranded form;

(d) attaching a first linker to the 5' end of said oligonucleotide and a second linker to the 3' end of said oligonucleotide, both said 5' and said 3' linkers of known nucleotide sequence, thereby generating an oligonucleotide having a 5' linker portion, an oligonucleotide portion and a 3' linker portion:

(e) amplifying the oligonucleotide of step d, thereby generating a duplex comprising a first strand having a 5' linker complement portion, an oligonucleotide complement portion and a 3' linker complement portion, and a second strand comprising a 5' linker portion, an oligonucleotide portion and a 3' linker portion;

(f) removing said 3' linker portion and said 5' linker portion;

(g) recovering said oligonucleotide in substantially single stranded form.

Another aspect of the invention (Method AU) is directed to the method of Method AT wherein said 5' linker has a restriction enzyme recognition site at or near the 3' end thereof and said 3' linker has a restriction enzyme recognition site at or near the 5' end thereof.

Another aspect of the invention (Method AV) is directed to the method of Method AU wherein said 3' linker portion is removed by attaching said duplex to solid support; digesting said attached duplex with a restriction enzyme capable of recognizing the restriction enzyme site at the 5' end thereof.

Another aspect of the invention (Method AW) is directed to a method for obtaining an aptamer containing at least one binding region that specifically binds a target which method comprises:

(a) incubating said target molecule with a mixture of oligonucleotides under conditions wherein complexation occurs with some, but not all, members of the mixture to form oligonucleotide-target complexes;

(b) separating the oligonucleotide-target complexes from uncompleted oligonucleotide;

(c) recovering and amplifying the completed oligonucleotide from said complexes; and (d) optionally determining the sequence of the recovered oligonucleotide, wherein said amplifying is conducted using at least one modified nucleotide, or wherein said mixture of oligonucleotides contains at least one modified oligonucleotide.

Another aspect of the invention (Method AX) is directed to a method to obtain an aptamer which specifically binds a first target and fails to bind a second substance, which method comprises:

incubating said first target with a mixture of member oligonucleotides under conditions wherein complexation occurs with some, but not all, members of said mixture;

separating complexed from uncompleted oligonucleotides;

recovering the complexed oligonucleotides to provide a first aptamer population;

incubating said second substance with said first aptamer population under conditions wherein complexation occurs with some, but not all, members of said mixture;

separating complexed from uncompleted oligonucleotides;

recovering the uncompleted oligonucleotides to provide a second aptamer population which specifically binds the first target; and recovering and amplifying the oligonucleotide(s) in said second aptamer population.

Another aspect of the invention (Method AY) is directed to a method to obtain an aptamer which specifically binds a first target and does not bind to a second substance, which method comprises:

contacting said second substance with a mixture of oligonucleotides under conditions wherein some but not all of the members of the mixture bind to the second substance;

separating away those members which do not bind to the second substance to obtain a first pool of oligonucleotides;

contacting the first pool with said first target;

separating away and isolating those oligonucleotides which bind to the first target to provide a second pool of aptamers;

recovering and amplifying the aptamers.

Another aspect of the invention (Aptamer BB) is directed to an aptamer prepared by the method of any of Method AF-AY.

Another aspect of the invention (Composition C) is directed to a complex formed by a target molecule and the aptamer of Aptamer N-AX, AY, AZ, BA, or BB.

Another aspect of the invention (Method AZ) is directed to method to detect the presence or absence of a target molecule, which method comprises contacting a sample suspected of containing said target molecule with the aptamer of Aptamer N-AX, AY, AZ, BA, or BB under conditions wherein a complex between said target molecule and the aptamer is formed, and detecting the presence or absence of said complex.

Another aspect of the invention (Method BA) is directed to a method to purify a target molecule, which method comprises contacting a sample containing said target molecule with the aptamer of Aptamer N-AX, AY, AZ, BA, or BB attached to solid support under conditions wherein said target molecule is bound to the aptamer coupled to solid support;

washing unbound components of the sample; and recovering the target molecule from said solid support.

Another aspect of the invention (Composition D) is directed to a pharmaceutical composition for medical use comprising the aptamer of Aptamer N-AX, AY, AZ, BA, or BB in admixture with a physiologically acceptable excipient.

Another aspect of the invention (Composition E) is directed to a composition for diagnostic use which comprises the aptamer of Aptamer N-AX, AY, AZ, BA, or BB.

Another aspect of the invention (Aptamer BC) is directed to the aptamer of Aptamer N-AX, AY, AZ, BA, or BB coupled to an auxiliary substance.

Another aspect of the invention (Aptamer BD) is directed to the aptamer of Aptamer BC wherein said auxiliary substance is selected from the group consisting of a drug, a toxin, a solid support, and specific binding reagent, a label, a radioisotope or a contrast agent.

Another aspect of the invention (Composition F) is directed to a conjugate for modulating immune response to a pathologic cell, comprising:

a targeting agent moiety that specifically binds to a surface feature of the pathologic cell; and an immunomodulatory moiety that induces an immunological response different from that elicited by the pathologic cell itself in the absence of the conjugate.

Another aspect of the invention (Composition G) is directed to a conjugate according to Composition F wherein said targeting agent is selected from the group consisting of oligonucleotides, antibodies and ligands for cell surface receptors.

Another aspect of the invention (Composition H) is directed to a conjugate according to Composition G wherein said targeting agent is the aptamer of Aptamer N-AX, AY, AZ, BA, or BB.

Another aspect of the invention (Composition I) is directed to a conjugate according to Composition F wherein the immunomodulatory moiety is selected from the group consisting of peptides and carbohydrates.

Another aspect of the invention (Method BB) is directed to a method for preparing a conjugate for modulating immune response to a pathologic cell, comprising:

identifying a targeting agent that specifically binds to a surface antigen of the pathologic cell; and associating said targeting agent with an immunomodulatory moiety that induces a desired immune response.

Another aspect of the invention (Method BC) is directed to method for modulating immune response to a pathologic cell, comprising:

administering an amount effective to modulate immune response of a conjugate in accordance with Composition F.

Another aspect of the invention (Method BD) is directed to an improved method to identify an oligonucleotide sequence which specifically binds a target substance, or a fragment of a target substance which method comprises incubating said target substance or said fragment with a mixture of randomized oligonucleotide sequences under conditions wherein complexation occurs with some, but not all, members of said mixture;

separating complexed from uncomplexed oligonucleotides;

recovering and amplifying the complexed nucleotides from said complexes; and optionally determining the sequence of the recovered oligonucleotides;

the improvement which comprises including in said mixture of randomized oligonucleotide sequences at least one modified nucleotide residue.

Another aspect of the invention (Method BE) is directed to the improvement of Method BD wherein said modification comprises substitution of at least one modified base for A, G, C, or T.

Another aspect of the invention (Method BF) is directed to the method according to Method BD wherein said target substance is a glycoprotein, a protein, a carbohydrate, a membrane structure, a receptor or an organelle.

Another aspect of the invention (Method BG) is directed to the method according to Method BD wherein said mixture of randomized oligonucleotide sequences is single-stranded DNA.

Another aspect of the invention (Composition J) is directed to a complex which comprises a target substance or a fragment of a target substance and at least one specifically-bound oligonucleotide, which complex is free of cellular components; and wherein said complex contains at least one modified nucleotide residue.

Another aspect of the invention (Composition K) is directed to the complex of Composition J wherein said at least one specifically-bound oligonucleotide is flanked by primer sequences adapted to permit application of PCR to said mixture.

Another aspect of the invention (Composition L) is directed to the complex of Composition J with the proviso that the target is other than an oligonucleotide.

Another aspect of the invention (Method BH) is directed to a method to identify an oligonucleotide sequence which specifically binds a target substance, or a fragment of a target substance which method comprises incubating said target substance or said fragment with a mixture of randomized oligonucleotide sequences under conditions wherein complexation occurs with some, but not all, members of said mixture;

separating complexed from uncomplexed oligonucleotides;

recovering and amplifying the complexed nucleotides from said complexes; and optionally determining the sequence of the recovered oligonucleotides;

wherein said mixture of randomized oligonucleotides includes oligonucleotides containing at least one modified nucleotide residue.

Another aspect of the invention (Method BI) is directed to the method according to Method BH wherein said target substance is a glycoprotein, a protein, a carbohydrate, a membrane structure, a receptor or an organelle.

Another aspect of the invention (Method BJ) is directed to the method of Method BI wherein said mixture of randomized oligonucleotide sequences is single-stranded DNA.

Another aspect of the invention (Composition M) is directed to a mixture of candidate aptamers comprising randomized nucleotide sequences, wherein said randomized sequences contain at least one modified nucleotide residue.

Another aspect of the invention (Composition N) is directed to the mixture of Composition M wherein said randomized sequences are flanked by primer sequences adapted to permit application of PCR to said mixture.

Another aspect of the invention (Composition O) is directed to the mixture of Composition M wherein said randomized sequences are single-stranded DNA.

Another aspect of the invention (Aptamer BE) is directed to an aptamer containing at least one binding region capable of binding specifically to a target molecule, wherein said aptamer is single stranded DNA and at least one modified oligonucleotide base.

Another aspect of the invention (Aptamer BF) is directed to an aptamer containing at least one binding region capable of binding specifically to a target molecule with a dissociation constant (Kd) of less than $10^{-9}$ and at least one modified oligonucleotide base.

Another aspect of the invention (Aptamer BG) is directed to an aptamer containing at least one binding region capable of binding specifically to a target molecule, wherein the Kd with respect to the aptamer and said target molecule is less by a factor of at least 10, as compared to the Kd for said aptamer and other unrelated molecules and at least one modified oligonucleotide base.

Another aspect of the invention (Aptamer BH) is directed to an aptamer containing at least one binding region capable of binding specifically to a target molecule wherein said binding region contains less than 14 nucleotide residues, and at least one modified oligonucleotide base.

Another aspect of the invention (Aptamer BI) is directed to the aptamer according to any one of Aptamer BE-BH wherein said modified base is alkylated by an alkyl, alkenyl, or alkynyl group containing from 1 to 6 carbon atoms.

Another aspect of the invention (Aptamer BJ) is directed to the aptamer according to Aptamer BI wherein the base is modified by alkylation of the 5-position of uridine, deoxyuridine, cytidine or deoxycytidine, the $N^4$-position of cytidine, or 2'-deoxycytidine, the $N^6$-position of adenosine or 2'-deoxyadenosine, or the 7-position of deazaguanosine, deaza-2'-deoxyguanosine, deazaadenosine or deaza-2'-deoxyadenosine.

Another aspect of the invention (Aptamer BK) is directed to the aptamer of Aptamer BJ wherein the modified base is 5-pentynyl deoxyuridine.

Another aspect of the invention (Aptamer BL) is directed to an aptamer according to any one of Aptamer BE-BH containing at least one binding region capable of binding specifically to a target molecule or to a fragment of a target molecule comprising:

bradykinin, PGF2, CD4, HER2, IL-1 receptor, Factor X, thrombin, PDGF, aFGF, ICAM-1, VCAM-1 or E-Selectin.

Another aspect of the invention (Aptamer BM) is directed to the aptamer of any one of Aptamer BE-BH wherein the target molecule exhibits one or more biological functions.

Another aspect of the invention (Aptamer BN) is directed to the aptamer of Aptamer BM wherein the target molecule does not exhibit the biological function of binding nucleic acids.

Another aspect of the invention (Aptamer BO) is directed to the aptamer of any one of Aptamer BE-BH wherein the target molecule is a protein or peptide.

Another aspect of the invention (Aptamer BP) is directed to the aptamer of Aptamer BO wherein the target molecule is an extracellular protein.

Another aspect of the invention (Aptamer BQ) is directed to the aptamer of Aptamer BP wherein the extracellular protein is selected from the group consisting of collagenase, tumor necrosis factor, antithrombin III, and interleukins.

Another aspect of the invention (Aptamer BR) is directed to the aptamer of Aptamer BQ wherein the target molecule is an intracellular protein.

Another aspect of the invention (Aptamer BS) is directed to the aptamer of Aptamer BR wherein the intracellular protein is selected from the group consisting of oncogene proteins, endotoxin and dihydrofolate reductase.

Another aspect of the invention (Aptamer BT) is directed to the aptamer of Aptamer BO wherein the target molecule is a cell surface protein.

Another aspect of the invention (Aptamer BU) is directed to the aptamer of Aptamer BT wherein the cell surface protein is selected from the group consisting of HLA antigens, tumor necrosis factor receptors, and EGF receptor.

Another aspect of the invention (Aptamer BV) is directed to the aptamer of Aptamer BO wherein the target molecule is a glycoprotein.

Another aspect of the invention (Aptamer BW) is directed to the aptamer of any one of Aptamer BE-BH wherein the target molecule is a carbohydrate.

Another aspect of the invention (Aptamer BX) is directed to the aptamer of Aptamer BW wherein the carbohydrate is a selected from the group consisting of monosaccharide, disaccharide, polysaccharide, or is a glucosaminoglycan or fragment thereof.

Another aspect of the invention (Aptamer BY) is directed to the aptamer of any one of Aptamer BE-BH wherein the target molecule is a lipid.

Another aspect of the invention (Aptamer BZ) is directed to the aptamer of Aptamer BY wherein the lipid is a glycolipid.

Another aspect of the invention (Aptamer CA) is directed to the aptamer of Aptamer BY wherein the lipid is a cholesterol, steroid, or triglyceride.

Another aspect of the invention (Aptamer CB) is directed to the aptamer of any one of Aptamer BE-BH wherein the target molecule is a small molecule selected from the group consisting of -bungarotoxin, botulinum toxin and diphtheria toxin.

Another aspect of the invention (Aptamer CC) is directed to the aptamer of any one of Aptamer BE-BH wherein the target molecule has a molecular weight from about 200 to about 1000 daltons.

Another aspect of the invention (Aptamer CD) is directed to the aptamer of any one of Aptamer BE-BH wherein the target molecule has a molecular weight from about $10^3$ to about $10^4$ daltons.

Another aspect of the invention (Aptamer CE) is directed to the aptamer of any one of Aptamer BE-BH wherein the target molecule has a molecular weight from about $10^4$ to about $10^6$ daltons.

Another aspect of the invention (Aptamer CF) is directed to the aptamer of any one of Aptamer BE-BH which contains a binding region of less than 14 nucleotide residues.

Another aspect of the invention (Aptamer CG) is directed to the aptamer of any one of Aptamer BE-BH which contains a binding region of less than 6 nucleotide residues.

Another aspect of the invention (Aptamer CH) is directed to the aptamer of any one of Aptamer BE-BH which contains 6-50 nucleotide residues.

Another aspect of the invention (Aptamer CI) is directed to the aptamer of any one of Aptamer BE-BH which contains 6-50 nucleotide residues.

Another aspect of the invention (Aptamer CJ) is directed to the aptamer of any one of Aptamer CJ wherein said aptamer is capable of binding specifically to a target molecule at physiological conditions.

Another aspect of the invention (Aptamer CK) is directed to the single-stranded DNA aptamer of Aptamer BE-BH wherein said aptamer binds to said target with a Kd of less than $10^{-9}$.

Another aspect of the invention (Aptamer CL) is directed to the aptamer of Aptamer CK wherein said aptamer binds to the target with a Kd of less than $10^{-9}$ at physiological conditions.

Another aspect of the invention (Aptamer CM) is directed to the aptamer of Aptamer BE-BH wherein the Kd with respect to the aptamer and said target molecule is less by a factor of at least 10, as compared to the Kd for said aptamer and other unrelated molecules.

Another aspect of the invention (Aptamer CN) is directed to the aptamer of Aptamer BE-BH wherein the aptamer further contains at least one modified linking group or sugar residue.

Another aspect of the invention (Aptamer CN) is directed to the aptamer of Aptamer CN wherein the aptamer contains at least one linking group wherein P(O)O is replaced by P(O)S, P(S)S, P(O)NR$_2$, P(O)R, P(O)OR', CO or CH$_2$, wherein each R or R' is independently H or substituted or unsubstituted alkyl (1–20C) optionally containing an ether (—O—) linkage, aryl, alkenyl, cycloalkyl, cycloalkenyl or aralkyl; or the aptamer contains at least one linking group attached to an adjacent nucleotide through S or N; or the aptamer contains at least one abasic site.

Another aspect of the invention (Aptamer CP) is directed to the aptamer of Aptamer CO which contains at least one linking group wherein P(O)o is replaced by P(O)S and said linking group is attached to each adjacent nucleotide through O; or which contains at least one linking group wherein P(O)O is replaced by P(O)NH(CH$_2$CH$_2$OCH$_3$) and said linking group is attached to each adjacent nucleotide through O; or contains at least one uracil (dU) base substituted for thymine; or contains at least one abasic site; or contains at least one modified or analogous sugar other than ribose.

Another aspect of the invention (Aptamer CQ) is directed to the aptamer of Aptamer BE-BH which is a secondary aptamer.

Another aspect of the invention (Method BK) is directed to a method for obtaining an aptamer containing at least one binding region that specifically binds a target, which method comprises:

(a) incubating said target with a mixture of member oligonucleotides under conditions wherein the target complexes with some, but not all, members of the mixture to form oligonucleotide-target complexes;

(b) separating the oligonucleotide-target complexes from uncomplexed oligonucleotides;

(c) recovering and amplifying the complexed oligonucleotides from said complexes to obtain an aptamer; and (d) optionally determining the sequence of the recovered aptamer, wherein said aptamer is a single-stranded DNA, or wherein said aptamer contains at least one binding region capable of binding specifically to a target molecule with a dissociation constant (Kd) of less than $10^{-9}$, or wherein said aptamer contains at least one binding region capable of binding specifically to a target molecule, wherein the Kd with respect to the aptamer and said target molecule is less by a factor of at least 10, as compared to the Kd for said aptamer and other molecules, or wherein said aptamer contains at least one binding region capable of binding specifically to a target molecule wherein said binding region contains less than 14 nucleotide residues, or wherein said aptamer contains at least one binding region capable of binding specifically to a target molecule wherein said aptamer contains less than 16 nucleotide residues, or wherein said aptamer contains at least one binding region capable of binding specifically to a target molecule selected from the group consisting of exemplified targets, and wherein said aptamer comprises at least one modified oligonucleotide base.

Another aspect of the invention (Method BL) is directed to the method of Method BK wherein said mixture of oligonucleotides contains at least one modified oligonucleotide.

Another aspect of the invention (Method BM) is directed to the method of Method BK wherein said amplifying is conducted using at least one modified nucleotide.

Another aspect of the invention (Method BN) is directed to the method of Method BK-BM wherein said mixture of oligonucleotides contains at least one randomized-sequence region.

Another aspect of the invention (Method BO) is directed to the method of Method BK-BN which further includes repeating steps (a)–(c) using the recovered and amplified complexed oligonucleotides resulting from step (c) in succeeding step (a).

Another aspect of the invention (Method BP) is directed to the method of Method BK-BO wherein the Kd with respect to the oligonucleotide mixture and target is at least 50-fold more than the Kd with respect to the aptamer and target.

Another aspect of the invention (Aptamer CR) is directed to an aptamer prepared by the method of Method BK-BP.

Another aspect of the invention (Method BQ) is directed to a method to obtain a secondary aptamer that specifically binds to a target molecule which method comprises:

(a) incubating said target molecule with a mixture of oligonucleotide sequences under conditions wherein complexation occurs with some, but not all, members of the mixture to form oligonucleotide-target complexes;

(b) separating the oligonucleotide-target complexes from uncomplexed oligonucleotides;

(c) recovering and amplifying the complexed oligonucleotides from said complexes;

(d) optionally repeating steps (a)–(c) with the recovered oligonucleotides of step (c);

(e) determining the sequences of the recovered oligonucleotides;

(f) determining a consensus sequence included in the recovered oligonucleotides; and (g) synthesizing a secondary aptamer which comprises the consensus sequence;

wherein said mixture of oligonucleotides contains at least one modified oligonucleotide base.

Another aspect of the invention (Aptamer CS) is directed to a secondary aptamer prepared by the method of Method BQ.

Another aspect of the invention (Method BR) is directed to a method for obtaining an aptamer containing at least one binding region that specifically binds a target, which method comprises:

(a) incubating said target with a mixture of member oligonucleotides under conditions wherein the target complexes with some, but not all, members of the mixture to form oligonucleotide-target complexes;

(b) separating the oligonucleotide-target complexes from uncomplexed oligonucleotides;

(c) recovering and amplifying the complexed oligonucleotides from said complexes to obtain an aptamer; and (d) optionally determining the sequence of the recovered aptamer, wherein the dissociation constant (Kd) with respect to said target and mixture of oligonucleotides is 1M, or wherein the Kd with respect to the aptamer and said target is less by a factor of at least 50 as compared to the Kd for said target and said mixture of oligonucleotides; or wherein steps (a) and (b) are conducted under physiological conditions, or wherein said mixture of oligonucleotides consists of single-stranded DNA, and wherein said mixture of oligonucleotides contains at least one modified oligonucleotide base.

Another aspect of the invention (Method BS) is directed to the method of Method BR wherein said amplifying is conducted using at least one modified nucleotide.

Another aspect of the invention (Method BT) is directed to the method of Method BR-BS wherein said mixture of oligonucleotides contains at least one randomized-sequence region.

Another aspect of the invention (Method BU) is directed to the method of Method BR-BT which further includes repeating steps (a)–(c) using the recovered and amplified complexed oligonucleotides resulting from step (c) in succeeding step (a).

Another aspect of the invention (Method BR) is directed to the method of Method BR wherein said mixture of oligonucleotides is of unpredetermined sequence.

Another aspect of the invention (Aptamer CT) is directed to an aptamer prepared by the method of Method BR-BV.

Another aspect of the invention (Method BW) is directed to a method to obtain an aptamer containing a binding region which specifically binds a target molecule which method comprises:

(a) incubating the target molecule reversibly coupled to a support with a mixture of oligonucleotide sequences under conditions wherein the coupled target molecule complexes with some, but not all, members of the mixture to form support-bound oligonucleotide complexes;

(b) decoupling and recovering the oligonucleotide target complex from the support to obtain free aptamer-target complexes;

(c) recovering and amplifying the complexed oligonucleotides from the free oligonucleotide-target complexes to obtain a population of aptamers;

(d) optionally repeating steps (a)–(c) using as said mixture the recovered population of aptamers of step (c); and (e) optionally determining the sequence of the recovered aptamers.

wherein said mixture of oligonucleotides contains at least one modified oligonucleotide base.

Another aspect of the invention (Method BX) is directed to the method of Method BW wherein in step (a) the target substance is reversibly coupled to the support using an activated thiol group on the support.

Another aspect of the invention (Method BY) is directed to the method of Method BW wherein in step (b), decoupling is accomplished by adding a reducing agent.

Another aspect of the invention (Method BZ) is directed to the method of Method BY wherein the reducing agent is dithiothreitol or -mercaptoethanol.

Another aspect of the invention (Method CA) is directed to the method of Method BW wherein the support is a lectin support and the target substance binds reversibly to lectin.

Another aspect of the invention (Method CB) is directed to the method of Method CA wherein in step (b), decoupling is accomplished by adding a monosaccharide.

Another aspect of the invention (Method CC) is directed to the method of Method CB wherein the monosaccharide is -methyl-mannoside.

Another aspect of the invention (CD) is directed to a method for obtaining aptamers capable of binding a target, said method comprising:

(a) providing a first pool of oligonucleotides of unpredetermined sequence, said pool comprising a quantity of oligonucleotides sufficiently reflective of the structural complexity of said target as to ensure the presence of at least one oligonucleotide capable of binding said target;

(b) incubating said pool of oligonucleotides, or a portion thereof with said target under conditions wherein complexation occurs between some oligonucleotides and said target, said complexed oligonucleotides defining a first aptamer population;

(c) recovering said first aptamers in substantially single stranded form from uncompleted oligonucleotides;

(d) attaching a known nucleotide sequence to at least one end of said first aptamers;

(e) amplifying said first aptamers;

(f) removing said known nucleotide sequence from said first aptamers;

(g) optionally repeating steps (a)–(f) a sufficient number of times to generate an optimal aptamer population having high affinity for target.

wherein said pool of oligonucleotides comprises at least one modified base.

Another aspect of the invention (CE) is directed to a method for obtaining an oligonucleotide capable of complexing to a target, said oligonucleotide being substantially non-predetermined sequence, said method comprising:

(a) incubating said target with a pool of oligonucleotides of non-predetermined or substantially non-predetermined sequence under conditions wherein some, but not all, oligonucleotides complex with said target;

(b) separating oligonucleotide:target complexes;

(c) recovering the oligonucleotides from step b in substantially single stranded form;

(d) attaching a first linker to the 5' end of said oligonucleotide and a second linker to the 3' end of said oligonucleotide, both said 5' and said 3' linkers of known nucleotide sequence, thereby generating an oligonucleotide having a 5' linker portion, an oligonucleotide portion and a 3' linker portion;

(e) amplifying the oligonucleotide of step d, thereby generating a duplex comprising a first strand having a 5' linker complement portion, an oligonucleotide complement portion and a 3' linker complement portion, and a second strand comprising a 5' linker portion, an oligonucleotide portion and a 3' linker portion;

(f) removing said 3' linker portion and said 5' linker portion;

(g) recovering said oligonucleotide in substantially single stranded form.

wherein said pool of oligonucleotides comprises at least one modified base.

Another aspect of the invention (Method CF) is directed to the method of Method CE wherein said 5' linker has a restriction enzyme recognition site at or near the 3' end thereof and said 3' linker has a restriction enzyme recognition site at or near the 5' end thereof.

Another aspect of the invention (Method CG) is directed to the method of Method CE wherein said 3' linker portion is removed by attaching said duplex to solid support; digesting said attached duplex with a restriction enzyme capable of recognizing the restriction enzyme site at the 5' end thereof.

Another aspect of the invention (Method CH) is directed to a method for obtaining an aptamer containing at least one binding region that specifically binds a target which method comprises:

(a) incubating said target molecule with a mixture of oligonucleotides under conditions wherein complexation occurs with some, but not all, members of the mixture to form oligonucleotide-target complexes;

(b) separating the oligonucleotide-target complexes from uncomplexed oligonucleotide;

(c) recovering and amplifying the complexed oligonucleotide from said complexes; and (d) optionally determining the sequence of the recovered oligonucleotide.

wherein said amplifying is conducted using at least one modified nucleotide, or wherein said mixture of oligonucleotides contains at least one modified oligonucleotide.

Another aspect of the invention (CI) is directed to a method to obtain an aptamer which specifically binds a first target and fails to bind a second substance, which method comprises:

incubating said first target with a mixture of member oligonucleotides under conditions wherein complexation occurs with some, but not all, members of said mixture;

separating complexed from uncomplexed oligonucleotides;

recovering the complexed oligonucleotides to provide a first aptamer population;

incubating said second substance with said first aptamer population under conditions wherein complexation occurs with some, but not all, members of said mixture;

separating complexed from uncompleted oligonucleotides;

recovering the uncomplexed oligonucleotides to provide a second aptamer population which specifically binds the first target; and recovering and amplifying the oligonucleotide(s) from said second aptamer population, wherein said mixture of oligonucleotides comprises at least one modified base.

Another aspect of the invention (Method CJ) is directed to a method to obtain an aptamer which specifically binds a first target and does not bind to a second substance, which method comprises:

contacting said second substance with a mixture of oligonucleotides under conditions wherein some but not all of the members of the mixture bind to the second substance;

separating away those members which do not bind to the second substance to obtain a first pool of oligonucleotides;

contacting the first pool with said first target;

separating away and isolating those oligonucleotides which bind to the first target to provide a second pool of aptamers;

recovering and amplifying the aptamers, wherein said mixture of oligonucleotides comprises at least one modified base.

Another aspect of the invention (Aptamer CU) is directed to an aptamer prepared by the method of any of Method BR-BV or BW-CJ.

Another aspect of the invention (Composition P) is directed to a complex formed by a target molecule and the aptamer of Aptamer BE-BH, CR, CS, CT, or CU.

Another aspect of the invention (Method CK) is directed to a method to detect the presence or absence of a target molecule, which method comprises contacting a sample suspected of containing said target molecule with the aptamer of Aptamer BE-BH, CR, CS, CT, or CU under conditions wherein a complex between said target molecule and the aptamer is formed, and detecting the presence or absence of said complex.

Another aspect of the invention (Method CL) is directed to a method to purify a target molecule, which method comprises contacting a sample containing said target molecule with the aptamer of Aptamer BE-BH, CR, CS, CT, or CU attached to solid support under conditions wherein said target molecule is bound to the aptamer coupled to solid support;

washing unbound components of the sample; and recovering the target molecule from said solid support.

Another aspect of the invention (Composition Q) is directed to a pharmaceutical composition for medical use comprising the aptamer of Aptamer BE-BH, CR, CS, CT, or CU in admixture with a physiologically acceptable excipient.

Another aspect of the invention (Composition R) is directed to a composition for diagnostic use which comprises the aptamer of Aptamer BE-BH, CR, CS, CT, or CU.

Another aspect of the invention (Composition S) is directed to the aptamer of Aptamer BE-BH, CR, CS, CT, or CU coupled to an auxiliary substance.

Another aspect of the invention (Composition T) is directed to the aptamer of Composition S wherein said auxiliary substance is selected from the group consisting of a drug, a toxin, a solid support, and specific binding reagent, a label, a radioisotope or a contrast agent.

Another aspect of the invention (Method CM) is directed to a method to identify an oligonucleotide sequence which specifically binds a target substance, which method comprises incubating said target substance with a mixture of randomized oligonucleotide sequences under conditions wherein complexation occurs with some, but not all, members of said mixture;

separating complexed from uncomplexed oligonucleotides;

recovering and amplifying the complexed nucleotides from said complexes; and optionally determining the sequence of the recovered oligonucleotides;

the improvement which comprises including in said mixture of randomized oligonucleotide sequences at least one modified nucleotide residue.

Another aspect of the invention (Method CN) is directed to the improvement of Method CM wherein said modification comprises substitution of at least one modified base for A, G, C, or T.

Another aspect of the invention (Composition U) is directed to a complex which comprises a target substance and at least one specifically-bound oligonucleotide, which complex is free of cellular components; and wherein said complex contains at least one modified nucleotide residue.

Another aspect of the invention (Method CO) is directed to a method to identify an oligonucleotide sequence which specifically binds a target substance, which method comprises incubating said target substance with a mixture of randomized oligonucleotide sequences under conditions wherein complexation occurs with some, but not all, members of said mixture;

separating complexed from uncompleted oligonucleotides;

recovering and amplifying the complexed nucleotides from said complexes; and optionally determining the sequence of the recovered oligonucleotides;

wherein said mixture of randomized oligonucleotides includes oligonucleotides containing at least one modified nucleotide residue.

Another aspect of the invention (Composition V) is directed to a mixture of candidate aptamers comprising randomized nucleotide sequences, wherein said randomized sequences contain at least one modified nucleotide residue.

Another aspect of the invention (Composition W) is directed to the mixture of Composition V wherein said randomized sequences are flanked by primer sequences adapted to permit application of PCR to said mixture.

Another aspect of the invention (Method CP) is directed to a method to identify an aptamer which specifically binds a kinin, which method comprises:
 incubating said kinin with a mixture of randomized oligonucleotide sequences under conditions wherein complexation occurs with some, but not all, members of said mixture;
 separating complexed oligonucleotides from uncomplexed oligonucleotides;
 recovering and amplifying the complexed oligonucleotide(s) from said complexes; and
 optionally determining the sequence of the recovered oligonucleotide(s).

Another aspect of the invention (Method CQ) is directed to the method of Method CP wherein said kinin is bradykinin.

Another aspect of the invention (Method CR) is directed to the method of Method CP wherein the oligonucleotide mixture is single-stranded DNA.

Another aspect of the invention (Method CS) is directed to the method of Method CP wherein said recovering and amplifying is conducted using the polymerase chain reaction (PCR).

Another aspect of the invention (Composition X) is directed to a mixture of oligonucleotide segments useful as a starting material in the recovery of an aptamer that specifically binds to a target kinin, which mixture comprises a randomized set of nucleotide sequences wherein each member of the set of said segments contains a random DNA sequence flanked with known primer sequences for use in the polymerase chain reaction (PCR).

Another aspect of the invention (Aptamer CV) is directed to an oligonucleotide comprising a sequence specific for a kinin, in purified and isolated form obtained by the process of Method CP.

Another aspect of the invention (Aptamer CW) is directed to the oligonucleotide of Aptamer CV wherein the target substance is a bradykinin.

Another aspect of the invention (Method CT) is directed to a method for recovering a target kinin from a sample, which method comprises:
 contacting said sample with an oligonucleotide containing a sequence specifically binding for said kinin under conditions wherein said kinin and said oligonucleotide form a complex;
 separating said complex from other materials in the sample; and
 recovering said kinin from the complex.

Another aspect of the invention (Method CU) is directed to a method to determine the presence or absence of a kinin in a sample, which method comprises:
 treating said sample with an oligonucleotide containing a sequence which specifically binds said kinin under conditions wherein a complex between said oligonucleotide and kinin is formed when analyte is present; and
 detecting the presence or absence of the complex.

Another aspect of the invention (Method CV) is directed to the method of Method CU wherein said kinin is bradykinin.

Another aspect of the invention (CW) is directed to a method to recover a target kinin from a sample, which method comprises:
 contacting said sample with a solid support having bound to it an oligonucleotide containing a sequence capable of specifically binding said kinin under conditions wherein said target kinin binds to said oligonucleotide;
 separating the solid support from the sample; and
 recovering the target kinin from the solid support.

Another aspect of the invention (Method CX) is directed to the method of Method CW wherein said target kinin is bradykinin.

Another aspect of the invention (Composition Y) is directed to a complex which comprises a kinin target substance and its specifically bound oligonucleotide, which complex is free of cellular components.

Another aspect of the invention (Composition Z) is directed to the complex of Composition Y wherein said target substance is bradykinin.

Another aspect of the invention (Method CY) is directed to a method to identify an aptamer which specifically binds a hydrophobic target substance, which method comprises:
 incubating said hydrophobic target substance with a mixture of randomized oligonucleotide sequences under conditions wherein complexation occurs with some, but not all, members of said mixture;
 separating complexed oligonucleotides from uncomplexed oligonucleotides;
 recovering and amplifying the complexed oligonucleotide(s) from said complexes; and
 optionally determining the sequence of the recovered oligonucleotide(s).

Another aspect of the invention (Method CZ) is directed to the method of Method CY wherein said hydrophobic target substance is an eicosanoid.

Another aspect of the invention (Method DA) is directed to the method of Method CZ wherein said eicosanoid is selected from the group consisting of prostaglandins, thromboxanes, leukotrienes and prostacyclin.

Another aspect of the invention (Method DB) is directed to the method of Method DA wherein said eicosanoid is PGF2.

Another aspect of the invention (Method DC) is directed to the method of Method CY wherein the oligonucleotide mixture is single-stranded DNA.

Another aspect of the invention (Method DE) is directed to the method of Method CY wherein said recovering and amplifying is conducted using the Polymerase chain reaction (PCR).

Another aspect of the invention (Composition AA) is directed to a mixture of oligonucleotide segments useful as a starting material in the recovery of an aptamer that specifically binds to a target hydrophobic substance, which mixture comprises a randomized set of nucleotide sequences wherein each member of the set of said segments contains a random DNA sequence flanked with known primer sequences for use in the polymerase chain reaction (PCR).

Another aspect of the invention (Aptamer CX) is directed to an oligonucleotide comprising a sequence specific for a hydrophobic target substance, in purified and isolated form obtained by the process of Method CY.

Another aspect of the invention (Aptamer CY) is directed to the oligonucleotide of Aptamer CX wherein the target substance is an eicosanoid.

Another aspect of the invention (Aptamer CZ) is directed to the oligonucleotide of Aptamer CY wherein said eicosanoid is selected from the group consisting of prostaglandins, thromboxanes, leukotrienes and prostacyclin.

Another aspect of the invention (Aptamer DA) is directed to the oligonucleotide of Aptamer CZ wherein said eicosanoid is PGF2.

Another aspect of the invention (Method DF) is directed to a method for recovering a target hydrophobic substance from a sample, which method comprises:

contacting said sample with an oligonucleotide containing a sequence specifically binding for said substance under conditions wherein said substance and said oligonucleotide form a complex;

separating said complex from other materials in the sample; and recovering said substance from the complex.

Another aspect of the invention (Method DG) is directed to a method to determine the presence or absence of a hydrophobic analyte in a sample, which method comprises:

treating said sample with an oligonucleotide containing a sequence which specifically binds said hydrophobic analyte under conditions wherein a complex between said oligonucleotide and analyte is formed when analyte is present; and detecting the presence or absence of the complex.

Another aspect of the invention (Method DH) is directed to the method of Method DG wherein said hydrophobic analyte is an eicosanoid.

Another aspect of the invention (Method DI) is directed to the method of Method DH wherein said eicosanoid is selected from the group consisting of prostaglandins, thromboxanes, leukotrienes and prostacyclin.

Another aspect of the invention (Method DJ) is directed to the method of Method DI wherein said eicosanoid is PGF2.

Another aspect of the invention (Method DK) is directed to a method to recover a target hydrophobic substance from a sample, which method comprises:

contacting said sample with a solid support having bound to it an oligonucleotide containing a sequence capable of specifically binding said substance under conditions wherein said target substance binds to said oligonucleotide;

separating the solid support from the sample; and recovering the target substance from the solid support.

Another aspect of the invention (Method DL) is directed to the method of Method DK wherein said target hydrophobic substance is an eicosanoid.

Another aspect of the invention (DM) is directed to the method of Method DL wherein said eicosanoid is selected from the group consisting of prostaglandins, thromboxanes, leukotrienes and prostacyclin.

Another aspect of the invention (Method DN) is directed to the method of Method DM wherein said eicosanoid is PGF2.

Another aspect of the invention (Composition AB) is directed to a complex which comprises a hydrophobic target substance and its specifically bound oligonucleotide, which complex is free of cellular components.

Another aspect of the invention (Composition AC) is directed to the complex of Composition AB wherein said hydrophobic target substance is an eicosanoid.

Another aspect of the invention (Composition AD) is directed to the complex of Composition AC wherein said eicosanoid is selected from the group consisting of prostaglandins, thromboxanes, leukotrienes and prostacyclin.

Another aspect of the invention (Composition AE) is directed to the complex of Composition AD wherein said eicosanoid is PGF2.

Another aspect of the invention (Method DO) is directed to a process for identifying single stranded aptamers capable of binding a target, said process comprising:

a. Generating at least one pool of oligonucleotides of random sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said complexed oligonucleotides defining an aptamer population;

c. recovering said aptamers in substantially single stranded form from uncomplexed oligonucleotides;

d. attaching a known nucleotide sequence to at least one end of said aptamers;

e. amplifying said aptamers;

f. removing said known nucleotide sequence from said aptamers.

Another aspect of the invention (Method DP) is directed to a process for identifying single stranded aptamers capable of binding a target, said process comprising:

a. generating a first pool of oligonucleotides of random sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said completed oligonucleotides defining a first aptamer population;

c. recovering said first aptamers in substantially single stranded form from uncompleted oligonucleotides;

d. attaching a known nucleotide sequence to at least one end of said first aptamers;

e. amplifying said first aptamers;

f. removing said known nucleotide sequence from said first aptamers;

g. repeating steps a–f a sufficient number of times to generate an optimal aptamer population having high affinity for target.

Another aspect of the invention (Method DQ) is directed to a process for identifying single stranded aptamers capable of binding a target, said process comprising:

a. generating a first pool of oligonucleotides of random sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said completed oligonucleotides defining a first aptamer population;

c. recovering said first aptamers in substantially single stranded form from uncomplexed oligonucleotides;

d. attaching a known nucleotide sequence to at least one end of said first aptamers;

e. amplifying said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–f using said second aptamers of step g, or a portion thereof, a sufficient number of times so as to identify an optimal aptamer population from which at least one consensus region may identified in at least two of the aptamers from said optimal aptamer population, the presence of which may be correlated with aptamer to target binding or to aptamer structure.

Another aspect of the invention (Method DR) is directed to a process for identifying single stranded aptamers capable of binding a target, said process comprising:

a. generating a first pool of oligonucleotides of random sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said completed oligonucleotides defining a first aptamer population;

c. recovering said first aptamers in substantially single stranded form from uncompleted oligonucleotides;

d. attaching a known nucleotide sequence to at least one end of said first aptamers;

e. amplifying said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–g at least 5 times, defining an optimal aptamer population.

Another aspect of the invention (Method DS) is directed to a process for identifying single stranded aptamers capable of binding a target, said process comprising:

a. generating a first pool of oligonucleotides of random sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said complexed oligonucleotides defining a first aptamer population;

c. recovering said first aptamers in substantially single stranded form from uncompleted oligonucleotides;

d. attaching a known nucleotide sequence to at least one end of said first aptamers;

e. amplifying said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–f using said second aptamers of step g, or a portion thereof, a sufficient number of times so that the diversity of said oligonucleotide pool is reduced to an optimal aptamer population, wherein at least about 50% of said aptamers of said optimal aptamer population are capable of complexing to target in step b, when the target:aptamer molar ratio is at least about 1000:1.

Another aspect of the invention (Method DT) is directed to a process for identifying single stranded aptamers capable of binding a target, said process comprising:

a. generating a first pool of oligonucleotides of random sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said completed oligonucleotides defining a first aptamer population;

c. recovering said first aptamers in substantially single stranded form from uncomplexed oligonucleotides;

d. attaching a known nucleotide sequence to at least one end of said first aptamers;

e. amplifying said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–f using said second aptamers of step g, or a portion thereof, a sufficient number of times so that the diversity of said oligonucleotide pool is reduced to an optimal aptamer population comprising aptamers which are capable of being eluted from immobilized target by target free in solution.

Another aspect of the invention (Method DU) is directed to a process for identifying single stranded aptamers capable of binding a target, said process comprising:

a. generating a first pool of oligonucleotides of random sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said complexed oligonucleotides defining a first aptamer population;

c. recovering said first aptamers in substantially single stranded form from uncompleted oligonucleotides;

d. attaching a known nucleotide sequence to at least one end of said first aptamers;

e. amplifying said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–f using said second aptamers of step g, or a portion thereof, a sufficient number of times so that the diversity of said oligonucleotide pool is reduced at least about five hundred thousand (500,000) fold to an optimal aptamer population.

Another aspect of the invention (Method DV) is directed to a process of any one of Method DO-DU wherein said known nucleotide sequence is 1–10 nucleotides in length.

Another aspect of the invention (Method DW) is directed to a process of any one of Method DO-DU wherein the oligonucleotides comprising said pool as first generated in step a is comprised of nucleotides randomly selected from the group consisting of guanine, arginine, thymine, cytostine, isocytostine and isoguanine.

Another aspect of the invention (Method DX) is directed to a process of any one of Method DO-DU wherein said oligonucleotides comprising said pool are modified to contain a cross-linking residue.

Another aspect of the invention (Method DY) is directed to a process of any one of Method DO-DU wherein the oligonucleotides comprising said oligonucleotide pool are between 15–100 nucleotides in length.

Another aspect of the invention (Method DZ) is directed to a process of any one of Method DO-DU wherein the oligonucleotides comprising said oligonucleotide pool are between 30–80 nucleotides in length.

Another aspect of the invention (Method EA) is directed to a process of any one of Method DO-DU wherein the oligonucleotides comprising said oligonucleotide pool are a mixture of at least 20-mers, 40-mers, 60-mers and 80-mers.

Another aspect of the invention (Method EB) is directed to a process of any one of Method DO-DU wherein the oligonucleotides comprising said pool are single stranded DNA.

Another aspect of the invention (Aptamer DB) is directed to an oligonucleotide capable of binding a target, such capability and the sequence responsible therefor, having first been determined by the process of any one of Method DO-DU.

Another aspect of the invention (Method EC) is directed to a process for identifying single stranded aptamers capable of binding a target, said process comprising:

a. generating at least one pool of oligonucleotides of non-predetermined or substantially non-predetermined sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said complexed oligonucleotides defining an aptamer population;

c. recovering said aptamers in substantially single stranded form from uncomplexed oligonucleotides;

d. attaching a known nucleotide sequence to at least one end of said aptamers;

e. amplifying said aptamers;

f. removing said known nucleotide sequence from said aptamers.

Another aspect of the invention (Method ED) is directed to a process for identifying single stranded aptamers capable of binding a target, said process comprising:

a. generating a first pool of oligonucleotides of nonpredetermined or substantially non-predetermined sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said complexed oligonucleotides defining a first aptamer population;

c. recovering said first aptamers in substantially single stranded form from uncomplexed oligonucleotides;

d. attaching a known nucleotide sequence to at least one end of said first aptamers;

e. amplifying said first aptamers;

f. removing said known nucleotide sequence from said first aptamers;

g. repeating steps a–f at least once using said first aptamers of step f, or a portion thereof, to comprise a second pool of oligonucleotides for use in step a, thereby generating a second aptamer population which may be used to reseat steps a–f.

Another aspect of the invention (Method EE) is directed to a process for identifying single stranded aptamers capable of binding a target, said process comprising:

a. generating a first pool of oligonucleotides of nonpredetermined or substantially non-predetermined sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said complexed oligonucleotides defining a first aptamer population;

c. recovering said first aptamers in substantially single stranded form from uncompleted oligonucleotides;

d. attaching a known nucleotide sequence to at least one end of said first aptamers;

e. said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–f using said second aptamers of step g, or a portion thereof, a sufficient number of times so as to identify an optimal aptamer population from which at least one consensus region may identified in at least two of the aptamers from said optimal aptamer population, the presence of which may be correlated with aptamer to target binding or to aptamer structure.

Another aspect of the invention (Method EF) is directed to a process for identifying single stranded aptamers capable of binding a target, said process comprising:

a. generating a first pool of oligonucleotides of nonpredetermined or substantially non-predetermined sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said complexed oligonucleotides defining a first aptamer population;

c. recovering said first aptamers in substantially single stranded form from uncompleted oligonucleotides;

d. attaching a known nucleotide sequence to at least one end of said first aptamers;

e. amplifying said first aptamers;

f. said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–g at least 5 times, defining an optimal aptamer population.

Another aspect of the invention (Method EG) is directed to a process for identifying single stranded aptamers capable of binding a target, said process comprising:

a. generating a first pool of oligonucleotides of nonpredetermined or substantially non-predetermined sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said completed oligonucleotides defining a first aptamer population;

c. recovering said first aptamers in substantially single stranded form from uncompleted oligonucleotides;

d. attaching a known nucleotide sequence to at least one end of said first aptamers;

e. amplifying said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–f using said second aptamers of step g, or a portion thereof, a sufficient number of times so that the diversity of said oligonucleotide pool is reduced to an optimal aptamer population, wherein at least about 50% of said aptamers of said optimal aptamer population are capable of complexing to target in step b, when the target:aptamer molar ratio is at least about 1000:1.

Another aspect of the invention (Method EH) is directed to a process for identifying single stranded aptamers capable of binding a target, said process comprising:

a. generating a first pool of oligonucleotides of nonpredetermined or substantially non-predetermined sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said completed oligonucleotides defining a first aptamer population;

c. recovering said first aptamers in substantially single stranded form from uncompleted oligonucleotides;

d. attaching a known nucleotide sequence to at least one end of said first aptamers;

e. amplifying said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–f using said second aptamers of step g, or a portion thereof, a sufficient number of times so that the diversity of said oligonucleotide pool is reduced to an optimal aptamer population comprising aptamers which are capable of being eluted from immobilized target by target free in solution.

Another aspect of the invention (Method EI) is directed to a process for identifying single stranded aptamers capable of binding a target, said process comprising:

a. generating a first pool of oligonucleotides of nonpredetermined or substantially non-predetermined sequence averaging about 10–400 nucleotides in length, said pool comprising a quantity of oligonucleotides sufficiently reflective of the structural complexity of said target as to ensure the presence of at least one oligonucleotide capable of binding said target;

b. incubating said pool of oligonucleotides, or a portion thereof with said target under conditions wherein complexation occurs between some oligonucleotides and said target, said complexed oligonucleotides defining a first aptamer population;

c. recovering said first aptamers in substantially single stranded form from uncomplexed oligonucleotides;

d. attaching a known nucleotide sequence to at least one end of said first aptamers;

e. amplifying said first aptamers;

f. removing said known nucleotide sequence from said first aptamers;

g. repeating steps a–f using said first aptamers of step f, or a portion thereof, to comprise a second pool of oligonucleotides for use in step a, thereby generating a second aptamer population which may be used to repeat steps a–f.

h. repeating steps a–f using said second aptamers of step g, or a portion thereof, a sufficient number of times so that the diversity of said oligonucleotide pool is reduced at least about five hundred thousand (500,000) fold to an optimal aptamer population.

Another aspect of the invention (Method EJ) is directed to a process of any one of Method EC-EI wherein said known nucleotide sequence is 1–10 nucleotides in length.

Another aspect of the invention (Method EK) is directed to a process of any one of Method EC-EI wherein the oligonucleotides comprising said pool as first generated in step a is comprised of nucleotides randomly selected from the group consisting of guanine, arginine, thymine, cytostine, isocytostine and isoguanine.

Another aspect of the invention (Method EL) is directed to a process of any one of Method EC-EI wherein said oligonucleotides comprising said pool are modified to contain a cross-linking residue.

Another aspect of the invention (Method EM) is directed to a process of any one of Method EC-EI wherein the oligonucleotides comprising said oligonucleotide pool are between 15–100 nucleotides in length.

Another aspect of the invention (Method EN) is directed to a process of any one of Method EC-EI wherein the oligonucleotides comprising said oligonucleotide pool are between 30–80 nucleotides in length.

Another aspect of the invention (Method EO) is directed to a process of any one of Method EC-EI wherein the oligonucleotides comprising said oligonucleotide pool are a mixture of at least 20-mers, 40-mers, 60-mers and 80-mers.

Another aspect of the invention (Method EP) is directed to a process of any one of Method EC-EI wherein the oligonucleotides comprising said pool are single stranded DNA.

Another aspect of the invention (Aptamer DC) is directed to an oligonucleotide capable of binding a target, such capability and the sequence responsible therefor, having first been determined by the process of any one of Method EC-EI.

Another aspect of the invention (Method EQ) is directed to a process for identifying and amplifying an oligonucleotide of non-predetermined or substantially non-predetermined sequence, said oligonucleotide being capable of complexing to a desired target, said method comprising:

a. incubate said target with a pool of oligonucleotides of non-predetermined or substantially non-predetermined sequence under conditions wherein some, but not all, oligonucleotides complex with said target;

b. separate oligonucleotide:target complexes;

c. recover oligonucleotides from step b in substantially single stranded form;

d. attach a first linker to the 5' end of said oligonucleotide and a second linker to the 3' end of said oligonucleotide, both said 5' and said 3' linkers of known nucleotide sequence, said 5' linker having a first type II restriction enzyme recognition site at or near the 3' end thereof and said 3' linker having a second type II restriction enzyme recognition site at or near the 5' end thereof, thereby generating an oligonucleotide having a 5' linker portion, an oligonucleotide portion and a 3' linker portion;

e. amplify the oligonucleotide of step d, thereby generating a duplex comprising a first strand having a 5' linker complement portion, an oligonucleotide complement portion and a 3' linker complement portion, and a second strand comprising a 5' linker portion, an oligonucleotide portion and a 3' linker portion;

f. remove said 3' linker portion and said 5' linker portion;

g. recover said oligonucleotide in substantially single stranded form.

Another aspect of the invention (Method ER) is directed to a method for identifying and amplifying an oligonucleotide of non-predetermined or substantially non-predetermined sequence, said oligonucleotide being capable of complexing to a desired target, said method comprising:

a. incubate said target with a pool of oligonucleotides of non-predetermined or substantially non-predetermined sequence under conditions wherein some, but not all, oligonucleotides form oligonucleotide:target complexes with said target;

b. separate oligonucleotide:target complexes from uncomplexed oligonucleotide;

c. recover complexed oligonucleotides from step b in substantially single stranded form;

d. attach a first DNA linker to the 5' end of said oligonucleotide and a second linker to the 3' end of said oligonucleotide, both said 5' and said 3' linkers of known nucleotide sequence, said 5' linker having a first type II restriction enzyme recognition site at or near the 3' end thereof and having at least 4 nucleotides covalently attached to the 5' end of said 5' linker, and said 3' linker having a second type II restriction enzyme recognition site at or near the 5' end thereof and said 3' linker comprising at least four nucleotides capable of hybridizing to the 3' end of said oligonucleotide, thereby generating an oligonucleotide having a 5' linker portion, an oligonucleotide portion and a 3' linker portion;

e. amplify the oligonucleotide of step d, thereby generating a duplex comprising a first strand having a 5' linker complement portion, an oligonucleotide complement portion and a 3' linker complement portion, and a second strand comprising a 5' linker portion, an oligonucleotide portion and a 3' linker portion;

f. remove said 3' linker portion as follows:
   (1) attach said duplex to a solid support;
   (2) remove said 3' linker portion by digesting with type II restriction enzyme capable of recognizing said second restriction enzyme restriction site;
   (3) remove said 5' linker complement portion and said oligonucleotide complement portion;
   (4) anneal 5' linker complement portion to said oligonucleotide portion;
   (5) remove said 5' linker portion by digesting with a type II restriction enzyme capable of recognizing said first restriction enzyme binding site.

g. recover said oligonucleotide in substantially single stranded form.

Another aspect of the invention (Method ES) is directed to a method for identifying and amplifying an oligonucleotide of non-predetermined or substantially non-predetermined sequence, said oligonucleotide being capable of complexing to a desired target, said method comprising:

a. incubate said target with a pool of oligonucleotides of non-predetermined or substantially non-predetermined sequence under conditions wherein some, but not all, oligonucleotides form oligonucleotide:target complexes with said target;

b. separate oligonucleotide:target complexes from uncomplexed oligonucleotides;

c. recover complexed oligonucleotides from step b in substantially single stranded form;

d. attach a single first linker containing a single RNA residue at the 3' end thereof, to the 5' end of said oligonucleotide and a second linker to the 3' end of said oligonucleotide, said 3' linker of known nucleotide sequence, said 3' linker having a type II restriction enzyme recognition site at or near the 5' end thereof and said 3' linker comprising at least four nucleotides capable of hybridizing to at least one of the ends of said oligonucleotide, thereby generating an oligonucleotide having a 5' linker portion, an oligonucleotide portion and a 3' linker portion;

e. amplify the oligonucleotide of step d, thereby generating a duplex comprising a first strand having a 5' linker complement portion, an oligonucleotide complement portion and a 3' linker complement portion, and a second strand comprising a 5' linker portion, an oligonucleotide portion and a 3' linker portion;

f. remove said 3' linker portion as follows:
  (1) attach said duplex to a solid support;
  (2) remove said 3' linker portion by digesting with type II restriction enzyme capable of recognizing said second restriction enzyme restriction site;
  (3) remove said 5' linker complement portion and said oligonucleotide complement portion;
  (4) remove said 5' linker portion by cleaving said RNA linkage;

g. recover said oligonucleotide in substantially single stranded form.

Another aspect of the invention (Aptamer DD) is directed to an oligonucleotide capable of binding a target such capability and the sequence responsible therefor, having first been determined by the process of Method EQ, ER, or ES.

Another aspect of the invention (Method ET) is directed to a method for determining the presence or amount of target in a sample, said method comprising:

a. contacting said sample with an aptamer capable of specifically binding said target under conditions wherein a complex forms between aptamer and target, said aptamer having attached thereto a label, said label capable of generating a detectable signal when said aptamer is complexed to said target as compared to when said aptamer is uncomplexed; and
  b. relating the detectable signal to the presence or amount of target in said sample.

Another aspect of the invention (Method EU) is directed to a method for determining the presence or amount of target in a sample, said method comprising:

a. bringing together said sample, or a portion thereof and an aptamer identified by any of the methods of Method DO-DQ, EC-EE, or EQ-ES, said aptamer having been selected to be shorter in length to said target which said aptamer binds;
  b. incubating said sample and said aptamer under conditions such that said aptamer binds to a detectably greater extent with said target than it does with other molecules in said sample, and;
  c. assaying for binding of said aptamer to said target.

Another aspect of the invention (Aptamer DE) is directed to an aptamer in purified and isolated form obtained by the process of any of Method DO-DQ, EC-EE, or EQ-ES.

Another aspect of the invention (Method EV) is directed to a process of any of Method EC-ES wherein the sequence of said oligonucleotides comprising said pool is at least about 70% non-predetermined.

Another aspect of the invention (Method EW) is directed to a process of any of Method EC-ES wherein the predetermined sequence of said oligonucleotides comprising said pool comprises an enzyme recognition site or a primer binding site.

Another aspect of the invention (Composition AF) is directed to a conjugate for modulating immune response to a pathologic cell, comprising:

a targeting agent moiety that specifically binds to a surface feature of the pathologic cell; and an immunomodulatory moiety that induces an immunological response different from that elicited by the pathologic cell itself in the absence of the conjugate.

Another aspect of the invention (Composition AG) is directed to a conjugate according to Composition AF, wherein said targeting agent is selected from the group consisting of oligonucleotides, antibodies and ligands for cell surface receptors.

Another aspect of the invention (Composition AH) is directed to a conjugate according to Composition AF, wherein the immunomodulatory moiety is selected from the group consisting of peptides and carbohydrates.

Another aspect of the invention (Composition AI) is directed to a conjugate according to Composition AF, wherein the immunomodulatory moiety is a peptide incorporating a sequence derived from an immunogenic protein of viral or bacterial origin.

Another aspect of the invention (Composition AJ) is directed to a conjugate according to Composition AF, wherein the immunomodulatory moiety elicits a cytotoxic lymphocyte response.

Another aspect of the invention (Composition AK) is directed to a conjugate according to Composition AJ, wherein the immunomodulatory moiety is cyclosporin A or interleukin-6.

Another aspect of the invention (Method EX) is directed to a method for preparing a conjugate for modulating immune response to a pathologic cell, comprising:

identifying a targeting agent that specifically binds to a surface antigen of the pathologic cell; and associating said targeting agent with an immunomodulatory moiety that induces a desired immune response.

Another aspect of the invention (Method EY) is directed to a method according to Method EX, wherein said immunomodulatory moiety is an antigen which elicits a strong cytotoxic T-lymphocyte response.

Another aspect of the invention (Method EZ) is directed to a method for modulating immune response to a pathologic cell, comprising:

administering an amount effective to modulate immune response of a conjugate in accordance with Composition AF.

Another aspect of the invention (Method FA) is directed to a method according to Method EZ, wherein the conjugate comprises an antigen which elicits a strong cytotoxic T-lymphocyte response, thereby marking cells for destruction.

Another aspect of the invention (Method FB) is directed to a method to identify an oligonucleotide sequence which specifically binds a complexation target expressed on a cell surface, which process comprises:

incubating a first set of cells having a set of surface materials including said complexation target on the cell surface with a mixture of randomized oligonucleotide sequences under conditions wherein complexation occurs with some, but not all, members of said mixture;

separating complexed from uncomplexed oligonucleotides;

recovering the complexed oligonucleotides to provide a first pool of binding oligonucleotides;

incubating a second set of cells having substantially the same set of surface materials as said first set of cells but lacking said complexation target with said first pool of binding oligonucleotides;

separating complexed from uncomplexed oligonucleotides;

recovering the uncomplexed oligonucleotides to provide a second pool of binding oligonucleotides which specifically bind the complexation target; and recovering and amplifying the oligonucleotide(s) from said second pool of binding oligonucleotides.

Another aspect of the invention (Method FC) is directed to the method of Method FB wherein said complexation target is a transmembrane or extracellular matrix protein.

Another aspect of the invention (Method FD) is directed to the method of Method FC, wherein the protein is CD4.

Another aspect of the invention (Method FE) is directed to the method of Method FC, wherein the protein is IL-1R.

Another aspect of the invention (Method FF) is directed to the method of Method FB, wherein the complexion target is a glycoprotein.

Another aspect of the invention (Method FG) is directed to the method of Method FB, wherein the complexion target is a carbohydrate.

Another aspect of the invention (Method FH) is directed to the method of Method FB, wherein the oligonucleotide sequences are labeled.

Another aspect of the invention (Method FI) is directed to the method of Method FH, wherein the oligonucleotide sequences are labeled with a label selected from the group consisting of enzymatic and chemiluminescent labels.

Another aspect of the invention (Method FJ) is directed to the method of Method FC, wherein the protein is a receptor protein.

Another aspect of the invention (Method FK) is directed to the method of Method FC, wherein the protein is a mutant protein.

Another aspect of the invention (Method FL) is directed to the method of Method FB, further comprising adding nucleases to enhance recovery of oligonucleotides.

Another aspect of the invention (Method FM) is directed to the method of Method FB, wherein the cells are primary human cells.

Another aspect of the invention (Method FN) is directed to the method of Method FB, wherein the cells are transformed human cells.

Another aspect of the invention (Method FO) is directed to the method of Method FB, wherein the oligonucleotides are recovered after binding in a serum-containing medium at about 37 C.

Another aspect of the invention (Method FP) is directed to the method of Method FB wherein the oligonucleotide mixture is single-stranded DNA.

Another aspect of the invention (Method FQ) is directed to the method of Method FB wherein said separating steps are conducted using electrophoresis mobility shift assay (EMSA).

Another aspect of the invention (Method FR) is directed to the method of Method FB wherein said recovering and amplifying is through the conduct of the polymerase chain reaction (PCR).

Another aspect of the invention (Aptamer DF) is directed to an oligonucleotide comprising a sequence specific for a complexation target, in purified and isolated form obtained by the process of Method FB.

Another aspect of the invention (Aptamer DG) is directed to the oligonucleotide of Aptamer DF wherein the complexation target is the HER2 glycoprotein.

Another aspect of the invention (Method FS) is directed to a process for recovering cells which express a target molecule on the surface thereof from a mixture of cells some of which cells do not express the target molecule, comprising the steps of:

obtaining an aptamer which binds to the target molecule on the cell surfaces by following the process of:

contacting a first set of cells having a specific target molecule on their surface with a randomized mixture of oligonucleotide sequences under conditions wherein some but not all of the sequences will bind to the cellular surfaces;

separating away those sequences which do not bind to the cellular surfaces;

isolating the cells having sequences bound thereto and recovering the bound sequences from the cellular surfaces to provide a first pool of sequences;

contacting the first pool of sequences with a second set of cells substantially the same as the first set of cells, but lacking the specific target molecule present on the surface of the first set of cells;

separating away and isolating those sequences which do not bind to the second set of cells to provide a second pool of sequences;

recovering the sequences of the second pool; p2 labeling the sequences in the second pool;

contacting the labeled sequences with the mixture of cells and determining which cells have the labeled sequences bound thereto; and separating and recovering the cells having the labeled sequences bound thereto.

Another aspect of the invention (Method FT) is directed to a method to modify target cells or tissues in a subject, which method comprises administering to a subject in need of such modification an oligonucleotide which comprises a sequence specifically binding to a substance characteristic of said target cell or tissue, wherein said oligonucleotide is optionally derivatized with a moiety which enhances said modification and wherein said sequence is obtained by the process of Method FB.

Another aspect of the invention (Method FU) is directed to a method to determine the presence or absence of a target substance in a sample, which method comprises treating said sample with a labeled oligonucleotide containing a sequence which specifically binds said target substance under conditions wherein a complex between said oligonucleotide and target substance is formed when target substance is present, and detecting the presence or absence of the complex, wherein the specifically binding sequence has been obtained by the process of Method FB.

Another aspect of the invention (Method FV) is directed to a method to recover a target substance from a sample, which method comprises contacting said sample with a solid support to which has been bound an oligonucleotide containing a sequence specifically binding said substance under conditions wherein said target substance binds to said oligonucleotide;

separating the solid support from the sample; and recovering the target substance from the solid support, wherein the specifically binding sequence has been determined by the process of Method FB.

Another aspect of the invention (Method FW) is directed to a method of obtaining an oligonucleotide sequence which binds to a specific target molecule on a cell surface, which comprises:

contacting a first set of cells having a specific target molecule on their surface with a randomized mixture of oligonucleotide sequences under conditions wherein some, but not all of the sequences will bind to the cellular surfaces;

separating away those sequences which do not bind to the cellular surfaces;

isolating the cells having sequences bound thereto and recovering the bound sequences from the cellular surfaces to provide a first pool of sequences;

contacting the first pool of sequences with a second set of cells substantially the same as the first set of cells, but lacking the specific target molecule present on the surface of the first set of cells;

separating away and isolating those sequences which do not bind to the second set of cells to provide a second pool of sequences; and recovering the sequences of the second pool.

Another aspect of the invention (Method FX) is directed to a method for identifying an aptamer which specifically binds a target substance comprising the following steps:

(a) incubating the target substance reversibly coupled to a support with a mixture of randomized oligonucleotide sequences under conditions wherein the coupled target substance complexes with some, but not all, members of the mixture to form support-bound aptamer-target complexes;

(b) decoupling and recovering the target substance from the support-bound aptamer-target complexes to form free aptamer-target complexes;

(c) recovering and amplifying the complexed aptamers from the free aptamer-target complexes; and (d) optionally determining the sequence of the recovered aptamers.

Another aspect of the invention (Method FY) is directed to the method of Method FX wherein the target substance is selected from the group consisting of a polypeptide, enzyme, protein, lipid, glycolipid, phospholipid, leukotriene, lipoprotein, glycoprotein, carbohydrate, or cell surface molecule.

Another aspect of the invention (Method FZ) is directed to the method of Method FX wherein in step (a) the target substance is reversibly coupled to the support using an activated thiol group on the support.

Another aspect of the invention (Method GA) is directed to the method of Method FZ wherein in step (b), decoupling is accomplished by adding a reducing agent.

Another aspect of the invention (Method GB) is directed to the method of Method GA wherein the reducing agent is dithiothreitol or -mercaptoethanol.

Another aspect of the invention (Method GC) is directed to the method of Method FY wherein the target substance is bradykinin.

Another aspect of the invention (Method GD) is directed to the method of Method GC wherein in step (a) the target substance is reversibly coupled to the support using an activated thiol group on the support, and wherein in step (b) decoupling is accomplished by adding dithiothreitol.

Another aspect of the invention (Method GE) is directed to the method of Method FX wherein the support is a lectin support and the target substance binds reversibly to lectin.

Another aspect of the invention (Method GF) is directed to the method of Method GE wherein the target substance is thrombin.

Another aspect of the invention (Method GG) is directed to the method of Method GE wherein in step (b), decoupling is accomplished by adding a monosaccharide.

Another aspect of the invention (Method GH) is directed to the method of Method GG wherein the monosaccharide is -methyl-mannoside.

Another aspect of the invention (Aptamer DH) is directed to an oligonucleotide comprising a sequence specific for a target substance, in purified and isolated form, wherein the sequence is determined by the process of Method FX.

Another aspect of the invention (Aptamer DI) is directed to the oligonucleotide of Aptamer DH wherein the target substance is thrombin.

Another aspect of the invention (Aptamer DJ) is directed to the oligonucleotide of Aptamer DH wherein the target substance is bradykinin.

Another aspect of the invention (Method GI) is directed to a process for recovering a target substance from a sample, which process comprises contacting said sample with an oligonucleotide containing a sequence that specifically binds said substance under conditions wherein said substance and said oligonucleotide form a complex;

separating the complex from other materials in the sample; and recovering the substance from the complex, wherein the specifically binding sequence has been determined by the process of Method FX.

Another aspect of the invention (Method GJ) is directed to a method to modify target cells or tissues in a subject, which method comprises administering to a subject in need of such modification an oligonucleotide which comprises a sequence specifically binding to a substance characteristic of said target cell or tissue, wherein said oligonucleotide is optionally derivatized with a moiety which enhances said modification and wherein said sequence is determined to specifically bind said substance by the process of Method FX.

Another aspect of the invention (Method GK) is directed to a method to determine the presence or absence of an analyte in a sample, which method comprises treating said sample with an oligonucleotide containing a sequence which specifically binds said analyte under conditions wherein a complex between said oligonucleotide and analyte is formed when analyte is present, and detecting the presence or absence of the complex, wherein the specifically binding sequence has been determined by the process of Method FX.

Another aspect of the invention (Method GL) is directed to a method to recover a target substance from a sample, which method comprises contacting said sample with a solid support to which has been bound an oligonucleotide containing a sequence specifically binding said substance under conditions wherein said target substance binds to said oligonucleotide;

separating the solid support from the sample; and recovering the target substance from the solid support, wherein the specifically binding sequence has been determined by the process of Method FX.

Another aspect of the invention (Method GM) is directed to a secondary aptamer which specifically binds a target substance made by a process comprising the following steps:

(a) incubating the target substance reversibly coupled to a support with a mixture of randomized oligonucleotide sequences under conditions wherein the coupled target substance complexes with some, but not all, members of the mixture to form support-bound aptamer-target complexes;

(b) decoupling and recovering the target substance from the support-bound aptamer-target complexes to form free aptamer-target complexes;

(c) recovering and amplifying the complexed aptamers from the free aptamer-target complexes;

(d) determining the sequences of the recovered aptamers;

(e) determining a consensus sequence included in the recovered aptamers;

(f) synthesizing a secondary aptamer which comprises the consensus sequence.

EXAMPLES

The following examples are meant to illustrate, but not to limit the invention.

Example 1

Selection of Aptamers that Bind to Bradykinin

A. Preparation of Bradykinin Column

Bradykinin derivatized Toyopearl (Toso Haas, Inc., Woburn, Mass.) support was used for all selections described. Bradykinin was coupled to the Toyopearl support through its amino termini according to the manufacturer's instructions. Bradykinin ($NH_2$-arg-pro-pro-gly-phe-ser-pro-phe-arg-COOH, acetate salt) was obtained from Bachem Feinchemikalien AG (Cat. No. H-1970). Toyopearl AF-carboxyl 650M was converted to the NHS-ester by treatment with N-hydroxy succinimide (NHS) and diisopropyl carbodiimide in dioxane/DMF (1:1) for 24 hours. The support was washed with DMF, $H_2O$, 200 mM $NaHCO_3$ and treated with a solution of bradykinin (20 mg of bradykinin/ml support) in 200 mM $NaHCO_3$ for 3 days. The support was then washed and the coupling yield was determined by HCl digestion of the support (80 C. for 8 hours) and a ninhydrin assay using free bradykinin as a standard. The yield was found to be 16 mg/ml support (16 mole/ml support). The coupled support was then capped by treatment with acetic acid (NHS-ester) in dioxane/200 mM $NaHCO_3$ buffer (1:1).

An underivatized capped support to be used as a control was made by treating Toyopearl AF-carboxyl 650M with acetic acid (NHS-ester) in dioxane/200 mM $NaHCO_3$ buffer (1:1), followed by washing.

B. Synthesis of Oligonucleotide Pool

DNA oligonucleotides containing a randomized sequence region were synthesized using standard solid phase techniques and phosphoramidite chemistry (Oligonucleotide Synthesis, Gait, M. J., ed. (IRL Press), 1984; Cocuzza, A., Tetrahedron Letters, (1989) 30:6287–6291.) A 1M small-scale synthesis yielded 60 nmole of HPLC-purified single-stranded randomized DNA. Each strand consisted of specific 18-mer sequences at both the 5' and 3' ends of the strand and a random 60-mer sequence in the center of the oligomer to generate a pool of 96-mers with the following sequence (N=G, A, T or C):

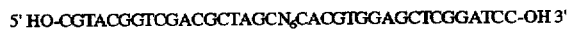
5' HO-CGTACGGTCGACGCTAGCN₆₀CACGTGGAGCTCGGATCC-OH 3'

DNA 18-mers with the following sequences were used as primers for PCR amplification of oligonucleotide sequences recovered from bradykinin columns. The 5' primer sequence was 5' HO-CGTACGGTCGACGCTAGC-OH 3' and the 3' primer sequence was 5' biotin-O-GGATCCGAGCTCCACGTG-OH 3'. The biotin residue was linked to the 5' end of the 3' primer using commercially available biotin phosphoramidite (New England Nuclear, Cat. No. NEF-707). The biotin phosphoramidite is incorporated into the strand during solid phase DNA synthesis using standard synthesis conditions.

C. Selection for Aptamers That Bind to an Immobilized Bradykinin Column 400 1 bradykinin-derivatized Toyopearl support was loaded on a 1.5 ml column housing. The column was washed with 3 ml of 20 mM Tris-acetate buffer (pH 7.4) containing 1 mM $MgCl_2$, 1 mM $CaCl_2$, 5 mM KCl and 140 mM NaCl (the "selection buffer"). An identical column was prepared using the underivatized Toyopearl control support described in Example 1-A.

An initial oligonucleotide pool (0.5 nmole, $3\times10^{14}$ unique sequences) of synthetic 96-mers prepared in Example 2 was amplified approximately 30-fold by large-scale PCR using known techniques. Assuming 10–20% readthrough of synthetic DNA and possible preferential amplification by the Taq polymerase, the estimated actual complexity was reduced to about $1\times10^{13}$ unique sequences.

This amplified oligonucleotide pool (0.1 nmoles, about 6 copies of $1\times10^{13}$ unique sequences), doped with 5'-$^{32}$P-labeled species, was used in the first selection round. The pool was heated to 94 C. for 3 minutes in selection buffer, allowed to cool to room temperature, applied to the control column in a volume of 100 1, and allowed to equilibrate for approximately 10 minutes. The column was then eluted with selection buffer and the eluent collected in 200 1 fractions. The bulk of the counts (approximately 95%) with little affinity for the matrix eluted in the first 2 or 3 fractions after the void volume. These fractions were combined, applied to the bradykinin-linked support (400 1 support, approximately 5 mole, washed with 3 ml of selection buffer), and eluted with selection buffer. The column was then eluted with selection buffer and the eluent collected in 200 1 fractions. Fractions were collected until the eluted counts in a fraction plateaued at less than about 0.05% total loaded counts. The column was then eluted with elution buffer (500 mM TrisHCl (pH 8.3), 20 mM EDTA) at room temperature. Aptamers were eluted in the first 2 or 3 fractions after the void volume. These fractions were combined and precipitated using ethanol and glycogen as the carrier. The aptamer pellet was resuspended in 200 1 of $ddH_2O$ (deionized distilled water) and divided into two 0.5 ml siliconized Eppendorf tubes for PCR. All remaining counts on the column were removed by treatment with 0.1N NaOH (0.5 ml), although these species were not used in subsequent amplification and selections.

D. Amplification of Selected Aptamers

Two groups of selected aptamers were amplified by PCR using standard techniques and the following protocol.

A 200 1 PCR reaction consisted of the following: 100 1 template aptamer (approximately 2 moles); 20 1 buffer (100 mM TrisCl (pH 8.3), 500 mM KCl, 20 mM $MgCl_2$); 32 1 NTP's (5 mM conc total, 1.25 mM each ATP, CTP, GTP, and TTP); 20 1 primer 1 (biotinylated 18-mer, 50 1); 20 1 primer 2 (18-mer, 50 1); 2 1 hot NTP's (approximately 2 mCi); 6 1 $ddH_2O$; and 2 1 Taq I Polymerase (10 units). The reaction was sealed with 2 drops NUJOL mineral oil. A control reaction was also performed without template aptamer.

Initial denaturation was at 94 C. for 3 minutes, but subsequent denaturation after each elongation reaction lasted 1 minute. Primer annealing occurred at 60 C. for 1 minute, and elongation of primed DNA strands using the Taq polymerase ran at 72 C. for 2 minutes. The final elongation reaction to completely fill in all strands ran for 10 minutes at 72 C., and the reaction was then held at 4 C.

Fifteen rounds of Taq polymerase elongation were carried out in order to amplify the selected aptamer DNA. After the reactions were completed, the NUJOL oil was removed by chloroform extraction. The two reactions were combined and chloroform extracted again. A 2 1 sample was removed from each of the aptamer and control reaction for counting and an analytical gel. The rest of the amplified aptamer was run over four Nick columns (G-50 Sephadex, washed with 3 ml TE buffer (10 mM TrisHCl (pH 7.6), 0.1 mM EDTA)) to remove unincorporated NTP'S, primers, and salt. 100 l of the amplified aptamer pool (400 l total) was applied to each Nick column. 400 l of TE buffer was then added to each column and the columns were eluted with an additional 400 l using 10 mM TrisHCl, pH 7.6, 0.1 mM EDTA (1600 l total). An 8 l sample was removed from the combined eluents for counting and an analytical gel. The remaining eluent was loaded on an avidin agarose column (Vector Laboratories, Cat. No. A-2010) (600 l settled support, washed with 3×800 l TE buffer). Approximately 90% of the loaded counts remained on the column. The column was washed with TE buffer (3×800 l) and then the nonbiotinylated strand was eluted with 0.15N NaOH (400 l fractions). More than 45% of the counts on the column were eluted in the first two fractions. These two fractions (800 l) were combined and neutralized with approximately 4 l of glacial acetic acid. The neutralized fractions were reduced to 200 l by speed vacuum or butanol extraction and then precipitated with ETOH. The resultant pellet was dissolved in 102 l selection buffer, heated at 94 C. for 3 min, and cooled to room temperature. A 2 l sample was removed for counting and an analytical gel.

E. Aptamer Recovery Profiles From the First Two Rounds of Selection

Aptamers eluted from the first round of bradykinin-linked column selection were obtained in two 100 l fractions that contained 0.07% of the total counts loaded. Recovery of three 100 l fractions from the second round selection yielded 0.26% of the total counts loaded therein, indicating that an increased proportion of the aptamers loaded onto the column had bound to bradykinin.

F. Further Rounds of Aptamer Selection on Bradykinin Columns

Additional rounds of selection and amplification were carried out in order to obtain a population of aptamers that consisted of species that bound to bradykinin. The cycle of Examples 1-C and 1-D was repeated 6 times until a significant portion of the oligonucleotide pool (as measured by cpm) remained on the column after washing with selection buffer. Under the selection and amplification conditions used, about 15% of input counts (0.5 nmole DNA, about 19 g) bound to the bradykinin column in rounds 5 and 6. About 6% of the counts bound to the control column. However, the proportion of counts that bound to the bradykinin column was higher, 40% of input cpm, when the initial amount of input DNA was reduced from 0.5 nmole to 0.1 nmole. Under these conditions (0.1 nmole input DNA, about 3.5 g) 19% of the counts bound to the capped control column. The relatively high proportion of counts bound to the control column was due to overloading of the control column during the prebinding process prior to adding aptamer to bradykinin columns at each round of selection. This high level of binding to the control column in the later round pools (rounds 5 and 6) can be reduced by reducing the molar ratio of input DNA to column during the selection process. This protocol is described in Example 1-G below. This high affinity aptamer pool was eluted, amplified by PCR, cloned, and sequenced (about 20 to 40 clones). From these clones, several homologous batches of aptamers and/or individual clones are prepared by solid phase DNA synthesis and tested for bradykinin binding affinity and specificity.

G. Aptamer Selection Using a Reduced Molar Ratio of Aptamer to Column

An initial oligonucleotide pool (0.5 nmole, $3 \times 10^{14}$ unique sequences) of synthetic 96-mer prepared as in Example 1-B is amplified approximately 30-fold by large-scale PCR using known techniques. Assuming 10–20% readthrough of synthetic DNA and possible preferential amplification by the Taq polymerase, the estimated actual complexity is reduced to about $1 \times 10^{13}$ unique sequences.

This amplified oligonucleotide pool (0.5 nmoles, about 30 copies of $1 \times 10^{13}$ unique sequences) doped with 5'-$^{32}$P-labeled species, is used in the first selection round. A bradykinin-linked column and control support column are prepared as in Example 1-B.

The pool is heated to 94 C. for 3 minutes in selection buffer, cooled to room temperature, then applied to 1 ml of control support washed with 3 ml of selection buffer, and allowed to equilibrate for about 10 minutes. The column is then eluted with selection buffer and the eluent collected in 200 l fractions. The bulk of the counts (approximately 90%), with little affinity for the matrix is eluted in the first 2 or 3 fractions after the void volume. These fractions are combined, applied to the bradykinin-linked support (1 ml, approximately 10 to 15 mole, washed with 3 ml of selection buffer), eluted with selection buffer, and the eluent collected in 200 l fractions. Fractions are collected until the eluted counts in a fraction plateau at less than 0.05% of the total counts loaded on the column (approximately 12 fractions). The column is then eluted with elution buffer (0.15N NaOH, 50 mM EDTA). The aptamers are eluted in the first 2 or 3 fractions after the void volume. These fractions are combined and precipitated using ethanol and glycogen as the carrier. The aptamer pellet is taken up in 100 l of ddH$_2$O and transferred to a 0.5 ml siliconized eppendorf tube for PCR. One aptamer PCR reaction and one control (without template) reaction are then run as described in Example 1-D.

The above procedure is then repeated, with the exception that the oligonucleotide pool used in subsequent selection cycles is reduced to 0.1 nmole and the control and bradykinin support volumes are reduced to about 330 l (about 3 to 5 moles bradykinin). The procedure is repeated (~5–6 times) until a significant portion of oligonucleotide remains on the column after washing with selection buffer. This high-affinity aptamer pool is eluted, converted to double stranded DNA by PCR, and cloned. About 20 clones are sequenced. From these clones, several homologous batches of aptamers are prepared and tested for binding affinity and target specificity. High affinity aptamers are mutagenized using the techniques described in Ellington et al., Nature (1990) 346:818–822 to yield a 15% mutation rate at each position and reselected to determine those bases which are involved in binding.

Example 2

Selection of Aptamers that Bind to PGF2

A. Preparation of PGF2 Linked to a Solid Support

PGF2 derivatized Toyopearl AF-amino 650M (Toso Haas, Inc., Woburn, Mass.) support (charged with 10 moles PGF2/ml matrix) was used for all selections described. The support was coupled through the free carboxyl group of PGF2 according to the manufacturer's instructions. PGF2 was purchased from Sigma Chemical Co. (Cat. No. P 3023) and tritiated PGF2 was purchased from New England Nuclear.

10 mg of PGF2 (Tris salt) was dissolved in 1 ml H$_2$O/methanol and converted to the sodium salt by passage over an ion exchange column. The column eluent was then evaporated, dissolved in dioxane and converted to the N-hydroxy-succinimide (NHS) ester by treatment with NHS and diisopropyl carbodiimide for 24 hrs. This mixture was then added to 1 ml of the settled support Toyopearl washed previously with 200 mM NaHCO$_3$. The mixture was shaken for 24 hrs., and washed with a NaHCO$_3$ solution. To determine the amount of coupling. the above described procedure was repeated except that a small amount of tritiated PGF2 was added. The coupling yield was determined by the amount of tritium associated with the support. The support was then capped by treatment with acetic acid (NHS-ester) in dioxane/200 mM NaHCO$_3$ buffer (1:1).

An underivatized capped support was made by treating Toyopearl AF-amino 650M with acetic acid (NHS-ester) in dioxane/200 mM NaHCO$_3$ buffer (1:1) to be used as a control.

B. Selection for Aptamers That Bind to an Immobilized PGF2 Column 200 l derivatized Toyopearl support containing 2 mole of PGF2 ligand was loaded on a 1.5 ml column housing. The column was washed with 3 ml of 20 mM Tris-acetate buffer (pH 7.4) containing 1 mM MgCl$_2$, 1 mM CaCl$_2$, 5 mM KCl and 140 mM NaCl (the "selection buffer"). An identical column was prepared using the underivatized Toyopearl control support described in Example 2-A.

0.5 nmoles of the oligonucleotide pool prepared in Example 1-B (doped with tracer amounts of 5'-$^{32}$P-end-labeled species) was resuspended in 400 l of selection buffer and heat denatured for 2 min at 95 C. The denatured DNA was immediately transferred to wet ice for 10 min. This material was applied to the control support (underivatized Toyopearl), flow initiated, and eluent collected. Flow-through was reapplied three times. At the end of the third application, the column was rinsed with 200 l selection buffer (1 bed volume). The flow-through was pooled and applied for a fourth time. A column profile was established using $^{32}$P quantification via Cerenkov counting. Flow-through material was then pooled for application to the PGF2 support.

Application of the flow-through pool to PGF2-derivatized Toyopearl was performed as described above. After the third application, the column was washed with 200 l of selection buffer and the material reapplied to establish a column profile. The support was washed with additional selection buffer until the eluting $^{32}$P material decreased to low levels, less than 0.2% of initial input cpm. The support was then washed with 1 ml of selection buffer containing 1M NaCl. Bound oligonucleotides were eluted with 20 mM EDTA/ 60% acetonitrile. The solvent was removed under vacuum and the material chromatographed on a Nick column (Pharmacia, G-50 Sephadex columns) as per the manufacturer's instructions using 10 mM Tris (pH 7.5)/0.1 mM EDTA/250 mM NaCl. The $^{32}$P-containing fraction was then precipitated with 20 g of carrier glycogen and absolute ethanol (2.5 vol) on dry ice for 15 minutes. The DNA was pelleted for 15 minutes at 4 C., washed with 70% ethanol, and dried under vacuum.

C. Amplification of Aptamers Obtained After Selection on a PFG2 Column

The DNA selected in Example 2-B above was amplified via PCR using known techniques under the following conditions: 1 nmole of 5' and 3' primer (biotinylated), 250 m dNTPs (containing 20 Ci each of dCTP, DGTP and dATP) in 200 l of 10 mM Tris (pH 8.3) containing 50 mM KCl and 1.5 mM MgCl$_2$'. The reaction vessel was sealed with mineral oil, and subjected to 25 cycles of amplification. The mineral oil was then removed, and 100 l CHCl$_3$ was added. The solution was then vortexed and separated via centrifugation. The aqueous layer was removed, concentrated via n-butanol extraction and brought to a final volume of 100 l. The $^{32}$P labeled DNA was then passed over a Nick column equilibrated in 100 mM Tris (pH 7.5)/100 mM NaCl to remove unincorporated primer and dNTPs. The column eluent was then applied to 400 l of avidin-agarose matrix (two applications resulted in more than 90% retention of the input). The matrix was extensively washed to remove contaminants and single-stranded aptamer eluted with 600 l washes of 0.15N NaOH (2×), yielding 40–48% recovery of input $^{32}$P DNA. The aptamer solution was brought to pH 6 with acetic acid and concentrated via n-butanol extraction to 40% of the initial volume. The material was precipitated with absolute ethanol (3 vols) on dry ice for 15 minutes. The DNA was pelleted, washed with 70% ethanol and dried under vacuum. The material was resuspended in selection buffer as described above. Subsequent rounds of selection were carried out using the same protocol: removal of aptamer by binding to the control support column; followed by binding to the PGF2 column. Each round of selection resulted in a pool enriched in the aptamer that specifically bound to the PGF2 immobilized on the column. Amplified material was always obtained from the PGF2 column by elution in 20 mM EDTA/60% acetonitrile.

D. Quantitation of Aptamer Recovery From PGF2 Columns After 6 Rounds of Selection The total radioactivity ($^{32}$P) associated with each oligonucleotide pool used for PGF2 selection was determined prior to addition to underivatized Toyopearl columns. DNA from underivatized and PGF2-derivatized columns was recovered and total radioactivity determined and expressed as % recovery. Data for 32P recovered (in cpm) after column washes are shown in Table 2 for selection rounds 1 through 6.

TABLE 2

| Round of selection | % Total cpm Eluted by CH$_3$CN/EDTA Wash |
| --- | --- |
| 1 | 0.37 |
| 2 | 2.31 |
| 3 | 7.98 |
| 4 | 16.97 |
| 5* | 17.34 |
| 6 | 17 |

*total cpm recovered after 2 column washes with CH$_3$CH/EDTA.

E. Characterization of Aptamers Eluted From the Round 6 Column (a) The recovery of specifically-binding oligonucleotides in each amplified pool from round 4, 5 and 6 selections remained constant at about 17% of total input cpm. Aptamers obtained from the round 6 column washes prior to addition of CH$_3$CN/EDTA were recovered by ethanol precipitation, pooled, and subjected to selection on a new PGF2 column. The total cpm recovered from CH$_3$CN/EDTA elution was about 17%.

This demonstrates that the aptamers eluted by CH$_3$CN/EDTA in round 6 specifically bind to the PGF2 ligand. The 17% recovery was due only to the limited binding capacity of the PGF2 column. This means that 1 to 10% of linked PGF2 is available for aptamer binding, giving a ligand:oligonucleotide loading ratio of about 40 to 400. Higher recovery values for round 4 through 6 selections have been reported but result from a higher ligand:oligonucleotide ratio of about 10–30,000 (Ellington and Szostak, Nature (1990) 346:818–822). Thus, the aptamers obtained after 6 rounds of PGF2 selection (the "round 6 pool") were a pool of molecules that resulted from competition among aptamer species for a limited number of PGF2 binding sites.

(b) The round 6 pool was further characterized by adding 1 ml of a 2.4 mg/ml solution (5 mole) of PGF2 in selection buffer to an PGF2 column (containing 2, mole of matrix-bound PGF2). This result shows ligand-specific elution of the pool—a classic property of affinity-selected ligands. See Schott, H., Affinity Chromatography, (Marcel Dekker, Inc., New York), 1984.

(c) The round 6 pool was additionally characterized for PGF2-binding specificity by monitoring hydroxypropionic acid (HP)-mediated elution (HP is chemically similar to PGF2). 0.4 ml of selection buffer containing 1.0 mM HP was added to a PGF2 column saturated with radiolabelled round 6 pool. The elution profile showed that less than it of applied radiolabeled aptamer DNA was eluted by HP. This step was followed by application of 0.4 ml of selection buffer containing 1.0 mM PGF2 using the same column, and resulted in the elution of over 95% of radiolabelled aptamer DNA from the column. This result demonstrated that the round 6 pool was binding specifically to PGF2 and did not bind to a chemically similar molecule such as HP.

(d) To further characterize the round 6 pool, the pool was incubated with 5 mole of PGF2 in selection buffer for 30 minutes at room temperature and then added to a PGF2 column as described above. Less than 2% of the total cpm associated with the pool bound to the column. A PGF2 column loaded with the round 6 pool in selection buffer adsorbs 75% of the input oligonucleotides (here 75% of the counts bound to the column because only 0.05 nmole of aptamer was added to the column).

(e) Analysis of the selection and elution buffers was carried out by incubating the round 6 pool with a PGF2 column by suspending the pool in selection buffer containing 20 mM EDTA to remove $Mg^{++}$ ions by chelation. Less than 2% of the total cpm associated with the pool bound to the column, while a control column loaded with the round 6 pool in selection buffer bound as described above (75% of the counts bound to the column because only 0.05 nmole of oligonucleotides was added to the column, resulting in a 10-fold increase in the PGF2:oligonucleotide molar ratio compared to the binding ratio used to generate the PGF2 aptamer pool). This indicated that specific binding of oligonucleotides involves structural features that required the presence of $Mg^{++}$ ion. The use of EDTA in the elution buffer efficiently removes $Mg^{++}$ ion from solution and thus prohibits specific binding of oligonucleotides to the PGF2 matrix.

(f) The following additional characterization method is proposed:

The round 6 pool is characterized by determining the elution profile obtained after washing a PGF2 column (200 l support volume) saturated with the round 6 pool. The washes are carried out using 0.4 ml of selection buffer containing 1.0 mM solutions of a series of compounds that resemble PGF2 more closely than HP does. In each case, the elution with a molecule similar to PGF2 will be followed by elution with 0.4 ml of selection buffer containing 1.0 mM PGF2 to determine the efficiency of PGF2 elution. The compounds that are tested include hydroxydecanoic acid, arachidonic acid, prostaglandin A, prostaglandin B, and other eicosanoids.

Washes using chemically similar molecules are utilized for isolation of aptamers that bind to specific compounds. Elution of a PGF2 column saturated with the round 6 pool using 1.0 mM 8-iso-PGF2 (Cayman Chemical Company, catalog No. 16350, an isomer of PGF2), followed by elution with selection buffer containing 1.0 mM PGF results in isolation of aptamers that preferentially bind to either PGF or the 8-iso-PGF isomer. Alternatively, columns made using equimolar amounts of PGF and 8-iso-PGF are used to generate a pool of aptamers containing species that bind to one or the other isomer or both. Some of these aptamers presumably bind to regions of the PGF structure that are unaffected by the isomerization. Chemically modified eicosanoids are used in a similar manner.

Example 3

Selection of Aptamers From Non-Predetermined Pools

A. Preparation of PGF2 Linked to a Solid Support PGF2 derivatized Toyopearl (Toyo Haas, Inc., Woburn, Mass.) support (charged with 10 moles PGF/mL matrix) was used for all selections described. Selections were carried out according to the manufacturer's instructions. PGF was purchased from Sigma Chemical Co. (Cat. No. P 3023) and $^3$H-PGF was purchased from New England Nuclear.

PGF (salt) (10 mg) is dissolved in $H_2O$/methanol (1 ml) and converted to the sodium salt by passage over an ion exchange column. The eluent is evaporated, dissolved in dioxane and converted to the NHS-ester by treatment with N-hydroxy-succinimide (NHS) and diisopropyl carbodiimide for 24 hrs. This mixture is then added to a toyopearl AF-amino 650M (Toyo Haas, Inc.) support (1 ml of settled support) which has been washed previously with 200 mM $NaHCO_3$). The mixture is shaken for 24 hours and the support is washed with 200 mM $NaHCO_3$ solution. To determine the amount of loading the above-described coupling procedure is repeated except that a small amount of tritiated PGF is added and the coupling yield is determined from the amount of $^3$H-label associated with the support.

After completed PGF2 coupling, the support is capped by treatment with acetic acid NHS-ester in dioxane/buffer 1:1. (The buffer is 200 mM $NaHCO_3$). The all-capped support is made by treatment of toyopearl AF-amino 650M with acetic acid NHS-ester in the same manner as described above.

B. Selection of Aptamers of Substantially Non"Predetermined Sequence That Bind to PGF Linked to Solid Support A pool of aptamers consisting of 60 bases of completely random sequence is synthesized by standard solid phase techniques using phosphoramidite chemistry (Gait M. J., Oligonucleotide Synthesis, IRL Press, 1984; Cocuzza, A., Tetrahedron Lett., (1989) 30:6287–6291). $1.3 \times 10^6$ different aptamer sequences are possible in a random 60-mer pool. A standard 1M scale synthesis followed by HPLC purification yields 60 nmoles of single stranded DNA. Assuming that each base residue has an average molecular weight of 350, the synthesis yields 1.26 mg of purified DNA. The aptamers are synthesized with a phosphate group at the 5' end. The biotin residue is linked to primer using a commercially available biotin phosphoramidite conjugate (New England Nuclear, Catalog No. NEF-707) that is incorporated into the strand after solid phase DNA synthesis using standard synthesis conditions. The biotin label is incorporated into DNA according to manufacturer's recommendations.

PGF derivatized support (charged with 10 moles PGF/mL resin) is used for all selections described. 200 l (2 mole of PGF ligand) support is poured into a 1.5 mL column housing. The support is washed with 3 mL of 20 mM Tris-Ac pH 7.4 containing 1 mM $MgCl_2$, 1 mM $CaCl_2$, 5 mM KCl and 140 mM NaCl (the "selection buffet"). Selection buffet mimics the ion and pH conditions found in the human circulatory system. A control column containing identical support is prepared in the same manner. This support is the parent matrix for attachment of selection ligand but has been capped as the acetamide to mimic the linkage used for attachment to PGF2.

1 nmole of aptamer (doped with tracer amounts of $^{32}$P-labeled species) is resuspended in 400 l of selection buffer and heat denatured for 2 minutes at 95 C. The denatured DNA is immediately transferred to wet ice for 10 minutes. This material is applied to the control support. Flow is initiated and eluent collected. Flow-through is reapplied up to three times. At the end of the third application the column is rinsed with selection buffer. A column profile is established using $^{32}P$ quantitation via Cerenkov counting. Flow through material (2 to 4 column volumes) is pooled for application to the PGF support.

Application to PGF2 matrix is identical to that described above. After application to the column, the matrix is washed with 200 l of selection buffer and the material reapplied to establish a column profile. The support is washed with additional selection buffer until the eluting $^{32}P$ material reaches a constant low level (less than about 0.2% of input DNA per 200 l of flow through). The support then is washed with 1 mL of selection buffer containing increased NaCl (1M) until counts per 200 l of wash are less than about 0.2% of input totals. Desired aptamer is eluted with a solution of 20 mM EDTA/60% acetonitrile (elution buffer). Specifically bound aptamers are recovered from the first 2 to 4 column volumes that are obtained after adding elution buffer. The solvent is removed in vacuo and the material is chromatographed on a G50 Sephadex Nick column (Pharmacia, catalog no. 17-0855-02) as per the manufacturer's instructions using 10 mM Tris pH 7.5/0.1 mM EDTA/250 mM NaCl. The $^{32}P$ fraction is then precipitated with 20 g of carrier glycogen (Boehringer Mannheim) and 2.5 volume absolute ethanol (dry ice 15 minutes). The DNA is pelleted at 14 K, 15 minutes @ 4 C., washed with 70% ethanol and dried in vacuo.

C. Covalent linkage of linkers to aptamers with completely random sequences

Linkers of known sequence that serve as primers for amplification of the aptamer by PCR or other methods are covalently attached to the DNA in the aptamer pool as follows. 1.0 mole of aptamer obtained as described in Section 1 (about 21 ng of which corresponds to about $6.0 \times 10^{14}$ molecules) is added to a solution containing 1 nmole of linker 1 which contains 40 nucleotide residues (about 14 g) and 1 nmole of linker 2 (about 14 g). Linker 1, which will be ligated to the 5' end of the aptamer and consists of a pool of 256 different species, has the structure shown below. Four random sequence residues at the 5' end of strand A of linker 1 gives rise to the 256 different species. Four random sequence residues at the 3' end of strand C of linker 2 result in a pool of 256 linker 2 species.

--- linker 1:

3' HO-ACGCCGCGGTACTTACGC-N—N—N—N—OH 5' strand A
5' biotin-TGCGGCGCCATGAATGCG-OH 3' strand B
Linker 2 has the following structure.
linker 2:

5' HO-AGCGGCCGCTCTTCTAGA-N—N—N—N—OH 3' strand C
3' HO-TCGCCGGCGAGAAGATCT-OPO3 5' strand D
The linker 1 sequence: 5' GAATGC 3' CTTACG

--- is the recognition sequence for cutting restriction enzyme Bsm I, which cuts as denotes the cut site in each strand):

5' GAATGCNx
3' CTTACxGN

Positioning of the BspMI site as shown in linker 1 permits subsequent precise removal of the attached linker from the aptamer after amplification. The linker 2 sequence:

5' CTCTTC 3'
3' GAGAAG 5' is the recognition sequence for cutting by the restriction enzyme Ear I, which cuts as follows (x denotes the cut site in each strand):

5' CTCTTCNx
3' GAGAAGNNNNx

Positioning of the Ear I site as shown in linker 2 permits subsequent precise removal of the attached linker from the aptamer after amplification.

Nucleotide residues labeled N are random A, T, G or C residues and serve to anneal with the terminal four bases at the 5' end, linker 1, and 3' end, linker 2, of each aptamer. Perfect matches between the random linker bases and the terminal four random bases of the aptamer permit annealing and ligation of the linkers to the aptamer. The ligation reaction is carried out in a 300 l volume using 1,000 units of T4 DNA ligase (New 5' GAATGC 3' CTTACG by the follows (New England Biolabs, Catalog No. 202CL) in standard reaction buffer (50 mM tris-HCl, pH 7.8 AT 20 C., 10 mM magnesium chloride, 20 mM dithiothreitol, 1 mM ATP, 50 g/ml bovine serum albumin) at 12 C. for 12 to 18 hours. The molar ratios of linker to matched aptamer end is approximately 1000:1, which drives the ligation reaction toward ligation of all aptamers in the pool. This ratio arises from input aptamer, 1 mole, that has 0.0039 mole of any given 4 base sequence at either end. 0.0039 nmole of either linker with a given 4 base overhang is present resulting in the 1000:1 ratio. For aptamers that have an end which participates in aptamer structure and/or binding, later rounds of selection and amplification will be enriched in species that have a nonrandom sequence at one or both ends. In this case, the ratio of specifically matched linker and aptamer will decrease by as much as 100 fold or more. Subsequent rounds of selection and amplification may then be carried out using linkers that reflect predominant aptamer end sequences to restore the ratio to a value near 1:1000. The conditions described generate aptamers with linkers covalently linked to each end. The ligation reaction generates two products. The first product is linker 1 ligated to the 5' end of the aptamer with linker 2 ligated to the 3' end of the aptamer. The second product is linker 2 ligated to itself to give a dimer. The dimers are removed by adding solid agarose-avidin support (Vector Labs, Inc. Catalog No. A2010), 2 mg of avidin per ml support with avidin linked to the support to the ligation reaction. Biotin attached to linker 1 strand A binds to the avidin solid support, permitting separation of dimers from aptamers with linkers covalently attached. The support is pelleted and washed three times in buffer (10 mM NaCl, 10 mM Tris-HCl, pH 7.5, 1 mM EDTA) to remove dimers and unligated linkers synthesized using linker strand C as a primer. The column is heated to 95 C. to melt off the aptamer complement.

The following method to separate linker dimers from the aptamer pool alternatively way be utilized. For example, E. coli polymerase I (New England Biolabs, Catalog Nos. 209L or 210L) is used to synthesize aptamer and strand B complement, using strand C as the primer. The resulting duplex aptamer-linker and complement is then separated from linker dimers using an avidin column by washing at room temperature. The complement containing flanking linker is eluted by heating to 94 C. and washing.

Protocols for adding linkers to only one end of an aptamer and amplifying it follow. For example, in a preferred embodiment, a pool of a very long linkers (several hundred nucleotides of known double stranded sequence having one 3' overhang (4 bases long) of random sequence at the 3' end of aptamer) is generated. This pool of linkers may be used to drive 3' ligation to the aptamer pool. Chain extension from the 3' overhang generates the aptamer complement. Standard blunt end ligation may then be used to circularize the double stranded structure. The structure then is cut using a restriction site in the linker, preferably one with an 8 base recognition sequence (to reduce the percentage of aptamers cut). Aptamers are then amplified using PCR or other known methods. In this method, the primers obviously may be placed anywhere within the large linker region, permitting amplification of only desired lengths of linker. Obviously, the long linker described above could be a replicon and directly used to generate an aptamer clone bank by transforming a desired host. For related protocols see PCR Technology, Principles and Applications for DNA Amplification, Chapter 10, p. 105–111 (Henry A. Erlich, ed. 1989) Stockton Press. For another variation which may be adapted see Eun H.-M., and Yoon, J.-W., Biotechniques (1989) 7:992–997. A less preferred (because yields are lower) embodiment for attaching a linker to a single stranded aptamer would be ligation of single stranded linker to single stranded aptamer.

D. PCR Amplification of Aptamers With Flanking Primer Sequences

The selected DNA is amplified via PCR using the following conditions: 1 nmole of each primer, 250M dNTPs (containing 20 Ci of dCTP, DGTP and dATP-total 60 Ci) in 200 l of 10 mM Tris pH 8.3 containing 50 mM KCl and 1.5 mM $MgCl_2$'. The reaction is sealed with mineral oil. This reaction is put through 15 cycles of amplification. One cycle of PCR amplification is carried out by bringing the temperature to 94 C. for 1 minute. This time is extended to 2 minutes for the initial denaturation step. The denaturation step is 60 C. for 1 minute. The hybridization step is 72 C. for 1 minute and then back to 94. After 15 cycles, the temperature is left at 72 C. for 2 minutes to completely fill in all primed single stranded regions. Upon completion, the mineral oil is removed by extraction with $CHCl_3$. The solution is then vortexed and separated via centrifugation. The aqueous layer is removed and concentrated via n-butanol extraction-final volume 100 pL. The $^{32}P$ labeled DNA is then passed over a Sephadex G50 Nick column (Pharmacia) equilibrated in 100 mM Tris pH 7.5/100 mM NaCl to remove unincorporated primer and dNTP's. The eluent is then applied to a 400 l avidin-agarose matrix (two applications results in >90% retention of the input). The matrix is extensively washed to remove contaminants and the single strand aptamers are eluted with 2 600 l washes of 0.15N NaOH. The aptamer solution is neutralized with acetic acid to pH 6 and concentrated via n-butanol extraction to 40% of the initial volume. The material is precipitated with 1 l of a 20 mg/ml glycogen solution (Boehringer Mannheim) followed by adding 3 volumes of absolute ethanol and cooling on dry ice for 15 minutes. The DNA is pelleted, washed with 70% ethanol and dried in vacuo. The material is resuspended in selection buffer as described above. The procedure is repeated with aptamer pools from subsequent rounds of selection on PGF columns.

E. Removal of Primers From the Amplified Aptamer Pool

Linker 2 is removed by digestion with Ear I (New England Biolabs, Catalog No. 528L) under recommended conditions using excess enzyme to insure complete cutting by the enzyme. Following Ear I digestion, the column is heated to 95 C. for 3 minutes to denature the aptamer complement-strand molecule followed by washing in TE buffer (10 mM Tris-HCl, pH 7.5, 1 mM EDTA) to remove all unbound strands.

The aptamer is removed from linker 1 strand A, which is bound to the agarose-avidin support, by suspending the support in 1 ml of BsmI restriction buffer (50 mM sodium chloride, 20 mM Tris-HCl, pH 7.4 at 20 C., 10 mM magnesium chloride, 10 mM 2-mercaptoethanol, 10 g/ml bovine serum albumin) and then annealing linker 1 strand A, followed by digestion with 300 units of BsmI enzyme at 65 C. for 1 hour. BsmI digestion releases the aptamer from linker 1 strand B which remains bound to the support by biotin-avidin binding. The resulting pool of sequences is referred to as round 1 aptamers because the pool has been selected once for aptamers that bind to the PGF molecule. The aptamer pool is then radiolabeled by incorporation of $^{32}P$ as described in Example 3-B. Alternatively, aptamers are labeled using radiolabeled nucleotide triphosphates during PCR amplification. The DNA is precipitated with ethanol as described in Example 3-D.

F. Chemical Linkage of Linkers to Aptamers with completely random sequences

Linkers are covalently coupled to the 5' end of aptamers obtained from column selection as described in Examples 3-A and 3-B. Aptamer DNA is synthesized with a free amine group at the 5' end. Amine phosphoramidite monomers are used to generate the 5' terminal amine-nucleoside residue (using equal amounts of A, T, G and C monomer at the final coupling step).

After selection and elution of DNA, the aptamer DNA is coupled to primer sequences as follows. Linker is coupled to the 3' end using linker 2 described in Example 3-C. Linker (carrying biotin at the 5' end) is attached to the aptamer free 5' amine group by chemical coupling between primer oligomer DNA with a free 3' phosphate group. The reaction is carried out for 4 hours at room temperature in 0.1M methylimidazole, pH 7.0 and 0.1M 1-(3-dimethylaminopropyl)-3-ethylcarbodiimide hydrochloride. The latter reagent acts as a water soluble condensing agent. The resulting aptamer contains the linkage, 5' X—O—P—$O_2$—NH—$CH_2$—Z 3', at the aptamer-linker junction; X is the 3' terminal residue of the linker and Z is the 5' terminal aptamer residue. Once linkers are attached at both ends of the aptamer, as described in the Examples above, PCR amplification is carried out and the DNA is attached to an avidin column. Free aptamer carrying a amino group at the 5' end is obtained by (i) digestion in excess Ear I enzyme, (ii) heat denaturing at 94 C., (iii) washing the column with TE, (iv) release of free aptamer after incubation of the column in 80% acetic acid for 4 hours at room temperature. The aptamers are then recovered by neutralizing with base and ethanol precipitation.

G. Linkers Containing a RNA Residue at the 5' Aptamer-Primer Junction

DNA oligomers containing even a single RNA nucleotide residue are sensitive to RNAses such as RNAse $T_1$ or $U_1$. $T_1$ and $U_1$ enzymes cleave specifically at guanine residues to yield two oligomers. One oligomer contains the RNA residue at the 3' end the phosphate group linked at the 3' position and the other oligomer contains a hydroxyl group at the 5' end. Cleavage of such an oligomer at the RNA residue is also possible by incubation of the oligomer in 0.1M NaOH for 30 minutes and yields essentially the same products as the $T_1$ or $U_1$ enzymes. RNAse sensitivity of DNA-RNA oligomers may be applied to selection and amplification of aptamers. Incorporation of an RNA residue (G*) at the 3' terminal position of linker I strand B (5' biotin-TGCGGCGCCATG AATGCG*-OH 3') will generate aptamer with a ribo-guanosine residue at the 5' end of the aptamer (i.e., at the primer 3' to 5' aptamer junction) when this oligomer is used to prime synthesis of aptamer using the complementary strand template. DNA polymerases have the capacity to initiate DNA synthesis from a free 3' hydroxyl group on either DNA or RNA oligomers. RNA-containing oligomer is synthesized using support bound protected G* monomer (Milligem/Biosearch, Catalog No. GEN 067570) that is used directly in a 1 mole scale DNA synthesis using phosphoramidite chemistry according to manufacturer's instructions.

Aptamer strands have the following structure. G* denotes the position of the guanine RNA residue. 5' biotin-TGCGGCGCCATGAATGCG*$N_{60}$TCTAGAAGAGCGGCCGCT-OH 3'

Aptamer selection for PGF2 target would be carried out as described in Examples 3-A through 3-D. DNA primers (strands B and C as described in Example 3-C) are attached to aptamer DNA eluted from the column and amplification using strand B of linker 1 with a ribosyl G residue at the 3' end is used as primer for synthesis of the aptamer strand containing an RNA residue in amplification. Removal of the linkers and recovery of aptamer would be accomplished by the following series of steps. The RNA containing strand has 5' biotin attached.

1. Ear I digestion to remove primer sequences at the 3' end of the aptamer,
2. heating to 94 C. for 2-3 minutes to denature the complementary strand,
3. washing the column to remove species released in steps 1 and 2,
4. aptamer release from the avidin column by $T_1$ RNAse digestion, and
5. recovery of aptamer from the column by washing and ethanol precipitation.

The aptamer thus obtained is then used in a subsequent round of selection on a PGF2 column. After recovery of aptamer from the column, DNA obtained in elution buffer washes is precipitated, and resuspended in buffer for kinase reaction and then ligated to flanking primer sequences as described. The kinase reaction prior to ligation of linkers is necessary to replace the 5' terminal phosphate group that is lost from the aptamer when $T_1$ digestion (or NaOH treatment) is carried out.

H. Selection of Aptamers With a 3' Bind That Does Not Participate in Target Molecule Binding or in Maintaining Aptamer Structure Aptamers are obtained as described in the Examples above, except that after two rounds of selection and amplification using aptamers without flanking primer sequences, alternate rounds of selection and amplification are carried out with linker left on the 3' end during a subsequent round of selection. The population of aptamers thus obtained bind to the PGF2 target regardless of the presence of linker at the 3' end. This population is a subset of all aptamers that bind to PGF2.

I. Selection of Aptamers With Several Bases of Known Base Sequence at One or Both Ends Aptamer DNA is synthesized as described in Example 3-B except that the 5' terminal four bases have a known sequence to generate a pool of aptamers with the following sequence 5' $PO_3$-AATTC$N_{55}$ 3'. A linker similar to linker 1 with the following structure is ligated to the 5' end of the aptamer, 3' HO-$X_{17}$CTTAAG-OH 5'
5' biotin-$X_{17}$G-OH 3' and linker 2 of Example 3-C is ligated to the 3' end of the aptamer pool after elution from target molecules. Ligation of this linker to the aptamer creates a EcoRI site and cutting of the aptamer with EcoRI releases aptamer without addition or deletion of any residues. The use of restriction enzymes such as EcoRI are preferred in the 5' linker because cutting occurs on short double stranded regions that carry the recognition site (such as the double stranded region that occurs when aptamer is removed from the avidin column by restriction enzyme cutting after removal of the 3' linker and complementary strand). Other restriction sites such as that for Hind III, or Xba I which leave a four base 5' overhang may be created and used at the 5' end to leave 5 bases of known sequence. Creation of a site for enzymes that leave either 2 (Cla I) or 0 (Pvu II) base 5' overhangs, respectively, will generate aptamers with 4 or 3 bases of known sequence at the 5' end of the aptamer. Sites created and used in this manner at the 3' end require the use of enzymes that leave a 0 (Sma I), 2 (Pvu I) or 4 (Apa I) base 3' overhang after cutting to generate aptamers with 3, 4 or 5 bases respectively at the 3' end with known sequence. If both ends of the aptamers have known sequences that constitute part of a restriction enzyme site, then the sites at the ends must differ from each other so that the linkers can be removed separately after amplification.

J. Selection of Aptamers Starting From a Pool of Aptamers That Vary in Length

Eleven pools of aptamers of random sequence are synthesized which vary in length from 50 to 60 bases for each pool. Equal molar amounts of each pool is mixed and the variable length pool is then used to select for aptamers that bind to PGF2 as described in Examples 3-B through 3-E or 3-I above.

Example 4

Preparation of Aptamers Specific for Cell Surface Proteins

A. CD4

The human lung fibroblast-like cell line, CCD-18LU (American Type Culture Collection No. CCL205), is transfected with the human CD4 gene cloned into an expression vector. Cells stably expressing human CD4 protein are obtained by standard methods for transfecting cells and obtaining clones (see Molecular Cloning: A Laboratory Manual Cold Springs Harbor, 1989). In this case, the bacterial neomycin phosphotransferase is coexpressed from the CD4 vector, permitting selection for cells carrying the vector in the antibiotic G418 (Gibco). The resulting cell line expressing CD4 is called CD4$^+$. A pool of aptamers consisting of 60 bases of random sequences flanked by 18 base primer sequences is obtained by standard solid phase synthesis techniques ("Oligonucleotide Synthesis—A Practical Approach", ed. M. J. Gait, IRL Press 1984). Next, 0.1 to 1 nmoles of aptamer are added to 6 ml of tissue culture medium (minimum Essential medium (Eagle)] without fetal bovine serum. Two confluent 10 cm tissue culture plates of CCD-18LU cells are washed twice in 5 ml medium lacking serum followed by addition of 3 ml of medium containing the aptamer pool. The plates are left at 37 C. for 30 minutes. Medium from the two CCD-18LU plates is then recovered and pooled.

The recovered aptamer in medium is added to 2 confluent plates of CD4$^+$ cells previously washed twice in 5 ml per wash of medium lacking serum. The plates are left at 37 C. for 30 min. After incubation, the plates are washed two times in medium and one time in saline using 5 ml per wash. The CD4$^+$ cells are then treated with trypsin (1.5 ml trypsin 0.01% solution in 10 mM EDTA) for 30 minutes at 37 C. The medium containing cells is briefly spun to pellet out the cells. The aptamers are recovered by ethanol precipitation and amplified. The procedure is repeated 3 to 6 times to enrich for aptamers that specifically bind to the CD4 cell surface protein. Binding to CD4 is monitored by measuring the amount of radiolabeled aptamer that is retained after binding to CD4$^+$ cells. Radiolabeled aptamers are obtained by a standard kinase reaction using -$^{32}$P-ATP to label the 5' end of aptamer after amplification. Alternatively, radiolabeled nucleoside triphosphates can be obtained by using PCR amplification to label the aptamer pool. The binding assay (positive selection) uses 0.1 nmole of labeled aptamer (approximately 3.4 g) binding to one confluent plate of CD4$^+$ cells for 30 min at 37 C., followed by two washes in medium and one saline wash. The retained radioactivity is determined by scintillation counting of cells lysed in 1 ml of it sodium dodecyl sulfate, 10 mM Tris pH 7.2, 10 mM EDTA. 0.05 ml of lysate is counted in a scintillation counter using standard methods and reagents (Aquasolve, New England Nuclear). Selection and amplification is continued until at least three rounds have been completed. After the third round and subsequent amplification rounds, 30–50 individual aptamers from the amplified pool are cloned and sequenced using a convenient vector such as pBluescript (Promega Biotech) and double-stranded dideoxy sequencing. Alternatively, pools of 10–20 individual clone sequences may be sequenced. When DNA sequencing reveals regions of conserved sequences, individual clones are synthesized and examined for their binding characteristics. The aptamers may be tested for their capacity to block the binding of HIV to T-cell lines such as SupTI or HUT-78 (Evans, L. A., et al., J. Immunol. (1987) 138:341S–3418) that are susceptible to infection.

Individual aptamer isolates or small pools consisting of 10 to 50 individual aptamer species that reduce HIV infectivity are used to identify optimal species for blocking HIV infectivity by interfering with the binding interaction between gp120 and CD4. Disruption of this interaction has been previously shown to reduce HIV infectivity (Clapham et al., Nature (1989) 337:368–370). After identification of optimal CD4 aptamer species, further modifications such as inclusion of covalent crosslinking base analogs (such as aziridinylcytosine as disclosed in copending commonly assigned application Ser. No. 529,346, incorporated herein by reference) or other substituents to enhance the efficacy of the aptamer are then tested in order to further improve the aptamer for therapeutic or diagnostic uses. Lead aptamer species identified on the basis of blocking HIV infectivity are also then modified by inclusion of terminal internucleotide linkage modifications that render the oligonucleotide substantially nuclease resistant. Methods to stabilize oligonucleotides are disclosed in publication number WO90/15065, and commonly assigned copending U.S. application Ser. No. 482,943, incorporated herein by reference.

B. HER2

HeLa cells stably transfected and expressing the gene for the HER2 oncogene referred to herein as the HER2 cell line are grown to confluency and washed two times with phosphate-buffered saline. Single-stranded oligonucleotide is generated by the random incorporation of 60 nucleotides between two primer binding sites using standard solid-phase synthesis techniques essentially as described in "Oligonucleotide Synthesisa Practical Approach" (IRL Press 1984, ed. M. J. Gait). Approximately 5×10$^6$ to 1×10$^7$ cells are then incubated with 2 to 5 ml of tissue culture medium containing 0.1 to 1 nmoles of oligonucleotide at 37 C. at a pH in the range of 7.0 to 7.4 containing between 1–5 mM of divalent cations, such as magnesium or calcium. After 1–2 hours of incubation, oligonucleotides which have binding specificity for any cell surface proteins, and structure including the target HER2 glycoproteins, are then released from the cell by cleavage with trypsin (or other protease which is capable of cleaving, and thereby dissociating from cells, the protein target of interest) in buffered saline. (Evans et al., J. Immunol. (1987) 138:3415–3418; Hoxie et al., Science (1986) 234:1123–1127).

Aptamers and cell proteins released by protease cleavage are then digested for an additional 30 minutes at 37 C. with protease to extensively degrade all cellular proteins. This process may be aided by a brief heat step (80 C. for 3 minutes) followed by readdition of fresh protease such a pronase (Sigma Chemical Company, catalog no. P4914). Alternatively, a protease from the thermophilic bacterium (Sigma Chemical Company, catalog no. P1512) may be used to aid recovery of aptamers from cell proteins. After digesting with enzymes, the aptamers recovered from binding to HER2 cells are recovered by precipitation with ethanol using glycogen as a carrier. The aptamers are then resuspended in medium (3 ml) and incubated with 5×10$^6$ HeLa cells for about 60 minutes. Cellular supernatants are recovered, and the oligonucleotides precipitated from the serum-free culture medium after adding 200 to 800 g glycogen (Boehringer Mannheim) followed by the addition of two volumes of ethanol.

The thus-recovered oligonucleotides, which form a reduced pool with cell surface protein binding specificity, are amplified using PCR techniques. The cycle is repeated 4–7 times followed by cloning of individual aptamer species. The sequences of individual clones are determined by standard methods. Individual aptamers are then synthesized and tested for binding by the method described in Example 4-C.

C. IL-1

The human HeLa cell line is transfected with two different genes to generate two lines that express the inserted gene. The first gene is the human IL-1 receptor (Sims et al., Proc. Natl. Acad. Sci. (1989) 86:8946–8950), giving rise to the IL-1R cell line and the second gene is the IL-1 receptor that has been genetically engineered by standard techniques to express IL-1R that has been mutated in the extracellular domain, giving rise to the IL-1Rm cell line. Transfected clones expressing each receptor are identified by immunoprecipitation using polyclonal antibodies against the IL-1R protein.

Aptamers that specifically bind to the IL-1Rm molecule at the cell surface are obtained by selection using the IL-1Rm cell line. The procedure starts with a pool of aptamers containing 60 random bases flanked by 18 base primer sequences as described above. Two confluent plates containing about 8,000,000 IL-1R cells are incubated with a total of 0.1 nmole of aptamer in a total of 4 ml of tissue culture medium lacking serum. 0.1 nmole of aptamer pool is estimated to contain approximately 6×10$^{13}$ different aptamer species, having a mass of approximately 3.4 g. The estimates of molecule numbers is based on the estimated molecular weight of 33,600 for a 96-mer. Each base residue in the aptamer has an average molecular weight near 350 da. The aptamer pool size may be reduced by as much as 10-fold if the initial DNA synthesis does not provide fully random sequences due to uncharacterized biases in the synthesis and purification steps.

The cells are washed three times in medium lacking serum prior to adding the aptamer pool. The IL-1R cells are incubated for 30 minutes at 37 C. followed by recovery of the medium containing aptamers from the cells. The aptamers in solution are then added to washed IL-1Rm cells and incubated for 30 minutes at 37 C., followed by three washes in medium lacking serum followed by three washes in buffered saline. The cells are then trypsinized for 30 minutes at 37 C. and intact cells are pelleted by a brief spin. Aptamers are recovered from the supernatant after enzyme digestion or heating by precipitation and amplified by standard PCR methods. The process is repeated using 0.1 nmole of amplified aptamer pools at the start of each round of selection.

Enrichment for aptamers that specifically bind to the IL-1Rm protein is monitored by measuring the binding of selected aptamer pools to IL-1Rm cells by the following method. Aptamers obtained after 6 rounds of selection and amplification are modified according to methods disclosed herein and in copending and commonly assigned application Ser. No. 07/594,147, filed Oct. 9, 1990, which application is incorporated herein by reference. Biotin is covalently attached at the 5' end via linkage to N-ethyl-diethanolamine linked to the 5' nucleotide of each aptamer in the amplified pool. Alternatively, aptamers labeled for chemiluminescent detection may be synthesized and used for in situ detection of bound aptamers (Bronstein et al., Clin. Chem. (1989) 35:1856; Bronstein et al., Anal. Biochem. (1989) 180:95). Aptamers attached to target IL-1Rm molecules on IL-1Rm cells are then assayed by standard protocols using avidin and biotinylated enzymes such as alkaline or acid phosphatases. Methods for detection of nucleic acids by enzymatic methods are generally described in numerous publications (Urdea et al., Nucleic Acids Res. (1988) 16:4937–4956; Gillam, Tibtech (1987) 5:332–334). Pools containing a significant proportion of aptamers that specifically bind to the IL-1Rm target are detected by incubating a washed, confluent IL-1Rm tissue culture plate containing about $5 \times 10^{-6}$ cells with 0.01 nmole of labeled aptamer from the selected pool mixed with 0.1 nmole of unlabeled aptamer from the initial random pool for 30 minutes at 23 C. After incubation, the plate is washed three times in buffered saline and bound labeled IL-1Rm aptamer is detected enzymatically. The presence of nitroblue tetrazolium dye (Gillam, Tibtech (1987) 5:332–334) indicates the presence of bound aptamer. Specific binding of selected aptamer is verified by coincubation of 0.01 nmole of labeled selected aptamer with 0.1 nmole of unlabeled selected aptamer for 30 minutes at 37 C. The unlabeled aptamer will compete with labeled aptamer and will reduce the enzyme generated dye production by about 70 to 95%. A control plate of IL-1R cells incubated with labeled selected aptamer alone and in mixture with the initial pool of unselected aptamer is included to demonstrate that binding is specific for the IL-1Rm molecule. Little or no binding of selected aptamer is observed on control IL-1R cells.

After a pool of aptamers that efficiently binds to the IL-1Rm molecule is identified, individual clones are obtained and sequenced by standard protocols (Chen et al., DNA (1985) 4:165–170). Individual aptamers are then synthesized and tested for their capacity to bind to the IL-1Rm molecule.

Aptamers that bind IL-1Rm efficiently but that do not bind to IL-1R are binding to structures in IL-1Rm that are present due to the mutation engineered into the parent IL-1R molecule. This type of selection procedure can be adapted to naturally occurring mutations, such as translocations that are correlated with pathological conditions. Protein structures uniquely associated with a mutation may be used to generate aptamers that specifically bind to those structures. Such aptamers would be useful for both diagnostic and therapeutic applications.

D. Serum-Enhanced IL-1 Selection

Aptamers which bind to IL-1R can be obtained by following a protocol as described in Example 15 above except that HeLa is used as the control cell line and the target is the IL-1R molecule on the IL-1R cell line. Nonradioactive methods can be used to detect bound aptamers.

In a variation of this protocol, aptamer recovered from the HeLa control cells is incubated with IL-1R cells in serum-free medium for 15 minutes at 37 C., then prewarmed calf serum is added to give a final concentration of 10% and incubate an additional 15 minutes. The serum contains enzymes that degrade aptamers that are not tightly bound to target molecules. The serum will enhance selection for aptamers that are not nuclease sensitive due to their tight association with IL-1R. After incubation, the cells are washed twice in medium without serum and once in saline, and aptamers are recovered and amplified.

Example 5

Selection of Aptamers that Bind to Factor X

A. Synthesis of Oligonucleotide Pool

DNA oligonucleotides containing a randomized sequence region were synthesized using standard solid phase techniques and phosphoramidite chemistry (Oligonucleotide Synthesis, Gait, M. J., ed. (IRL Press), 1984; Cocuzza, A., Tetrahedron Letters, (1989) 30:6287–6291). A 1M small-scale synthesis yielded 60 nmole of HPLC-purified single-stranded randomized DNA. Each strand consisted of specific 19-mer sequences at both the 5' and 3' ends of the strand and a random 30-mer sequence in the center of the oligomer to generate a pool of 68-mers with the following sequence (N=G, A, T or C):

5' TCTCCGGATCCAAGCTTATN$_{30}$CGAATTCCTCGAGTCTAGA 3'

DNA 19-mers with the following sequences were used as primers for PCR amplification of oligonucleotide sequences recovered from selection columns. The 5' primer sequence was 5' TCTCCGGATCCAAGCTTAT 3' and the 3' primer sequence was 5' biotin-O-TCTAGACTCGAGGAATTCG 3'. The biotin residue was linked to the 5' end of the 3' primer using commercially available biotin phosphoramidite (New England Nuclear, Cat. No. NEF-707). The biotin phosphoramidite is incorporated into the strand during solid phase DNA synthesis using standard synthesis conditions.

B. Isolation of Factor X Aptamers Using Factor X Immobilized on a Lectin Column

A pool of aptamer DNA 68 bases in length was synthesized as described in Example 5-A, and then PCR-amplified to construct the initial pool. An aliquot of the enzymatically-synthesized DNA was further amplified in the presence of -$^{32}$P-dNTPs to generate labeled aptamer to permit quantitation from column fractions.

A Factor X column was prepared by washing 1 mL (58 nmole) agarose-bound concanavalin A ("Con-A") (Vector Laboratories, cat. no. AL-1003) with 20 mM Tris-acetate buffer (pH 7.4) containing 1 mM MgCl$_2$, 1 mM CaCl$_2$, 5 mM KCl and 140 mM NaCl (the "selection buffer") (4×10 ml). 1 ml of settled support was then incubated overnight at 4 C. in 10 mL selection buffer containing 368 g (6.24 nmole) Factor X (Haematologic Technologies Inc, Cat No. HCXA-0060). After shaking overnight to permit Factor X binding to the Con-A beads, the mixture was briefly centrifuged and the supernatant removed. The beads were resuspended in fresh selection buffer and transferred to a column which was then washed with selection buffer (5×1 mi). A column containing 1 mL of settled beads had a void volume of approximately 300 L. A control Con-A column was prepared by adding 1 mL of settled support to a column followed by 5 washes of 1 mL of selection buffer.

Prior to application of the aptamer DNA pool to Con-A columns, the DNA was heated in selection buffer at 95 C. for 3 minutes and then cooled to room temperature for 10 minutes. The pool, consisting of 100 mole DNA in 0.5 mL selection buffer, was then prerun on the control Con-A column at room temperature to remove species that bound to the control support. Three additional 0.5 mL aliquots of selection buffer were added and column fractions 2, 3 and 4 (0.5 mL each) were pooled and then reapplied to the column twice. The DNA in 1.5 mL selection buffer was then recovered. Approximately 16% of total input cpm were retained on the column.

The recovered DNA was then applied to a Con-A-Factor X column as a 0.5 mL aliquot followed by a 1.0 mL aliquot. Flow-through was retained and reapplied to the column twice. DNA added to the column on the final application was left on the column for 1 hour at room temperature. The column was then eluted with 0.5 mL aliquots of selection buffer. 0.5 mL fractions were collected and radioactivity was determined in each fraction. Radioactivity in eluted fractions 7 through 12 were low and relatively constant. After recovery of fraction 12, the column was washed with 0.5 mL aliquots of 0.1M -methyl-mannoside (Sigma Cat. no. M-6882) in selection buffer to elute the bound Factor X along with Factor X-bound aptamers. Fractions 14 and 15 showed a significant peak of Factor X protein level, as determined spectrophotometrically by Bradford protein stain (Bio-Rad, Cat No. 500-0006). 0.0851 of the input DNA eluted in these two fractions.

Aptamer DNA (Round 1 DNA) was recovered from the Factor X by phenol extraction (2×0.5 mL). The aqueous phase volume was reduced to about 250 l by n-butanol extraction. Aptamer DNA was precipitated on dry ice using 3 volumes of ethanol and 20 g of glycogen as a carrier. The DNA was pelleted, washed once in 70% ethanol and then dried.

C. Amplification of Factor X Selected Aptamers

Round 1 DNA from Example 5-B was resuspended in 100 L of $H_2O$ and amplified by PCR. A 200 L PCR reaction consisted of the following: 100 L template 96-mer DNA (approximately 0.01 moles); 20 l 10×buffer (100 mM Tris-Cl (pH 8.3), 500 mM KCl, 20 mM $MgCl_2$); 32 l dNTP's (5 mM conc total, 1.25 mM each dATP, dCTP, DGTP, and dTTP); 20 l primer 1 (biotinylated 18-mer, 50M); 20 L primer 2 (18-mer, 50M); 6 l - $^{32}$P-dNTP's (approximately 60 Ci); and 4 L Taq I Polymerase (20 units). The reaction was covered with 2 drops NUJOL mineral oil. A control reaction was also performed without template aptamer.

Initial denaturation was at 94 C. for 3 minutes, but subsequent denaturation after each elongation reaction lasted 1 minute. Primer annealing occurred at 56 C. for 1 minute, and elongation of primed DNA strands using the Taq polymerase ran at 72 C. for 2 minutes, with 5-second extensions added at each additional cycle. The final elongation reaction to completely fill in all strands ran for 10 minutes at 72 C., and the reaction was then held at 4 C.

18 rounds of Taq polymerase elongation were carried out in order to amplify the selected aptamer DNA. After the reactions were completed, the aqueous layer was retrieved and any residual NUJOL oil was removed by n-butanol extraction, reducing the volume to 100 L. A sample may be removed from each of the aptamer and control reaction for quantitation and analytical PAGE. The amplified aptamer pool (100 go was fractionated over a Nick column (G-50 Sephadex, equilibrated with 3 mL TE buffer (10 mM TrisHCl (pH 7.6), 0.1 mM EDTA)) to remove unincorporated NTP'S, primers, and salt. 400 L of TE buffer was then added to the column and the DNA pool was eluted from the column with an additional 400 l using TE buffer. (A sample may be removed from the eluent for quantitation and analytical PAGE.) The eluent (400 L) was loaded on an avidin agarose column (Vector Laboratories, Cat. No. A-2010) (500 l settled support, washed with 3×1 mL Tris/NaCl buffer (0.1M Tris, 0.1M NaCl, pH 7.5)). Approximately 90% of the loaded radioactivity remained on the column. The column was washed with Tris/NaCl buffer (4×400 L) and then the nonbiotinylated strand was eluted with 0.15N NaOH (3×300 L fractions). More than 45% of the radioactivity on the column eluted in these three fractions. These fractions (900 L) were combined and neutralized with approximately 5.5 L of glacial acetic acid. The neutralized fractions were reduced to 250 L by speed vacuum or butanol extraction and the nucleic acids were precipitated with ETOH. The resultant pellet was dissolved in 102 L selection buffer. A 2 L sample was removed for quantitation and analytical PAGE. The resulting amplified Round 1 Pool was applied to a new Con-A-Factor X column as in Example 5-B to obtain Round 2 aptamers.

D. Characterization of Round 1 Through Round 11 Factor X Aptamers Obtained from Selection on Lectin Columns Eleven rounds of Factor X aptamer selection and amplification were carried out using Con-A-Factor X columns as in Examples 5-B and 5-C. As shown in Table 3, the -methyl-mannoside eluate in fractions 14 and 15 contained a maximum of about 18% of input DNA at selection round 11 using the described conditions.

TABLE 3

| % DNA eluted by | % DNA bound to | |
| --- | --- | --- |
| Round | -methyl-mannoside* | control support |
| 1 | 0.085 | 14.0 |
| 2 | 1.400 | 37.0 |
| 3 | 14.000** | 27.0 |
| 4 | 1.800 | 21.0 |
| 5 | 1.100 | 18.0 |
| 6 | 1.500 | 10.5 |
| 7 | .620 | 4.8 |
| 8 | 1.100 | 10.6 |
| 9 | 1.500 | 12.1 |
| 10 | 5.700 | 2.8 |
| 11 | 17.800 | 19.0 |

*0.1M -methyl-mannoside in selection buffer was added beginning at fraction 13 in each elution, and fractions 14 and 15 were retained and the DNA amplified. Fraction 16 was also included in rounds 7–11. Due to slow leeching of Factor X from the column, DNA bound to Factor X could also be seen in earlier fractions in rounds 10 and 11.
**A high proportion of DNA was bound in round 3 due to a low input ratio of DNA to Factor X.

After amplification, approximately 5 picomoles of radiolabeled round 11 aptamer DNA was analyzed for specificity in a filter binding assay. In this assay, nitrocellulose filters (1 cm diameter) presoaked in selection buffer overnight at 4 C. and DNA in 100 l of selection buffer was incubated at room temperature for 10 minutes with: (1) An unselected 68-mer oligonucleotide DNA pool, (2) unselected DNA with Factor X (1M), (3) Round 11 aptamer DNA and Factor X (1M), and (4) Round 11 aptamer DNA alone. The filters were then washed 3 times with 3.0 mL of selection buffer at 37 and radioactivity was counted to determine the amount of DNA that was retained as a Factor X complex. The results are shown in Table 4.

TABLE 4

| DNA | A DNA Bound to Filter |
|---|---|
| Unselected 68-mer | 1.2 |
| Unselected 68-mer + Factor X | 1.3 |
| Round 11 aptamer + Factor X | 24.6 |
| Round 11 aptamer | 0.9 |

Unselected DNA did not show significant binding to the Factor X while selected aptamer DNA bound to Factor X. Binding results show specific Factor X binding. Based on the filter binding results in Table 10, a $K_D$ of approximately 2 m can be estimated for the round 11 pool.

Example 6

Selection of Aptamers that Bind to Thrombin

Thrombin has a heparin binding region, which is a locus of positive charge. Heparin is a polyanion which has a large number of negatively charred sulfate groups. We have postulated that DNA may bind to thrombin at the heparin binding region(s). The precise theoretical explanation of this phenomenon is not entirely clear, however, and the inventors do not wish to be bound to any particular theory. Characteristics of thrombin, including its heparin binding region(s) are well described in The Thrombin. Vols. 1 and 2, (CRC Press, Inc. (R. Machovich, Ed. (1984)). Also described therein are the targets (protein, cellular and "surfaces") to which thrombin binds.

Thrombin is a multifunctional enzyme which may react with several proteins and cells (via receptors). Its targets include plasma protein, including fibrinogen and Factors V, VIII and IX, platelets, and endothelial cells. The regulatory activities of thrombin and the thrombin structures associated therewith will be discussed briefly to illustrate the utility and application of this invention to drug discovery.

Thrombin is well-known to convert fibrinogen to fibrin in the process of clot formation. In the presence of thrombin and calcium ions, plasma Factor XIII is converted to an enzyme (Factor XIIIa). When Factor XIIIa is formed, it establishes cross-links between the gamma chains of fibrinogens. Thrombin also catalyzes the proteolysis of the single chain Factor V by cleaving the parent molecule into intermediates. It has also been demonstrated that thrombin at low concentration (in the absence of clots) activates Factor VIII in the fluid phase blood. Thrombin also generates Factor IXa activity from purified Factor IX. These activation processes are part of the positive feedback regulatory functions of thrombin. Thrombin also has negative feedback regulatory functions, since, for example, activation of Factor XIV results in the inactivation of Factor Va and VIIIa. By cleaving C3 and C5 to generate C3a-like and C5a-like fragments, thrombin causes platelet mediated activation of the complement system. Thrombin also is involved in the formation of enzyme-inhibitor complexes. Antithrombin III, -2-macroglobulin, -1-proteinase inhibitor and heparin cofactor II, all are substrates for thrombin.

Thrombin also reacts with cells and vessel walls. It is one of the most important triggers of platelet adhesion and aggregation. Thrombin binds via a specific receptor protein and this generates a signal response in the platelets. Heparin inhibits the binding of thrombin to platelets via enzyme-polysaccharide interaction. Accordingly, the binding site of thrombin for platelet and heparin is located in the same region of the enzyme. This suggests that aptamers made according to this invention may be linked or used in various combinations to regulate activity. Thrombin also binds to endothelial cells, resulting in prostacyclin release, protein C activation and inhibition of plasminogen activator activity.

Data in the literature suggests a model for the binding regions of thrombin. According to published data, the fibrinogen binding site extends over a large portion of the surface of the enzyme, which involves the low affinity platelet binding sites. The high affinity platelet binding site overlaps with the heparin binding site, which contains a specific lysine residue. The same lysine is necessary for the high affinity endothelial binding site. Little is known about the localization of the low affinity endothelial cell binding site.

Thrombin also stimulates DNA synthesis and cell division in nonproliferating fibroblasts. The binding of thrombin to fibroblasts involves regions of -thrombin which are distinct from the catalytic site. These sites are related to regions involved in fibrinogen recognition. Thrombin binding to fibroblasts stimulates the production and release of the surface associated glycoprotein fibronectin. Fibronectin operates in the coagulation system and in cellular motility, malignant transformation, cell-to-cell adhesion to collagen or fibrin-coated surfaces. These thrombin activities are integral to wound healing and tissue repair.

Thrombin also has been shown to be selectively immobilized by surface bound fibrin on erythrocytes and may interact with components of the complement system to affect lymphocytes. It also is known to bind hepatoma cells. Finally, thrombin is known to readily bind surfaces with negative charges. As previously mentioned, thrombin readily binds heparin and heparin-like molecules (e.g., heparinoids, glycosaminoglycans). Heparin is used clinically in the treatment and prevention of thrombolytic diseases. Moreover, bound thrombin does not lose its activity toward fibrinogen substrate. For example, thrombin bound to calcium phosphate retains its ability to clot fibrinogen. This characteristic may be applied to drug discovery.

In using the teachings of this invention to generate first and second-generation aptamers to thrombin, the role of heparin in coagulation and thrombolysis should be considered. Thrombin is inactivated by antithrombin III, and heparin has a role in this reaction. Two hypotheses have been postulated. According to the "inhibitor-fitting hypothesis," heparin binds to the inhibitor, thereby activating it. According to the "enzyme-fitting hypothesis," a thrombin-heparin interaction induces a conformational chance in the enzyme, rendering it more susceptible to the inhibitor. Data supports both hypotheses. Specifically, the binding of heparin to both thrombin and antithrombin III is tight: $K_d$ for thrombin is $1.5 \times 10^{-9}$ M, and for antithrombin III, the Kd is $4.4 \times 10^{-7}$ M. The modification of lysine or arginine residues of both thrombin and antithrombin III inhibits the rate-enhancing effect of heparin on the thrombin-antithrombin III reaction. Kinetic analyses also underline the primary importance of the thrombin-heparin interaction.

Since the reaction between thrombin and antithrombin III is accelerated by nonstoichiometric amounts of heparin, an apparent catalytic role of this polysaccharide has been suggested. Heparin qualitatively fulfills several criteria of a catalyst, to wit: binding nature (high affinity for proteins involved in the reaction), reaction rate enhancement (through increasing activation entropy), recyclization of the heparin molecule in the reaction, Michaelis-Menten saturation kinetics, and specificity (heparin accelerates only the inactivation of proteinases of blood coagulation by antithrombin III).

On the basis of these data, a model may be proposed for the role of heparin in the thrombin-antithrombin III reaction. Namely, thrombin binds to the nonspecific binding site of heparin, while antithrombin II binds to a specific one. The interactions result in a conformation change in the proteins as well as in the polysaccharide. Furthermore, reaction components on a surface, like heparin, are concentrated in an ordered structure. The interaction between the enzyme and its inhibitor is thereby facilitated, resulting in a minimum one order of magnitude rate-enhancement of the reaction. During the interaction of thrombin and antithrombin III several labile intermediates may form, although in the final complex thrombin is bound covalently to antithrombin III, resulting in the inactivation of the enzyme as well as the inhibitor. The final complex binds less tightly to heparin than thrombin or antithrombin III alone. As a result, heparin is released and the free polysaccharide reacts again with free enzyme and inhibitor molecules. Accordingly, there are five possible molecular effects in the mechanism of the heparin-enhanced inactivation rate of proteinase by its inhibitor. They are:

1. A conformational change in the thrombin molecule induced by heparin binding;
2. Alteration of the three-dimensional structure of antithrombin III in the presence of heparin;
3. An increase in the local concentration of the reactants on the "surface" of heparin;
4. Heparin orders the enzyme and inhibitor molecule into an adequate orientation;
5. The reaction pathways may be altered so that various labile intermediates of thrombin-antithrombin III complexes form in the presence of heparin as a catalyst.

Likely, multifunctional action is involved. Although the inventors do not wish to be bound to any particular theory, the state of the knowledge of heparin action may be considered in practicing this invention.

On a related point, the rate of inactivation of the other proteinases of blood coagulation by antithrombin III is also accelerated by heparin. Comparison and kinetic analysis of the inactivation of thrombin, Factor Xa, and plasmin demonstrates that the heparin-enzyme interactions are of primary importance in the rate enhancement of the antithrombin III reaction with proteinases of coagulation in the presence of heparin. The enzyme-fitting hypothesis and its extension to other proteinases is further supported by other data in the literature, especially since, besides thrombin, Factor Xa, plasmin, and other proteinases of blood coagulation have been shown to bind tightly to heparin. Several authors accept that the role of heparin in the reaction of the various proteinases with the inhibitor must be the same, or at least similar. Moreover, these actions may depend on the concentrations of heparin, as well.

As demonstrated by the discussion above, one of the important aspects of this invention is the recognition that aptamers having little to no predetermined sequence constraints should be identified and selected for. One cannot eliminate A priori the potentially deleterious effects of particular sequences which might arise in putative aptamers. For this reason, in the inventive methods for identifying aptamers according to this invention, one generates a completely random or substantially completely random pool of oligonucleotides to be incubated with the target. In particular, flanking regions of known sequence are minimized in length, or wherever possible, eliminated altogether.

Nothing herein is intended or should be construed as limiting this invention to the identification of first generation aptamers (i.e., those of entirely random, unknown or non-predetermined sequence). As one skilled in the art will recognize, once optimal binding aptamers are identified using these inventive methods, the aptamers may be sequenced and further studied to determine the nucleotide sequence(s) involved in function and/or determining conformation. Thereafter, second and third generation aptamers may be specifically designed therefrom, building on the structure/function determinants and designing in other desirable features or characteristics.

Targets such as thrombin which contain a net positive charge, either localized in a region or as reflected as an overall net positive charge present a particular problem in aptamer development. These results demonstrating the development of aptamers to thrombin may be extensible to other positively charged molecules, positively charged serum proteases and serum proteins, including immuno globulins, gamma globulin and human serum albumin. Prior art references disclosing aptamers have used only nucleic acid binding proteins as targets or dyes. To date, no protein target has been described which does not normally bind to DNA or RNA. This invention represents the first time aptamers have been generated to protein targets that do not normally bind nucleic acids.

A. Synthesis of Oligonucleotide Pool

DNA oligonucleotides containing a randomized sequence region were synthesized using standard solid phase techniques and phosphoramidite chemistry (Oligonucleotide Synthesis, Gait, M. J., ed. (IRL Press), 1984; Cocuzza, A., Tetrahedron Letters, (1989) 30:6287–6291). A 1 m small-scale synthesis yielded 60 nmole of HPLC-purified single-stranded randomized DNA. Each strand consisted of specific 18-mer sequences at both the 5' and 3' ends of the strand and a random 60-mer sequence in the center of the oligomer to generate a pool of 96-mers with the following sequence (N=G, A, T or C):

5' HO-CGTACGGTCGACGCTAGCN$_{60}$CACGTGGAGCTCGGATCC-OH 3'

DNA 18-mers with the following sequences were used as primers for PCR amplification of oligonucleotide sequences recovered from selection columns. The 5' primer sequence was 5' HO-CGTACGGTCGACGCTAGC-OH 3' and the 3' primer sequence was 5' biotin-O-GGATCCGAGCTCCACGTG-OH 3'. The biotin residue was linked to the 5' end of the 3' primer using commercially available biotin phosphoramidite (New England Nuclear, Cat. No. NEF-707). The biotin phosphoramidite is incorporated into the strand during solid phase DNA synthesis using standard synthesis conditions.

In another, similar experiment, a pool of 98-mers with the following sequence was synthesized:

5' HO-AGAATACTCAAGCTTGCCG-N$_{60}$-ACCTGAATTCGCCCTATAG-OH 3'.

DNA 19-mers with the following sequences can also be used as primers for PCR amplification of oligonucleotides recovered from selection columns. The 3' primer sequence is 5' biotin-O-CTATAGGGCGAATTCAGGT-OH 3' and the 5' primer sequence is

5' HO-AGAATACTCAAGCTTGCCG-OH 3'.

It will be noted that in all cases, the duplex form of the primer binding sites contain restriction enzyme sites.

B. Isolation of Thrombin Aptamers Using Thrombin Immobilized on a Lectin Column A pool of aptamer DNA 96 bases in length was synthesized as described in Example 6-A, and then PCR-amplified to construct the initial pool. A small amount of the enzymatically-synthesized DNA was further amplified in the presence of $-^{32}$P-dNTPs to generate labeled aptamer to permit quantitation from column fractions.

A thrombin column was prepared by washing 1 ml (58 nmole) agarose-bound concanavalin A ("Con-A") (Vector Laboratories, cat. no. AL-1003) with 20 mM Tris-acetate buffer (pH 7.4) containing 1 mM MgCl$_2$, 1 mM CaCl$_2$, 5 mM KCl and 140 mM NaCl (the "selection buffer") (4×10 ml). 1 ml of settled support was then incubated overnight at 4 C. in 10 mi selection buffer containing 225 g (6.25 nmole) thrombin (Sigma, Cat. no. T-6759). After shaking overnight to permit thrombin binding to the Con-A beads, the mixture was briefly centrifuged and the supernatant removed. The beads were resuspended in fresh selection buffer and transferred to a column which was then washed with selection buffer (5×1 ml). A column containing 1 ml of settled beads had a void volume of approximately 300 L. A control Con-A column was prepared by adding 1 ml of settled support to a column followed by 5 washes of 1 ml of selection buffer.

Prior to application of the aptamer DNA pool to Con-A columns, the DNA was heated in selection buffer at 95 C. for 3 minutes and then cooled on ice for 10 minutes. The pool, consisting of 100 mole DNA in 0.5 ml selection buffer, was then prerun on the control Con-A column at room temperature to remove species that bound to the control support. Three additional 0.5 ml aliquots of selection buffer were added and column fractions 2, 3 and 4 (0–5 ml each) were pooled and then reapplied to the column twice. The DNA in 1.5 ml selection buffer was then recovered. Approximately 1% of total input cpm were retained on the column.

The recovered DNA was then applied to a Con-A-thrombin column as a 0.5 ml aliquot followed by a 1.0 ml aliquot. Flow-through was retained and reapplied to the column twice. DNA added to the column on the final application was left on the column for 1 hour at room temperature. The column was then eluted with 0.5 ml aliquots of selection buffer. 0.5 ml fractions were collected and radioactivity was determined in each fraction. Radioactivity in eluted fractions 7 through 12 were low and relatively constant. After recovery of fraction 12, the column was washed with 0.5 ml aliquots of 0.1M -methyl-mannoside (Sigma Cat. no. M-6882) in selection buffer to elute the bound thrombin along with thrombin-bound aptamers. Fractions 14 and 15 showed a significant peak of thrombin enzyme activity, as determined spectrophotometrically by conversion of a chromogenic substrate (Kabi Diagnostica, Cat. no. S-2238). 0.01% of the input DNA eluted in these two fractions.

Aptamer DNA (Round 1 DNA) was recovered from the thrombin by phenol extraction (2×0.5 ml). The aqueous phase volume was reduced to about 250 1 by n-butanol extraction. Aptamer DNA was precipitated on dry ice using 3 volumes of ethanol and 20 g of glycogen as a carrier. The DNA was pelleted, washed once in 70% ethanol and then dried.

C. Amplification of Selected Thrombin Aptamers

Round 1 DNA from Example 6-B was resuspended in 100 l of H$_2$O and amplified by PCR. A 200 1 PCR reaction consisted of the following: 100 1 template 96-mer DNA (approximately 0.01 moles); 20 1 10×buffer (100 mM Tris-Cl (pH 8.3), 500 mM KCl, 20 mM MgCl$_2$); 32 1 dNTP's (5 mM conc total, 1.25 mM each dATP, dCTP, DGTP, and dTTP); 20 1 primer 1 (biotinylated 18-mer, 50M); 20 1 primer 2 (18-mer, 50M); 6 L $-^{32}$P-dNTP's (approximately 60 Ci); and 2 1 Taq I Polymerase (20 units). The reaction was covered with 2 drops NUJOL mineral oil. A control reaction was also performed without template aptamer.

Initial denaturation was at 94 C. for 3 minutes, but subsequent denaturation after each elongation reaction lasted 1 minute. Primer annealing occurred at 56 C. for 1 minute, and elongation of primed DNA strands using the Taq polymerase ran at 72 C. for 2 minutes, with 5-second extensions added at each additional cycle. The final elongation reaction to completely fill in all strands ran for 10 minutes at 72 C., and the reaction was then held at 4 C.

18 rounds of Taq polymerase elongation were carried out in order to amplify the selected aptamer DNA. After the reactions were completed, the aqueous layer was retrieved and any residual NUJOL oil was removed by n-butanol extraction, reducing the volume to 100 L. A sample may be removed from each of the aptamer and control reaction for quantitation and analytical PAGE. The amplified aptamer pool (100 L) was run over a Nick column (G-50 Sephadex, washed with 3 mL TE buffer (10 mM TrisHCl (pH 7.6), 0.1 mM EDTA)) to remove unincorporated NTP's, primers, and salt. 400 L of TE buffer was then added to the column and the DNA pool was eluted from the column with an additional 400 1 using TE buffer. (A sample may be removed from the eluent for quantitation and analytical PAGE.) The eluent (400 L) was loaded on an avidin agarose column (Vector Laboratories, Cat. No. A-2010) (500 L settled support, washed with 3×1 mL Tris/NaCl buffer (0.1M Tris, 0.1M NaCl, pH 7.5)). Approximately 90% of the loaded radioactivity remained on the column. The column was washed with Tris/NaCl buffer (4×400 l) and then the nonbiotinylated strand was eluted with 0.15N NaOH (3×300 1 fractions). More than 45% of the radioactivity on the column eluted in these three fractions. These fractions (900 1) were combined and neutralized with approximately 3.5 1 of glacial acetic acid. The neutralized fractions were reduced to 250 1 by speed vacuum or butanol extraction and the nucleic acids were precipitated with ETOH. The resultant pellet was dissolved in 102 1 selection buffer. A 2 1 sample was removed for quantitation and analytical PAGE. The resulting amplified Round 1 Pool was applied to a new Con-A-thrombin column as in Example 22 to obtain Round 2 aptamers.

D. Characterization of Round 1 Through Round 5 Thrombin Aptamers Obtained from Selection on Lectin Columns Five rounds of thrombin aptamer selection and amplification were carried out using Con-A-thrombin columns as in Examples 6-B and 6-C. As shown in Table 5, the combined fractions 14 and 15 contained a maximum of about 10% of input DNA using the described conditions.

TABLE 5

| % DNA eluted by | % DNA bound to | |
|---|---|---|
| Round | -methyl-mannoside* | control support |
| 1 | 0.01 | 0.7 |
| 2 | 0.055 | 1.9 |

TABLE 5-continued

| % DNA eluted by | % DNA bound to | |
|---|---|---|
| Round | -methyl-mannoside* | control support |
| 3 | 5.80 | 2.3 |
| 4 | 10.25 | 1.1 |
| 5 | 9.70 | 1.0 |

*0.1M -methyl-mannoside in selection buffer was added as fraction 13 in each elution, and fractions 14 and 15 were retained and the DNA amplified. Due to slow leeching of thrombin from the column, DNA bound to thrombin could also be seen in earlier fractions in rounds 3–5.

After amplification, round 5 aptamer DNA was analyzed for specificity in a filter binding assay. In this assay, nitrocellulose filters (1 cm diameter) prebound with salmon sperm DNA were used to bind either: (1) An unselected 96-mer oligonucleotide DNA pool, (2) unselected DNA with thrombin (60 mole), (3) Round 5 aptamer DNA and thrombin (60 mole), (4) Round 5 aptamer DNA alone, or (5) Round 5 aptamer DNA and ovalbumin (60 mole). In each case 3.5 mole of DNA was used and the incubation was in 200 L selection buffer at room temperature for 1 hour. The filters were then washed 3 times with 3.0 ml of selection buffer and radioactivity was counted to determine the amount of DNA that was retained as a thrombin complex. The results are shown in Table 6.

TABLE 6

| DNA | % DNA Bound to Filter |
|---|---|
| Unselected 96-mer | 0.08 |
| Unselected 96-mer + thrombin | 0.06 |
| Round 5 aptamer + thrombin | 20.42 |
| Round 5 aptamer | 0.07 |
| Round 5 aptamer + ovalbumin | 0.05 |

Unselected DNA did not show significant binding to the thrombin while selected aptamer DNA bound to thrombin. Binding results show specific thrombin binding with no detectable ovalbumin binding.

Round 5 aptamer DNA was then amplified using the following 3' primer sequence:

5' HO-TAATACGACTCACTATAGGGATCCGAGCTCCACGTG-OH 3' and the 5' 18-mer primer sequence shown in Example 21. The 36-mer primer was used to generate internal BamHI restriction sites to aid in cloning. The amplified Round 5 aptamer DNA was then cloned into pGEM 3Z (Promega). 32 of the resulting clones were then amplified directly using the following 5' primer sequence:

5' HO-CTGCAGGTCGACGCTAGC-OH 3' and the 3' biotinylated 18-mer primer sequence shown in Example 21, and then sequenced.

Filter binding assays using aptamer DNA from 14 of the clones were used to determine the dissociation constants ($K_D$) for thrombin as follows: Thrombin concentrations between 10 m and 1 nM were incubated at room temperature in selection buffer for 5 minutes in the presence of 0.08 mole of radiolabeled 96-mer derived from cloned Round 5 aptamer DNA. After incubation, the thrombin and aptamer mixture was applied to nitrocellulose filters (0.2 micron, 2.4 cm diameter) that were pretreated with salmon sperm DNA (1 mg/ml DNA in selection buffer) and washed twice with 1 ml selection buffer. After application of thrombin mixture, the filters were washed three times with 1 ml selection buffer. The radioactivity retained on the filters was then determined. $K_D$ values for the individual clones ranged from 50 to >2000 nM.

The DNA sequence of the 60-nucleotide randomly-generated region from 32 clones was determined in order to examine both the heterogeneity of the selected population and to identify homologous sequences. Sequence analysis showed each of the 32 clones to be distinct. However, striking sequence conservation was found. The hexamer 5' GGTTGG 3' was found at a variable location within the random sequence in 31 of 32 clones, and five of the six nucleotides are strictly conserved in all 32. Additionally, in 28 of the 32 clones a second hexamer 5' GGNTGG 3', where N is usually T and never C, is observed within 2–5 nucleotides from the first hexamer. Thus, 28 clones contain the consensus sequence 5' GGNTGG(N)ZGGNTGG 3' where z is an integer from 2 to 5. The remaining 4 clones contain a "close variant sequence" (a sequence differing by only a single base). A compilation of the homologous sequences are shown in FIG. 1. It should be noted that DNA sequencing of several clones from the unselected DNA population or from a population of aptamers selected for binding to a different target revealed no homology to the thrombin-selected aptamers. From these data we conclude that this consensus sequence contains a sequence which is responsible either wholly or in part, for conferring thrombin affinity to the aptamers.

Clotting time for the thrombin-catalyzed conversion of fibrinogen (2.0 mg/ml in selection buffer) to fibrin at 37 C. was measured using a precision coagulation timer apparatus (Becton-Dickinson, Cat. nos. 64015, 64019, 64020). Thrombin (10 nM) incubated with fibrinogen alone clotted in 40 sec, thrombin incubated with fibrinogen and P1 nuclease (Boehringer-Mannheim, Indianapolis, Ind.) clotted in 39 sec, thrombin incubated with fibrinogen and aptamer clone #5 (200 nM) clotted in 115 sec, and thrombin incubated with fibrinogen, clone #5 (200 nM) and 1 nuclease clotted in 40 sec. All incubations were carried out at 37 C. using reagents prewarmed to 37 C. Aptamer DNA or, when present, P1 nuclease, was added to the fibrinogen solution prior to addition of thrombin. These results demonstrated that (i) thrombin activity was inhibited specifically by intact aptamer DNA and (ii) that inhibitory activity by aptamer did not require a period of prebinding with thrombin prior to mixing with the fibrinogen substrate.

Inhibition of thrombin activity was studied using a consensus-related sequence 7-mer, 5' GGTTGGG 3', or a control 7-mer with the same base composition but different sequence (5' GGGGGTT 3'). Clotting times were measured using the timer apparatus as above. The thrombin clotting time in this experiment was 24 sec using thrombin alone (10 nM), 26 sec with thrombin and the control sequence at 20M and 38 sec with thrombin plus the consensus sequence at 20M, indicating specificity for thrombin inhibition at the level of the 7-mer.

The inhibitory aptamers were active at physiological temperature under physiologic ion conditions and were able to bind to thrombin in the presence of the fibrinogen substrate, a key requirement for therapeutic efficacy.

Example 7

Modified Thrombin Aptamers

Modified forms of the single-stranded, thrombin consensus sequence-containing deoxynucleotide 15-mer described in Example 7, 5' GGTTGGTGTGGTTGG 3', and a closely related 17-mer, were synthesized using conventional techniques. These aptamers for the most part contain the identical nucleotide sequences, bases, sugars and phosphodiester linkages as conventional nucleic acids, but substitute one or more modified linking groups (thioate or MEA), or modified bases (uracil or 5-(1-pentynyl-2'-deoxy)uracil). The aptamers containing 5-(1-pentynyl)-2'-deoxyuridine were generated by replacing thymidine in the parent aptamers. Thrombin aptamers containing 5-(1-pentynyl)-2'-deoxyuridine were also obtained by selection as described in Examples 13 and 14 below.

Independent verification of the $K_i$ for the nonmodified 15-mer was made by determining the extent of thrombin inhibition with varying DNA concentration. The data revealed 50% inhibition of thrombin activity at approximately the same concentration as the derived $K_i$, strongly suggesting that each bound thrombin was largely, if not completely, inhibited, and that binding occurred with a 1:1 stoichiometry.

TABLE 7

| Compound | $K_i$ (nM) |
| --- | --- |
| GGTTGGTGTGGTTGG | 20 |
| GGTTGGTGTGGTTGG#G#T | 35 |
| GGTTGGTGTGGTT*G*G | 40 |
| G*G*T*T*G*G*T*G*T*G*G*T*T*G*G | 280 |
| GGTTGG(dU)G(dU)GGTTGG | 15 |
| GG(dU)TGGTGTGG(dU)TGG | 80 |
| GGTTGGTGTGGTU'GG | 20 |

*indicates a thioate (i.e., P(O)S) linkage
indicates a MEA linkage
U'indicates 5-(1-pentynyl)uracil

Example 8

Incorporation of 5-(1-pentynyl)-2'-deoxyuridine Into Aptamer Candidate DNA 5-(1-pentynyl)-2'-deoxyuridine was synthesized and converted to the triphosphate as described in Otvos, L., et al., Nucleic Acids Res (1987) 1763–1777. The pentynyl compound was obtained by reacting 5-iodo-2'-deoxyuridine with 1-pentyne in the presence of palladium catalyst. 5-(1-pentynyl)-2'-deoxyuridine triphosphate was then used as a replacement for thymidine triphosphate in the standard PCR reaction.

A pool of 96-mer single-stranded DNA was synthesized, each strand consisting of specific 18-mer PCR primer sequences at both the 5' and 3' ends and a random 60-mer sequence in the center of the oligomer. Details of synthesis of the pool of single-stranded DNA is disclosed in Examples 1–6 above. PCR conditions were the same as those described above, with the following changes. dATP, DGTP and dCTP were all used at a concentration of 200M. The optimal concentration for synthesis of full-length 96-mer DNA via PCR using 5-(1-pentynyl)-2'-deoxyuridine was 800M. Generation of PCR-amplified fragments demonstrated that the Taq polymerase both read and incorporated the base as a thymidine analog. Thus, the analog acted as both substrate and template for the polymerase. Amplification was detected by the presence of a 96-mer band on an EtBr-stained polyacrylamide gel.

Example 9

Incorporation of Other Base Analogs Into Candidate Aptamer DNA

Ethyl, propyl and butyl derivatives at the 5-position of uridine, deoxyuridine, and at the $N^4$ position of cytidine and 2'-deoxycytidine are synthesized using methods described above. Each compound is converted to the triphosphate form and tested in the PCR assay described in Example 1 using an appropriate mixture of three normal deoxytriphosphates or ribotriphosphates along with a single modified base analog.

This procedure may also be performed with $N^6$ position alkylated analogs of adenosine and 2'-deoxyadenosine, and the 7-position alkylated analogs of deazaguanosine, deaza-2'-deoxyquanosine, deazaadenosine and deaza-2'-deoxyadenosine, synthesized using methods described in the specification.

Example 10

Thrombin Aptamer Containing Substitute Internucleotide Linkages

Modified forms of the 15-mer thrombin aptamer, 5' GGTTGGTGTGGTTGG 3' containing one or two formacetal internucleotide linkages (O—$CH_2$—O) in place of the phosphodiester linkage (O—PO(O$^-$)—O) were synthesized and assayed for thrombin inhibition as described above. The H-phosphonate dimer synthon was synthesized as described in Matteucci, M. D., Tet. Lett. (1990) 31:2385–2387. The formacetal dimer, 5' T-O-$CH_2$-O-T 3', was then used in solid phase synthesis of aptamer DNA. Control unmodified aptamer DNA was used as a positive control.

The results that were obtained are shown in Table 8.

TABLE 8

| Compound | clot time (sec) | | |
| --- | --- | --- | --- |
| | 100 nM | 20 nM | 0 nM |
| GGTTGGTGTGGTTGG | 105 | 51 | — |
| GGTTGGTGTGGTTGG | 117 | 48 | — |
| GGTTGGTGTGGTTGG | 84 | 60 | — |
| GGTTGGTGTGGTTGG | 125 | 49 | — |
| NO DNA CONTROL | — | — | 25 | indicates a formacetal linkage

Example 11

Thrombin Aptamer Containing Abasic Nucleotide Residues

Modified forms of the 15-mer thrombin aptamer, 5' GGTTGGTGTGGTTGG 3' containing one abasic residue at each position in the aptamer were synthesized and assayed for thrombin inhibition as described above. The abasic residue, 1,4-anhydro-2-deoxy-D-ribitol was prepared as described in Eritja, R., et al, Nucleosides and Nucleotides (1987) 6:803–814. The N,N-diisopropylamino cyanoethylphosphoramidite synthon was prepared by standard methods as described in Caruthers, M. H. Accounts Chem. Res. (1991) 24:278–284, and the derivatized CGP support was prepared by the procedures described in Dahma, M. J., et al, Nucleic Acids Res. (1990) 18:3813. The abasic residue was singly substituted into each of the 15 positions of the 15-mer. Control unmodified aptamer DNA was used as a positive control. The results that were obtained are shown in Table 9.

TABLE 9

| Compound | clot time (sec) | |
|---|---|---|
| | 100 nM | 0 nM |
| GGTTGGTGTGGTTGX | 27 | — |
| GGTTGGTGTGGTTXG | 27 | — |
| GGTTGGTGTGGTXGG | 27 | — |
| GGTTGGTGTGGXTGG | 56 | — |
| GGTTGGTGTGXTTGG | 27 | — |
| GGTTGGTGTXGTTGG | 29 | — |
| GGTTGGTGXGGTTGG | 43 | — |
| GGTTGGTXTGGTTGG | 51 | — |
| GGTTGGXGTGGTTGG | 161 | — |
| GGTTGXTGTGGTTGG | 27 | — |
| GGTTXGTGTGGTTGG | 27 | — |
| GGTXGGTGTGGTTGG | 27 | — |
| GGXTGGTGTGGTTGG | 62 | — |
| GXTTGGTGTGGTTGG | 27 | — |
| XGTTGGTGTGGTTGG | 28 | — |
| GGTTGGTGTGGTTGG | 136 | — |
| NO DNA CONTROL | — | 26 |

X - indicates an abasic residue

Example 12

Thrombin Aptamers Containing -5-(1-Propynyl)-2'-deoxyuridine Nucleotide Residues Modification of the 15-mer thrombin aptamer, 5' GGTTGGTGTGGTTGG 3' to contain 5-(1-propynyl)-2'-deoxyuridine nucleotide analogs at the indicated positions in the aptamer was effected by the synthesis of these aptamers. They were assayed for thrombin inhibition as described above. The aptamer and the H-phosphonate were prepared as described in DeClercq, E., et al., J. Med.Chem. (1983) 26:661–666; Froehler, B. C., et al, Nucleosides and Nucleotides (1987) 6:287–291; and Froehler, B. C., et al, Tet. Lett. (1986) 27:469. This analog residue was substituted at the indicated positions and the aptamer assayed for inhibition of thrombin. The results that were obtained are shown in Table 10.

TABLE 10

| Compound | clot time (sec) | |
|---|---|---|
| | 100 nM | 0 nM |
| GGTTGGTGTGGTZGG | 147 | — |
| GGTTGGTGTGGZTGG | 129 | — |
| GGTTGGTGZGGTTGG | 120 | — |
| GGTTGGZGTGGTTGG | 118 | — |
| GGTZGGTGTGGTTGG | 187 | — |
| GGZTGGTGTGGTTGG | 138 | — |
| GGTTGGTGTGGTTGG | 125 | — |
| NO DNA CONTROL | — | 23 |

Z - indicates a 5-propynyl-2'-deoxyuridine residue

Example 13

Incorporation of 5-(1-pentynyl)-2'-deoxyuridine Into Aptamer Candidate DNA 5-(1-pentynyl)-2'-deoxyuridine was synthesized and converted to the triphosphate as described in Otvos, L., et al., Nucleic Acids Res (1987) 1763–1777. The pentynyl compound was obtained by reacting 5-iodo-2'-deoxyuridine with 1-pentyne in the presence of a palladium catalyst. 5-(1-pentynyl)-2'-deoxyuridine triphosphate was then used as a replacement for thymidine triphosphate in the standard PCR reaction.

A pool of 60-mer single-stranded DNA was synthesized, each strand consisting of specific 18-mer PCR primer sequences at both the 5' and 3' ends and a random 20-mer sequence in the center of the oligomer. Details of synthesis of the pool of single-stranded DNA is disclosed in Example 1.

Because of the poor substrate activity of pentynyl dUTP when used with TAQ polymerase, VENT-thermostable polymerase, (New England Biolabs, Cat. No. 254) was employed. Amplification was performed as per the manufacturers instructions. Pentynyl dUTP was included in the reaction as a substitute for dTTP. The single-stranded 60-mer was isolated by a modification of standard procedures. The 200 L PCR amplification reaction was divided into two samples which were applied to two NICK® columns equilibrated (5 mL) as described. The eluent was collected, pooled and applied to avidin-agarose as described. This column was washed with buffer followed by elution of single-stranded 60-mer DNA with 0.15N NaOH, pooled and neutralized with glacial acetic acid. Single-stranded 60-mer DNA was desalted on a NAP5 column equilibrated in 20 mM Tris OAc (pH 7.4). 10×selection buffer salts were added to the sample, heated to 95 C. for 3 minutes, and transferred to wet ice for 10 minutes.

Example 14

Isolation of Thrombin Aptamers Using DNA Containing 5-(1-Pentynyl)-2'-deoxyuridine The pool of aptamer DNA 60 bases in length was used essentially as described in Example 13. The aptamer pool sequence was

5' TAGAATACTCAAGCTTCGACG-$N_{20}$-AGTTTGGATCCCCGGGTAC 3', while the 5' primer sequence was

5' TAGAATACTCAAGCTTCGACG 3' and the 3' biotin-linked primer was

5' GTACCCGGGGATCCAAACT 3'.

Thrombin immobilized on a Con-A lectin column served as the target as described.

After five rounds of selection, aptamer DNA was recovered and amplified using thymidine triphosphate (dTTP) in place of 5-(1-pentynyl)-2'-deoxyuridine in order to facilitate subsequent cloning and replication of aptamer DNA in E. coli. At this stage, the presence of a thymidine nucleotide at a given location in an aptamer corresponded to the location of a 5-(1-pentynyl)-2'-deoxyuridine nucleotide in each original round five aptamer. Thus, dTTP served to mark the location of 5-(1-pentynyl)-2'-deoxyuridine residues in the original selected DNA pools.

The round five amplified DNA containing dTTP was digested with BamHI and HindIII and cloned into the corresponding sites of pGEM 3Z (Promega Biotech) and transformed into E. coli. DNA from 21 clones was analyzed by dideoxy sequencing. Three of the clones contained aptamer sequences that were identical. Only one of the 21 clones contained a sequence that closely resembled the original 5' GGTTGG 3' binding motif obtained using thymine in the selection protocol.

One of these two clones (#17) and the original unselected pool was analyzed for thrombin binding by nitrocellulose filter assay described above using DNA labeled with $^{32}P$ to permit analysis of thrombin binding characteristics. The labeled DNA was synthesized by PCR and contained 5-(1-pentynyl)-2'-deoxyuridine in order to retain the original selected DNA structures. The DNA was incubated with thrombin at various concentrations between 10 nM and 10M to obtain the $K_D$ values for thrombin binding. The $K_D$ of the unselected pool was >10 m while the $K_D$ of clone 17 was 400 nM.

Radiolabeled clone 17 DNA was synthesized using thymidine in place of 5-(1-pentynyl)-2'-deoxyuridine and the resulting DNA had a $K_D$ of >10M, demonstrating that the 5-(1-pentynyl)-2'-deoxyuracil heterocycle could not be replaced by thymine in the selected aptamer without loss of binding affinity.

Representative sequences that were obtained are as follows.

```
5' TAGTATGTATTATGTGTAG 3'
5' ATAGAGTATATATGCTGTCT 3'
5' GTATATAGTATAGTATTGGC 3'
5' AGGATATATGATATGATTCGG 3'
5' TACTATCATGTATATTACCC 3'
5' CATTAAACGCGAGCTTTTTG 3'
5' CTCCCATAATGCCCTAGCCG 3'
5' GACGCACCGTACCCCGT 3'
5' CACCAAACGCATTGCATTCC 3'
5' GTACATTCAGGCTGCCTGCC 3'
5' TACCATCCCGTGGACGTAAC 3'
5' GACTAAACGCATTGTGCCCC 3'
5' AACGAAGGGCACGCCGGCTG 3'
5' ACGGATGGTCTGGCTGGACA 3'
```

Example 15

Isolation of Thrombin Aptamers Using

DNA Containing 5-Methyl-2'-deoxycytidine 5-methyl-2'-deoxycytidine triphosphate was obtained commercially (Pharmacia, Cat. No. 27-4225-01) and used to synthesize DNA containing random sequences 60 bases in length flanked by primers 19 bases in length. The pool of aptamer DNA 98 bases in length was used essentially as described in Example 6. Thrombin immobilized on a Con-A lectin column served as the target as described.

Briefly, a 200 L PCR reaction was set up using: 10 mM Tris-HCl, pH 8.3 at 25 C., 1.5 mM $MgCl_2$, 50 mM NaCl and 200 m of each of dATP, DGTP, dTTP and 5-methyl-2'-deoxycytidine triphosphate. 20 Ci each of -$^{32}$P-dATP and dGTP were added to label the DNA. 1 nmole of 5' and 3' primer were added followed by addition of 0.2 mole of 98-mer template pool DNA. Amplification was initiated by addition of 2 l (10 U) of Taq polymerase followed by sealing of the reaction with a mineral oil overlay. About 16 cycles of amplification were performed followed by a 10 minute final extension to complete all duplex synthesis.

Amplified DNA was recovered (100 L aqueous phase), n-butanol extracted (650 L) and applied to a Nick column prewashed with 5 mL of buffer containing 100 mM TrisHCl pH 7.5 and 100 mM NaCl. Eluted DNA was applied to a 0.5 mL avidin-agarose column prewashed in the same buffer and washed until DNA loss from the column was <1000 cpm. Single stranded DNA was eluted from the avidin column by washing with 0.15N NaCl and the eluate was neutralized to pH 7.0 using glacial acetic acid. The 98-mer DNA was exchanged into selection buffer on a second Nick column and, after heat denaturation for 3 min at 95 C. followed by cooling on ice for 10 min, used in aptamer selection on thrombin lectin columns. 1 mL ConA/thrombin columns were equilibrated in selection buffer prior to addition of single-stranded DNA. The single-stranded DNA was recirculated for three complete passes. Upon completion of the third pass the peak radioactive element was then applied to a 1 mL ConA/thrombin column (charged with 3 nmoles of thrombin). Radioactive single-stranded 98-mer was applied three times to this matrix. At the third application, the column was stoppered and allowed to stand for 1 hr. The column was then washed with selection buffer and 0.5 mL aliquot fractions collected. A total wash volume of 6 mL was employed. At this time, 0.1 m -methyl-mannoside in selection buffer was then added, followed by a 4 mL total volume wash. Thrombin enzymatic activity was detected via chromogenic substrate monitored by absorbance at 405 nm. Peak thrombin fractions were pooled, extracted with phenol, and the volume reduced by nBuOH extraction. 20 g glycogen was added, the single-stranded 98-mer precipitated via ethanol addition and pelleted via centrifugation. The pelleted DNA was resuspended in water and used as a template for PCR amplification. This protocol was repeated to obtain a pool of DNA that resulted from 5 rounds of selection on thrombin columns.

Double-stranded DNA was digested with EcoRI and HinDIII and cloned into pGEM3Z. Aptamers were then transformed into *E. coli* and analyzed by dideoxy sequencing. Round five aptamer pool DNA bound to thrombin with a $K_D$ of approximately 300 nM.

Example 16

Demonstration of Aptamer Specificity for Binding to and Inhibition of Thrombin

The specificity of aptamer binding was demonstrated using $^{32}$P radiolabeled DNA and a series of proteins. To determine the binding specificity of the thrombin aptamer, 96-mer clone #29, having the partial sequence 5' CGGG-GAGAGGTTGGTGTGGTTGGCAATGGCTA-GAGTAGTGAC GTTTTCGCGGTGAGGTCC 3' was used. The consensus sequence is shown underlined. In addition, a 21-mer aptamer, 5' GGTTGGGCTGGTTGGGT-TGGG 3' was tested for inhibition of another fibrinogen-cleaving enzyme ancrod, which was obtained commercially (Sigma, Cat. No. A-5042). The 21-mer had a of $K_I$ for thrombin of about 100 nM and its $K_D$ was about 350 nM. Clone #29 had a $K_D$ of about 200 nM for thrombin.

The aptamer was shown to specifically bind to thrombin by a filter binding assay. Briefly, radiolabeled aptamer DNA at about a concentration of about 1 nM was incubated with the indicated protein for several minutes at room temperature, followed by filtration of the aptamer-protein mixture through a nitrocellulose filter. The filter was washed with 3 mL of selection buffer and then radioactivity bound to the filters was determined as a % of input radioactivity. Results obtained are shown in Table 11. Binding data is shown for both unselected 96-mer DNA and for two separate experiments with clone #29 96-mer. All proteins were tested at about 1M concentration except human serum albumin which was used at 100M. The results that were obtained demonstrated that the 96-mer specifically bound to thrombin and had little affinity for most of the other proteins tested.

TABLE 11

| Protein | Input CPM | Bound CPN | % Bound |
|---|---|---|---|
| Unselected DNA | | | |
| Control | 75573 | 230 | 0 |
| Thrombin | 74706 | 6732 | 9.0 |

TABLE 11-continued

| Protein | Input CPM | Bound CPN | % Bound |
|---|---|---|---|
| Prothrombin | 75366 | 183 | <0.5 |
| Albumin | 16560 | 1851 | 2.0 |
| Chymotrypsin | 75566 | 225 | <0.5 |
| Trypsin | 73993 | 306 | <0.5 |
| Kallikrein | 76066 | 122 | <0.5 |
| Plasmin | 74513 | 3994 | 5.0 |
| Clone 29 DNA | | | |
| Control | 81280 | 126 | 0 |
| Thrombin | 81753 | 48160 | 59.0 |
| Prothrombin | 81580 | 8849 | 11.0 |
| Albumin | 85873 | 1778 | 2.0 |
| Chymotrypsin | 82953 | 207 | <0.5 |
| Trypsin | 75673 | 318 | <0.5 |
| Kallikrein | 84013 | 143 | <0.5 |
| Plasmin | 82633 | 12323 | 15.0 |
| TPA | 81960 | 192 | <0.5 |
| Clone 29 DNA | | | |
| Control | 81886 | 917 | 0 |
| Thrombin | 82940 | 48796 | 59.0 |
| Prothrombin | 91760 | 8719 | 9.5 |
| Albumin | 92473 | 234 | <0.5 |
| Chymotrypsin | 97060 | 186 | <0.5 |
| Trypsin | 97846 | 429 | <0.5 |
| Kallikrein | 95053 | 1275 | <0.5 |
| Plasmin | 66565 | 9704 | 15.0 |
| TPA | 98166 | 644 | <0.5 |

The thrombin 21-mer ancrod assay was conducted as follows. Ancrod was suspended in sterile water at a concentration of 44 U/mL. 10 L ancrod solution was added to 95 L of selection buffer prewarmed to 37 C. 100 L of this mixture was transferred to the coagulation cup of the fibrometer described above, followed by addition of 200 L of fibrinogen and 20 L of 21-mer DNA (both prewarmed to 37 C). TE buffer pH 7.0 was used as a control lacking DNA. The control clot time was 25 seconds while the clot time in the presence of 500 nM 21-mer was 24 seconds and was 26 seconds in the presence of 33M 21-mer. This result demonstrated the specificity on inhibition of fibrinogen cleavage was limited to thrombin; ancrod was not affected.

Example 17

Thrombin Aptamer Pharmacokinetic Studies

A 15-mer single-stranded deoxynucleotide, 5' GGTTG-GTGTGGTTGG 3', identified as a consensus sequence from 30 thrombin aptamer clones as described in Example 6 above, was used. Young adult rats of mixed gender and strain were used. The animals were anaesthetized and a diester of the 15-mer was injected through a catheter in 200 l volumes (in 20 mM phosphate buffer, pH 7.4, 0.15M NaCl) at two concentrations, so that the final concentration of 15-mer in the blood was about 0.5 and 5.0M respectively, although the exact concentration depends on the volume of distribution (which is unknown for this oligonucleotide). These values are 10 to 100 times greater than the human in vitro $K_d$ value. No heparin was used for catheterization.

At 0, 5, 20 and 60 minutes, blood was withdrawn from the animals (approx. 500 l aliquots), transferred into tubes containing 0.1 volume citrate buffer, and centrifuged. Rat plasma was removed and tested in a thrombin clotting-time assay. Six animals were used at each concentration, and three animals were injected with the control carrier solution containing no 15-mer.

A prolonged clotting time was observed at the 5 minute time point at both concentrations, with the most significant prolongation occurring at the higher dose concentration. Little or no activity was observed at 20 minutes. Thus, the 15-mer in blood withdrawn from rats 5 minutes post-injection was able to inhibit exogenously added human thrombin. A separate APTT test at the 5 minute time point showed that the 15-mer also inhibited rat blood coagulation, presumably by inhibiting rat thrombin to a significant degree. The half-life of the 15-mer in rats appears to be about 2 minutes or less.

Example 18

Thrombin Aptamer Primate Studies

Two thrombin aptamers were administered to adult male cynomologous monkeys. Unsubstituted 15-mer DNA with the sequence 5' GGTTGGTGTGGTTGG 3' and an analog, 5' GGTTGGTGTGGTT*G*G 3', containing thioate internucleotide linkages at the indicated positions were used. Aptamer was delivered as an intravenous bolus or infusion and then blood samples were withdrawn at various times after delivery of the bolus or during and after infusion. The catheter was heparinized after the 10 minute timepoint. The animals were not systematically heparinized.

Thrombin inhibition was measured by a prothrombin time test (PT) using a commercially available kit, reagents and protocol (Sigma Diagnostics, St. Louis, catalog Nos. T 0263 and 870-3). Inhibition of thrombin was indicated by an increased clot time compared to the control in the PT test. Clot times were obtained by withdrawing a sample of blood, spinning out red cells and using the plasma in the PT test. Control thrombin PT clot time values were obtained several minutes prior to administration of aptamer. Briefly, the PT assay was conducted using 0.1 mL of monkey plasma prewarmed to 37 C. and 0.2 mL of a 1:1 mixture of thromboplastin (used according to manufacturers instructions) and $CaCl_2$ (25 mM), also prewarmed to 37 C. Thrombin clot times were measured with a fibrometer as described above.

The animals were at least two years old and varied in weight from 4 to 6 kg. Doses of aptamer were adjusted for body weight. Aptamer DNA was dissolved in sterile 20 mM phosphate buffer (pH 7.4) at a concentration of 31.8 to 33.2 mg/mL and diluted in sterile physiological saline prior to delivery. Bolus injections were administered to give a final concentration of 22.5 mg/Kg (1 animal) of the diester aptamer or 11.25 mg/Kg (1 animal) of the diester aptamer. Infusions were administered over a 1 hour period to three groups of animals: (i) 0.5 mg/kg/min of diester 15-mer (4 animals), (ii) 0.1 mg/kg/min of diester 15-mer (2 animals) and (iii) 0.5 mg/kg/min of thioate analog 15-mer (2 animals).

PT assay results from the bolus injections showed thrombin inhibition times of 7.8, 3.3 and 1.35 times control at 2.5, 5.0 and 10.0 min respectively after delivery of the aptamer for the high dose animal. Inhibition times of 5.6, 2.2 and 1.2 times control were obtained from the low dose animal at the same time points.

FIG. 2 shows a plot of the PT times from the 4 animals that received the high dose diester infusion compared to pretreatment control values. The data points show the PT clot time as an average value obtained from the 4 animals in the group. The arrows indicate time points at the beginning and end of the infusion period. Thrombin inhibition peaked at about 10 to 20 min after the infusion was initiated and remained level until the infusion period was terminated. Inhibitory activity decreased rapidly after the infusion of aptamer terminated.

High dose diester and high dose thioate animals showed comparable inhibition of thrombin-mediated clotting, with the high dose thioate giving a sustained clot time of 2.5 to 2.7 times the control value during the course of the infusion. The low dose diester compound gave a clot time of 1.4 to 1.5 times the control value. These results demonstrated the efficacy of the native and thioate analog aptamers in primates.

Example 19

Inhibition of Extracorporeal Blood Clotting By Thrombin Aptamer

Anticoagulation of a hemodialysis filter was demonstrated using the 15-mer 5' GGTTGGTGTGGTTGG 3' thrombin aptamer with human blood. A bolus of 15-mer DNA was delivered to human blood at 37 C. to give an aptamer concentration of 10M. The blood was contained in an extracorporeal hemodialysis circuit (Travenol, Model No. CA-90). Pressure proximal to the hemodialysis filter was monitored to determine the time after administration of aptamer that coagulation occurred. Blood coagulation was marked by a pressure increase from about 50 mm Hg observed with uncoagulated blood (blood flow rate 200 mL/min) to pressure of at least 400 mm Hg.

Using citrated whole blood (recalcified at time zero), coagulation occurred at about 9 minutes after fresh blood was placed in the hemodialysis unit and circulation was begun. (In a repeat of this control experiment, coagulation occurred at 11 minutes.) A heparin control (1 U/mL) gave sustained anticoagulation until the experiment was terminated at 80 minutes after start of circulation in the unit. Blood coagulation occurred at 51 minutes in one trial with the 15-mer. In a second trial, coagulation did not occur during the 80 minute course of the experiment.

Example 20

Modified Thrombin Aptamers

Two distinct hydrophobic additions, 5-methyl-2'-deoxycytidine (5-methyl dC) and 5-pentynyl-2'-deoxyuridine (5-pentynyl dU) were used to capture a novel interaction in thrombin-DNA interaction unavailable with natural nucleotides. Using chemical synthesis a 98-base DNA oligomer containing a random region of 60 bases flanked by defined sequences for use in PCR amplification was prepared. This initial oligomer pool was subjected to large scale PCR amplification in the presence of 5-methyl dCTP to prepare an initial 98-base pool containing complete substitution of 5-methyl dC for dC. This pool was then used in a multi-round selection protocol towards human thrombin immobilized on a concavalin A-agarose column (Con A-agarose).

After the sixth cycle of this process, forty percent of the input DNA was retained on the thrombin containing column and was specifically eluted with -methyl mannoside. This dissociation constant of the DNA-protein complex was then determined via nitrocellulose filter binding and the Kd of the pool was estimated to be 200 nM compared to the unselected 5-methyl dC pool of 10M.

In a previous example, it was observed that aptamer-thrombin complex formation results in a loss of enzymatic activity when assayed with a purified system. Large scale PCR amplification isolated the single strand 98 base oligomer, and analyzed the enzyme inhibition properties of this pool using this purified system. This pool inhibited thrombin (77 sec @ 200 nM verses 28.9 sec for the control in the absence of DNA). However, it was also observed that clotting was not dependent on the methyl group of 5-methyl dC.

In parallel, the sixth round pool was cloned and sequenced. All clones characterized were found to contain the consensus sequence (i.e. GGNTGGNNNGGTNGG).

5-methyl deoxycytidine triphosphate was from Pharmacia and the corresponding suitably protected phosphoramidite from Milligen. 5-pentynyl deoxyuridine (5' DMT or $P_3O_9Na_3$) was synthesized via Pd/Cu-mediated coupling of the corresponding iodoalkyne and 5-iodo-deoxyuridine (Hobbs, F. W., (1989) J. Org. Chem., 54:3420–3422). 5-pentynyl deoxyuridine triphosphate ($-P(OCH_2CH_2CN)(N(CH(CH_3)_2)_2)$) was then prepared via the method of Kohler et al. (1980) Helv. Chim. Acta 63:2488–2492, and the protected phosphoramidite prepared via the method of Koster (1984) Nuc. Acids Res. 12:4539–4557.

To determine the effect of introducing a larger hydrophobic element into the random oligomer, a random pool containing 5-pentynyl dU was prepared. A second oligomer pool was chemically synthesized containing 20 random bases flanked by two constant regions for use in PCR. This template was then amplified in the presence of 5-pentynyl dUTP to construct the initial pool completely substituted with 5-pentynyl dU in place of thymidine. The selection procedure was then repeated in an identical format to that described above. After six rounds of selection and amplification, a second modified base aptamer pool towards thrombin was isolated.

Of the twenty-seven sequences analyzed, only one fit the GT-rich pattern highlighted above. Three sequences, representing different levels of 5-pentynyl dU substitution were chosen for further study (clone 3, clone 7 & clone 24). In addition, and more importantly, clone 24 represented a sequence observed in three distinct clones. Dissociation constants of these clones were determined to be 800, 1000 and 400 nM, respectively. Using an electrophoretic mobility shift assay (EMSA) the protein specificity of this pool was analyzed (Chodosh, L. in Current Protocols in Molecular Biology (eds Ausubel, F. M. et al.) 12.2.1–12.21.0 (Wiley-Interscience, New York 1987)).

A radiolabelled clone 24 oligomer was prepared, incubated with various concentrations of thrombin and then assayed via native polyacrylamide gel electrophoresis; a thrombin dependent band-shift was observed.

This radiolabelled oligonucleotide was incubated with a series of related proteins: trypsin, chymotrypsin, albumin, Factor X, prothrombin, -thrombin and thrombin. A protein dependent band shift was observed only in the case of thrombin. An electrophoretic mobility shift assay (EMSA) was employed to assay protein/ssDNA aptamer interaction as follows: Lane 1, no protein, lane 2, thrombin; lane 3, prothrombin; lane 4, -thrombin; lane 5, human albumin; lane 6, Factor X; lane 7, chymotrypsin; lane 8, trypsin.

5'-$^{32}$P-labelled pentynyl dU clone 24 aptamer was prepared using -$^{32}$P-ATP (Amersham) and T4 polynucleotide kinase (U.S. Biochemical) using standard procedures (Sambrook et al. in Molecular Cloning, A Laboratory Manual, 2nd Ed. 10.59–10.61). The $^{32}$P aptamer was heated to 95 C. in selection buffer (Bock (1992) Nature 355:564–566) for 5 minutes and cooled to room temperature. This DNA was then added to the respective protein equilibrated at 4 C. (final concentration-500 nM in selection buffer). This was allowed to stand on ice for 90 minutes. The sample was then brought to 10% glycerol and electrophoresised at 4 C. using 20 mM NaCl/50 mM HEPES pH 7.1 in a 4% (39:1) native acrylamide gel. Human thrombin, prothrombin, -thrombin and Factor X were from Haemotologics Technologies Inc.; human albumin, chymotrypsin and trypsin were from Sigma.

From these results it was concluded that this pool contained high affinity aptamers towards thrombin, and that the modified pyrimidine was required for the binding interaction, in distinct contrast to results obtained using 5-methyl dC. Furthermore, the results in the EMSA with -thrombin, a modified form of thrombin where the anion binding exosite has been proteolytically cleaved (Bing et al. (1977) J. Biol. Chem. 252:8027–8034), implicated the involvement of this exosite as at least one component of the binding site for this class of aptamers.

Nitrocellulose filter binding with purified human thrombin was performed to determine the Kd of the initial 5-pentynyl dU random pool and the sixth round pentynyl dU aptamers. The dissociation constant of the initial pool was greater than 10M while the selected pool was 400 nM. In addition, it was observed that the sixth round selected pool required 5-pentynyl dU; no significant binding was observed when the pool was prepared with thymidine (Kd>10M). The final 5-pentynyl dU pool was then cloned and a number of clones sequenced.

FIG. 3 illustrates the sequences obtained from the round 6 with 5-pentynyl dU pool as follows: Sixth round single stranded DNA was amplified, digested and cloned into pGEM3z using HindIII and EcoRI. Twenty-seven clones were sequenced via dideoxy methodology. Aptamer selection was performed as in (Bock 1992, supra) including the use of negative selection with Concavalin A/agarose (Con A/agarose). A general protocol for the selection method is as follows: a 60 nucleotide oligomer of the sequence 5'-TAGAATACTCAAGCTTCGACG(N)$_{20}$ AGTTTGGATCCCCGGGTAC-3' was prepared via automated synthesis using standard phosphoramidite chemistry. After deprotection in NH$_4$OH, followed by desalting using a NAP10 column (Pharmacia), the DNA was amplified using PCR in a 200 L reaction containing: 10M primer 5'-TAGAATACTCAAGCTTCGACG-3'; 10M 5'-biotin-GTACCCGGGGATCCAAACT-3'; 250M dGTP, 250M DATP, 250M dCTP and 250M pentynyl dUTP; 10 mM KCl, 10 mM (NH4)$_2$SO$_4$, 2 mM MgSO$_4$, 0.1% Triton X-100 in 20 mM Tris pH 8.8 in the presence of 60 Ci -$^{32}$P-dNTPs (dCTP, dATP & dGTP). The reaction was brought to 100 C. for 3 minutes and 10 U of Vent Polymerase (New England Biolabs) was added. This was cycled 18 times through 100 C., 1 min.; 56 C., 1 min.; 75 C., 2 min. using an extension of 5 sec/cycle at this temperature. The replacement of thymidine by 5-pentynyl dU in this and in all subsequent amplifications results in DNA containing solely this modified pyrimidine in the locations originally containing thymidine in the synthetic oligonucleotide. The resulting 60 nt ds DNA product was applied to a Nick column (Pharmacia) equilibrated in 100 mM NaCl/100 mM Tris pH 7.5 and eluted following the manufacturer's instructions. Single stranded 60 nt DNA was then isolated via the use of avidin agarose; single stranded 60 nt DNA was eluted from the matrix using 0.25N NaOH, neutralized with glacial acetic acid to pH 6 and the buffer exchanged via Nick column equilibrated in 10 mM Tris-acetate pH 7.4. The eluent was then brought to 20 mM Tris-acetate containing 140 mM NaCl, 5 mM KCl, 1 mM MgCl$_2$ and 1 mM CaCl$_2$. Selection was performed as described in Bock et al. (1992) supra.

A correlation between protein-DNA binding and the inhibition of enzymatic activity was observed. Furthermore, this property resides solely in the random region of selected clones. Oligonucleotides of the 20 base variable region of two clones (3 & 24) were then prepared via chemical synthesis.

These two 20 base oligomers were then analyzed for clotting inhibition activity using purified human thrombin (Haemetologic Technologies Inc.) and human fibrinogen pre-equilibrated at 37 C. was added. The final concentration of thrombin and fibrinogen in the mixture was 13 nM and 5.9M respectively. Oligonucleotides concentrations were as listed above and were at/or greater than their respective Kd as determined via nitrocellulose filter binding. Clotting times were measured using an automated fibrometer. Results of this assay is set forth in Table 12 below.

TABLE 12

Clotting Inhibition by Modified Base Containing Oligonucleotides

|   | Concentration | Time (sec) |
|---|---|---|
| (1) Clone 24 GXAXAXAGXAXAGXAXXGGC 20 nucleotide variable region | (1M) | 24 |
| (2) Clone 24 GCXGXAGAXAXXAGXAXAGX 20 nucleotide variable region scrambled | (1M) | 24 |
| (3) GGTTGGTGTGGTTGG | (20 nM) | 43 |
| (4) Clone 24-60 nucleotide fragment with pentynyl dU | (4M) | 104.5 |
| (5) Clone 3-60 nucleotide fragment | (4M) | 37.5 |
| (6) Clone 24/T-substituted-60 nucleotide fragment | (4M) | 25.1 |
| (7) Control |  | 24.3 |

X = pentynyl dU

All three molecules were inactive. The entire 60 base sequences of clones 3 & 24 were then prepared containing the random region flanked by the two constant regions and incorporated 5-pentynyl dU in the 3' constant region and T in the 5' constant region, analogous to the PCR product. In addition, a clone 24 analog was also prepared replacing all 5-pentynyl dU residues with thymidine. Each was then analyzed for its ability to inhibit thrombin (Table 12 above). Clotting inhibition was observed with full length clone 24, and furthermore this activity was dependent on the presence of 5-pentynyl dU (table 12 entry 6).

From these results it was concluded that one or both of the constant regions of the oligomer play a significant role for thrombin inhibition. In addition, it was independently verified, via this coagulation assay, that the interaction by this aptamer was dependent on the 5-pentynyl dU hydrophobic functionality as judged by the clone 24 thymidine substitution result. Sequence analysis has not established a consensus oligonucleotide which is responsible for the biological activity. Instead, the data points to the involvement of a conserved secondary or tertiary structure dependent on 5-pentynyl dU for its formation and interaction with thrombin.

The above results demonstrates that modified nucleotides can dramatically change the sequence of the aptamers isolated through in vitro selection, and in studies with 5-pentynyl dU the observed biochemical activity was dependent on the modified nucleotide. The inclusion of modified nucleotides therefore clearly broader the repertoire of the selection process. A major functionality change. Dramatic changes such as 5-pentynyl dU were able to alter the outcome of the process, whether this is related to a dominant structural feature of the anion binding site on thrombin is not known at present.

Example 21

Selection of Aptamers That Bind to bFGF

A control matrix comprised heparin-agarose 0.2 ml equilibrated with selection buffer. Aptamer DNA (Round 1 DNA) was obtained by incubating a 0.2 mL support with 6.2 nmole of bFGF for one hour at room temperature. The resulting column was washed with 10×0.5 mL selection buffer. The bFGF column was treated with 3×0.5 mL in selection buffer containing 2M NaCl. The second fraction of elution reflected the true eluted material.

Aptamer DNA (Round 1 DNA) from bFGF peak was brought to 0.1% SDS concentration and 20 mM ethylenediaminetetraacetic acid (EDTA), vortexed and extracted with a mixture of 180 L phenol and 180 L chloroform. The volume reduced to about 250 L. The resulting material was diluted with 0.5 mL and chromatographed on a NAP5 column in TE buffer. A 1 mL volume sample was collected and the volume was reduced by repeated n-butanol extraction to a final volume of 0.3 mL. Glycogen (20 g) was added and the solution adjusted with 0.25M NaCl and precipitated with 0.9 mL absolute ethanol at −70 C.

Approximately 2.59 pmole of template eluted and 25% was used in the PCR.

Two PCR amplification was conducted similar to Example 5C with 50 l template 97-mer, 20 l 10×-buffer (100 mM Tris Cl, 500 mM KCl, 1.5 mM $MgCl_2$), 8 L dNTP (25×), and 1 L each of $-^{32}P$ dATP, dCTP and dGTP (80 Ci total), 3 L Taq I Polymerase (15 units), 3 L 5'-primer (1 nmole), 2.4 L 3'-primer (1 nmole).

A control was also performed without template aptamer. PCR was conducted for 18 rounds, concluding with a final 10 minute extension at 72 C. The resulting material was transferred to a 1.5 mL Eppendorf tube and extracted with 800 L of n-butanol. The resulting 100 L sample was applied to a NICK™ column equilibrated in 100 mM Tris/100 mM NaCl. The second 400 L fraction was collected. Blank retained <1.5% of the template and was not further utilized.

The resulting material was also applied to 400 L avidin-agarose column in the same 100 mM Tris/100 mM NaCl buffer. The column was washed three times with 1.5 mL of high salt followed by 0.8 mL TE. The desired compound was removed and the column was treated with 0.8 mL of 0.15N NaOH. The first 200 L fraction was discarded and the remaining volume was collected, neutralized with glacial acetic acid, and reduced by n-butanol extraction to 200 l final volume. This material was chromatographed on 2-NICK™ columns equilibrated in 10 mM Tris; pH 7.4. The recovered material was heated at 95 C. for 5 minutes and slowly cooled to room temperature for 1 hr. to give 550 pmole of the desired aptamer for bFGF.

Example 22

Selection of Aptamers that Bind to Factor X

Figure 6:
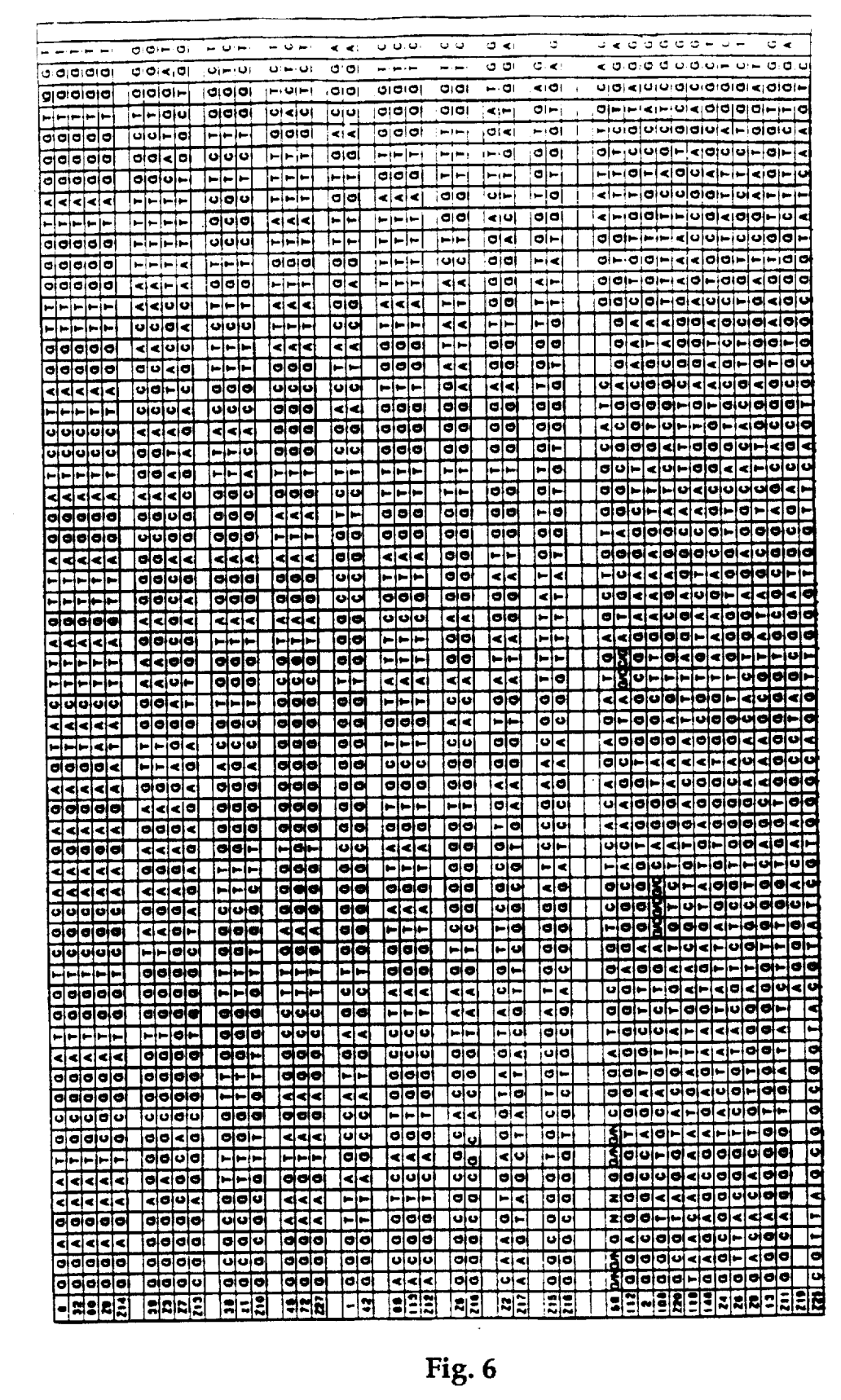

An improved selection process for obtaining aptamers that bind to Factor X was used to obtain specific binding species. Base sequences from the random region of individual DNA clones is shown in FIG. 6. The protocol used is similar to that described in Example 5 but differs by utilizing DNA molecules with a 60 base random region instead of a 30 base random region. Details of the selection are as follows.

A. Synthesis of Oligonucleotide Pool

DNA oligonucleotides containing a randomized sequence region were synthesized using standard solid phase techniques and phosphoramidite chemistry (oligonucleotide Synthesis, Gait, M. i., ed. (IRL Press), 1984; Cocuzza, A., Tetrahedron Letters, (1989) 30:6287 6291). A 1M scale synthesis yielded 60 nmole of HPLC-purified single-stranded randomized DNA. Each strand consisted of defined primer 19-base and 20-base sequences at both the 5' and 3' ends of the strand, respectively, and a random region 60 bases in length in the center of the oligomer to generate a pool of 99-mers with the following sequence (N=G, A, T or C):

5' TGG-CAG-ATG-ACC-CGA-ATT-C-$N_{60}$-GGA-TCC-AGT-GCT-CAA-ATG-TT 3'

DNA 19 and 20-mers with the following sequences were used as primers for PCR amplification of oligonucleotide sequences recovered from selection columns. The 5' primer sequence was 5' TGG-CAG-ATG-ACC-CGA-ATT-C (19-mer) 3' and the 3' primer sequence was 5' biotin-0-AACATTTGAGCACTGGATCC (20 mer) 3'. The biotin residue was linked to the 5' end of the 3' primer using commercially available biotin phosphoramidite (New England Nuclear, Cat. No. NEF-707). The biotin phosphoramidite is incorporated into the strand during solid phase DNA synthesis using standard synthesis conditions.

B. Isolation of Factor X Aptamers Using Factor X Immobilized on a Lectin Column

A pool of aptamer DNA 99 bases in length was synthesized as described in Example 22-A, and then PCR-amplified to construct the initial pool of about $10^{13}$ different molecules. An aliquot of the enzymatically-synthesized DNA was further amplified in the presence of $-^{32}P$-dNTPs to generate labeled aptamer to permit quantitation from column fractions.

A Factor X column was prepared by washing 1 mL (58 nmole) agarose-bound concanavalin A ("Con-A") (Vector Laboratories, cat. no. AL-1003) with 20 mM Tris-acetate buffer (pH 7.4) containing 1 mM $MgCl_2$, 1 mM $CaCl_2$, 5 mM KCl and 140 mM NaCl (the "selection buffer") (4 washes with 10 mL each). 1 mL of settled support was then incubated overnight at 4 C. in 10 mL selection buffer containing 368 ng (6.24 nmole) Factor X (Haematologic Technologies Inc, Cat No. HCXA-0060). After shaking overnight at 4 C. to permit Factor X binding to the Con-A beads, the mixture was briefly centrifuged and the supernatant removed. The beads were resuspended in fresh selection buffer and transferred to a column which was then washed with selection buffer (5×1 mL). A column containing 1 mL of settled beads had a void volume of approximately 300 L. A control Con-A column was prepared by adding 1 mL of settled support to a column followed by 5 washes with 1 mL of selection buffer per wash.

Prior to application of the aptamer DNA pool to Con-A columns, the DNA was heated in selection buffer at 95 C. for 3 minutes and then cooled to room temperature for 10 minutes. The pool, consisting of 100 pmole DNA in 0.5 mL selection buffer, was then prerun on the control Con-A column at room temperature to remove species that bound to the control support. Three additional 0.5 mL aliquots of selection buffer were added and column fractions 2, 3 and 4 (0.5 mL each) were pooled and then reapplied to the column twice. The DNA in 1.5 mL selection buffer was then recovered. Approximately 12% of total input cpm were retained on the column.

The recovered DNA was then applied to a Con-A-Factor X column as a 0.5 mL aliquot followed by a 1.0 mL aliquot.

Flow-through was retained and reapplied to the column twice. DNA added to the column on the final application was left on the column for 1 hour at room temperature. The column was then eluted with 0.5 mL aliquots of selection buffer. 0.5 mL fractions were collected and radioactivity was determined in each fraction. Radioactivity in eluted fractions 7 through 12 were low and relatively constant. After recovery of fraction 12, the column was washed with 0.5 mL aliquots of 0.1M -methyl-mannoside (Sigma Cat. no. M-6882) in selection buffer to elute the bound Factor X along with Factor X-bound aptamers. Fractions 13, 14 and 15 showed a significant peak of Factor X protein level, as determined spectrophotometrically by Bradford protein stain (BioRad, Cat No. 500-0006). 0.090% of the input DNA eluted in these two fractions.

Aptamer DNA (Round 1 DNA) was recovered from the Factor X by phenol extraction (2×0.5 mL). The aqueous phase volume was reduced to about 250 L by n-butanol extraction. Aptamer DNA was precipitated on dry ice using 3 volumes of ethanol and 20 g of glycogen as a carrier. The DNA was pelleted, washed once in 70% ethanol and then dried.

C. Amplification of Factor X Selected Aptamers

Round 1 DNA from Example 22-B was resuspended in 100 L of $H_2O$ and amplified by PCR. A 200 L PCR reaction consisted of the following: 100 L template 99-mer DNA (approximately 0.05 pmoles); 20 L 10X buffer (100 mM Tris-Cl (pH 8.3), 500 mM KCl, 20 mM $MgCl_2$); 32 L dNTP's (5 mM conc total, 1.25 mM each dATP, dCTP, DGTP, and dTTP); 20 L primer 1 (biotinylated 20-mer, 50M); 20 L primer 2 (19-mer, 50M); 6 L -$^{32}$P-dNTP's (approximately 60 Ci); and 4 L Taq I Polymerase (20 units). The reaction was covered with 2 drops NUJOL mineral oil. A control reaction was also performed without template aptamer.

Initial denaturation was at 94 C. for 3 minutes, but subsequent denaturation after each elongation reaction lasted 1 minute. Primer annealing occurred at 56 C. for 1 minute, and elongation of primed DNA strands using the Taq polymerase ran at 72 C. for 2 minutes, with 5-second extensions added at each additional cycle. The final elongation reaction to completely fill in all strands ran for 10 minutes at 72 C., and the reaction was then held at 4 C.

24 rounds of Taq polymerase elongation were carried out in order to amplify the selected aptamer DNA. After the reactions were completed, the aqueous layer was retrieved and any residual NUJOL oil was removed by n butanol extraction, reducing the volume to 100 L. A sample may be removed from each of the aptamer and control reaction for quantitation and analytical PAGE. The amplified aptamer pool (100 L) was fractionated over a Nick column (G-50 Sephadex, equilibrated with 3 mL TE buffer (10 mM Tris-HCl (pH 7.6), 0.1 mM EDTA)) to remove unincorporated NTP'S, primers, and salt. 400 L of TE buffer was then added to the column and the DNA pool was eluted from the column with an additional 400 L using TE buffer. (A sample may be removed from the eluent for quantitation and analytical PAGE.) The eluent (400 L) was loaded on an avidin agarose column (Vector Laboratories, Cat. No. A-2010) (500 L settled support, washed with 3×1 mL Tris/NaCl buffer (0.1M Tris, 0.1M NaCl, pH 7.5)). Approximately 90% of the loaded radioactivity remained on the column. The column was washed with Tris/NaCl buffer (4×400 L) and then the nonbiotinylated strand was eluted with 0.15N NaOH (4×300 L fractions). More than 45% of the radioactivity on the column eluted in the last three fractions. These fractions (900 L) were combined and neutralized with approximately 5.5 L of glacial acetic acid. The neutralized fractions were reduced to 200 L by speed vacuum or butanol extraction and the nucleic acids were exchange over a NICK™ column. A 5 L sample was removed for quantitation and analytical PAGE. The resulting amplified Round 1 Pool was applied to a new Con-A-Factor X column as in Example 22-B to obtain Round 2 aptamers.

D. Characterization of Round 1 Through Round 7 Factor X Aptamers Obtained from Selection on Lectin Columns Seven rounds of Factor X aptamer selection and amplification were carried out using Con-A-Factor X columns as in Examples 22-B and 22-C. As shown in Table 13, the -methyl-mannoside eluate in fractions 14, 15 and 16 contained a maximum of about 18% of input DNA at selection round 7 using the described conditions.

TABLE 13

| | % DNA eluted by -methyl-mannoside* | % DNA bound to control support |
|---|---|---|
| 1 | .09 | 12% |
| 2 | .134 | 6% |
| 3 | .513 | 9.5% |
| 4 | 1.3 | 6.2% |
| 5 | 3.7% | 2.3% |
| 6 | 8.4% | 3.2% |
| 7 | 17.9% | 2.7% |

*0.1M -methyl-mannoside in selection buffer was added beginning at fraction 13 in each elution, and fractions 14 and 15 and 16 were retained and the DNA amplified. Due to slow leeching of Factor X from the column, DNA bound to Factor X could also be seen in earlier fractions in rounds 6 and 7.

Figure 4:
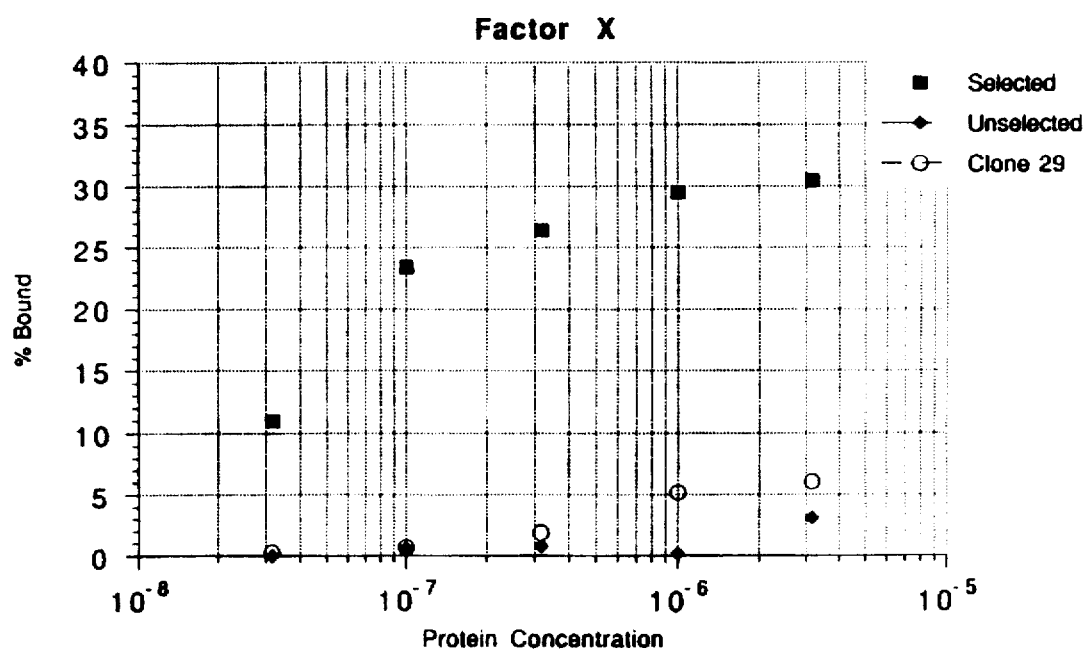
FIG. 4 is a graph of a Factor X binding assay.

After amplification, approximately 5 picomoles of radio-labeled round 7 aptamer DNA was analyzed for specificity in a filter binding assay. In this assay, nitrocellulose filters (1 cm diameter) pre-washed and also presoaked in selection buffer overnight at 4 C. was used in 100 L of selection buffer (containing 30 nM to 3 M Factor X) was incubated at room temperature for 10 minutes with: (1) 96-mer (IIa clone 29); (2) unselected DNA; (3) Round 7 aptamer DNA. The mixtures were applied to the filters by vacuum. The filters were then washed with 1.0 mL of selection buffer at 37 and radioactivity was counted to determine the amount of DNA that was retained as a Factor X complex. The results are shown in FIG. 4.

Figure 5:
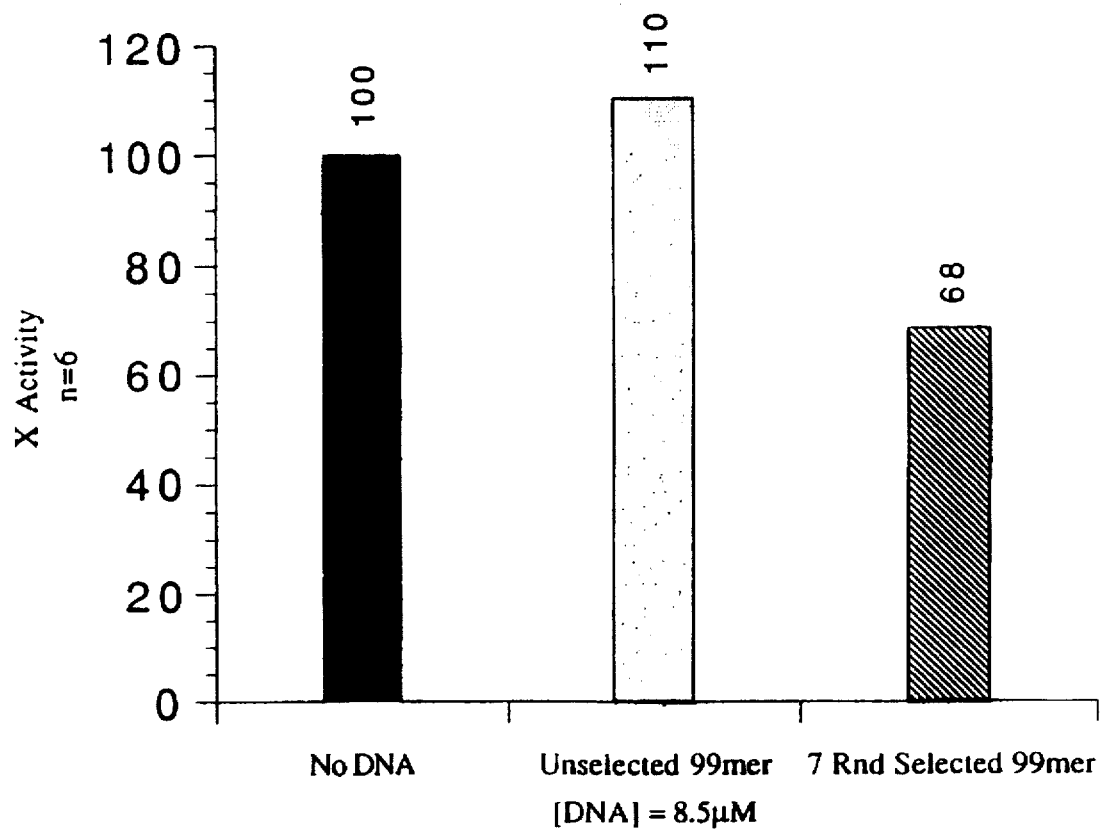
FIG. 5 is a graph of a Factor X inhibition assay.

Unselected DNA did not show significant binding to the Factor X while selected aptamer DNA bound to Factor X. Binding results show specific Factor X binding. Factor X inhibition was determined by conventional commercial assay using Russell Viper Venom (Sigma) with the results set forth in FIG. 5 for the 99-mer pool of Example 22.

The Viper Venom assay was carried out in a 250 L well of a microtiter plate. Factor X, (2 pM final concentration) 47 ng of protein is incubated with or without DNA [21.25 uM] in 40 L of Selection Buffer at 37 for 2–3 min. 10 L of $RVV/CaCl_2$ (0.066 mg/mL in 0.133M $CaCl_2$) is added and incubated at 37 for 60 sec. 50 L of 0.5 mM Spectrozyme FXa No. 222 (American Diagnostica) in 45 nM Tris. Cl pH 8.3 and allowed to react for 120 sec at 37. The reaction was stopped with 10 L of 20% acetic acid.

Tissue factor has minimal procoagulant activity prior to replipidation. The apoprotein was relipidated by incubation at 37 C. for 30 min in a relipidation mixture containing 800 L of TBSA (50 mM tris HCl, pH 7.5, 100 mM NaCl, 0.1% BSA) and 50 L of a 5 mg/ml solution of phosphatidylcholine in 0.25% deoxycholic acid and 25 L of 100 mM $CdCl_2$. The relipidated TF was then incubated for 5 minutes at 37 C. in 50 L of TBSA containing Factor X incubated with DNA and Factor VII and 100 L of 25 mM $CaCl_2$. Fifty microliters of the FXa substrate was then added and incubated for an additional 10 min at 37 C. The reaction was stopped by the addition of 50% acetic acid and absorbance at 405 nm was then detected.

Example 23

Selection of Aptamers that bind to ICAM-1

Five peptides (between 17 and 19 residues) encompassing the active domains of ICAM-1 were selected and obtained from commercial sources. Each peptide was 80% pure. Peptide sequences used were:

(25) YDQPKLLGIETPLPKKEL (43)
(35) TPLPKKELLLPGNNRKVYE (53)
(44) LPGNNRKVYELSNVQEDSQ (62)
(66) YSNCPDGQSTAKTFLTVY (83)
(162) YELDLRPQGLELFENTS (178)

Numbers in parentheses indicate the amino acid number from the amino terminus of ICAM-1.

Each peptide was dissolved in sterile water as a concentrated solution. Each peptide at 10M was incubated with a DNA pool consisting of 60 bases of random DNA flanked by PCR primer sequences in 50 L selection buffer. The DNA was radiolabeled with $^{32}P$ to permit localization of the DNA on gels described below. DNA that specifically interacted with the peptides was separated from the free DNA by electrophoresis in a low salt (50 mM HEPES, pH 7.5, 1 mM $MgCl_2$, 2 mM KCl), 4 or 6% polyacrylamide gel or a 2.5% agarose gel (Seakem, ME). DNA molecules that migrated more slowly, i.e. gel shifted, than the free pool DNA were isolated from the gel and subjected to 20 rounds of PCR amplification. DNA was recovered from acrylamide gels by soaking gel regions containing the desired DNA overnight at room temperature in 15 mL of 0.3M NaOAc followed by ethanol precipitation. DNA was recovered from agarose gels using Mermaid™ according to manufacturer's instructions (Bio 101). Approximately 1% of the molecules migrated more slowly than the bulk pool. After four rounds of selection, a DNA species was selected for that migrated more slowly than the starting pool even in the absence of peptide (presumably due to binding to the gel matrix) along with DNA species that were selected due to specific ICAM peptide binding. A negative selection process was therefore introduced to remove these DNAs. Round 4 DNA without added peptide was fractionated as before and the fast migrating DNA was isolated and reintroduced into the peptide selection process. The negative selection efficiently removed the presumptive gel matrix binding species.

Example 24

Selection of Aptamers that bind to VCAM-1 and E-Selectin

Aptamers that bind specifically to VCAM-1 and E-Selectin are obtained and characterized using methods essentially as described above for thrombin, Factor X or ICAM-1. VCAM-1 or E-Selectin protein or active domain peptide is used with lectin columns or in gel shift selections to obtain specifically binding aptamers. The selection process is conducted using a combination of lectin columns with gel shift selections or by using either method alone.

Thus, methods for obtaining aptamers that specifically bind serum proteins such as thrombin and Factor X, growth factors such as FGF, adhesion molecules such as ICAM-1, eicosanoids, kinins such as bradykinin, and cell surface ligands are described, as well as the therapeutic utility of these aptamers and the use of the aptamers in the detection and isolation of such substances. Although preferred embodiments of the subject invention have been described in some detail, it is understood that obvious variations can be made without departing from the spirit and scope of the appended claims.

TABLE 1

A. Extracellular Proteins:

lipoprotein lipase
lecithinlist-cholesterol acyl transferase
apolipoprotein A-1
apolipoprotein II
apolipoprotein IV
apolipoprotein B-48
apolipoprotein B-100
apolipoprotein CI
apolipoprotein CII
apolipoprotein CIII
apolipoprotein D
apolipoprotein E
insulin
insulin-like growth factors I and II
angiotensin I
angiotensin II
renin
angiotensin converting enzyme
atrial natriuretic peptide
immunoglobulin IgA constant region
innunoglobulin IgG constant region
immunoglobulin IgE constant region
immunoglobulin IgM constant region
immunoglobulin light chain kappa
immunoglobulin light chain lambda
immunoglobulin IgG Fc portion
immunoglobulin IgM Fc portion
immunoglobulin IgE Fc portion
amyloid protein
beta- amyloid protein
substance P
leu-enkephalin
met-enkephalin
somatostatin
interleukin-1
interleukin-2
interleukin-3
interleukin-4
interleukin-5
interleukin-6
interleukin-7
interleukin-8
interleukin-9
interleukin-10
interleukin-11
interleukin-12
interleukin-13
colony stimulating factor-macrophage
colony stimulating factor-granulocyte
colony stimulating factor-macrophage/granulocyte
erythropoietin
myelin basic protein
carcinoembryonic antigen
collagen type I
collagen type II
collagen type III
collagen type IV
collagen type V
vitronectin
fibronectin
fibrinogen
albumin
aminopeptidase
amylase
avidin
B-cell growth factor
Bence-Jones protein
prothrombin (Factor II)
thrombin (Factor IIa)

TABLE 1-continued tissue factor (Factor III)
proaccelerin (Factor V)
accelerin (Factor Va)
proconvertin (Factor VII)
antihemophiliac factor (Factor VIII)
Christmas factor (Factor IX)
Stuart factor (Factor X)
plasma thromboplastin antecedent (Factor XI)
Hageman factor (Factor XII)
Fibrin-stabilizing factor (Factor XIII)
prekallikrein
high molecular weight kininogen
bradykinin
kinins
calcitonin
carboxypeptidase A
carboxypeptidase B
carboxypeptidase C
catalase
ceruloplasmin
cholinesterase
chymotrypsin
lipase
amylase
collagenase
complement protein C1q
complement protein C1r2
complement protein C1s2
complement protein C2
complement protein C2a
complement protein C2b
complement protein C3 convertase
complement protein C3
complement protein C3b
complement protein C4
complement protein C4a
complement protein C4b
complement protein C5a
complement protein C5
complement protein C5b
complement protein C5 convertase
complement protein C6
complement protein C7
complement protein C8
complement protein C9
complement protein lytic complex
adrenocorticotropic hormone
corticotropin releasing hormone
pepsin A
pepsin B
pepsin C
trypsin
elastase
enterokinase
leucine aminopeptidase
aminotripeptidase
dipeptidase
prolidase
prolinase
alpha-glucosidase
sucrase
maltase
beta-galactosidase
oligo glucosidase
lipase
phospholipase A and B
cholesterol esterase
monoacylglycerol lipase
carboxylic acid esterase
alkaline phosphatase
elastin
myelin protein A1
proenkephalin
enteropeptidase
L-asparaginase
E-asparaginase
epidermal growth factor
fibrin
fibrinopeptide A TABLE 1-continued fibrinopeptide B
filaggrin
follicle-stimulating hormone
follicle-stimulating hormone releasing hormone
gastrin releasing peptide
growth hormone
glucagon
leutinizing hormone
leutinizing hormone releasing hormone
human menopausal gonadotropin
prolactin
chorionic gonadotropin
growth hormone releasing hormone
hemosiderin
placental lactogen
inhibin
kallikrein
acid keratin
vimentin
desmin
glial fibrillary acidic protein
leukokinin
leupeptin
luciferase
melanin
melanotropin
melatonin
melanotropin release inhibiting hormone
nerve growth factor
oxytocin
vasopressin
neurophysin
neurotensin
beta-endorphin
adrenorphin
dynorphin
alpha neoendorphin
phospholipase A2
papain
plasmin
acidic alpha1 glycoprotein
alpha 1 lipoprotein
alpha trypsin inhibitor
beta 1 lipoprotein
hemopexin
alpha 1 antitypsin
transferrin
plasminogen
platelet derived growth factor (alpha and beta)
acidic fibroblast growth factor
basic fibroblast growth factor
somatotropin release inhibiting hormone
somatotropin releasing hormone
superoxide dismutase
thymosin
thyrotropin
thyrotropin releasing hormone
alpha fetoprotein
tumor necrosis factor-alpha
tumor necrosis factor-beta
vasoactive intestinal opeptide
von Willebrand factor
tissue plasminogen activator
gondatropin releasing hormone
parathyroid hormone
antithrombin III
protein C
protein S
activated protein C
interferon alpha
interferon beta
interferon gamma
ferritin
haptoglobin
HDL
LDL
VLDL
TGF (alpha and beta)
Steel Factor (stem cell growth factor)

TABLE 1-continued

HB-epidermal growth factor
FGF-6
SLF
KGF
DDNF
NT-3
sis oncogene protein
int-2 oncogene protein
hst oncogene protein B. Cell Surface Proteins

| | |
|---|---|
| CD1a | thymocyte cell surface protein |
| CD1b | cortical thymocyte, dermal cell surface protein |
| CD1c | cortical thymocyte cell surface protein |
| CD2 | E rosette receptor |
| CD3 | T cell receptor complex |
| CD4 | T helper/inducer cell surface protein |
| CD5 | T cells, B cell, cell surface protein |
| CD6 | Pan T, B cells of CLL cell surface protein |
| CD7 | T cells, NK cell surface protein |
| CD8 | T cytotoxic/suppressor, NK cell surface protein |
| CD9 | Monocytes, Pre-B, platelet cell surface protein |
| CD10 | CALLA, Pre-B, granulocyte cell surface protein |
| CD11a | LFA-1 Alpha chain |
| CD11b | Mac 1 (adhesion molecule) |
| CD11c | p150-95 (adhesion molecule) |
| CDw12 | Monocyte, granulocyte platelet cell surface protein |
| CD13 | Pan myeloid (CA++ mobilization) cell surface protein |
| CD14 | Monocyte cell surface protein |
| CD15 | Hapten X (fucosyl N acetyllactosamine), granulocyte |
| CD16 | IgG Fc Receptor III, low affinity |
| CDw17 | Lactoceramide |
| CD18 | chain of LFA-1, Mac 1, p150-95 |
| CD19 | Pan B, cell surface protein |
| CD20 | B cells, dendritic reticular cell surface protein |
| CD21 | B cells, dendritic cells, CR2 (EBV Rc) Epstein Barr Virus Receptor |
| CD22 | B cell, cell surface protein |
| CD23 | IgE Fc Receptor low affinity |
| CD24 | B cell, cell surface protein |
| CD25 | IL2 Receptor |
| CD26 | Dipeptylpeptidase IV of activated T lymphocytes |
| CD27 | Mature T cell surface protein |
| CD28 | Tp44 Ag, T cells, plasma cell surface protein |
| CD29 | VLA Beta chain |
| CD30 | Activation antigen |
| CD31 | Myeloid Ag. gpIIa Antigen |
| CD32 | IgG Fc Receptor |
| CD33 | Pan myeloid cell surface protein |
| CD34 | Lymphoid and myeloid precursor cell surface protein |
| CD35 | CR1, granulocytes, monocytes, dendritic cell surface protein |
| CD36 | gpIV, thrombospondin receptor |
| CD37 | B cell, cell surface protein |
| CD38 | B & T cells and plasmocyte cell surface protein |
| CD39 | B cells, macrophages, endothelial cell surface protein |
| CD40 | B cells, El lymphocytes carcinoma (BLCA) cell surface protein |
| CD41a | gpIIb/IIIa |
| CD41b | gpIIb |
| CD42a | gpIX |
| CD42b | gpIb |
| CD43 | T cells, granulocytes, RBC, cell surface protein |
| CD44 | T cells, pre-B, granulocytes, cell surface protein |
| CD45 | Leukocyte common antigen (LCA) |
| CD45Ra | Restricted LCA, subset of CD4 + T cells |
| CD45Rb | Leukocyte cell surface protein |
| CD45Ro | Restricted LCA |
| CD46 | Membrane Cofactor Protein (MCP) |
| CD47 | N-linked glycan |
| CD48 | Leukocytes (PI-PLC linked) |
| CDw49a | a1 VLA chain |
| CDw49b | gpIaIIa, a2 VLA chain, collagen receptor |
| CDw49c | a3 VLA chain |
| CDw49d | a4 VLA chain |
| CDw49e | gpIc, a5 VLA chain |
| CDw49f | gpIcIIa, a6 VLA chain, laminin receptor |
| CDw50 | Leukocyte cell surface protein |
| CD51 | a chain vitronectin Rc (VNR) receptor |
| CDw52 | Campath-1, leukocyte cell surface protein |
| CD53 | Leukocyte cell surface protein |
| CD54 | ICAM-1 (Intracellular Adhesion Molecule), leukocytes |
| CD55 | DAF (Decay Accelerating Factor) |
| CD56 | N-CAM (NKH-1), Adhesion Molecule |
| CD57 | HNK1, Natural Killer cell surface protein |
| CD58 | Leukocyte functional antigen cell surface protein |
| CD59 | Leukocyte cell surface protein |
| CDw60 | Neu AC-Neu Gal, T lymphocytes subset |
| CD61 | gpIIIa, VNR B chain, Integrin B3 |
| CD62 | GMP-140 (PADGEM) |
| CD63 | Activated platelet cell surface protein |
| CD64 | Fc receptor, monocytes |
| CDw65 | Fucoganglioside |
| CD66 | Granulocyte cell surface protein |
| CD67 | Granulocyte (PI linked) cell surface protein |
| CD68 | Macrophage cell surface protein |
| CD69 | Activation Inducer Molecule |
| CDw70 | Activated B & T cells, Reed Sternberg cell, cell surface protein |
| CD71 | Transferrin receptor |
| CD72 | Pan B cell surface protein |
| CD73 | Ecto5'Nucleotidase |
| CD74 | Class II associated invariant chain- |
| CDw75 | Mature B cell surface protein |
| CD76 | Mature B cells, T cell subset, granulocyte cell surface protein |
| CD77 | Globotrioasylceramide (Gb3), Burkitt's lymphoma cell surface protein |
| CDw78 | Pan B (monocyte) cell surface protein |
| ICAM-1 | Thrombin Receptor |
| ICAM-2 | p-glycoprotein (MDR-1 gene product) |
| LPAM-2 | (MDR-2 gene product) |

VCAM-1
ELAM-1
T-cell receptor
LAN-1

Histocompatibility antigens (Cell surface antigens)

HLA-A1, HLA-A2, HLA-A3, HLA-A11, HLA-A23(9), HLA-A24(9), HLA-A25(10), HLA-A26(10), HLA-A29(w19), HLA-A30(w19), HLA-A31(w19), HLA-A32(w19), HLA-A33(w19), HLA-AW34(10), HLA-Aw36, HLA-Aw43, HLA-Aw66(10), HLA-Aw68(28), HLA-Aw69(28), HLA-Aw74(w19), HLA-Bw4(4a), HLA-Bw6(4b), HLA-B7, HLA-B8, HlA-B13, HLA-B18, HLA-B27, HLA-B35, HLA-B37, HLA-B38(16), HLA-B39(16), HLA-Bw41, HLA-Bw42, HLA-B44(12), HLA-B45(12), HLA-Bw46, HLA-Bw47, HLA-Bw48, HLA-B49(21), HLA-Bw50(21), HLA-B51(5), HLA-Bw52(5), HLA-Bw53, HLA-Bw54(22), HLA-Bw55(22), HLA-Bw56(22), HLA-Bw57(17), HLA-Bw58(17), HLA-Bw59, HLA-Bw60(40), HLA-Bw61(40), HLA-BW 62(15), HLA-Bw63(15), HLA-Bw64(14), HLA-Bw65(14), HLA-Bw67, HLA-Bw71(70), HLA-Bw72(70), HLA-Bw73, HLA-Bw75(15), HLA-Bw76(15), HLA-Bw77(15), HLA-Cw1, HLA-Cw2, HLA-Cw3, HLA-CW4, HLA-Cw5, HLA-Cw6, HLA-Cw1 HLA-Cw8, HLA-Cw9(3), HLA-Cw10(3), HLA-Cw11, HLA-Dw1, HLA-Dw2, HLA-Dw3, HLA-Dw4, HLA-Dw5, HLA-Dw8, HLA-Dw9, HLA-Dw10, HLA-Dw11(7), HLA-Dw12, HLA-Dw13, HLA-Dw14, HLA-Dw15, HLA-Dw16, HLA-Dw17(7), HLA-Dw18(6), HLA-Dw19(w6), HLA-Dw20, HLA-Dw21, HLA-Dw22, HLA-Dw23, HLA-Dw24, HLA-Dw25, HLA-Dw26, HLA-DR1, HLA-DR2, HLA-DR3, HLA-DR4, HLA-DR5, HLA-DRw6, HLA-DR7, HLA-DRw8, HLA-DR9, HLA-DRw10, Hhk-DRw11(5), HLA-DRWI2(5), HLA-DRW13(6), HLA-DRw14(6), HLA-DRWI5(2), HLA-DRw16(2), HLA-DRw17(3), HLA-DRw18(3), HLA-DRw52, HLA-DRw53, HLA-DQw1, HLA-DQw2, HLA-DQw3, HLA-DQw4, HLA-DQw5(w1), HLA-DQw6(w1), HLA-DQw7(w3), HLA-DQw8(w3), HLA-DQw9(w3), HLA-DPw1, HLA-DPw2, HLA-DPw3, HLA-DPw4, HLA-DPw5, HLA-DPw6

Insulin receptor
Insulin-like growth factor receptor
Sodium/potassium ATPase
Sodium/chloride cotransporter
IL-1 receptor
IL-3 receptor TABLE 1-continued IL-4 receptor
Parathyroid hormone receptor
GnRH receptor
CSF-M receptor
CSF-GM receptor
CSF-G receptor
Erythropoietin receptor
Complement receptor
C1b receptor
EGF receptor
Follicle stimulating hormone receptor
Follicle stimulating hormone releasing hormone receptor
Growth hormone receptor
Glucagon receptor
Leutinizing hormone receptor
Leutinizing hormone releasing hormone receptor
Growth hormone releasing hormone receptor
Nerve growth factor receptor
Melanotropin release inhibiting hormone receptor
Platelet derived growth factor receptor (alpha and beta)
Fibroblast growth factor receptor (i and 2)
Somatotropin release inhibiting hormone receptor
Somatotropin releasing hormone receptor
Thyrotropin receptor
Thyrotropin releasing hormone receptor
Tumor necrosis factor alpha receptor
Tumor necrosis factor beta receptor
Complement C3a receptor
Complement C5a receptor
Complement C3b receptor
Complement CR2 receptor
Complement CR3 receptor
CSF-1 receptor
GMCSF receptor
SLF receptor
flg oncogene protein
c-ros oncogene protein
erb-B2 oncogene protein
trk-B oncogene protein
trk oncogene protein
c-fems oncogene protein
c-kit oncogene protein
erb-B oncogene protein
HER-2/neu oncogene protein
kit oncogene protein
C. Virus and Bacterial Targets

HIV-1/HIV-2 reverse transcriptase (including RNAse H)
protease
integrase
gag proteins (including p17,p24, p15)
tat protein
rev protein
nef protein
vif protein
vpr protein
vpu protein
envelope proteins (including gp 120, gp41)
HTLV-I/II gag proteins (including gp24, gp19, gp15) protease
pol (including reverse transcriptase and RNAse H)
envelope genes (including gp46 and gp41)
tax
rex
Human papillomaviruses E7 protein E6 protein
E6* protein
E4 protein
E1 proteins
E1-E4 proteins
E2 proteins
capsid proteins (L1 and L2)
Influenza A and B polymerase proteins (including PA, PB1, and PB2)

TABLE 1-continued hemagglutinin (HA)
neuraminidase (NA)
nucleoprotein (NP)
M1 and M2 proteins
NS1 and NS2 proteins
Hepatitis B Envelope (surface antigenP proteins (including pre-S1, pre-S2 and S)
Nucleocapsid (core) proteins
P-gene product
X-gene product
Cytomegalovirus Immediate early (alpha) gene products (including IE1 and IE2)
Early (beta) gene products (including DNA pol p140, DBP52 EDBP 140)
Late (gamma) structural gene products
Herpes Simplex Virus thymidine kinase
ribonucleotide reductase
virus-encoded envelope glycoproteins
Epstein-Barr Virus immediate early gene products (including ZLF1 protein and RLF1 protein)
early gene products (including SMLF1, MRF1, ALF2, HRF1, ribonucleotide reductase, thymidine kinase [XLF1])
virus-encoded glycoproteins
lipopolysaccharides (from gram negative or gram positive bacteria)

botulinum toxin
diphtheria toxin
cholera toxin
endotoxin
D. Intracellular Targets (proteins/lipids/Enzymes Lipids fatty acids
glycerides
glycerylethers
phospholipids
sphingolipids
steroids
fat soluble vitamins
glycolipid
phospholipids
lecithins
phosphatidic acids (cephalins)
sphingomyelin
plasmalogens
phosphatidyl inositol
phosphatidyl choline
phosphatidyl serine
phosphatidyl inositol
diphosphatidyl glycerol
oleic
palmitic
stearic acids
linoleic acid
acylcoenzyme A
phosphoglyceride
phosphitidate
retinoic acid
retinoids
lipoprotein A
proteolipid
sphingolipids
sphingosine
ceramides
cerebrosides
gangliosides
sphingomyelins
terpenes
sesquiterpenes

TABLE 1-continued diterpenes
triterpenes
tetraterpenes
steroids
cholesterol
cholesterol esters
cholic acid
phosphatidylcholine
estrogen
testosterone
androgens
2-keto-3-deoxyoctanoate
Intracellular proteins p53
pRB retinoblastoma gene product)
methemoglobin
hemoglobin A
hemoglobin A1
hemoglobin A2
hemoglobin Barcelona
hemoglobin Barts
hemoglobin Beth Isreal
hemoglobin Bunbury
hemoglobin Cochin-Port Royal
hemoglobin Cowtown
hemoglobin Cranston
hemoglobin Creteil
hemoglobin D
hemoglobin D-Los Angeles
hemoglobin D-Punjab
hemoglobin F
hemoglobin Gower
hemoglobin Hammersmith
hemoglobin Hiroshima
hemoglobin Indianapolis
hemoglobin Kansas
hemoglobin Kariya
hemoglobin Kempsey
hemoglobin Kenya
hemoglobin Lepore
hemoglobin M
hemoglobin M Hyde Park
hemoglobin M Iwate
hemoglobin M Saskatoon
hemoglobin Nancy
hemoglobin Philly
hemoglobin Quong Sze
hemoglobin Ranier
hemoglobin Raleigh
hemoglobin S
hemoglobin Sealy
hemoglobin Seattle
hemoglobin St. Louis
hemoglobin St. Mande
hemoglobin Titusville
hemoglobin Torino
hemoglobin Wayne
hemoglobin York
hemoglobin Zurich
src oncogene protein
abl oncogene protein
met oncogene protein
Ha-ras oncogene protein
Ki-ras oncogene protein
N-ras oncogene protein
fps oncogene protein
mos oncogene protein
raf oncogene protein
pim oncogene protein
crk oncogene protein
dbl oncogene protein
rel oncogene protein
yes oncogene protein
fgr oncogene protein
L-myc oncogene protein
int-1 oncogene protein
ets oncogene protein
bcl-2 oncogene protein

TABLE 1-continued 1-acylglycerol-3-phosphate acyltransferase
3-b-hydroxy-steroid dehydrogenase(EC5.3.3.1)
3-hydroxybutyrate dehydrogenase
3-ketothiolase
5'-nucleotidase
8-oxoguanosine deglycosylase
11b-hydroxylase (EC 1.14.15:4)
18-hydroxylase
21-steroid hydroxylase(EC 1119910)
2,3-oxidosqualene lanosterol cyclase
24,28-sterol reductase
a-actin
a-mannosidase
a-melogenin
a-tubulin
acetolactate synthase
acetyl cholinesterase
acetyl glucosaminyl transferase
acetyl spermine deactylase
acetyl transacylase
acetyl-CoA carboxylase
acetyl-CoA malate citrate synthase
acid phosphatase
acid protease
aconitase
actin
adenosine deaminase
adenosylhomocysteine hydrolase
adenosylmethionine decarboxylase
adenylate cyclase
adenylate deaminase
adenylate kinase
adenylsuccinate lyase
adenylsuccinate synthase
alanine aminotransferase
alcohol dehydrogenase
aldolase
adose reducase
alkaline phosphatase
amidophosphodbosylanine transferase
AMP phosphodiesterase
amyloid b/A4 protein
amyloid precursor protein
ankarin
arginase
argininosuccinate lyase
argininosuccinate synthetase
aromatase
aryl sulfatase
aspartate aminotransferase
aspartate transcarbamoylase
ATP diphosphohydrolase
ATPase
b-actin
b-glucuronidase
b-glycerophosphatase
b-ketoacyl-ACP reductase
b-ketoacyl-ACP sythetase
b-spectrin
b-tropomyosin
b-tubulin
C5a inactivation factor
calcitoin
calmodulin
calpain I
calreticulin
carbamoyl-phosphate synthetase
carbonic anhydrase
casein kinase 1
casein kinase 2
catalase
catechol methyltransferase
cathepsin
cathepsin B and L
cdc 2 p34
cdc 10
cdc 13 p60
cdc 25 p80
chaparonin

TABLE 1-continued cholesterol esterase
cholesterol monooxygenase
citrate synthetase
clathrin
collagenase
connective tissue activating peptide
core protein
cortisol dehydrogenase
cyclin A and B
cyclophilin
cytidine deaminase
cytidylate deaminase
cytochrome C peroxidase
cytochrome P450
cytosine methyl transferase
defensin
diacylglycerol acyltransferase
dihydrofolate reductase
dihydrouracil dehydrogenase
dihydroorotatase
dihydroorotate dehydrogenase
dioxygenase
dopamine monooxygenase
dynenin
elastase
elastin
elongation factor Tu
endo-rhamosidase
enolase
enoyl-ACP hydratase
enoyl-ACP reductase
fatty acid synthetase
ferritin
ferrodoxin
fructose bisphosphate aldolase
fumarase
GABA aminotransferase
galactosidase
gelatinase
gelsolin
glucophosphate isomerase
glucosylceramide galactosyl transferase
glutaminase
glutamine phosphoribosylpyrophosphate aminotransferase
glycerol phosphate acyl transferase
glycerol phosphate dehydrogenase
glycinamide ribonucleotide transfomylase
GTP binding protein
heavy meromyosin
hexokinase
histaminase
histidine decarboxylase
HSP 27
hydropyrimidine hydrokse
hydroxy acyl CoA dehydrogenase
hydroxy steriod dehydrogenase
hydroxy-methylglutaryl CoA cleavage enzyme
hydroxy-methylglutaryl CoA reductase
hydroxy-methylglutaryl CoA sythetase
hypoxanthine-guanine phosphoribosyl transferas
IMP dehydrogenase
indole lyase
inositol phosphate phosphatase
isocitate lyase
kinin generating enzyme
lactate dehydrogenase
lactoferrin
laminin
leukocyte elastase
lipocortin
lipoxygenase
long chain fatty acid CoA ligase
lysozyme
major basic protein
malate dehydrogenase
malate synthase
malonyl transacylase
mannosidase
methionine adenosyltransferase

TABLE 1-continued mixed function oxygenase
myloperoxidase
myofilament
myristoyltransferase
N-acetyl glucuronidase
Na/K ATPase
NAD-dependent sterol 4-carboxylase
NADase
NADPH-dependent 3-oxosteroid reductase
nexin
nucleolar protein B23
nucleoside diphosphate kinase
ornithine aminotransferase
ornithine carbamoyltransferase
ornithine decarboxylase
orotate decarboxylase
orotate phosphoribosyl transferase
peptidyl prolyl isomerase
peptidylamidoglycolate lyase
phenylalanine hydroxylase
phosphatidate phosphatase
phosphoenol pyruvate carboxykinase
phosphofructokinase
phosphoglucokinase
phosphoglucomutase
phosphoglycerate kinase
phosphoglyceromutase
phospholipase A2
phospholipase C
phospholipase CG1
phospholipase D
phospholipase S
phosphoribomutase
phosphoribosylphosphate transferase
plasminogen activator inhibitor
platelet factor 4
porin
pRb rentinablastoma gene product
properidin
prostaglandin synthase
Protein kinase C
purine nucleoside phosphorylase
pyruvate dehydrogenase
pyruvate kinase
ribonucleotide reductase
ribosephosphate pyrophosphate kinase
ricin tropoelastin
serine/threonine kinase
spectrin
spermine synthase
squalene epoxidase
squalene monooxygenase
sterol methyltansferase
suc 1 p13
succinyl CoA synthetase
superoxide dismutase
tartrate dehydrogenase
thioesterase
thioredoxin
thrombospondin
thromboxane A2 synthetase
thymidylate synthetase
transacylase
triosephosphate dehydrogenase
triosephosphate isomerase
tRNA synthetase
tropomyosin
tryptophan synthase
tubulin
tyrosine kinase
ubioquinone reductase
uridine monophosphate kinase
urokinase type plasminogen activator
vitamin K reductase
wee −1 gene product
xanthine dehydrogenase
xanthine oxidase
xylosyl transferase

TABLE 1-continued

E. Small Molecules and Other Compounds 2-phosphoglycerate
3-hydroxy acyl-CoA
3-phospho-5-pyrophosphomevalonate
3-phosphoglycerate
3-phosphohydroxypyruvate
3-phosphoserine
5-alpha-dihydrotestosterone
5-phospho-beta-ribosylamine
5-phosphoribosyl 1-pyrophosphate
5-phospho-alpha-ribosyl-l-pyrophosphate
5-phosphoribosyl-4-carboxamide-5-aminoimidazole
6-benzylaminopurine
17-hydroxyprogesterone
acetominophen
aceyt-coenzyme A
acetylcholine
acetylsalicylic acid
adenine
adenosine
ADP
aflatoxin B1
aflatoxin G1
aflatoxin M1
aldosterone
allantoin
allodeoxycholic acid
allopurinol
alpha ketoglutarate
alpha,beta-dihydroxy-beta-methylvalerate
alpha-aceto-alpha-hydroxybutyrate
alpha-amino-beta-ketoadipate
alpha-bungarotoxin
alpha-carotine
alpha-keto-beta-methylvalerate
alpha-ketoglutarate
alpha-ketobutyrate
alpha-ketoglutarate
amiloride
aminopterin
AMP
amylopectin
amylose
anti-diuretic hormone
antipyrine
arachidic acid
arachidonic acid
arecoline
arginine
argininosuccinate
ascorbic acid
aspartate semialdehyde
aspartyl phosphate
ATP
atropine
bacitracine
benztropine
beta-caratine
betamethazone
bilirubin
biliverdin
biotin
carbachol
carbamoyl phosphate
carboline
carnitine
CDP
cholesterol
cholic acid
chorismic acid
cis aconitate
citrate
citrulline
CMP
cocaine
codeine
Coenzyme Q
coenzyme A
corticosterone
cortisol
cortisone
coumarin
creatine
creatinine
CTP
cyanocobalamin
cyclic AMP
cyclic CMP
cyclic GMP
cyclic TMP
cystathionine
cytnidine
cytochrome
D-Erythrose
D-Fructose
D-Galactosamine
D-glucose
D-Glucuronic acid
dADP
dAMP
dATP
dCDP
dCMP
dCTP
delta-4-androstenedione
deoxyadenosyl cobalamin
deoxycholic acid
dGDP
dGMP
dGTP
dihydroorotate
dihydroxyphenylalanine
diphosphoglycerate
dopanane
dTDP
dTMP
dTTP
dUDP
dUMP
dUTP
eosinophil chemotactic factor of anaaphyaxis-A
epinephrine
estriol
esdone
ethynylestrdiol
FAD
farnesyl pyrophosphate
fatty Acyl-s-CoA
ferrodoxin
FMN
FMNH2
folic acid
fructose 2,6-diphosphate
fructose
fructose 1,6-diphosphate
fructose 6-phosphate
Fructose1,6-diphosphate
fumarate
galactose
galactose
GalNAC
gama-aminolevulinate
gamma-carotene
gastric inhibitory protein
gaunidinoacetate
GDP
gentamycin
glucosamine
glucosamine 6-phosphate
glucose
glucose 1,6-diphosphate
glucose 1-phosphate
glucose 6-phosphate
Glutamate
glutamate semialdehyde
glutaryl-CoA
glutathione TABLE 1-continued glyceraldehyde 3-phosphate
glycerol 1-phosphate
glychocholate
glycine
glyoxylate
GMP
GTP
guanine
hemicholine
histamine
homogentisate
homoserine
hydrocortisone
hydroxyproline
indole
inosine
inositol
inositol phosphate
intermediate molecular weight eosinophil chemotactic factor of isocitrate
isopentenyl pyrophosphate
L-alanine
L-arginine
L-asparagine
L-aspartic acid
L-aspartic acid
L-azoserine
L-cysteine
L-Fucose
L-glutamic acid
L-glutamine
L-histidine
L-isoleucine
L-leucine
L-lysine
L-malate
L-methionine
L-phenylalanine
L-proline
L-serine
L-threonine
L-typtophane
L-tyrosine
L-valine
lanosterol
leukotriene B4
leukotriene C4
leukotriene D4
leukotrienes
lipoic acid
luciferin
malonate
malonyl-CoA
methocholine
methotrexate
methylenetetrahydrofolate
mtethylmalonyl-CoA
mevalonate
mevalonate-5-phosphate
muscarin
N-Formylmethionine
NAD
NADH
NADP
NADPH
neostigmine
nicotinamide
nicotine
nicotinic acid
norepinephrine
ornithine
oxaloacetate
oxotremorine
p-benzoquinone
pancuronium
pantothenic acid
para-aminobenzoic acid
phosphenolpyruvate TABLE 1-continued phosphocreatinine
physostigmine
pilocarpine
piperidine
pirenzipine
plastoquinone
platelet-activating factor
porphobilinogen
pregnenolone
progesterone
prolinanide
propionyl-CoA
prostaglandin D2
protoporphyrin IX
pteridine
pyridoxal
pyridoxal phosphate
pyridoxal phosphate
pyridoxamine
pyridoxamine phosphate
pyrodoxine
pyroglutamic acid
pyrophosphate
pyrrolidine
pyrroline-5-carboxylate
pyrrolizidine
quinplizidine
quinuclidinylbromide
RGD peptide
riboflavin
ribose
s-adenosylhomocysteine
s-adenosylmethionine
scopolamine
serotonin
slowreacting substance of anaphylaxis
squalene
suberyldicholine
succinate
succinyl-CoA
taurocholate
testosterone
tetrahydrofolic acid
thiamine
thioredoxin
thromboxane A2
thromboxane B2
thymine
tropane
ubiquinol
ubiquinone
UDP
UDP-galactose
UMP
uracil
urea
uric acid
UTP
vitamin A
vitamin D
vitamin E
vitamin K

---

We claim:

1. A method to detect the presence or absence of thrombin, which method comprises:
   a) contacting a sample suspected of containing thrombin with a single-stranded DNA aptamer coupled to a label under conditions wherein a complex between thrombin and the aptamer is formed; and
   b) detecting the presence or absence of said complex indicating the presence or absence of thrombin;
   wherein said aptamer comprises the sequence:

5'GGNTGG3' wherein N is A, T or G.

2. The method of claim 1 wherein N is T.

3. The method of claim 1 wherein said aptamer comprises the sequence:

5'GGNTGG(N)$_Z$GGNTGG3' (SEQ ID NO: 28)

wherein:
   N is A, T, or G; and
   Z is an integer from 2 to 5.

4. The method of claim 3 wherein Z is 3.

5. The method of claim 4 wherein said aptamer comprises the sequence:

5'GGNTGGTGTGGNTGG3' (SEQ ID NO: 38).

6. The method of claim 5 wherein N is T (SEQ ID NO: 29).

7. A method to purify thrombin, which method comprises:
   a) contacting a sample containing thrombin with a single-stranded DNA aptamer coupled to solid support under conditions wherein thrombin is bound to the aptamer coupled to solid support;
   b) washing unbound components of the sample; and
   c) recovering purified thrombin from said solid support;
   wherein said aptamer comprises the sequence:

5'GGNTGG3' wherein N is A, T or G.

8. The method of claim 7 wherein N is T.

9. The method of claim 7 wherein said aptamer comprises the sequence:

5'GGNTGG(N)$_Z$GGNTGG3' (SEQ ID NO: 28)

wherein:

N is A, T, or G; and

Z is an integer from 2 to 5.

10. The method of claim 9 wherein Z is 3.

11. The method of claim 10 wherein said aptamer comprises the sequence:

5'GGNTGGTGTGGNTGG3' (SEQ ID NO: 38).

12. The method of claim 11 wherein N is T (SEQ ID NO: 29).

* * * * *

SEQUENCE LISTING ( 1 ) GENERAL INFORMATION:

( i i i ) NUMBER OF SEQUENCES: 181

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( x i ) SEQUENCE DESCRIPTION: SEQ ID NO:1:

Cys Pro Arg Thr Asn Arg
1               5

( 2 ) INFORMATION FOR SEQ ID NO:2:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( x i ) SEQUENCE DESCRIPTION: SEQ ID NO:2:

Asp Pro Arg Leu Ile Asp
1               5

( 2 ) INFORMATION FOR SEQ ID NO:3:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:3:

Arg Pro Pro Gly Phe Ser Pro Phe Arg
1               5

( 2 ) INFORMATION FOR SEQ ID NO:4:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i x ) FEATURE:
      ( A ) NAME/KEY: misc_difference
      ( B ) LOCATION: replace(20, "")
      ( D ) OTHER INFORMATION: /note= "This is a 60 nucleotide
         stretch of random sequences."

( x i ) SEQUENCE DESCRIPTION: SEQ ID NO:4:

CGTACGGTCG ACGCTAGCNC ACGTGGAGCT CGGATCC      37

( 2 ) INFORMATION FOR SEQ ID NO:5:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:5:

CGTACGGTCG ACGCTAGC      18

( 2 ) INFORMATION FOR SEQ ID NO:6:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(1, "")
    ( D ) OTHER INFORMATION: /note= "This position is biotin-O- G."

( x i ) SEQUENCE DESCRIPTION: SEQ ID NO:6:

GGATCCGAGC TCCACGTG                    18

( 2 ) INFORMATION FOR SEQ ID NO:7:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

ACGCCGCGGT ACTTACGCNN NN                22

( 2 ) INFORMATION FOR SEQ ID NO:8:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(1, "")
    ( D ) OTHER INFORMATION: /note= "This position is biotin-T."

( x i ) SEQUENCE DESCRIPTION: SEQ ID NO:8:

TGCGGCGCCA TGAATGCG                    18

( 2 ) INFORMATION FOR SEQ ID NO:9:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

AGCGGCCGCT CTTCTAGANN NN                22

( 2 ) INFORMATION FOR SEQ ID NO:10:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

TCGCCGGCGA GAAGATCT                    18

( 2 ) INFORMATION FOR SEQ ID NO:11:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

GAGAAGNNNN        10

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note= "This position is biotin-T."

( i x ) FEATURE:
        ( A ) NAME/KEY: misc_difference
        ( B ) LOCATION: replace(18, "")
        ( D ) OTHER INFORMATION: /note= "This position is a thioate linkage."

( x i ) SEQUENCE DESCRIPTION: SEQ ID NO:12:

TGCGGCGCCA TGAATGCG        18

( 2 ) INFORMATION FOR SEQ ID NO:13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note= "This position is biotin-T."

( i x ) FEATURE:
        ( A ) NAME/KEY: misc_difference
        ( B ) LOCATION: replace(18, "")
        ( D ) OTHER INFORMATION: /note= "This position is a thioate linkage."

( i x ) FEATURE:
        ( A ) NAME/KEY: misc_difference
        ( B ) LOCATION: replace(19, "")
        ( D ) OTHER INFORMATION: /note= "This is a 60 nucleotide stretch of random sequences."

( x i ) SEQUENCE DESCRIPTION: SEQ ID NO:13:

TGCGGCGCCA TGAATGCGNT CTAGAAGAGC GGCCGCT        37

( 2 ) INFORMATION FOR SEQ ID NO:14:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note= "This position is PO3-A."

( i x ) FEATURE:
        ( A ) NAME/KEY: misc_difference ( B ) LOCATION: replace(6, "")
            ( D ) OTHER INFORMATION: /note= "This position is a 55
                nucleotide stretch of random sequences."

( x i ) SEQUENCE DESCRIPTION: SEQ ID NO:14:

N A T T C N    6

( 2 ) INFORMATION FOR SEQ ID NO:15:

( i ) SEQUENCE CHARACTERISTICS:
            ( A ) LENGTH: 7 base pairs
            ( B ) TYPE: nucleic acid
            ( C ) STRANDEDNESS: single
            ( D ) TOPOLOGY: linear ( i x ) FEATURE:
            ( A ) NAME/KEY: misc_difference
            ( B ) LOCATION: replace(1, "")
            ( D ) OTHER INFORMATION: /note= "This is a 17 nucleotide
                stretch of abasic residues."

( x i ) SEQUENCE DESCRIPTION: SEQ ID NO:15:

N C T T A A G    7

( 2 ) INFORMATION FOR SEQ ID NO:16:

( i ) SEQUENCE CHARACTERISTICS:
            ( A ) LENGTH: 2 base pairs
            ( B ) TYPE: nucleic acid
            ( C ) STRANDEDNESS: single
            ( D ) TOPOLOGY: linear ( i x ) FEATURE:
            ( A ) NAME/KEY: misc_difference
            ( B ) LOCATION: replace(1, "")
            ( D ) OTHER INFORMATION: /note= "This is a biotin-17
                nucleotide stretch of abasic residues."

( x i ) SEQUENCE DESCRIPTION: SEQ ID NO:16:

N G    2

( 2 ) INFORMATION FOR SEQ ID NO:17:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i x ) FEATURE:
            ( A ) NAME/KEY: misc_difference
            ( B ) LOCATION: replace(20, "")
            ( D ) OTHER INFORMATION: /note= "This is a 30 nucleotide
                stretch of random sequences."

( x i ) SEQUENCE DESCRIPTION: SEQ ID NO:17:

TCTCCGGATC CAAGCTTATN CGAATTCCTC GAGTCTAGA    3 9

( 2 ) INFORMATION FOR SEQ ID NO:18:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:18:

TCTCCGGATC CAAGCTTAT    1 9

( 2 ) INFORMATION FOR SEQ ID NO:19:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i x ) FEATURE:
  ( A ) NAME/KEY: misc_difference
  ( B ) LOCATION: replace(1, "")
  ( D ) OTHER INFORMATION: /note= "This position is biotin-O- T."

( x i ) SEQUENCE DESCRIPTION: SEQ ID NO:19:

TCTAGACTCG AGGAATTCG  19

( 2 ) INFORMATION FOR SEQ ID NO:20:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(19, "")
    ( D ) OTHER INFORMATION: /note= "This is a 60 nucleotide stretch of random sequences."

( x i ) SEQUENCE DESCRIPTION: SEQ ID NO:20:

CGTACGGTCG ACGCTAGCNC ACGTGGAGCT CGGATCC  37

( 2 ) INFORMATION FOR SEQ ID NO:21:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

CGTACGGTCG ACGCTAGC  18

( 2 ) INFORMATION FOR SEQ ID NO:22:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

GGATCCGAGC TCCACGTG  18

( 2 ) INFORMATION FOR SEQ ID NO:23:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(20, "")
    ( D ) OTHER INFORMATION: /note= "This is a 60 nucleotide stretch of random sequences."

( x i ) SEQUENCE DESCRIPTION: SEQ ID NO:23:

AGAATACTCA AGCTTGCCGN ACCTGAATTC GCCCTATAG  39

( 2 ) INFORMATION FOR SEQ ID NO:24:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note= "This position is biotin-O- C."

( x i ) SEQUENCE DESCRIPTION: SEQ ID NO:24:

CTATAGGGCG AATTCAGGT                                                          19

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

AGAATACTCA AGCTTGCCG                                                          19

( 2 ) INFORMATION FOR SEQ ID NO:26:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

TAATACGACT CACTATAGGG ATCCGAGCTC CACGTG                              36

( 2 ) INFORMATION FOR SEQ ID NO:27:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CTGCAGGTCG ACGCTAGC                                                            18

( 2 ) INFORMATION FOR SEQ ID NO:28:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(3, "")
        ( D ) OTHER INFORMATION: /note= "This position is usually T and never C."

( i x ) FEATURE:
        ( A ) NAME/KEY: misc_difference
        ( B ) LOCATION: replace(7, "")
        ( D ) OTHER INFORMATION: /note= "This position is Nz where N is usually T and never C, and z is an integer from 2 to 5."

( i x ) FEATURE:
   ( A ) NAME/KEY: misc_difference
   ( B ) LOCATION: replace(10, "")
   ( D ) OTHER INFORMATION: /note= "This position is usually T
    and never C."

( x i ) SEQUENCE DESCRIPTION: SEQ ID NO:28:

GGNTGGNGGN TGG                    13

( 2 ) INFORMATION FOR SEQ ID NO:29:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:29:

GGTTGGTGTG GTTGG                   15

( 2 ) INFORMATION FOR SEQ ID NO:30:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( i x ) FEATURE:
   ( A ) NAME/KEY: misc_difference
   ( B ) LOCATION: replace(15..17, "")
   ( D ) OTHER INFORMATION: /note= "These positions are linked
    by MEA."

( x i ) SEQUENCE DESCRIPTION: SEQ ID NO:30:

GGTTGGTGTG GTTGGGT                 17

( 2 ) INFORMATION FOR SEQ ID NO:31:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( i x ) FEATURE:
   ( A ) NAME/KEY: misc_difference
   ( B ) LOCATION: replace(13..15, "")
   ( D ) OTHER INFORMATION: /note= "These positions are thioate
( i . e . ,  P ( O)S) linked."

( x i ) SEQUENCE DESCRIPTION: SEQ ID NO:31:

GGTTGGTGTG GTTGG                   15

( 2 ) INFORMATION FOR SEQ ID NO:32:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( i x ) FEATURE:
   ( A ) NAME/KEY: misc_difference
   ( B ) LOCATION: replace(1..15, "")
   ( D ) OTHER INFORMATION: /note= "These positions are thioate
( i . e . ,  P ( O)S) linked."

( x i ) SEQUENCE DESCRIPTION: SEQ ID NO:32:

```
GGTTGGTGTG GTTGG                                                                15
```

( 2 ) INFORMATION FOR SEQ ID NO:33:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(7, "")
        ( D ) OTHER INFORMATION: /note= "This position is deoxyuridine."

( i x ) FEATURE:
        ( A ) NAME/KEY: misc_difference
        ( B ) LOCATION: replace(9, "")
        ( D ) OTHER INFORMATION: /note= "This position is deoxyuridine."

( x i ) SEQUENCE DESCRIPTION: SEQ ID NO:33:

```
GGTTGGNGNG GTTGG                                                                15
```

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(3, "")
        ( D ) OTHER INFORMATION: /note= "This position is deoxyuridine."

( i x ) FEATURE:
        ( A ) NAME/KEY: misc_difference
        ( B ) LOCATION: replace(12, "")
        ( D ) OTHER INFORMATION: /note= "This position is deoxyuridine."

( x i ) SEQUENCE DESCRIPTION: SEQ ID NO:34:

```
GGNTGGTGTG GNTGG                                                                15
```

( 2 ) INFORMATION FOR SEQ ID NO:35:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(13, "")
        ( D ) OTHER INFORMATION: /note= "This position is 5-(1- pentynyl)uracil."

( x i ) SEQUENCE DESCRIPTION: SEQ ID NO:35:

```
GGTTGGTGTG GTNGG                                                                15
```

( 2 ) INFORMATION FOR SEQ ID NO:36:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear

```
    ( i x ) FEATURE:
              ( A ) NAME/KEY: misc_difference
              ( B ) LOCATION: replace(3..4, "")
              ( D ) OTHER INFORMATION: /note= "This is a formacetal
                    linkage."

( x i ) SEQUENCE DESCRIPTION: SEQ ID NO:36:

GGTTGGTGTG GTTGG                                                         15

( 2 ) INFORMATION FOR SEQ ID NO:37:

( i ) SEQUENCE CHARACTERISTICS:
              ( A ) LENGTH: 15 base pairs
              ( B ) TYPE: nucleic acid
              ( C ) STRANDEDNESS: single
              ( D ) TOPOLOGY: linear ( i x ) FEATURE:
              ( A ) NAME/KEY: misc_difference
              ( B ) LOCATION: replace(12..13, "")
              ( D ) OTHER INFORMATION: /note= "This is a formacetal
                    linkage."

( x i ) SEQUENCE DESCRIPTION: SEQ ID NO:37:

GGTTGGTGTG GTTGG                                                         15

( 2 ) INFORMATION FOR SEQ ID NO:38:

( i ) SEQUENCE CHARACTERISTICS:
              ( A ) LENGTH: 15 base pairs
              ( B ) TYPE: nucleic acid
              ( C ) STRANDEDNESS: single
              ( D ) TOPOLOGY: linear ( i x ) FEATURE:
              ( A ) NAME/KEY: misc_difference
              ( B ) LOCATION: replace(3..4, "")
              ( D ) OTHER INFORMATION: /note= "This is a formacetal
                    linkage."

( i x ) FEATURE:
              ( A ) NAME/KEY: misc_difference
              ( B ) LOCATION: replace(12..13, "")
              ( D ) OTHER INFORMATION: /note= "This is a formacetal
                    linkage."

( x i ) SEQUENCE DESCRIPTION: SEQ ID NO:38:

GGTTGGTGTG GTTGG                                                         15

( 2 ) INFORMATION FOR SEQ ID NO:39:

( i ) SEQUENCE CHARACTERISTICS:
              ( A ) LENGTH: 15 base pairs
              ( B ) TYPE: nucleic acid
              ( C ) STRANDEDNESS: single
              ( D ) TOPOLOGY: linear ( i x ) FEATURE:
              ( A ) NAME/KEY: misc_difference
              ( B ) LOCATION: replace(15, "")
              ( D ) OTHER INFORMATION: /note= "This position indicates an
                    abasic residue."

( x i ) SEQUENCE DESCRIPTION: SEQ ID NO:39:

GGTTGGTGTG GTTGN                                                         15

( 2 ) INFORMATION FOR SEQ ID NO:40:

( i ) SEQUENCE CHARACTERISTICS:
              ( A ) LENGTH: 15 base pairs
              ( B ) TYPE: nucleic acid
```

(C) STRANDEDNESS: single
(D) TOPOLOGY: linear (ix) FEATURE:
(A) NAME/KEY: misc_difference
(B) LOCATION: replace(14, "")
(D) OTHER INFORMATION: /note= "This position is an abasic residue."

(xi) SEQUENCE DESCRIPTION: SEQ ID NO:40:

GGTTGGTGTG GTTNG 15

(2) INFORMATION FOR SEQ ID NO:41:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(13, "")
(D) OTHER INFORMATION: /note= "This position is an abasic residue."

(xi) SEQUENCE DESCRIPTION: SEQ ID NO:41:

GGTTGGTGTG GTNGG 15

(2) INFORMATION FOR SEQ ID NO:42:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(12, "")
(D) OTHER INFORMATION: /note= "This position is an abasic residue."

(xi) SEQUENCE DESCRIPTION: SEQ ID NO:42:

GGTTGGTGTG GNTGG 15

(2) INFORMATION FOR SEQ ID NO:43:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(11, "")
(D) OTHER INFORMATION: /note= "This position is an abasic residue."

(xi) SEQUENCE DESCRIPTION: SEQ ID NO:43:

GGTTGGTGTG NTTGG 15

(2) INFORMATION FOR SEQ ID NO:44:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:

(A) NAME/KEY: misc_difference
(B) LOCATION: replace(10, "")
(D) OTHER INFORMATION: /note= "This position is an abasic residue."

(x i) SEQUENCE DESCRIPTION: SEQ ID NO:44:

GGTTGGTGTN GTTGG                                        15

(2) INFORMATION FOR SEQ ID NO:45:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (i x) FEATURE:
    (A) NAME/KEY: misc_difference
    (B) LOCATION: replace(9, "")
    (D) OTHER INFORMATION: /note= "This position is an abasic residue."

(x i) SEQUENCE DESCRIPTION: SEQ ID NO:45:

GGTTGGTGNG GTTGG                                        15

(2) INFORMATION FOR SEQ ID NO:46:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (i x) FEATURE:
    (A) NAME/KEY: misc_difference
    (B) LOCATION: replace(8, "")
    (D) OTHER INFORMATION: /note= "This position is an abasic residue."

(x i) SEQUENCE DESCRIPTION: SEQ ID NO:46:

GGTTGGTNTG GTTGG                                        15

(2) INFORMATION FOR SEQ ID NO:47:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (i x) FEATURE:
    (A) NAME/KEY: misc_difference
    (B) LOCATION: replace(7, "")
    (D) OTHER INFORMATION: /note= "This position is an abasic residue."

(x i) SEQUENCE DESCRIPTION: SEQ ID NO:47:

GGTTGGNGTG GTTGG                                        15

(2) INFORMATION FOR SEQ ID NO:48:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (i x) FEATURE:
    (A) NAME/KEY: misc_difference
    (B) LOCATION: replace(6, "")
    (D) OTHER INFORMATION: /note= "This position is an abasic residue."

( x i ) SEQUENCE DESCRIPTION: SEQ ID NO:48:

GGTTGNTGTG GTTGG  15

( 2 ) INFORMATION FOR SEQ ID NO:49:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(5, "")
    ( D ) OTHER INFORMATION: /note= "This position is an abasic
        residue."

( x i ) SEQUENCE DESCRIPTION: SEQ ID NO:49:

GGTTNGTGTG GTTGG  15

( 2 ) INFORMATION FOR SEQ ID NO:50:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(4, "")
    ( D ) OTHER INFORMATION: /note= "This position is an abasic
        residue."

( x i ) SEQUENCE DESCRIPTION: SEQ ID NO:50:

GGTNGGTGTG GTTGG  15

( 2 ) INFORMATION FOR SEQ ID NO:51:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(3, "")
    ( D ) OTHER INFORMATION: /note= "This position is an abasic
        residue."

( x i ) SEQUENCE DESCRIPTION: SEQ ID NO:51:

GGNTGGTGTG GTTGG  15

( 2 ) INFORMATION FOR SEQ ID NO:52:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(2, "")
    ( D ) OTHER INFORMATION: /note= "This is an abasic residue."

( x i ) SEQUENCE DESCRIPTION: SEQ ID NO:52:

GNTTGGTGTG GTTGG  15

( 2 ) INFORMATION FOR SEQ ID NO:53:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note= "This is an abasic residue."

( x i ) SEQUENCE DESCRIPTION: SEQ ID NO:53:

NGTTGGTGTG GTTGG     15

( 2 ) INFORMATION FOR SEQ ID NO:54:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(13, "")
        ( D ) OTHER INFORMATION: /note= "This position is a
            5-propynyl- 2'-deoxyuridine residue."

( x i ) SEQUENCE DESCRIPTION: SEQ ID NO:54:

GGTTGGTGTG GTNGG     15

( 2 ) INFORMATION FOR SEQ ID NO:55:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(12, "")
        ( D ) OTHER INFORMATION: /note= "This is a
            5-propynyl- 2'-deoxyuridine residue."

( x i ) SEQUENCE DESCRIPTION: SEQ ID NO:55:

GGTTGGTGTG GNTGG     15

( 2 ) INFORMATION FOR SEQ ID NO:56:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(9, "")
        ( D ) OTHER INFORMATION: /note= "This position is a
            5-propynyl- 2'-deoxyuridine residue."

( x i ) SEQUENCE DESCRIPTION: SEQ ID NO:56:

GGTTGGTGNG GTTGG     15

( 2 ) INFORMATION FOR SEQ ID NO:57:

( i ) SEQUENCE CHARACTERISTICS:
        ( A ) LENGTH: 15 base pairs (B) TYPE: nucleic acid
(C) STRANDEDNESS: single
(D) TOPOLOGY: linear (ix) FEATURE:
(A) NAME/KEY: misc_difference
(B) LOCATION: replace(7, "")
(D) OTHER INFORMATION: /note= "This position is a 5-propynyl- 2'-deoxyuridine residue."

(xi) SEQUENCE DESCRIPTION: SEQ ID NO:57:

GGTTGGNGTG GTTGG                                          15

(2) INFORMATION FOR SEQ ID NO:58:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(4, "")
(D) OTHER INFORMATION: /note= "This position is a 5-propynyl- 2'-deoxyuridine residue."

(xi) SEQUENCE DESCRIPTION: SEQ ID NO:58:

GGTNGGTGTG GTTGG                                          15

(2) INFORMATION FOR SEQ ID NO:59:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(3, "")
(D) OTHER INFORMATION: /note= "This position is a 5-propynyl- 2'-deoxyuridine residue."

(xi) SEQUENCE DESCRIPTION: SEQ ID NO:59:

GGNTGGTGTG GTTGG                                          15

(2) INFORMATION FOR SEQ ID NO:60:

(i) SEQUENCE CHARACTERISTICS:
(A) LENGTH: 41 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(22, "")
(D) OTHER INFORMATION: /note= "This is a 20 nucleotide stretch of random sequences."

(xi) SEQUENCE DESCRIPTION: SEQ ID NO:60:

TAGAATACTC AAGCTTCGAC GNAGTTTGGA TCCCCGGGTA C              41

(2) INFORMATION FOR SEQ ID NO:61:

(i) SEQUENCE CHARACTERISTICS:
(A) LENGTH: 21 base pairs
(B) TYPE: nucleic acid
(C) STRANDEDNESS: single
(D) TOPOLOGY: linear ( x i ) SEQUENCE DESCRIPTION: SEQ ID NO:61:

TAGAATACTC AAGCTTCGAC G 21

( 2 ) INFORMATION FOR SEQ ID NO:62:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:62:

GTACCCGGGG ATCCAAACT 19

( 2 ) INFORMATION FOR SEQ ID NO:63:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:63:

TAGTATGTAT TATGTGTAG 19

( 2 ) INFORMATION FOR SEQ ID NO:64:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:64:

ATAGAGTATA TATGCTGTCT 20

( 2 ) INFORMATION FOR SEQ ID NO:65:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:65:

GTATATAGTA TAGTATTGGC 20

( 2 ) INFORMATION FOR SEQ ID NO:66:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:66:

AGGATATATG ATATGATTCG G 21

( 2 ) INFORMATION FOR SEQ ID NO:67:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:67:

-continued

TACTATCATG TATATTACCC 20

( 2 ) INFORMATION FOR SEQ ID NO:68:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

CATTAAACGC GAGCTTTTTG 20

( 2 ) INFORMATION FOR SEQ ID NO:69:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

CTCCCATAAT GCCCTAGCCG 20

( 2 ) INFORMATION FOR SEQ ID NO:70:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

GACGCACCGT ACCCCGT 17

( 2 ) INFORMATION FOR SEQ ID NO:71:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

CACCAAACGC ATTGCATTCC 20

( 2 ) INFORMATION FOR SEQ ID NO:72:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

GTACATTCAG GCTGCCTGCC 20

( 2 ) INFORMATION FOR SEQ ID NO:73:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

TACCATCCCG TGGACGTAAC 20

( 2 ) INFORMATION FOR SEQ ID NO:74:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:74:

GACTAAACGC ATTGTGCCCC     20

( 2 ) INFORMATION FOR SEQ ID NO:75:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:75:

AACGAAGGGC ACGCCGGCTG     20

( 2 ) INFORMATION FOR SEQ ID NO:76:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:76:

ACGGATGGTC TGGCTGGACA     20

( 2 ) INFORMATION FOR SEQ ID NO:77:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:77:

CGGGGAGAGG TTGGTGTGGT TGGCAATGGC TAGAGTAGTG ACGTTTTCGC GGTGAGGTCC     60

( 2 ) INFORMATION FOR SEQ ID NO:78:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:78:

GGTTGGGCTG GTTGGGTTGG G     21

( 2 ) INFORMATION FOR SEQ ID NO:79:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(13..15, "")
    ( D ) OTHER INFORMATION: /note= "These positions are linked
      by thioate internucleotide linkages."

( x i ) SEQUENCE DESCRIPTION: SEQ ID NO:79:

GGTTGGTGTG GTTGG 15

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(2, "")
        ( D ) OTHER INFORMATION: /note= "This position is pentynyl dU."

( i x ) FEATURE:
        ( A ) NAME/KEY: misc_difference
        ( B ) LOCATION: replace(4, "")
        ( D ) OTHER INFORMATION: /note= "This position is pentynyl dU."

( i x ) FEATURE:
        ( A ) NAME/KEY: misc_difference
        ( B ) LOCATION: replace(6, "")
        ( D ) OTHER INFORMATION: /note= "This position is pentynyl dU."

( i x ) FEATURE:
        ( A ) NAME/KEY: misc_difference
        ( B ) LOCATION: replace(9, "")
        ( D ) OTHER INFORMATION: /note= "This position is pentynyl dU."

( i x ) FEATURE:
        ( A ) NAME/KEY: misc_difference
        ( B ) LOCATION: replace(11, "")
        ( D ) OTHER INFORMATION: /note= "This position is pentynyl dU."

( i x ) FEATURE:
        ( A ) NAME/KEY: misc_difference
        ( B ) LOCATION: replace(14, "")
        ( D ) OTHER INFORMATION: /note= "This position is pentynyl dU."

( i x ) FEATURE:
        ( A ) NAME/KEY: misc_difference
        ( B ) LOCATION: replace(16, "")
        ( D ) OTHER INFORMATION: /note= "This position is pentynyl dU."

( i x ) FEATURE:
        ( A ) NAME/KEY: misc_difference
        ( B ) LOCATION: replace(17, "")
        ( D ) OTHER INFORMATION: /note= "This position is pentynyl dU."

( x i ) SEQUENCE DESCRIPTION: SEQ ID NO:80:

GNANANAGNA NAGNANNGGC 20

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(3, "")
        ( D ) OTHER INFORMATION: /note= "This position is pentynyl dU."

( i x ) FEATURE:
    ( A ) NAME/KEY: misc_difference
    ( B ) LOCATION: replace(5, "")
    ( D ) OTHER INFORMATION: /note= "This position is pentynyl dU."

( i x ) FEATURE:
    ( A ) NAME/KEY: misc_difference
    ( B ) LOCATION: replace(9, "")
    ( D ) OTHER INFORMATION: /note= "This position is pentynyl dU."

( i x ) FEATURE:
    ( A ) NAME/KEY: misc_difference
    ( B ) LOCATION: replace(11, "")
    ( D ) OTHER INFORMATION: /note= "This position is pentynyl dU."

( i x ) FEATURE:
    ( A ) NAME/KEY: misc_difference
    ( B ) LOCATION: replace(12, "")
    ( D ) OTHER INFORMATION: /note= "This position is pentynyl dU."

( i x ) FEATURE:
    ( A ) NAME/KEY: misc_difference
    ( B ) LOCATION: replace(15, "")
    ( D ) OTHER INFORMATION: /note= "This position is pentynyl dU."

( i x ) FEATURE:
    ( A ) NAME/KEY: misc_difference
    ( B ) LOCATION: replace(17, "")
    ( D ) OTHER INFORMATION: /note= "This position is pentynyl dU."

( i x ) FEATURE:
    ( A ) NAME/KEY: misc_difference
    ( B ) LOCATION: replace(20, "")
    ( D ) OTHER INFORMATION: /note= "This position is pentynyl dU."

( x i ) SEQUENCE DESCRIPTION: SEQ ID NO:81:

GCNGNAGANA NNAGNANAGN                                                       20

( 2 ) INFORMATION FOR SEQ ID NO:82:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(20, "")
        ( D ) OTHER INFORMATION: /note= "This is a 60 nucleotide stretch of random sequences."

( x i ) SEQUENCE DESCRIPTION: SEQ ID NO:82:

TGGCAGATGA CCCGAATTCN GGATCCAGTG CTCAAATGTT                     40

( 2 ) INFORMATION FOR SEQ ID NO:83:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

TGGCAGATGA CCCGAATTC                                                     19

( 2 ) INFORMATION FOR SEQ ID NO:84:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:84:

AACATTTGAG CACTGGATCC        20

( 2 ) INFORMATION FOR SEQ ID NO:85:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( x i ) SEQUENCE DESCRIPTION: SEQ ID NO:85:

Tyr Asp Gln Pro Lys Leu Leu Gly Ile Glu Thr Pro Leu Pro Lys Lys
1               5                   10                  15
Glu Leu ( 2 ) INFORMATION FOR SEQ ID NO:86:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: linear ( x i ) SEQUENCE DESCRIPTION: SEQ ID NO:86:

Thr Pro Leu Pro Lys Lys Glu Leu Leu Pro Gly Asn Asn Arg Lys
1               5                   10                  15
Val Tyr Glu ( 2 ) INFORMATION FOR SEQ ID NO:87:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: linear ( x i ) SEQUENCE DESCRIPTION: SEQ ID NO:87:

Leu Pro Gly Asn Asn Arg Lys Val Tyr Glu Leu Ser Asn Val Gln Glu
1               5                   10                  15
Asp Ser Gln ( 2 ) INFORMATION FOR SEQ ID NO:88:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( x i ) SEQUENCE DESCRIPTION: SEQ ID NO:88:

Tyr Ser Asn Cys Pro Asp Gly Gln Ser Thr Ala Lys Thr Phe Leu Thr
1               5                   10                  15
Val Tyr ( 2 ) INFORMATION FOR SEQ ID NO:89:

( i ) SEQUENCE CHARACTERISTICS:
  ( A ) LENGTH: 17 amino acids (B) TYPE: amino acid
(C) STRANDEDNESS: single
(D) TOPOLOGY: linear (xi) SEQUENCE DESCRIPTION: SEQ ID NO:89:

Tyr Glu Leu Asp Leu Arg Pro Gln Gly Leu Glu Leu Phe Glu Asn Thr
1               5                   10                  15

Ser (2) INFORMATION FOR SEQ ID NO:90:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:90:

GGGTTGGGTC GGTTGGT                                                17

(2) INFORMATION FOR SEQ ID NO:91:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:91:

GGGATGGTTT GGTTGGG                                                17

(2) INFORMATION FOR SEQ ID NO:92:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (xi) SEQUENCE DESCRIPTION: SEQ ID NO:92:

AGGTTGGGAG GGTGGG                                                 16

(2) INFORMATION FOR SEQ ID NO:93:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:93:

TGGTTGGCGA GGATGGA                                                17

(2) INFORMATION FOR SEQ ID NO:94:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:94:

AGGTTGGGTA GTGTTGGT                                               18

(2) INFORMATION FOR SEQ ID NO:95:

(i) SEQUENCE CHARACTERISTICS:

(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:95:

AGGTTGGGCT GGTTGGG 17

(2) INFORMATION FOR SEQ ID NO:96:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:96:

GGGTTGGGAG GTTGGA 16

(2) INFORMATION FOR SEQ ID NO:97:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:97:

TGGTTGGGTC GGTTGGG 17

(2) INFORMATION FOR SEQ ID NO:98:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:98:

GGGATGGTGT GGTTGGC 17

(2) INFORMATION FOR SEQ ID NO:99:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:99:

TGGTTGGCAG GGATGGG 17

(2) INFORMATION FOR SEQ ID NO:100:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:100:

TGGATGGTGA GGTTGGA 17

(2) INFORMATION FOR SEQ ID NO:101:

(i) SEQUENCE CHARACTERISTICS:
(A) LENGTH: 17 base pairs
(B) TYPE: nucleic acid ( C ) STRANDEDNESS: single
        ( D ) TOPOLOGY: linear ( x i ) SEQUENCE DESCRIPTION: SEQ ID NO:101:

GGGGTGGTTA GGTTGGT                                                                              17

( 2 ) INFORMATION FOR SEQ ID NO:102:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:102:

AGGGTGGTTA GGTTGGT                                                                              17

( 2 ) INFORMATION FOR SEQ ID NO:103:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:103:

CGGTTGGGTT GGGATGGA                                                                             18

( 2 ) INFORMATION FOR SEQ ID NO:104:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:104:

CGGTTGGTGT GGTTGGT                                                                              17

( 2 ) INFORMATION FOR SEQ ID NO:105:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:105:

AGGTTGGTGT GGGTGGG                                                                              17

( 2 ) INFORMATION FOR SEQ ID NO:106:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

CGGGTGGATA GGTTGGA                                                                              17

( 2 ) INFORMATION FOR SEQ ID NO:107:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

GGTGTGGTAG TTTGTTGGG                                                                 19

( 2 ) INFORMATION FOR SEQ ID NO:108:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

TGGTTGGTTA CTGGTTGGG                                                                 19

( 2 ) INFORMATION FOR SEQ ID NO:109:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

GGGTTGGTCT GGGTGGA                                                                   17

( 2 ) INFORMATION FOR SEQ ID NO:110:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

TGGTTGGGTT GGGTGGA                                                                   17

( 2 ) INFORMATION FOR SEQ ID NO:111:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:111:

TGGTTGGCCA GGTTGGA                                                                   17

( 2 ) INFORMATION FOR SEQ ID NO:112:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:112:

CTAGCGGCAG TGGTTGGG                                                                  18

( 2 ) INFORMATION FOR SEQ ID NO:113:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:113:

TGGGTGGGGA GGTTGGT                                              17

( 2 ) INFORMATION FOR SEQ ID NO:114:

( i ) SEQUENCE CHARACTERISTICS:
　　　　　　　　( A ) LENGTH: 17 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:114:

AGGTTGGTTT GGGTGGT                                              17

( 2 ) INFORMATION FOR SEQ ID NO:115:

( i ) SEQUENCE CHARACTERISTICS:
　　　　　　　　( A ) LENGTH: 18 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:115:

AGGTTGGTTA GGGTTGGT                                             18

( 2 ) INFORMATION FOR SEQ ID NO:116:

( i ) SEQUENCE CHARACTERISTICS:
　　　　　　　　( A ) LENGTH: 17 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:116:

GGGATGCGGT GGTTGGG                                              17

( 2 ) INFORMATION FOR SEQ ID NO:117:

( i ) SEQUENCE CHARACTERISTICS:
　　　　　　　　( A ) LENGTH: 18 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:117:

TGGTTGGTTA TGGTTGGT                                             18

( 2 ) INFORMATION FOR SEQ ID NO:118:

( i ) SEQUENCE CHARACTERISTICS:
　　　　　　　　( A ) LENGTH: 17 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:118:

AGGTTGGTGT GGTTGGC                                              17

( 2 ) INFORMATION FOR SEQ ID NO:119:

( i ) SEQUENCE CHARACTERISTICS:
　　　　　　　　( A ) LENGTH: 17 base pairs
　　　　　　　　( B ) TYPE: nucleic acid
　　　　　　　　( C ) STRANDEDNESS: single
　　　　　　　　( D ) TOPOLOGY: linear ( x i ) SEQUENCE DESCRIPTION: SEQ ID NO:119:

AGGTTGGTGT GGGTGGG                                              17

( 2 ) INFORMATION FOR SEQ ID NO:120:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:120:

TGGTTGGGAG GTTGGT                           16

( 2 ) INFORMATION FOR SEQ ID NO:121:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:121:

GGGTTGGTGG GTGGATGGT                        19

( 2 ) INFORMATION FOR SEQ ID NO:122:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:122:

AGGATATATG ATATGATTCG                       20

( 2 ) INFORMATION FOR SEQ ID NO:123:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:123:

TCAGTATTAG GCCCCTCGAA                       20

( 2 ) INFORMATION FOR SEQ ID NO:124:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:124:

CAGAGTACAG GCCATGTGCA                       20

( 2 ) INFORMATION FOR SEQ ID NO:125:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:125:

TAGTATGTAT TATGTGTAG                        19

( 2 ) INFORMATION FOR SEQ ID NO:126:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:126:

GTATATAGTA TAGTATTGGC  20

( 2 ) INFORMATION FOR SEQ ID NO:127:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:127:

GACTAAACGC ATTGTGCCCC  20

( 2 ) INFORMATION FOR SEQ ID NO:128:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

TACCATCCCG TGGACGTAAC  20

( 2 ) INFORMATION FOR SEQ ID NO:129:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

GTACATTCAG GCTGCCTGCC  20

( 2 ) INFORMATION FOR SEQ ID NO:130:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:130:

GACGCATCCA GTTTAGGTCG  20

( 2 ) INFORMATION FOR SEQ ID NO:131:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

AACGAAGGGC ACGCCGGCTG  20

( 2 ) INFORMATION FOR SEQ ID NO:132:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:132:

GTATATAGTA TAGTATTGGC 20

( 2 ) INFORMATION FOR SEQ ID NO:133:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:133:

TACTATCATG TATATTACCC 20

( 2 ) INFORMATION FOR SEQ ID NO:134:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:134:

ATAGAGTATA TATGCTGTCT 20

( 2 ) INFORMATION FOR SEQ ID NO:135:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:135:

CACCAAACGC ATTGCATTCC 20

( 2 ) INFORMATION FOR SEQ ID NO:136:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:136:

ACGGATGGTC TGGCTGGACA 20

( 2 ) INFORMATION FOR SEQ ID NO:137:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:137:

CATTAAACGC GAGCTTTTTG 20

( 2 ) INFORMATION FOR SEQ ID NO:138:

( i ) SEQUENCE CHARACTERISTICS:
     ( A ) LENGTH: 17 base pairs ( B ) TYPE: nucleic acid
                    ( C ) STRANDEDNESS: single
                    ( D ) TOPOLOGY: linear ( x i ) SEQUENCE DESCRIPTION: SEQ ID NO:138:

GACGCACCGT ACCCCGT                                                                                  17

( 2 ) INFORMATION FOR SEQ ID NO:139:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:139:

GTATATAGTA TAGTATTGGC                                                                               20

( 2 ) INFORMATION FOR SEQ ID NO:140:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:140:

CTCCCATAAT GCCCTAGCCG                                                                               20

( 2 ) INFORMATION FOR SEQ ID NO:141:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:141:

CAGTTTACGT GCCACTGTAC                                                                               20

( 2 ) INFORMATION FOR SEQ ID NO:142:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:142:

TGGATAGCAC ATTGGGTGTA                                                                               20

( 2 ) INFORMATION FOR SEQ ID NO:143:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:143:

GTGTAGTTTA CGTCCCACCC                                                                               20

( 2 ) INFORMATION FOR SEQ ID NO:144:

( i ) SEQUENCE CHARACTERISTICS:
                    ( A ) LENGTH: 20 base pairs
                    ( B ) TYPE: nucleic acid
                    ( C ) STRANDEDNESS: single ( D ) TOPOLOGY: linear ( x i ) SEQUENCE DESCRIPTION: SEQ ID NO:144:

GAACAAAACG CATTGTCCCC                                                                        20

( 2 ) INFORMATION FOR SEQ ID NO:145:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:145:

TATAGAGTAT AGTATGTGCT                                                                        20

( 2 ) INFORMATION FOR SEQ ID NO:146:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:146:

AGTACATGCA GGTAGTTCAC                                                                        20

( 2 ) INFORMATION FOR SEQ ID NO:147:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:147:

GCCCAACACG CATTGTTCCC                                                                        20

( 2 ) INFORMATION FOR SEQ ID NO:148:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:148:

GAGTTCACGT GCGATGTGAC                                                                        20

( 2 ) INFORMATION FOR SEQ ID NO:149:

( i ) SEQUENCE CHARACTERISTICS:
            ( A ) LENGTH: 60 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:149:

GGAGAATGCG GATGGTCGCA AGAGAGTACT TAGTTAGGAT CCTAGGTTGG GTAGGGTGGT                             60

( 2 ) INFORMATION FOR SEQ ID NO:150:

( i ) SEQUENCE CHARACTERISTICS:
            ( A ) LENGTH: 60 base pairs
            ( B ) TYPE: nucleic acid
            ( C ) STRANDEDNESS: single
            ( D ) TOPOLOGY: linear (xi) SEQUENCE DESCRIPTION: SEQ ID NO:150:

GGGGAGGGCG GGTGGGTAGA GAGAGTTGGA AGAGGGCGAG GACCGACAAT TTTGGCTGGG    60

(2) INFORMATION FOR SEQ ID NO:151:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:151:

GGGGGAGGCG GGTGGGTAGA GAGAGTTGGA AGAGGGCGAG GACGCACAAT TTTGGCTGGG    60

(2) INFORMATION FOR SEQ ID NO:152:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:152:

GGGGCGCAGG GGGGGGGGGA GAGAGAGGAC GCGCCAGCAA TACTACGCTT TTTCATGGAT    60

(2) INFORMATION FOR SEQ ID NO:153:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:153:

CGGGAGGGCG GGTGGGCTAG AGAGAGAGTT GGAAGAGGCG AGACGCACAA TTTTGGCTGG    60

(2) INFORMATION FOR SEQ ID NO:154:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:154:

GCGCGTTGGT TGGGTTGGCT TGGGGACGTG GTAGGAGGGT TACGTTCTGT CGCTCTGGCT    60

(2) INFORMATION FOR SEQ ID NO:155:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:155:

GCGCGTTGGT TGGGTTGGCT TGGGGGCGTG GTAGGAGGGT TACGTTCTGT CCGTCTGGTC    60

(2) INFORMATION FOR SEQ ID NO:156:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:156:

GGCGCGTTGG TTGGGTTGGC TTGGGACCTG GTAGGAGGCA CACGTTCTGT CGCTCTGGCT        60

( 2 ) INFORMATION FOR SEQ ID NO:157:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:157:

GGGAAGTAGA GGCCTTGAGG GTGGGGGGGC GTAGGATAGT GGGCGATATG TATTTGCTCT        60

( 2 ) INFORMATION FOR SEQ ID NO:158:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:158:

GGGAAGTAGA GGCCTTGAGG GGGGGGGGGC GTAGGATAGT GGGCGATATG TATTTGACTC        60

( 2 ) INFORMATION FOR SEQ ID NO:159:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

GGGTTAGCCA TGAGCTGGGG GCGGGGGGGT GGGCCGGTCT CGACTACGGG TTGTGACGGA        60

( 2 ) INFORMATION FOR SEQ ID NO:160:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:160:

GGGTTAGCCA TGAGCTGGGG GCGGGGGGGT GGGCCGGTCT CGACTACGAG TTGTGACGGA        60

( 2 ) INFORMATION FOR SEQ ID NO:161:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:161:

ACGGTCAGTG GCCTAGGTAG TAGTGCTGTA TTCGTAGGTT GGGTGGTATT TTAGTGGGTC        60

( 2 ) INFORMATION FOR SEQ ID NO:162:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:162:

GGGCGCGCAC GGTAAGTCGG GGGTGGCACA GGAGGGGGTT GGGGATATAC TGGTTTGGTC        60

( 2 ) INFORMATION FOR SEQ ID NO:163:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:163:

GGGCGCGCAC GGTAAGTCGG GGGTGGCACA GGAGGGGGTT GGGAATATAC TGGTTTGGTC  60

( 2 ) INFORMATION FOR SEQ ID NO:164:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:164:

CAAGTGAGGT AGTACGTTCG CGTGAGGTGA TAGGATGGGT GGGAGGTGGG GACTTGATGG  60

( 2 ) INFORMATION FOR SEQ ID NO:165:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:165:

AAGTAGCTAG TACGTTCGGC GTGAAGGTGA TAGGATGGGT GGGAGGTGGG ACTTGATGGA  60

( 2 ) INFORMATION FOR SEQ ID NO:166:

( i ) SEQUENCE CHARACTERISTICS:
    ( A ) LENGTH: 59 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:166:

GGCGGGTGCT GCGATGGGGA TCCGAACGGT TTTATGGTGT GGGTGGTTAT GGTGGTGAG  59

( 2 ) INFORMATION FOR SEQ ID NO:167:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:167:

GGGCGGGTGC TGCGACGGGG ATCCGAACGG TTTTATGGTG TGGGTGGTTA TGGTGGTGAG  60

( 2 ) INFORMATION FOR SEQ ID NO:168:

( i ) SEQUENCE CHARACTERISTICS:
    ( A ) LENGTH: 57 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(1, "")
    ( D ) OTHER INFORMATION: /note= "This position is G/N."

( i x ) FEATURE:

( A ) NAME/KEY: misc_difference
                    ( B ) LOCATION: replace(2, "")
                    ( D ) OTHER INFORMATION: /note= "This position is G/N."

( i x ) FEATURE:
                    ( A ) NAME/KEY: misc_difference
                    ( B ) LOCATION: replace(7, "")
                    ( D ) OTHER INFORMATION: /note= "This position is G/N."

( i x ) FEATURE:
                    ( A ) NAME/KEY: misc_difference
                    ( B ) LOCATION: replace(8, "")
                    ( D ) OTHER INFORMATION: /note= "This position is G/N."

( x i ) SEQUENCE DESCRIPTION: SEQ ID NO:168:

NNGNNGNNCG GATGCGGTCG TCACAGAGAT GAGCTGTGGG CATCGGGGAA TGTGCAC            57

( 2 ) INFORMATION FOR SEQ ID NO:169:

( i ) SEQUENCE CHARACTERISTICS:
                    ( A ) LENGTH: 60 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: misc_difference
                    ( B ) LOCATION: replace(30, "")
                    ( D ) OTHER INFORMATION: /note= "This position is G/C."

( i x ) FEATURE:
                    ( A ) NAME/KEY: misc_difference
                    ( B ) LOCATION: replace(31, "")
                    ( D ) OTHER INFORMATION: /note= "This position is C/G."

( x i ) SEQUENCE DESCRIPTION: SEQ ID NO:169:

GGAGGGGTGG GGGGGAGGGC ACAAGCGTAN NATGCGAGGC GCGAGGGGGT GTTTCTGGA          60

( 2 ) INFORMATION FOR SEQ ID NO:170:

( i ) SEQUENCE CHARACTERISTICS:
                    ( A ) LENGTH: 60 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:170:

GGCGGCCAGA TGCTTGAGGG GTGGGTGGGC GGAAAGGCTT GGGCAAACTG TGTGCGTAGG          60

( 2 ) INFORMATION FOR SEQ ID NO:171:

( i ) SEQUENCE CHARACTERISTICS:
                    ( A ) LENGTH: 60 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: misc_difference
                    ( B ) LOCATION: replace(18, "")
                    ( D ) OTHER INFORMATION: /note= "This position is G/C."

( i x ) FEATURE:
                    ( A ) NAME/KEY: misc_difference
                    ( B ) LOCATION: replace(19, "")
                    ( D ) OTHER INFORMATION: /note= "This position is G/C."

( i x ) FEATURE:
                    ( A ) NAME/KEY: misc_difference
                    ( B ) LOCATION: replace(20, "")
                    ( D ) OTHER INFORMATION: /note= "This position is G/C."

( x i ) SEQUENCE DESCRIPTION: SEQ ID NO:171:

5,756,291

209 210

-continued

GGGTACTGCA GTCCTGANNN CAGGTAGGCT TGAAAAGTTA GTGGGTAGGG TGGTCCACGG    60

( 2 ) INFORMATION FOR SEQ ID NO:172:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:172:

GCGTAGGTAC GTATGATGTC TAGGAAGAGT GGCGAGGATC ACGGCAATTT TTCAGCTCGG    60

( 2 ) INFORMATION FOR SEQ ID NO:173:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:173:

TAACAAAATG ATTGAACGCT GTGACAATTT AGGAGGCACT TTTCGGGGAA ATCGTGCGCG    60

( 2 ) INFORMATION FOR SEQ ID NO:174:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:174:

GAGAGCGAGA GAAGTGAGTA TGAGGAGCGT GTACTGCAAG GTGAGGGAGA CCGCAGACGG    60

( 2 ) INFORMATION FOR SEQ ID NO:175:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:175:

GGCGGGGTAC TAATATTAGG GTGGGTGGGT AAAGACGGCG GGTAATACTG CGGAGCGGCT    60

( 2 ) INFORMATION FOR SEQ ID NO:176:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:176:

GTTACGGTCG GTACGTCTCG TGGGCAGGTT GGGTGGTTCA GTGCGCGCGG TATTCAGGTC    60

( 2 ) INFORMATION FOR SEQ ID NO:177:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:177:

GACACACTGT TGGGATGGCT TGGGACACAC TGGAGAGGCA CACGTTCTGT CGCTCTGGCT    60

( 2 ) INFORMATION FOR SEQ ID NO:178:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( x i ) SEQUENCE DESCRIPTION: SEQ ID NO:178:

GGGAGGGGTG GGGGGTGGG CAGCAAAGCG TATAGCGTCT TGGAGGGGAT CGAATGGAT                59

( 2 ) INFORMATION FOR SEQ ID NO:179:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( x i ) SEQUENCE DESCRIPTION: SEQ ID NO:179:

GGCAGGGGTG ATATCTTTGG TGGTGGGGGG TGCGCGGAGC ACGGTGAAGT GTTGGGTGGG              60

( 2 ) INFORMATION FOR SEQ ID NO:180:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( x i ) SEQUENCE DESCRIPTION: SEQ ID NO:180:

AGGGCACAAG GCCTAGCGGA TGCGACGCGC GTGGGGGCTT TCTGGA                            46

( 2 ) INFORMATION FOR SEQ ID NO:181:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( x i ) SEQUENCE DESCRIPTION: SEQ ID NO:181:

CGTTAGCGGC GGTACGTATC GTGGGCAGGT TGGGTGGTTC AGTGCGGCGG TATCAAGTC              59